(12) United States Patent
Fischer et al.

(10) Patent No.: US 10,368,545 B2
(45) Date of Patent: Aug. 6, 2019

(54) SUBSTITUTED 2-THIOIMIDAZOLYLCARBOXAMIDES AS PESTICIDES

(71) Applicant: BAYER CROPSCIENCE AKTIENGESELLSCHAFT, Monheim am Rhein (DE)

(72) Inventors: Reiner Fischer, Monheim (DE); Markus Heil, Leichlingen (DE); Johannes-Rudolf Jansen, Monheim (DE); Susanne Kuebbeler, Duesseldorf (DE); David Wilcke, Duesseldorf (DE); Adeline Koehler, Langenfeld (DE); Matthieu Willot, Duesseldorf (DE); Sascha Eilmus, Leichlingen (DE); Kerstin Ilg, Cologne (DE); Olga Malsam, Roesrath (DE); Peter Loesel, Leverkusen (DE); Daniela Portz, Vettweiss (DE); Wolfram Andersch, Bergisch Gladbach (DE)

(73) Assignee: BAYER CROPSCIENCE AKTIENGESELLSCHAFT, Monheim am Rhen (DE)

( * ) Notice: Subject to any disclaimer, the term of this patent is extended or adjusted under 35 U.S.C. 154(b) by 0 days.

(21) Appl. No.: 15/546,234

(22) PCT Filed: Feb. 5, 2016

(86) PCT No.: PCT/EP2016/052445
§ 371 (c)(1),
(2) Date: Jul. 25, 2017

(87) PCT Pub. No.: WO2016/128298
PCT Pub. Date: Aug. 18, 2016

(65) Prior Publication Data
US 2018/0007900 A1 Jan. 11, 2018

(30) Foreign Application Priority Data
Feb. 9, 2015 (EP) .................................. 15154252

(51) Int. Cl.
| | | |
|---|---|---|
| *A01N 43/50* | (2006.01) | |
| *A01N 43/52* | (2006.01) | |
| *A01N 43/54* | (2006.01) | |
| *A01N 43/60* | (2006.01) | |
| *A01N 43/76* | (2006.01) | |
| *A01N 43/78* | (2006.01) | |
| *A01N 43/82* | (2006.01) | |
| *A01N 43/88* | (2006.01) | |

(Continued)

(52) U.S. Cl.
CPC ............. *A01N 43/50* (2013.01); *A01N 43/52* (2013.01); *A01N 43/54* (2013.01); *A01N 43/60* (2013.01); *A01N 43/653* (2013.01); *A01N 43/76* (2013.01); *A01N 43/78* (2013.01); *A01N 43/82* (2013.01); *A01N 43/88* (2013.01); *A01N 43/90* (2013.01); *C07D 401/12* (2013.01); *C07D 401/14* (2013.01); *C07D 405/14* (2013.01); *C07D 409/14* (2013.01); *C07D 413/14* (2013.01); *C07D 417/14* (2013.01); *C07D 471/04* (2013.01); *C07D 513/04* (2013.01)

(58) Field of Classification Search
CPC .. C07D 413/14; C07D 409/14; C07D 405/14; C07D 401/12; C07D 401/14; C07D 417/14; C07D 471/04; C07D 513/04; A01N 43/50; A01N 43/76; A01N 43/88; A01N 43/52; A01N 43/54; A01N 43/60; A01N 43/653; A01N 43/78; A01N 43/82; A01N 43/90
See application file for complete search history.

(56) References Cited

U.S. PATENT DOCUMENTS

2012/0122681 A1* 5/2012 Le Vezouet ............ A01N 43/50
504/100

FOREIGN PATENT DOCUMENTS

| EP | 0312960 A2 | 4/1989 |
|---|---|---|
| WO | 2011009804 A2 | 1/2011 |

(Continued)

OTHER PUBLICATIONS

Norris, et al., "Synthesis of imidazo[1,5-a]quinoxalin-4(5H)-one template via a novel intramolecular cyclization process," Tetrahedron Letters (2001) vol. 42: 4297-4299.

(Continued)

*Primary Examiner* — John Pak
(74) *Attorney, Agent, or Firm* — McBee Moore Woodward & Vanik IP, LLC

(57) ABSTRACT

The present invention relates to compounds of the general formula (I)

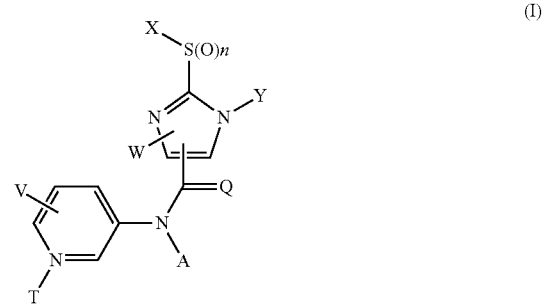

in which Q, V, T, W, X, Y, n and A have the meanings given in the description—and to a process for their preparation and to their use for controlling animal pests.

17 Claims, No Drawings

(51) Int. Cl.
*A01N 43/90* (2006.01)
*A01N 43/653* (2006.01)
*C07D 401/12* (2006.01)
*C07D 401/14* (2006.01)
*C07D 405/14* (2006.01)
*C07D 409/14* (2006.01)
*C07D 413/14* (2006.01)
*C07D 417/14* (2006.01)
*C07D 471/04* (2006.01)
*C07D 513/04* (2006.01)

(56) References Cited

FOREIGN PATENT DOCUMENTS

| WO | 2012084670 A1 | 6/2012 |
|----|---------------|--------|
| WO | 2014063942 A1 | 5/2014 |

OTHER PUBLICATIONS

Hay, et al., "Design, Synthesis and Evaluation of Imidazolylvethyl Carbamate Prodrugs of Alkylating Agents," Tetrahedron (2000) vol. 56: 645-657.

Bierer, et al., "Regiospecific Synthesis of the Aminoimidazoquinoxaline (IQx) Mutagens from Cooked Foods," J. Org. Chem. (1992) vol. 57, No. 5: 1390-1405.

Jordaan, et al., "The Synthesis of 1-Methyl-5-(a-indolyl)imidazole and 1-Methyl-2-ethylthiol-5-(a-indolyl)imidazole," J. Heterocyclic Chem. (1968) vol. 5: 723-725.

Hadizadeh, et al., "Syntheses of Substituted 2-(2-Alkylthio-1-benzyl-5-imidazolyl)-1,3,4-oxadiazoles," J. Heterocyclic Chem. (2002) vol. 39: 841-844.

Bossio, et al., "Synthesis and Properties of Some S-Derivatives of 1-Benzyl- and 1-(2-Pyridylmethyl)-5-Substituted 2-Mercaptoimidazoles," Heterocycles (1986) vol. 42, No. 4: 983-989.

* cited by examiner

SUBSTITUTED 2-THIOIMIDAZOLYLCARBOXAMIDES AS PESTICIDES

CROSS-REFERENCE TO RELATED APPLICATIONS

This application is a National Stage entry of International Application No. PCT/EP2016/052445, filed Feb. 5, 2016, which claims priority to European Patent Application No. 15154252.9, filed Feb. 9, 2015.

BACKGROUND

Field

The present application relates to novel heterocyclic compounds, to processes and intermediates for the preparation thereof, and their use for controlling animal pests.

Description of Related Art

WO 2011/009804 A2 describes heterocyclic compounds including, inter alia, imidazolylcarboxamides which can be used as insecticides.

Modern insecticides have to meet many demands, for example in relation to extent, persistence and spectrum of their action and possible use. Questions of toxicity, sparing of beneficial species and pollinators, environmental properties, application rates, combinability with other active ingredients or formulation auxiliaries play a role, as does the question of the effort required for the synthesis of an active ingredient; furthermore, resistances may occur, to mention only some parameters. For all these reasons alone, the search for novel crop protection compositions cannot be considered complete, and there is a constant need for novel compounds having improved properties compared to the known compounds, at least in relation to individual aspects.

SUMMARY

It was an object of the present invention to provide compounds which widen the spectrum of the pesticides in various aspects.

This object, and further objects which are not stated explicitly which can be discerned or derived from the connections discussed herein, are achieved by the provision of compounds of the formula (I)

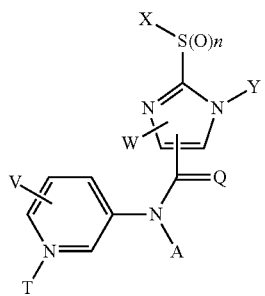

(I)

in which
Q represents oxygen or sulphur,
V represents a radical from the series hydrogen, halogen, alkyl, haloalkyl, alkoxy, haloalkoxy and cyano,
W represents a radical from the series hydrogen, halogen, alkyl, haloalkyl, alkoxy, haloalkoxy and cyano,
X represents a radical from the series optionally substituted alkyl, alkenyl, alkynyl, optionally substituted cycloalkyl which is saturated or unsaturated and optionally interrupted by heteroatoms, optionally substituted cycloalkylalkyl which is saturated or unsaturated and optionally interrupted by heteroatoms, optionally substituted aryl, hetaryl, optionally substituted arylalkyl, hetarylalkyl and cyano,
Y represents a radical from the series hydrogen, optionally substituted alkyl, alkenyl, alkynyl, optionally substituted cycloalkyl which is optionally interrupted by heteroatoms, optionally substituted cycloalkylalkyl which is optionally interrupted by heteroatoms, arylalkyl, hetarylalkyl and cyano,
n represents a number 0, 1 or 2,
A represents a radical from the series hydrogen, optionally substituted alkyl, alkenyl, alkynyl and optionally substituted cycloalkyl and cycloalkylalkyl which are optionally interrupted by heteroatoms,
T represents oxygen or an electron pair,
and salts thereof.

DETAILED DESCRIPTION OF A PREFERRED EMBODIMENT

Preferred substituents or ranges for the radicals shown in the compounds of the formula (I) are illustrated below. The combination thereof forms the range of preference (1).
Q represents oxygen or sulphur,
V represents a radical from the series hydrogen, halogen, $C_1$-$C_4$-alkyl, $C_1$-$C_4$-haloalkyl, $C_1$-$C_4$-alkoxy, $C_1$-$C_4$-haloalkoxy and cyano,
W represents a radical from the series hydrogen, halogen, $C_1$-$C_4$-alkyl, $C_1$-$C_4$-haloalkyl, $C_1$-$C_4$-alkoxy, $C_1$-$C_4$-haloalkoxy and cyano,
X represents a radical from the series $C_1$-$C_8$-alkyl, $C_3$-$C_8$-alkenyl, $C_3$-$C_8$-alkynyl, optionally mono- or polysubstituted independently of one another by halogen, $C_1$-$C_4$-alkoxy, $C_1$-$C_4$-alkyl-S(O)$_m$—, cyano, C(O)OR$^2$, CONR$^2$R$^3$, C(G)R$^2$; $C_3$-$C_8$-cycloalkyl or $C_5$-$C_8$-cycloalkenyl, optionally interrupted once or twice independently of one another by O, S(O)$_m$, C(G)R$^2$, NR$^4$ and optionally mono- to tetrasubstituted independently of one another by halogen, $C_1$-$C_4$-alkyl, $C_1$-$C_4$-haloalkyl, $C_1$-$C_4$-alkoxy, cyano; straight-chain or branched $C_3$-$C_8$-cycloalkyl-$C_1$-$C_4$-alkyl or $C_5$-$C_8$-cycloalkenyl-$C_1$-$C_4$-alkyl, optionally interrupted once or twice independently of one another by O, S(O)$_m$, C(G)R$^2$, NR$^4$ and optionally mono- to tetrasubstituted independently of one another by halogen, $C_1$-$C_4$-alkyl, $C_1$-$C_4$-haloalkyl, $C_1$-$C_4$-alkoxy, cyano; aryl, optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-S(O)$_m$—, $C_1$-$C_4$-haloalkoxy, $C_1$-$C_4$-haloalkyl-S(O)$_m$—, nitro and cyano; or hetaryl, which can be optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-S(O)$_m$—, $C_1$-$C_4$-haloalkoxy, $C_1$-$C_4$-haloalkyl-S(O)$_m$—, nitro and cyano; straight-chain or branched aryl-$C_1$-$C_4$-alkyl, hetaryl-$C_1$-$C_4$-alkyl, optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-S(O)$_m$—, $C_1$-$C_4$-haloalkoxy, $C_1$-$C_4$-haloalkyl-S(O)$_m$—, nitro and cyano,
G represents O, N—CN, N—OR$^2$, Y represents a radical from the series hydrogen; $C_1$-$C_6$-alkyl, $C_3$-$C_6$-alkenyl, $C_3$-$C_6$-alkynyl, optionally mono- or polysubstituted independently of one another by halogen, $C_1$-$C_4$-alkoxy, $C_1$-$C_4$-alkyl-$S(O)_m$—, cyano; $C_3$-$C_8$-cycloalkyl, optionally mono- or disubstituted independently of one another by halogen, $C_1$-$C_4$-alkyl, $C_1$-$C_4$-haloalkyl, $C_1$-$C_4$-alkoxy, cyano; straight-chain or branched $C_3$-$C_8$-cycloalkyl-$C_1$-$C_4$-alkyl, optionally interrupted once or twice independently of one another by O, $S(O)_m$, CO, $NR^4$ and optionally mono- to tetrasubstituted independently of one another by halogen, $C_1$-$C_4$-alkyl, $C_1$-$C_4$-haloalkyl, $C_1$-$C_4$-alkoxy, cyano; arylalkyl or hetarylalkyl, optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-$S(O)_m$—, $C_1$-$C_4$-haloalkoxy, $C_1$-$C_4$-haloalkyl-$S(O)_m$—, nitro and cyano; and cyano, m represents a number 0, 1 or 2, n represents a number 0, 1 or 2, A represents a radical from the series hydrogen; $C_1$-$C_6$-alkyl, $C_3$-$C_6$-alkenyl, $C_3$-$C_6$-alkynyl, optionally mono- or polysubstituted independently of one another by halogen, $C_1$-$C_4$-alkoxy, $C_1$-$C_4$-alkyl-$S(O)_m$—, cyano; $C_3$-$C_6$-cycloalkyl, optionally mono- or disubstituted independently of one another by halogen, $C_1$-$C_4$-alkyl, $C_1$-$C_4$-haloalkyl, $C_1$-$C_4$-alkoxy, cyano; and straight-chain or branched $C_3$-$C_8$-cycloalkyl-$C_1$-$C_4$-alkyl, optionally mono- or disubstituted independently of one another by halogen, $C_1$-$C_4$-alkyl, $C_1$-$C_4$-haloalkyl, $C_1$-$C_4$-alkoxy, cyano, $R^2$ represents a radical from the series hydrogen; $C_1$-$C_8$-alkyl, $C_3$-$C_8$-alkenyl, $C_3$-$C_8$-alkynyl, optionally mono- or polysubstituted independently of one another by halogen, $C_1$-$C_4$-alkoxy, $C_1$-$C_4$-alkyl-$S(O)_m$—; $C_3$-$C_8$-cycloalkyl, optionally interrupted once by O, $S(O)_m$ and optionally mono- or disubstituted independently of one another by halogen, $C_1$-$C_4$-alkyl, $C_1$-$C_4$-haloalkyl, $C_1$-$C_4$-alkoxy, cyano; straight-chain or branched $C_3$-$C_8$-cycloalkyl-$C_1$-$C_4$-alkyl, optionally interrupted once by O, $S(O)_n$ and optionally mono- or disubstituted independently of one another by halogen, $C_1$-$C_4$-alkyl, $C_1$-$C_4$-haloalkyl, $C_1$-$C_4$-alkoxy, cyano; aryl, hetaryl, optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-$S(O)_m$—, $C_1$-$C_4$-haloalkoxy, $C_1$-$C_4$-haloalkyl-$S(O)_m$—, nitro and cyano; and straight-chain or branched aryl-$C_1$-$C_4$-alkyl, hetaryl-$C_1$-$C_4$-alkyl, optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-$S(O)_m$—, $C_1$-$C_4$-haloalkoxy, $C_1$-$C_4$-haloalkyl-$S(O)_m$—, nitro and cyano, $R^3$ represents a radical from the series hydrogen; $C_1$-$C_6$-alkyl, $C_3$-$C_6$-alkenyl, $C_3$-$C_6$-alkynyl, optionally mono- or polysubstituted independently of one another by halogen, $C_1$-$C_4$-alkoxy, $C_1$-$C_4$-alkyl-$S(O)_m$—, cyano, $R^4$ represents a radical from the series hydrogen; $C_1$-$C_6$-alkyl, $C_3$-$C_6$-alkenyl, $C_3$-$C_6$-alkynyl, optionally mono- or polysubstituted independently of one another by halogen, $C_1$-$C_4$-alkoxy, $C_1$-$C_4$-alkyl-$S(O)_m$—, cyano, and represents the radicals $CONR^2R^3$ and $COR^2$, where the above definitions of the preferred range (1) apply to $R^2$ and $R^3$, T represents oxygen or an electron pair, and salts thereof.

Particularly preferred substituents or ranges for the radicals shown in the compounds of formula (I) are elucidated below. The combination thereof forms the range of preference (2).

Q represents oxygen,

Y represents a radical from the series hydrogen, fluorine, chlorine, bromine, methyl, ethyl, difluoromethyl, trifluoromethyl, methoxy, ethoxy, difluoromethoxy, trifluoromethoxy and cyano, W represents a radical from the series hydrogen, fluorine, chlorine, bromine, methyl, ethyl, difluoromethyl, trifluoromethyl, methoxy, ethoxy, difluoromethoxy, trifluoromethoxy and cyano, X represents a radical from the series $C_1$-$C_6$-alkyl, $C_3$-$C_6$-alkenyl, $C_3$-$C_6$-alkynyl, optionally mono- to heptasubstituted independently of one another by fluorine, chlorine, bromine, methoxy, ethoxy, methyl-$S(O)_m$—, ethyl-$S(O)_m$—, cyano, $C(O)OR^2$, $CONR^2R^3$, $C(G)R^2$; $C_3$-$C_6$-cycloalkyl, optionally interrupted once or twice independently of one another by O, $S(O)_m$, CO, $NR^4$ and optionally mono- or disubstituted independently of one another by fluorine, chlorine, bromine, methyl, ethyl, trifluoromethyl, methoxy, ethoxy, cyano; straight-chain or branched $C_3$-$C_6$-cycloalkyl-$C_1$-$C_2$-alkyl, optionally interrupted once or twice independently of one another by O, $S(O)_m$, CO, $NR^4$ and optionally mono- or disubstituted independently of one another by fluorine, chlorine, bromine, methyl, ethyl, trifluoromethyl, methoxy, ethoxy, cyano; phenyl, naphthyl, pyridyl, pyrimidyl, pyridazinyl, pyrazinyl, triazinyl, furanyl, thienyl, oxazolyl, isoxazolyl, thiazolyl, isothiazolyl, pyrazolyl, imidazolyl, oxadiazolyl, thiadiazolyl, triazolyl, benzimidazolyl, imidazopyridinyl, which may optionally be substituted by phenyl which is mono- to trisubstituted independently of one another by fluorine, chlorine, methyl, ethyl, difluoromethyl, trifluoromethyl, methoxy, ethoxy, methyl-S(O)m-, ethyl-S(O)n-, difluoromethoxy, trifluoromethoxy, trifluoromethyl-S(O)m-, difluoroethyl-S(O)m-, trifluoromethyl-S(O)m-, nitro and cyano, optionally mono- or disubstituted independently of one another by fluorine, chlorine, bromine, methyl, ethyl, difluoromethyl, trifluoromethyl, methoxy, ethoxy, methyl-$S(O)_m$—, ethyl-$S(O)_n$—, difluoromethoxy, trifluoromethoxy, trifluoromethyl-$S(O)_m$—, difluoroethyl-$S(O)_m$—, trifluoroethyl-$S(O)_m$—, nitro and cyano; straight-chain or branched phenyl-$C_1$-$C_2$-alkyl, pyridyl-$C_1$-$C_2$-alkyl, pyrimidyl-$C_1$-$C_2$-alkyl, thiazolyl-$C_1$-$C_2$-alkyl, pyrazolyl-$C_1$-$C_2$-alkyl, optionally mono- or disubstituted independently of one another by fluorine, chlorine, bromine, methyl, ethyl, difluoromethyl, trifluoromethyl, methoxy, ethoxy, Me-$S(O)_m$—, Et-$S(O)_m$—, difluoromethoxy, trifluoromethoxy, trifluoromethyl-$S(O)_m$—, difluoroethyl-$S(O)_m$—, trifluoroethyl-$S(O)_m$—, nitro and cyano; and cyano, G represents O, N—$OR^2$, Y represents a radical from the series hydrogen; $C_1$-$C_4$-alkyl, $C_3$-$C_4$-alkenyl, $C_3$-$C_4$-alkynyl, optionally mono- to pentasubstituted independently of one another by fluorine, chlorine, bromine, methoxy, ethoxy, methyl-$S(O)_m$—, ethyl-$S(O)_m$—, cyano; $C_3$-$C_6$-cycloalkyl, optionally mono- or disubstituted independently of one another by fluorine, chlorine, bromine, methyl, ethyl, trifluoromethyl, methoxy, ethoxy, cyano; straight-chain or branched $C_3$-$C_6$-cycloalkyl-$C_1$-$C_2$-alkyl, optionally interrupted once or twice independently of one another by O, $S(O)_m$, CO, $NR^4$ and optionally mono- to tetrasubstituted independently of one another by fluorine, chlorine, bromine, methyl, ethyl, trifluoromethyl, methoxy, ethoxy, cyano; aryl-$C_1$-$C_2$-alkyl or hetaryl-$C_1$-$C_2$-alkyl, optionally mono- or disubstituted independently of one another by fluorine, chlorine, bromine, methyl, ethyl, $C_1$-$C_4$-haloalkyl, trifluoromethyl, methoxy, ethoxy, cyano, nitro; and cyano, m represents a number 0, 1 or 2, n represents a number 0, 1 or 2, A represents a radical from the series hydrogen; $C_1$-$C_6$-alkyl, $C_3$-$C_6$-alkenyl, $C_3$-$C_6$-alkynyl, optionally mono- to pentasubstituted independently of one another by fluorine, chlorine, bromine, methoxy, ethoxy, methyl-$S(O)_m$—, ethyl-$S(O)_m$—, cyano; $C_3$-$C_6$-cycloalkyl, optionally mono- or disubstituted independently of one another by fluorine, chlorine, bromine, methyl, ethyl, trifluoromethyl, methoxy, ethoxy, cyano; straight-chain or branched $C_3$-$C_6$-cycloalkyl-$C_1$-$C_2$-alkyl, optionally mono- or disubstituted independently of one another by fluorine, chlorine, bromine, methyl, ethyl, trifluoromethyl, methoxy, ethoxy, cyano, $R^2$ represents a radical from the series hydrogen; $C_1$-$C_6$-alkyl, $C_3$-$C_6$-alkenyl, $C_3$-$C_6$-alkynyl, optionally mono- to pentasubstituted independently of one another by fluorine, chlorine, bromine, methoxy, ethoxy, methyl-$S(O)_m$—, ethyl-$S(O)_m$—; $C_3$-$C_6$-cycloalkyl, optionally interrupted once by O, $S(O)_m$ and optionally mono- or disubstituted independently of one another by fluorine, chlorine, bromine, methyl, ethyl, trifluoromethyl, methoxy, ethoxy, cyano; straight-chain or branched $C_3$-$C_6$-cycloalkyl-$C_1$-$C_2$-alkyl, optionally interrupted once by O, $S(O)_m$ and optionally mono- or disubstituted independently of one another by fluorine, chlorine, bromine, methyl, ethyl, trifluoromethyl, methoxy, ethoxy, cyano; phenyl or pyridyl, optionally mono- or disubstituted independently of one another by fluorine, chlorine, bromine, methyl, ethyl, difluoromethyl, trifluoromethyl, methoxy, ethoxy, methyl-$S(O)_m$—, ethyl-$S(O)_m$—, difluoromethoxy, trifluoromethoxy, trifluoromethyl-$S(O)_m$—, difluoroethyl-$S(O)_m$—, trifluoroethyl-$S(O)_m$—, nitro and cyano and straight-chain or branched phenyl-$C_1$-$C_2$-alkyl, pyridyl-$C_1$-$C_2$-alkyl, pyrimidyl-$C_1$-$C_2$-alkyl, thiazolyl-$C_1$-$C_2$-alkyl, optionally mono- or disubstituted independently of one another by fluorine, chlorine, bromine, methyl, ethyl, difluoromethyl, trifluoromethyl, methoxy, ethoxy, methyl-$S(O)_m$—, ethyl-$S(O)_m$—, difluoromethoxy, trifluoromethoxy, trifluoromethyl-$S(O)_n$—, difluoroethyl-$S(O)_n$—, trifluoroethyl-$S(O)_n$—, nitro and cyano, $R^3$ represents a radical from the series hydrogen; $C_1$-$C_4$-alkyl, $C_3$-$C_4$-alkenyl, $C_3$-$C_4$-alkynyl, optionally mono- to pentasubstituted independently of one another by fluorine, chlorine, bromine, methoxy, ethoxy, methyl-$S(O)_m$—, ethyl-$S(O)_m$—, cyano, $R^4$ represents a radical from the series hydrogen; $C_1$-$C_4$-alkyl, $C_3$-$C_4$-alkenyl, $C_3$-$C_4$-alkynyl, optionally mono- to pentasubstituted independently of one another by fluorine, chlorine, bromine, methoxy, ethoxy, methyl-$S(O)_m$—, ethyl-$S(O)_m$—, cyano, and represents the radicals $CONR^2R^3$ and $COR^2$, where the above definitions of the preferred range (2) apply to $R^2$ and $R^3$, T represents oxygen or an electron pair, and salts thereof.

Very particularly preferred substituents or ranges of the radicals shown in the compounds of the formula (I) are elucidated below. Taking into account the position of the carboxamide group at the imidazole radical, the very particularly preferred structure (I-A) is obtained. The combination thereof forms the range of preference (3-A).

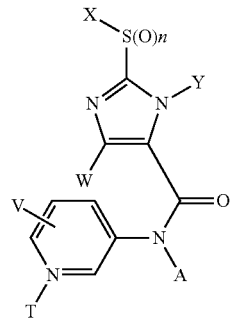

(I-A)

V represents a radical from the series hydrogen, fluorine, chlorine, methyl and cyano, W represents a radical from the series hydrogen, fluorine, chlorine, bromine, methyl, ethyl and cyano, X represents a radical from the series $C_1$-$C_6$-alkyl, $C_3$-$C_4$-alkenyl, $C_3$-$C_4$-alkynyl, which are optionally mono-, di-, tri-, tetra-, pentasubstituted independently of one another by fluorine, chlorine, bromine, methoxy, ethoxy, methyl-$S(O)_m$—, ethyl-$S(O)_m$—, cyano and may optionally be monosubstituted by the groups $C(O)OR^2$, $CONR^2R^3$, $C(G)R^2$; $C_3$-$C_6$-cycloalkyl, optionally interrupted once or twice independently of one another by O, $S(O)_m$, CO, $NR^4$ and optionally mono- or disubstituted independently of one another by fluorine, chlorine, methyl, ethyl, trifluoromethyl, methoxy, cyano; $C_3$-$C_6$-cycloalkylmethyl, optionally interrupted once or twice independently of one another by O, $S(O)_m$, CO, $NR^4$ and optionally mono- or disubstituted independently of one another by fluorine, chlorine, methyl, ethyl, trifluoromethyl, methoxy, cyano; phenyl, pyridyl, pyrimidyl, thienyl, thiazolyl, oxazolyl, imidazolyl, oxadiazolyl, thiadiazolyl, triazolyl, benzimidazolyl, imidazopyridinyl which may optionally be substituted by phenyl which is mono- or disubstituted independently of one another by fluorine, chlorine, methyl, ethyl, difluoromethyl, trifluoromethyl, methoxy, ethoxy, methyl-S(O)m-, ethyl-S(O)n-, difluoromethoxy, trifluoromethoxy, trifluoromethyl-S(O)m-, difluoroethyl-S(O)m-, trifluoroethyl-S(O)m-, nitro and cyano, optionally mono- or disubstituted independently of one another by fluorine, chlorine, bromine, methyl, ethyl, difluoromethyl, trifluoromethyl, methoxy, ethoxy, methyl-$S(O)_m$—, ethyl-$S(O)_m$—, difluoromethoxy, trifluoromethoxy, trifluoromethyl-$S(O)_m$—, difluoroethyl-$S(O)_m$—, trifluoroethyl-$S(O)_m$—, nitro and cyano; benzyl, pyridylmethyl, pyrimidylmethyl, thiazolylmethyl, pyrazolyl-$C_1$-$C_2$-alkyl, optionally mono- or disubstituted independently of one another by fluorine, chlorine, bromine, methyl, ethyl, difluoromethyl, trifluoromethyl, methoxy, ethoxy, Me-S$(O)_m$—, Et-S$(O)_m$—, difluoromethoxy, trifluoromethoxy, trifluoromethyl-$S(O)_n$—, difluoroethyl-$S(O)_m$—, trifluoroethyl-$S(O)_m$—, nitro and cyano; and cyano, G represents O, N—$OR^2$, Y represents a radical from the series hydrogen; methyl, ethyl, propyl, allyl, propargyl and benzyl, optionally mono- to trisubstituted independently of one another by fluorine, methoxy, ethoxy, cyano, m represents a number 0, 1 or 2, n represents a number 0, 1 or 2, A represents a radical from the series hydrogen; methyl, ethyl, propyl, allyl, propargyl, cyclopropyl or cyclopropylmethyl, optionally mono- to trisubstituted independently of one another by fluorine, methoxy, ethoxy, cyano,
$R^2$ represents a radical from the series hydrogen; $C_1$-$C_6$-alkyl, $C_3$-$C_6$-alkenyl, $C_3$-$C_6$-alkynyl, optionally mono- to trisubstituted independently of one another by fluorine, chlorine, methoxy, ethoxy, methyl-$S(O)_m$—, ethyl-$S(O)_m$—; $C_3$-$C_6$-cycloalkyl, optionally interrupted once by O, $S(O)_m$ and optionally mono- or disubstituted independently of one another by fluorine, chlorine, methyl, ethyl, trifluoromethyl, methoxy, cyano; $C_3$-$C_6$-cycloalkyl-methyl, optionally interrupted once by O, $S(O)_m$ and optionally mono- or disubstituted independently of one another by fluorine, chlorine, methyl, ethyl, trifluoromethyl, methoxy, cyano; phenyl or pyridyl, optionally mono- or disubstituted independently of one another by fluorine, chlorine, bromine, methyl, ethyl, difluoromethyl, trifluoromethyl, methoxy, ethoxy, methyl-$S(O)_m$—, ethyl-$S(O)_m$—, difluoromethoxy, trifluoromethoxy, trifluoromethyl-$S(O)_m$—, difluoroethyl-$S(O)_m$—, trifluoroethyl-$S(O)_m$—, nitro and cyano; and benzyl, pyridylmethyl, pyrimidylmethyl, thiazolylmethyl, optionally mono- or disubstituted independently of one another by fluorine, chlorine, bromine, methyl, ethyl, difluoromethyl, trifluoromethyl, methoxy, ethoxy, methyl-$S(O)_m$—, ethyl-$S(O)_m$—, difluoromethoxy, trifluoromethoxy, trifluoromethyl-$S(O)_m$—, difluoroethyl-$S(O)_m$—, trifluoroethyl-$S(O)_m$—, nitro and cyano,
$R^3$ represents a radical from the series hydrogen; $C_1$-$C_4$-alkyl, $C_3$-$C_4$-alkenyl, $C_3$-$C_4$-alkynyl, optionally mono- to trisubstituted independently of one another by fluorine, chlorine, bromine, methoxy, ethoxy, methyl-$S(O)_m$—, ethyl-$S(O)_m$—, cyano,
$R^4$ represents a radical from the series hydrogen; $C_1$-$C_4$-alkyl, $C_3$-$C_4$-alkenyl, $C_3$-$C_4$-alkynyl, optionally mono- to trisubstituted independently of one another by fluorine, chlorine, bromine, methoxy, ethoxy, methyl-$S(O)_m$—, ethyl-$S(O)_m$—, cyano, and represents the radicals $CONR^2R^3$ and $COR^2$, where the above definitions of the preferred range (3A) apply to $R^2$ and $R^3$,
T represents oxygen or an electron pair,
and salts thereof.

Very particularly preferred substituents or ranges of the radicals shown in the compounds of the formula (I) are elucidated below. Taking into account the position of the carboxamide group at the imidazole radical, the very particularly preferred structure (I-B) is obtained. The combination thereof forms the range of preference (3-B).

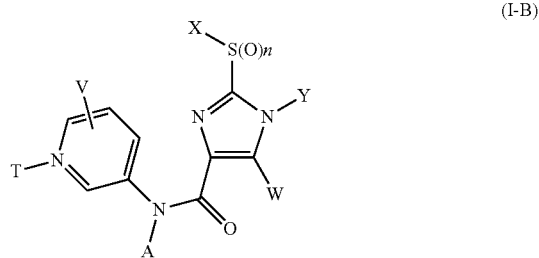

(I-B)

V represents a radical from the series hydrogen, fluorine, chlorine, methyl and cyano,
W represents a radical from the series hydrogen, fluorine, chlorine, bromine, methyl, ethyl and cyano,
X represents a radical from the series $C_1$-$C_6$-alkyl, $C_3$-$C_4$-alkenyl, $C_3$-$C_4$-alkynyl, which are optionally mono- to pentasubstituted independently of one another by fluorine, chlorine, bromine, methoxy, ethoxy, methyl-$S(O)_m$—, ethyl-$S(O)_m$—, cyano and may optionally be monosubstituted by the groups $C(O)OR^2$, $CONR^2R^3$, $C(G)R^2$; $C_3$-$C_6$-cycloalkyl, optionally interrupted once or twice independently of one another by O, $S(O)_m$, CO, $NR^4$ and optionally mono- or disubstituted independently of one another by fluorine, chlorine, methyl, ethyl, trifluoromethyl, methoxy, cyano; $C_3$-$C_6$-cycloalkyl-methyl, optionally interrupted once or twice independently of one another by O, $S(O)_m$, CO, $NR^4$ and optionally mono- or disubstituted independently of one another by fluorine, chlorine, methyl, ethyl, trifluoromethyl, methoxy, cyano; phenyl, pyridyl, pyrimidyl, thienyl, thiazolyl, oxazolyl, imidazolyl, oxadiazolyl, thiadiazolyl, triazolyl, benzimidazolyl, imidazopyridinyl, which may optionally be substituted by phenyl which is mono- or disubstituted independently of one another by fluorine, chlorine, methyl, ethyl, difluoromethyl, trifluoromethyl, methoxy, ethoxy, methyl-S(O)m-, ethyl-S(O)n-, difluoromethoxy, trifluoromethoxy, trifluoromethyl-S(O)m-, difluoroethyl-S(O)m-, trifluoroethyl-S(O)m-, nitro and cyano, optionally mono- or disubstituted independently of one another by fluorine, chlorine, bromine, methyl, ethyl, difluoromethyl, trifluoromethyl, methoxy, ethoxy, methyl-$S(O)_m$—, ethyl-$S(O)_m$—, difluoromethoxy, trifluoromethoxy, trifluoromethyl-$S(O)_m$—, difluoroethyl-$S(O)_m$—, trifluoroethyl-$S(O)_m$—, nitro and cyano; benzyl, pyridylmethyl, pyrimidylmethyl, thiazolylmethyl, pyrazolyl-$C_1$-$C_2$-alkyl, optionally mono- or disubstituted independently of one another by fluorine, chlorine, bromine, methyl, ethyl, difluoromethyl, trifluoromethyl, methoxy, ethoxy, Me-$S(O)_m$—, Et-$S(O)_m$—, difluoromethoxy, trifluoromethoxy, trifluoromethyl-$S(O)_m$—, difluoroethyl-$S(O)_m$—, trifluoroethyl-$S(O)_m$—, nitro and cyano; and cyano,
G represents O, N—$OR^2$,
Y represents a radical from the series hydrogen; methyl, ethyl, propyl, allyl, propargyl and benzyl, optionally mono- to trisubstituted independently of one another by fluorine, methoxy, ethoxy, cyano,
m represents a number 0, 1 or 2,
n represents a number 0, 1 or 2,
A represents a radical from the series hydrogen; methyl, ethyl, propyl, allyl, propargyl, cyclopropyl or cyclopropylmethyl, optionally mono- to trisubstituted independently of one another by fluorine, methoxy, ethoxy, cyano,
$R^2$ represents a radical from the series hydrogen; $C_1$-$C_6$-alkyl, $C_3$-$C_6$-alkenyl, $C_3$-$C_6$-alkynyl, optionally mono- to trisubstituted independently of one another by fluorine, chlorine, methoxy, ethoxy, methyl-$S(O)_m$—, ethyl-$S(O)_m$—; $C_3$-$C_6$-cycloalkyl, optionally interrupted once by O, $S(O)_m$ and optionally mono- or disubstituted independently of one another by fluorine, chlorine, methyl, ethyl, trifluoromethyl, methoxy, cyano; $C_3$-$C_6$-cycloalkylmethyl, optionally interrupted once by O, $S(O)_m$ and optionally mono- or disubstituted independently of one another by fluorine, chlorine, methyl, ethyl, trifluoromethyl, methoxy, cyano; phenyl or pyridyl, optionally mono- or disubstituted independently of one another by fluorine, chlorine, bromine, methyl, ethyl, difluoromethyl, trifluoromethyl, methoxy, ethoxy, methyl-$S(O)_m$—, ethyl-$S(O)_m$—, difluoromethoxy, trifluoromethoxy, trifluoromethyl-$S(O)_m$—, difluoroethyl-$S(O)_m$—, trifluoroethyl-$S(O)_m$—, nitro and cyano; and benzyl, pyridylmethyl, pyrimidylmethyl, thiazolylmethyl, optionally mono- or disubstituted independently of one another by fluorine, chlorine, bromine, methyl, ethyl, difluoromethyl, trifluoromethyl, methoxy, ethoxy, methyl-S(O)$_m$—, ethyl-S(O)$_m$—, difluoromethoxy, trifluoromethoxy, trifluoromethyl-S(O)$_m$—, difluoroethyl-S(O)$_m$—, trifluoroethyl-S(O)$_m$—, nitro and cyano, R$^3$ represents a radical from the series hydrogen; C$_1$-C$_4$-alkyl, C$_3$-C$_4$-alkenyl, C$_3$-C$_4$-alkynyl, optionally mono- to trisubstituted independently of one another by fluorine, chlorine, bromine, methoxy, ethoxy, methyl-S(O)$_m$—, ethyl-S(O)$_m$—, cyano, R$^4$ represents a radical from the series hydrogen; C$_1$-C$_4$-alkyl, C$_3$-C$_4$-alkenyl, C$_3$-C$_4$-alkynyl, optionally mono- to trisubstituted independently of one another by fluorine, chlorine, bromine, methoxy, ethoxy, methyl-S(O)$_m$—, ethyl-S(O)$_m$—, cyano, and represents the radicals CONR$^2$R$^3$ and COR$^2$, where the above definitions of the preferred range (3B) apply to R$^2$ and R$^3$, T represents oxygen or an electron pair, and salts thereof.

Especially preferred substituents or ranges for the radicals shown in the compounds of the formula (I) are elucidated below. Taking into account the position of the carboxamide group at the imidazole radical, the especially preferred structure (I-A) is obtained. Its combination with the especially preferred substituents forms the preferred range (4-A).

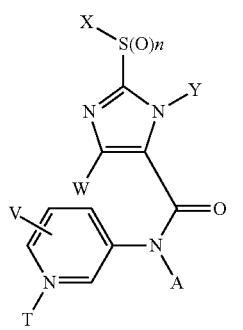

(I-A)

V represents hydrogen or fluorine,

W represents a radical from the series hydrogen, chlorine, bromine and methyl,

X represents a radical from the series methyl, ethyl, propyl, isopropyl, butyl, isobutyl, sec-butyl, tert-butyl, pentyl, isopentyl, 2,2-dimethylpropyl, hexyl, neohexyl, allyl, methallyl, 2-butenyl, propargyl, 2-butynyl, which are optionally mono- to trisubstituted independently of one another by fluorine, chlorine, bromine, methoxy, ethoxy, methylsulphanyl, ethylsulphanyl, methylsulphinyl, ethylsulphinyl, methylsulphonyl, ethylsulphonyl and may optionally be monosubstituted by the groups C(O)OR$^2$, CONR$^2$R$^3$, C(G)R$^2$; cyclopropyl, cyclobutyl, cyclopentyl, cyclohexyl, optionally interrupted once or twice independently of one another by O, S(O)$_m$, CO, NR$^4$ and optionally mono- or disubstituted independently of one another by fluorine, chlorine, methyl, ethyl, trifluoromethyl, methoxy, cyano; cyclopropylmethyl, cyclobutylmethyl, cyclopentylmethyl, cyclohexylmethyl, optionally interrupted once or twice independently of one another by O, S(O)$_m$, CO, NR$^4$ and optionally mono- or disubstituted independently of one another by fluorine, chlorine, methyl, ethyl, trifluoromethyl, methoxy, cyano; phenyl, pyridyl, pyrimidyl, thienyl, thiazolyl, oxazolyl, imidazolyl, oxadiazolyl, thiadiazolyl, triazolyl, benzimidazolyl, imidazopyridinyl which may optionally be substituted by phenyl, optionally mono- or disubstituted independently of one another by fluorine, chlorine, bromine, methyl, ethyl, difluoromethyl, trifluoromethyl, methoxy, ethoxy, methylsulphanyl, ethylsulphanyl, methylsulphinyl, ethylsulphinyl, methylsulphonyl, ethylsulphonyl, difluoromethoxy, trifluoromethoxy, trifluoromethylsulphanyl, trifluoromethylsulphinyl, trifluoromethylsulphonyl, difluoromethylsulphanyl, difluoromethylsulphinyl, difluoromethylsulphonyl, trifluoroethylsulphanyl, trifluoroethylsulphinyl trifluoroethylsulphonyl, nitro and cyano; benzyl, pyridylmethyl, pyrimidylmethyl, thiazolylmethyl, pyrazolyl-C$_1$-C$_2$-alkyl, optionally mono- or disubstituted independently of one another by fluorine, chlorine, bromine, methyl, ethyl, difluoromethyl, trifluoromethyl, methoxy, ethoxy, methylsulphanyl, ethylsulphanyl, methylsulphinyl, ethylsulphinyl, methylsulphonyl, ethylsulphonyl, difluoromethoxy, trifluoromethoxy, trifluoromethylsulphanyl, trifluoromethylsulphinyl, trifluoromethylsulphonyl, difluoromethylsulphanyl, difluoromethylsulphinyl, difluoromethylsulphonyl, trifluoroethylsulphanyl, trifluoroethylsulphinyl trifluoroethylsulphonyl, nitro and cyano; and cyano, G represents O, N—OR$^2$, Y represents a radical from the series hydrogen, methyl, ethyl, propyl, difluoroethyl, trifluoroethyl, methoxymethyl, ethoxymethyl, cyanomethyl and benzyl, m represents a number 0, 1 or 2, n represents a number 0, 1 or 2, A represents a radical from the series hydrogen, methyl, ethyl, propyl, difluoroethyl, trifluoroethyl, methoxymethyl, ethoxymethyl, cyanomethyl, allyl, propargyl, cylopropyl or cyclopropylmethyl, R$^2$ represents a radical from the series hydrogen; methyl, ethyl, propyl, isopropyl, n-butyl, isobutyl, sec-butyl, tert-butyl, allyl, methallyl, 2-butenyl, propargyl, 2-butynyl, optionally mono- to trisubstituted independently of one another by fluorine, chlorine, methoxy, ethoxy; cyclopropyl, cyclobutyl, cyclopentyl, cyclohexyl, optionally interrupted once by O, S(O)$_m$ and optionally mono- or disubstituted independently of one another by fluorine, chlorine, methyl, ethyl, trifluoromethyl, methoxy, cyano; cyclopropylmethyl, cyclobutylmethyl, cyclopentylmethyl, cyclohexylmethyl, optionally interrupted once by O, S(O)$_m$ and optionally mono- or disubstituted independently of one another by fluorine, chlorine, methyl, ethyl, trifluoromethyl, methoxy, cyano; phenyl or pyridyl, optionally mono- or disubstituted independently of one another by fluorine, chlorine, bromine, methyl, ethyl, difluoromethyl, trifluoromethyl, methoxy, ethoxy, methylsulphanyl, ethylsulphanyl, methylsulphinyl, ethylsulphinyl, methylsulphonyl, ethylsulphonyl, difluoromethoxy, trifluoromethoxy, trifluoromethylsulfanyl, trifluoromethylsulphinyl, trifluoromethylsulphonyl, difluoromethylsulphanyl, difluoromethylsulphinyl, difluoromethylsulphonyl, trifluoroethylsulphanyl, trifluoroethylsulphinyl, trifluoroethylsulphonyl, nitro and cyano; and benzyl, pyridylmethyl, pyrimidylmethyl, thiazolylmethyl, optionally mono- or disubstituted independently of one another by fluorine, chlorine, bromine, methyl, ethyl, difluoromethyl, trifluoromethyl, methoxy, ethoxy, difluoromethoxy, trifluoromethoxy, nitro and cyano, R$^3$ represents a radical from the series hydrogen, methyl, ethyl, propyl, isopropyl, butyl, isobutyl and allyl, R$^4$ represents a radical from the series hydrogen, optionally once to three times independently of one another by fluorine, methoxy, ethoxy, cyano methyl, ethyl, propyl, isopropyl, butyl, isobutyl, and allyl and represents the radicals CONR²R³ and COR², where the above definitions of the preferred range (4A) apply to R² and R³, T represents oxygen or an electron pair, and salts thereof.

Especially preferred substituents or ranges for the radicals shown in the compounds of the formula (I) are elucidated below. Taking into account the position of the carboxamide group at the imidazole radical, the especially preferred structure (I-B) is obtained. Its combination with the especially preferred substituents forms the preferred range (4-B).

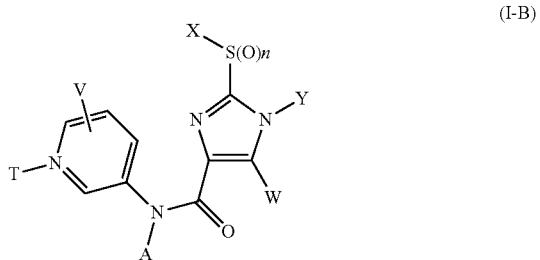

(I-B)

V represents hydrogen or fluorine,

W represents a radical from the series hydrogen, chlorine, bromine and methyl,

X represents a radical from the series methyl, ethyl, propyl, isopropyl, n-butyl, isobutyl, sec-butyl, tert-butyl, pentyl, isopentyl, 2,2-dimethylpropyl, hexyl, neohexyl, allyl, methallyl, 2-butenyl, propargyl, 2-butynyl, which are optionally mono- to trisubstituted independently of one another by fluorine, chlorine, bromine, methoxy, ethoxy, methylsulphanyl, ethylsulphanyl, methylsulphinyl, ethylsulphinyl, methylsulphonyl, ethylsulphonyl, cyano and may optionally be monosubstituted by the groups C(O)OR², CONR²R³, C(G)R²; cyclopropyl, cyclobutyl, cyclopentyl, cyclohexyl, optionally interrupted once or twice independently of one another by O, S(O)$_m$, CO, NR⁴ and optionally mono- or disubstituted independently of one another by fluorine, chlorine, methyl, ethyl, trifluoromethyl, methoxy, cyano; cyclopropylmethyl, cyclobutylmethyl, cyclopentylmethyl, cyclohexylmethyl, optionally interrupted once or twice independently of one another by O, S(O)$_m$, CO, NR⁴ and optionally mono- or disubstituted independently of one another by fluorine, chlorine, methyl, ethyl, trifluoromethyl, methoxy, cyano; phenyl, pyridyl, pyrimidyl, thienyl, thiazolyl, oxazolyl, imidazolyl, oxadiazolyl, thiadiazolyl, triazolyl, benzimidazolyl, imidazopyridinyl which may optionally be substituted by phenyl, optionally mono- or disubstituted independently of one another by fluorine, chlorine, bromine, methyl, ethyl, difluoromethyl, trifluoromethyl, methoxy, ethoxy, methylsulphanyl, ethylsulphanyl, methylsulphinyl, ethylsulphinyl, methylsulphonyl, ethylsulphonyl, difluoromethoxy, trifluoromethoxy, trifluoromethylsulphanyl, trifluoromethylsulphinyl, trifluoromethylsulphonyl, difluoromethylsulphanyl, difluoromethylsulphinyl, difluoromethylsulphonyl, trifluoroethylsulphanyl, trifluoroethylsulphinyl trifluoroethylsulphonyl, nitro and cyano; benzyl, pyridylmethyl, pyrimidylmethyl, thiazolylmethyl, pyrazolyl-C₁-C₂-alkyl, optionally mono- or disubstituted independently of one another by fluorine, chlorine, bromine, methyl, ethyl, difluoromethyl, trifluoromethyl, methoxy, ethoxy, methylsulphanyl, ethylsulphanyl, methylsulphinyl, ethylsulphinyl, methylsulphonyl, ethylsulphonyl, difluoromethoxy, trifluoromethoxy, trifluoromethylsulphanyl, trifluoromethylsulphinyl, trifluoromethylsulphonyl, trifluoromethylsulphanyl, difluoromethylsulphinyl, difluoromethylsulphonyl, trifluoroethylsulphanyl, trifluoroethylsulphinyl trifluoroethylsulphonyl, nitro and cyano; and cyano, G represents O, N—OR², Y represents a radical from the series hydrogen, methyl, ethyl, propyl, difluoroethyl, trifluoroethyl, methoxymethyl, ethoxymethyl, cyanomethyl and benzyl, m represents a number 0, 1 or 2, n represents a number 0, 1 or 2, A represents a radical from the series hydrogen, methyl, ethyl, propyl, difluoroethyl, trifluoroethyl, methoxymethyl, ethoxymethyl, cyanomethyl, allyl, propargyl, cyclopropyl or cyclopropylmethyl, R² represents a radical from the series hydrogen; methyl, ethyl, propyl, isopropyl, n-butyl, isobutyl, sec-butyl, tert-butyl, allyl, methallyl, 2-butenyl, propargyl, 2-butynyl, optionally mono- to trisubstituted independently of one another by fluorine, chlorine, methoxy, ethoxy; cyclopropyl, cyclobutyl, cyclopentyl, cyclohexyl, optionally interrupted once by O, S(O)$_m$ and optionally mono- or disubstituted independently of one another by fluorine, chlorine, methyl, ethyl, trifluoromethyl, methoxy, cyano; cyclopropylmethyl, cyclobutylmethyl, cyclopentylmethyl, cyclohexylmethyl, optionally interrupted once by O, S(O)$_m$ and optionally mono- or disubstituted independently of one another by fluorine, chlorine, methyl, ethyl, trifluoromethyl, methoxy, cyano; phenyl or pyridyl, optionally mono- or disubstituted independently of one another by fluorine, chlorine, bromine, methyl, ethyl, difluoromethyl, trifluoromethyl, methoxy, ethoxy, methylsulphanyl, ethylsulphanyl, methylsulphinyl, ethylsulphinyl, methylsulphonyl, ethylsulphonyl, difluoromethoxy, trifluoromethoxy, trifluoromethylsulfanyl, trifluoromethylsulphinyl, trifluoromethylsulphonyl, difluoromethylsulphanyl, difluoromethylsulphinyl, difluoromethylsulphonyl, trifluoroethylsulphanyl, trifluoroethylsulphinyl, trifluoroethylsulphonyl, nitro and cyano; and benzyl, pyridylmethyl, pyrimidylmethyl, thiazolylmethyl, optionally mono- or disubstituted independently of one another by fluorine, chlorine, bromine, methyl, ethyl, difluoromethyl, trifluoromethyl, methoxy, ethoxy, difluoromethoxy, trifluoromethoxy, nitro and cyano, R³ represents a radical from the series hydrogen, methyl, ethyl, propyl, isopropyl, n-butyl, isobutyl and allyl, R⁴ represents a radical from the series hydrogen, optionally once to three times independently of one another by fluorine, methoxy, ethoxy, cyano methyl, ethyl, propyl, isopropyl, n-butyl, isobutyl, and allyl and represents the radicals CONR²R³ and COR², where the above definitions of the preferred range (4B) apply to R² and R³, T represents oxygen or an electron pair, and salts thereof.

Very particularly preferred substituents or ranges of the radicals shown in the compounds of the formula (I) are elucidated below. The combination thereof forms the range of preference (5).

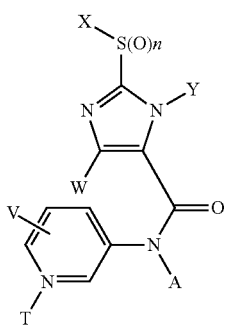

(I-A)

V represents hydrogen,
W represents a radical from the series hydrogen, chlorine and bromine and preferably represents hydrogen,
X represents a radical from the series methyl, ethyl, n-butyl, n-pentyl, n-propyl, isopropyl, allyl, 3,3-dimethylallyl, propargyl, cyclohexyl, tetrahydropyranyl, tetrahydrothiopyranyl, 3-oxetanyl, 5-oxa-[3.3.0]-bicycloheptanyl, methoxyethyl, methoxypropyl, ethoxyethyl, ethylthioethyl, methylthioethyl, difluoromethyl, trifluoromethyl, 2,2,2-trifluoroethyl, 3,3,3-trifluoropropyl, 3-chloro-2,2,3,3-tetrafluoropropyl, 3-fluoropropyl, 3,3-difluoropropyl, 2,2,2-trifluoroethylthioethyl, methylcarbonylmethyl, cyclopropylcarbonylmethyl, tert-butylcarbonylmethyl, methoxycarbonylmethyl, ethoxycarbonylmethyl, hydroxycarbonylmethyl, carbamoylmethyl, N-methylcarbamoylmethyl, N-cyclopropylcarbamoylmethyl, N,N-dimethylcarbamoylmethyl, 2-methoximinopropyl, cyclopropylmethyl, phenyl, 4-methylphenyl, 2-nitrophenyl, 3-methylthiophenyl, 4-chlorophenyl, 4-fluorophenyl, 4-tert-butylphenyl, 4-methoxyphenyl, 4-nitrophenyl, 4-diemethylaminophenyl, 2-fluorophenyl, 2-methoxyphenyl, 2-dimethylaminosulphonylphenyl, 2-dimethylaminocarbamoylphenyl, 3-nitrophenyl, 3-trifluoromethylphenyl, 3-chlorophenyl, 2,5-dichlorophenyl, 3,5-dichlorophenyl, 4-chloro-3-trifluoromethylphenyl, 2,4,5-trichlorophenyl, 2-pyridyl, 5-(2-chloro)pyridyl, 2-(5-methyl)pyridyl, 2-(6-methyl)pyridyl, 2-(3-trifluoromethyl)pyridyl, 2-pyrimidyl, 2-(4-methyl)pyrimidyl, 2-(5-methyl)pyrimidyl, 2-(4-methoxy)pyrimidyl, 2-(5-fluoro)pyrimidyl, 2-(4-trifluoromethyl)pyrimidyl, 2-(5-trifluoromethyl)pyrimidyl, 2-(4,6-dimethyl)pyrimidyl, 2-(4,5-dimethyl)pyrimidyl, 2-(4,6-dimethoxy)pyrimidyl, —CH$_2$-2-pyrimidyl, —CH$_2$-2-pyrazinyl, —CH$_2$-5-(1-methyl)imidazolyl, —CH$_2$-3-(1-methyl)pyrazolyl, —CH$_2$-4-pyridyl, —CH$_2$-2-pyridyl, —CH$_2$-2-(1-methyl)imidazolyl, —CH$_2$-3-pyridyl, —CH$_2$-2-furanyl, —CH$_2$-5-(2-chloro)pyridyl, benzyl, 3,4-dichlorobenzyl, 2,6-difluorobenzyl, 2-fluoro-6-methoxybenzyl, 2,6-dichlorobenzyl, 2-chloro-6-trifluoromethylbenzyl, 2-chloro-6-fluorobenzyl, —CH$_2$-2-(4,6-dimethoxy)pyrimidyl, 2,6-dimethylbenzyl, —CH$_2$-1-(3-nitro-5-methyl)pyrazolyl, 2-(1-methyl)benzimidazolyl, 2-(5-methyl)oxadiazolyl, 2-[3-methyl-6-(trifluoromethyl) imidazo[4.5]pyridinyl, 3-[4-ethyl-5-(trifluoromethyl)]-1,2,4-triazolyl, 3-[4-methyl-5-(trifluoromethyl)]-1,2,4-triazolyl, 3-[4-methyl-5-(difluoromethyl)]-1,2,4-triazolyl, 2-(5-phenyl)-1,3,4-thiadiazolyl, 2-(1-methyl-5-phenyl) imidazolyl, 2-(4,5-dimethyl)oxazolyl, 2-(1-methyl-5-methoxycarbonyl)imidazolyl, 2-(1-methyl)imidazolyl, 1,2-ethanediyl, Y represents methyl, ethyl or benzyl,
n represents a number 0 or 2 and preferably represents 0,
A represents a radical from the series hydrogen and methyl and preferably represents methyl,
T represents an electron pair
and
compounds of the formula (I-B)

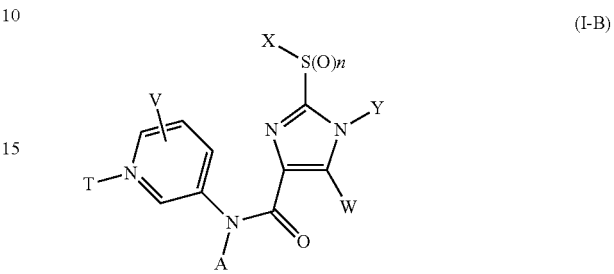

(I-B)

where
V represents hydrogen,
W represents a radical from the series hydrogen, chlorine and bromine and preferably represents hydrogen,
X represents a radical from the series 4,6-dimethylpyrimidyl, n-butyl, n-pentyl, benzyl, methyl, 3-methylthiophenyl, 2,2,2-trifluoroethyl, phenyl, 4-methylphenyl, 2-pyrimidyl, ethylthioethyl, 2-nitrophenyl, cyclopropylmethyl and preferably represents a 2-pyrimidyl radical,
Y represents methyl,
n represents a number 0 or 2 and preferably represents 0,
A represents a radical from the series hydrogen and methyl and preferably represents methyl,
T represents an electron pair,
and salts thereof.

It is also possible that, in one of the preferred ranges (1-5), X and Y together with the atoms to which they are attached represent a saturated or unsaturated cycle. Preferably, X and Y together with the atoms to which they are attached represent a saturated or unsaturated 5- to 7-membered ring. Very particularly preferably, X and Y together with the atoms to which they are attached represent a saturated 5-membered ring.

In preferred range (1), unless stated otherwise,
halogen is selected from the group consisting of fluorine, chlorine, bromine and iodine, preferably in turn from the group consisting of fluorine, chlorine and bromine,
hetaryl (synonymous with heteroaryl, including as part of a larger unit, for example hetarylalkyl) is selected from the group consisting of furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzoisofuryl, benzothienyl, benzoisothienyl, indolyl, isoindolyl, indazolyl, benzothiazolyl, benzoisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl,
heterocyclyl represents a saturated 3-, 4-, 5- or 6-membered ring which contains 1 or 2 nitrogen atoms and/or one oxygen atom and/or one sulphur atom, but where 2 nitrogen atoms shall not be directly vicinal, for example aziridinyl, azetidinyl, azolidinyl, azinanyl, oxiranyl, oxetanyl, oxolanyl, oxanyl, dioxanyl, thiiranyl, thietanyl, thiolanyl, thianyl and tetrahydrofuryl.

In preferred range (2), unless stated otherwise,
halogen represents fluorine, chlorine, bromine and iodine, preferably fluorine, chlorine and bromine,
hetaryl (including as part of a larger unit, such as hetarylalkyl) represents pyridyl, pyrimidyl, thiazolyl, oxazolyl, pyrazolyl, thienyl, furanyl, benzyl, pyridinylmethyl and thiazolylmethyl, and
heterocyclyl (including as part of a larger unit, such as heterocyclylalkyl) represents a saturated or unsaturated 3-, 4- or 5-membered ring which contains 1 or 2 nitrogen atoms and/or one oxygen atom and/or one sulphur atom, but where 2 nitrogen atoms shall not be directly vicinal, for example 1- or 2-aziridinyl, 2-oxiranyl, 2-thiiranyl, 1- or 2-azetidinyl, 2- or 3-oxetanyl, 2- or 3-thietanyl, 1,3-dioxetan-2-yl, 1-, 2- or 3-pyrrolidinyl.

In preferred range (3), unless stated otherwise,
halogen represents fluorine, chlorine, bromine and iodine, preferably fluorine, chlorine and bromine, and
heterocyclyl (including as part of a larger unit, such as heterocyclylalkyl) represents a saturated or unsaturated 3- or 4-membered ring which contains 1 or 2 nitrogen atoms and/or one oxygen atom and/or one sulphur atom, but where 2 nitrogen atoms shall not be directly vicinal, for example 1- or 2-aziridinyl, 2-oxiranyl, 2-thiiranyl, 1- or 2-azetidinyl, 2- or 3-oxetanyl, 2- or 3-thietanyl or 1,3-dioxetan-2-yl. Halogen-substituted radicals, for example haloalkyl, are, unless otherwise specified, monohalogenated or polyhalogenated up to the maximum number of possible substituents. In the case of polyhalogenation, the halogen atoms can be identical or different. In this case, halogen is fluorine, chlorine, bromine or iodine, especially fluorine, chlorine or bromine.

Saturated or unsaturated hydrocarbon radicals, such as alkyl or alkenyl, may each be straight-chain or branched if possible, including in combination with heteroatoms, as, for example, in alkoxy.

Unless stated otherwise, optionally substituted radicals may be mono- or polysubstituted, where the substituents in the case of polysubstitution may be the same or different.

If, in the compounds of the formula (I), T represents oxygen, these compounds are present as N-oxides.

If, in the compounds of the formula (I), T represents an electron pair, these compounds are present as pyridines.

The radical definitions or elucidations given above in general terms or within areas of preference apply to the end products and correspondingly to the starting materials and intermediates. These radical definitions can be combined with one another as desired, i.e. including combinations between the respective ranges of preference.

Preference according to the invention is given to using compounds of the formula (I) which contain a combination of the meanings listed above as being preferred (preferred range (1)).

Particular preference according to the invention is given to using compounds of the formula (I) which contain a combination of the meanings listed above as being particularly preferred (preferred range (2)).

Very particular preference according to the invention is given to using compounds of the formula (I) which contain a combination of the definitions listed above as being very particularly preferred (preferred range (3A and/or 3B)).

Special preference according to the invention is given to using compounds of the formula (I) which contain a combination of the definitions listed above as being very particularly preferred (preferred range (4A and/or 4B)).

Even more preference according to the invention is given to using compounds of the formula (I) which contain a combination of the meanings listed above as being very particularly preferred (preferred range (5)).

Depending on the nature of the substituents, the compounds of the formula (I) may be in the form of geometric and/or optically active isomers or corresponding isomer mixtures in different compositions. These stereoisomers are, for example, enantiomers, diastereomers, atropisomers or geometric isomers. Accordingly, the invention encompasses both pure stereoisomers and any mixtures of these isomers. It has additionally been found that the novel compounds of the formula (I) can be prepared by the processes described below.

The compounds of the formula (I-A) can be synthesized, for example, according to processes A to D, as shown in the schemes below.

Process A-1

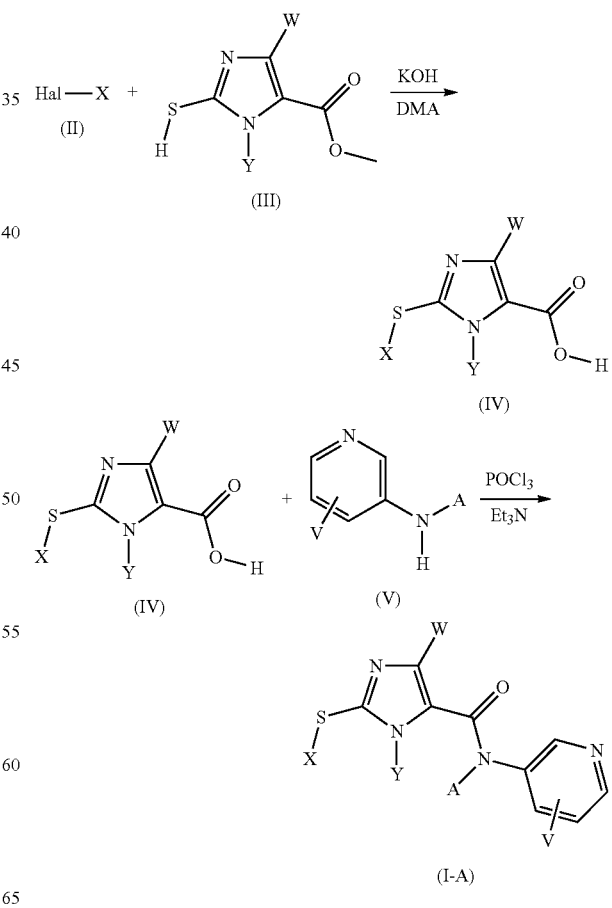

DMA=dimnethylacetamnide; Et$_3$N=trietlwlamnine

Process A-2
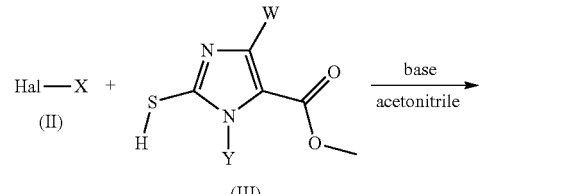
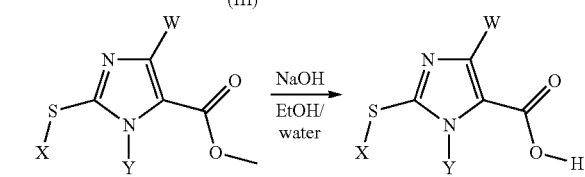
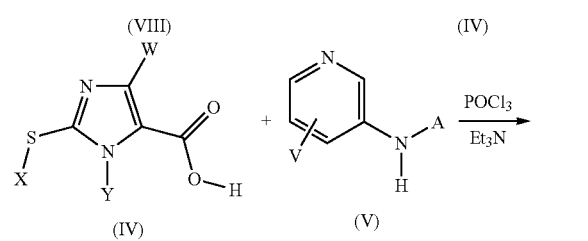
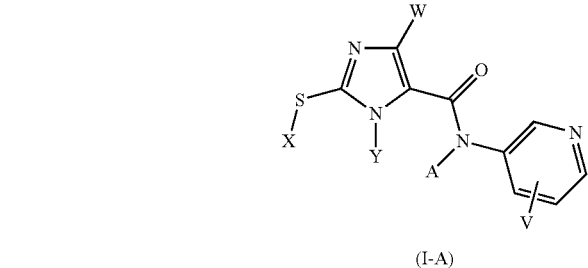
Process B
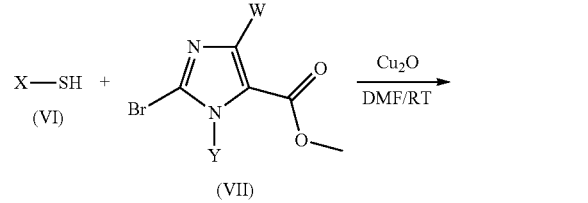
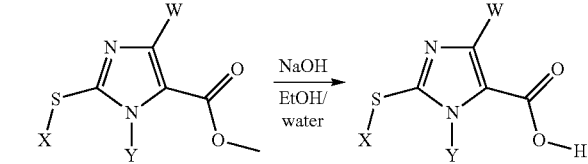
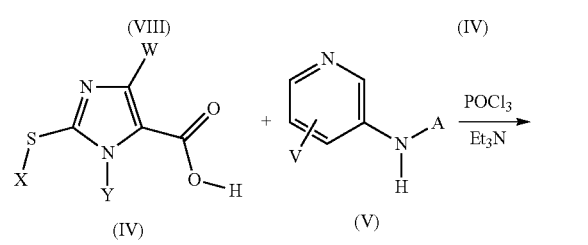
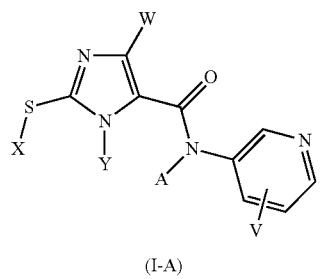
DMF=dimethylformamide; Et₃N=triethylamine
Process C-1
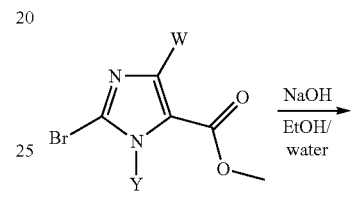
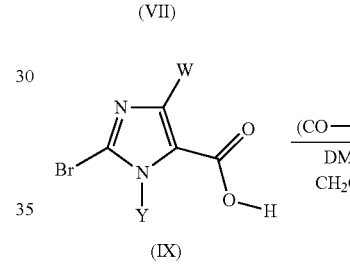
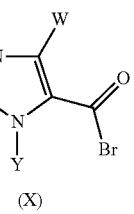
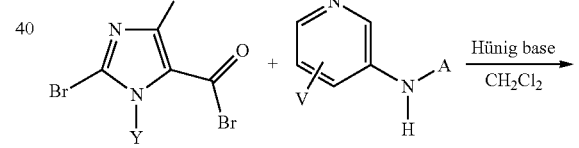
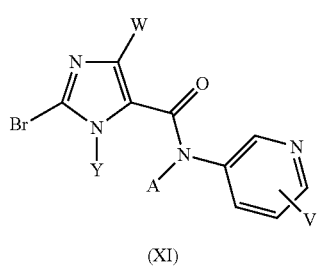
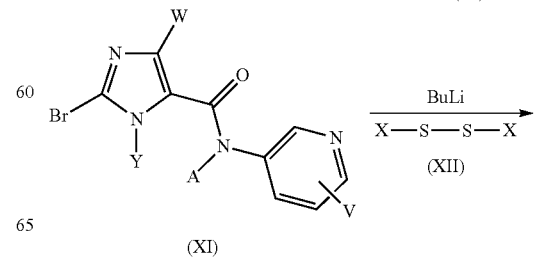

-continued
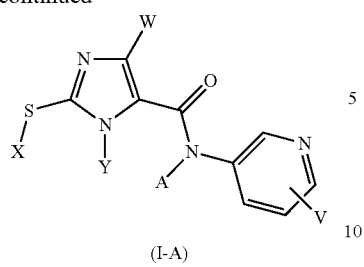
(I-A)
BuLi=n-butyllithiumn; Hünig base=N,N-diisopropylethylamnine
Process C-2
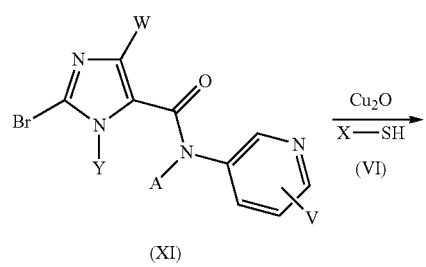
(XI)
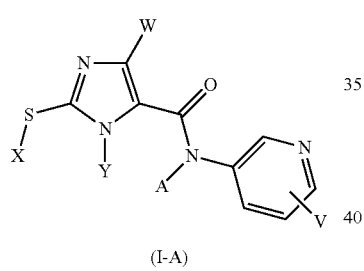
(I-A)
Process D
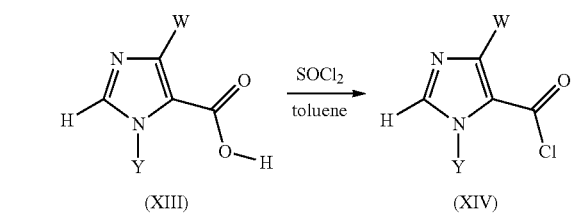
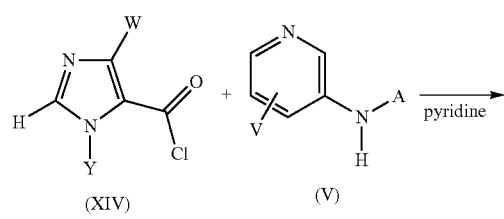 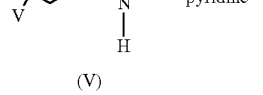
-continued
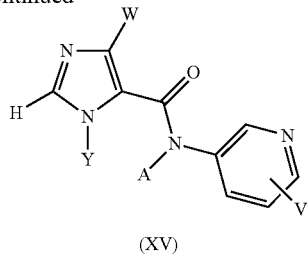
(XV)
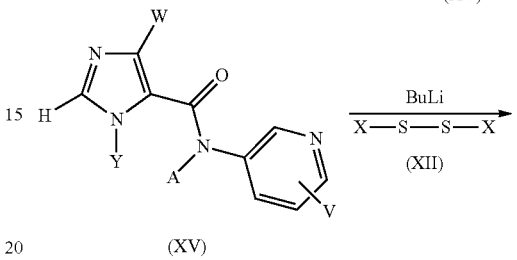
(XV)
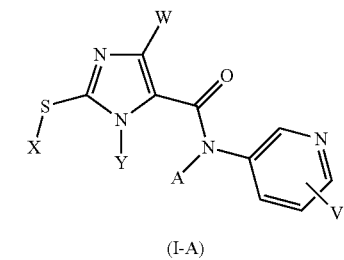
(I-A)
BuLi=n-butyllithium
The compounds of the formula (I-B) can be synthesized, for example, according to process E, as shown in the scheme below.
Process E
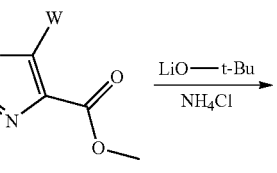
(XVI)
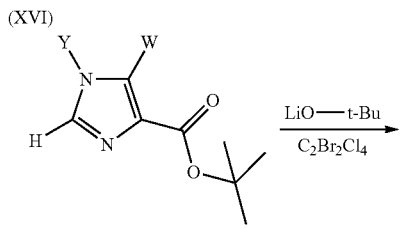
(XVII)
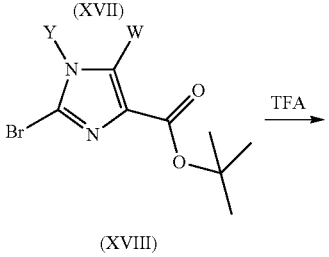
(XVIII)

-continued

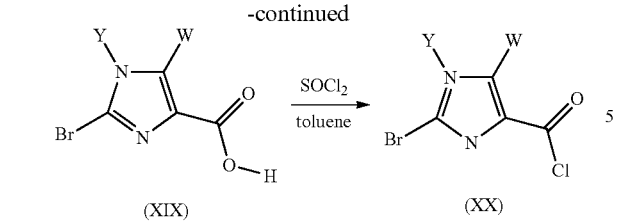

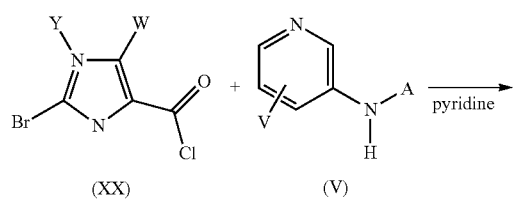

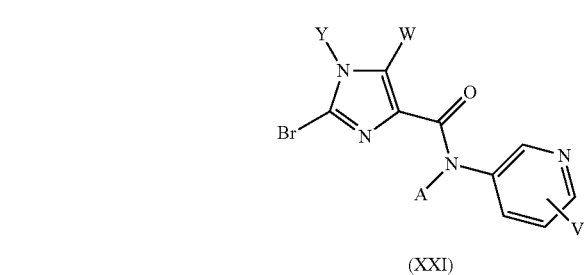

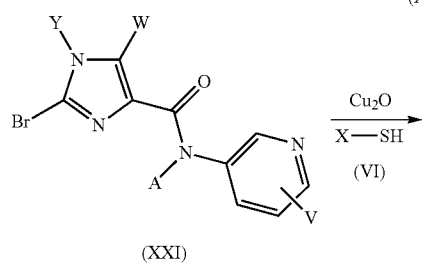

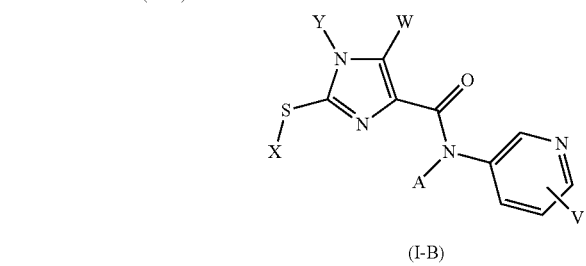

LiO-t-Bu=lithium tert-butoxide. TFA=trifluoroacetic acid

Process F

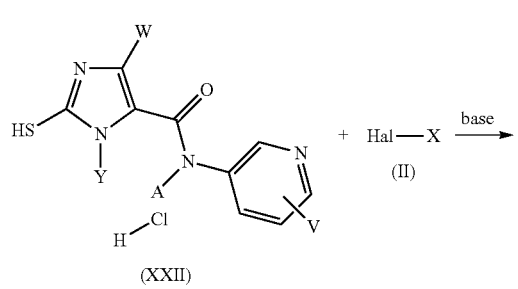

-continued

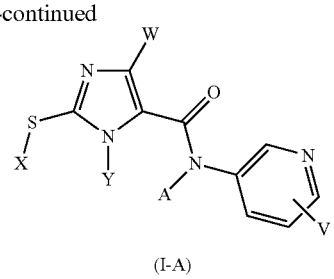

Process G

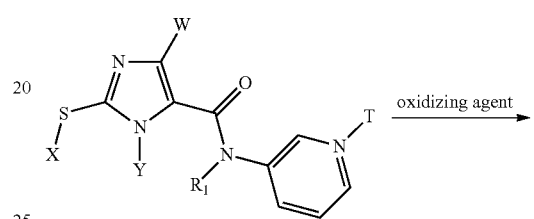

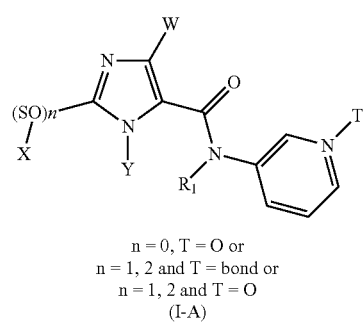

n = 0, T = O or
n = 1, 2 and T = bond or
n = 1, 2 and T = O
(I-A)

Most of the halides (e.g. alkyl halides, hetaryl halides, etc.) of the formula (II) required for process A are commercial products or can be prepared by processes generally known in organic chemistry.

The 2-mercaptoimidazolylcarboxylic esters of the formula (III) required for process A are commercially available or can be prepared, for example, by processes known from the literature, e.g. H. Rapoport et. al.; Synthesis 1988, 10, 767-771.

Most of the thiols of the formula (VI) (e.g. alkyl mercaptans, thiophenols, mercaptopyrimidines, mercaptopyridines, etc.) required for process B are commercially available or can be prepared by processes generally known in organic chemistry.

The 2-bromoimidazolylcarboxylic esters of the formula (VII) required for processes B and C are commercially available or can be prepared, for example, by processes known from the literature, e.g. H. Rapoport et. al.; Synthesis 1988, 10, 767-771.

Most of the dithioethers of the formula (XII) (e.g. pyrimidyl dithioethers, pyridyl dithioethers, etc.) required for processes C-1 and D are commercially available or can be prepared by processes generally known in organic chemistry, e.g. Zeynizadeh, Behzad, Journal of Chemical Research—Part S, 2002, 564-566, Ritgerswerke Aktiengesellschaft patent: U.S. Pat. No. 4,256,892 A1, 1981, Kesavan, Venkitasamy; Bonnet-Delpon, Daniele; Begue, Jean-Pierre Synthesis 2000, 2, 223-225.

The imidazolylcarboxylic acids of the formula (XIII) required for process D are commercially available or can be prepared, for example, by processes known from the literature, e.g. H. Rapoport et. al.; Synthesis 1988, 10, 767-771, BASF Aktiengesellschaft patent: U.S. Pat. No. 4,864,030 A1, 1989, Takeda Pharmaceutical Company Limited patent: EP2530078 A1, 2012, TAISHO PHARMACEUTICAL CO., LTD. patent: US2012/10414 A1, 2012, Subrayan, Ramachandran P.; Thurber, Ernest L.; Rasmussen, Paul G. Tetrahedron, 1994, 50, 2641-2656.

The imidazolylcarboxylic esters of the formula (XVI) required for process E are commercially available or can be prepared, for example, by processes known from the literature, e.g. Nunami; Yamada; Fukui; Matsumoto, Journal of Organic Chemistry, 1994, vol. 59, 7635-7642, H. Rapoport et. al.; Synthesis 1988, 10, 767-771.

The 3-aminopyridines of the formula (V) required for processes A to E are commercially available or can be prepared, for example, by processes known from the literature, e.g. Liu, Zhen-Jiang; Vors, Jean-Pierre; Gesing, Ernst R. F.; Bolm, Carsten, Advanced Synthesis and Catalysis, 2010, 352, 3158-3162, BAYER CROPSCIENCE AG patent: US2010/305124 A1, 2010, Shafir, Alexandr; Buchwald, Stephen L., Journal of the American Chemical Society, 2006, 128, 8742-8743.

As can be seen from process schemes A to E, the compounds of the formulae (I-A) and (I-B) are, in principle, accessible via an amidation process or a coupling process at the last stage.

Amidation Process

The compounds of the formula (I-A) and the intermediates of the formulae (XI), (XV) and (XXI) in the processes A to E according to the invention can be synthesized using amidation reactions known from the literature, or analogously to the examples explicitly mentioned.

A number of reaction conditions have been described for the amidation step, for example G. Benz in Comprehensive Organic Synthesis, 1$^{st}$ Ed., Pergamon Press, Oxford, 1991, Vol. 6, pp. 381-417; P. D. Bailey et al. in Comprehensive Organic Functional Group Transformation, 1st Ed., Elsevier Science Ltd., Oxford, 1995, Vol. 5, pp. 257-308 and R. C. Larock in Comprehensive Organic Transformations, 2nd Ed., Wiley-VCH, New York, Weinheim, 1999, pp. 1929-1994. Some of these reactions proceed via intermediate carbonyl chlorides, which can be employed in isolated form or in in-situ-generated form.

The amidation reactions are optionally carried out in the presence of a condensing agent, optionally in the presence of an acid acceptor and optionally in the presence of a solvent.

Useful condensing agents are all the condensing agents typically usable for such amidation reactions. Examples include activators such as phosgene, phosphorus trichloride, phosphorus oxychloride, oxalyl chloride, oxalyl bromide or thionyl chloride; carbodiimides such as N,N'-dicyclohexyl-carbodiimide (DCC) and 1-(3-dimethylaminopropyl)-3-ethylcarbodiimide (EDCI), or other customary condensing agents such as phosphorus pentoxide, polyphosphoric acid, N,N'-carbonyldiimidazole, 2-chloropyridine 1-methoiodide (Mukaiyama's reagent), 2-ethoxy-N-ethoxycarbonyl-1,2-dihydroquinoline (EEDQ), triphenylphosphine/carbon tetrachloride, bromotripyrrolidinophosphonium hexafluorophosphate (BROP), O-(1H-benzotriazol-1-yloxy)tris(dimethylamino)phosphonium hexafluorophosphate (BOP), N,N,N',N'-bis(tetramethylene)chlorouronium tetrafluoroborate, O-(1H-benzotriazol-1-yl)-N,N,N',N'-tetramethyluronium hexafluorophosphate (HBTU), O-(1H-benzotriazol-1-yl)-N,N,N',N'-bis(tetramethylene)uronium hexafluorophosphate, O-(1H-benzotriazol-1-yl)-N,N,N',N'-tetramethyluronium tetrafluoroborate (TBTU), O-(1H-benzotriazol-1-yl)-N,N,N',N'-bis(tetramethylene)uronium tetrafluoroborate, O-(7-azabenzotriazol-1-yl)-N,N,N',N'-tetramethyluronium hexafluorophosphate (HATU), 1-hydroxybenzotriazole (HOBt) and 4-(4,6-dimethoxy-1,3,5-triazin-2-yl)-4-methylmorpholinium salt (DMT.MM), usually available as a chloride. These reagents can be used separately or in combination.

Suitable acid acceptors are all customary inorganic or organic bases, for example organic amines such as triethylamine, diisopropylethylamine, N-methylmorpholine, pyridine or N,N-dimethylaminopyridine, alkali metal and alkaline earth metal carbonates such as lithium carbonate, sodium carbonate, potassium carbonate or caesium carbonate; alkali metal bicarbonates such as sodium bicarbonate or potassium bicarbonate. The amidation reaction in the processes according to the invention is optionally carried out in the presence of a suitable reaction auxiliary such as, for example, N,N-dimethylformamide or N,N-dimethylaminopyridine. Suitable solvents or diluents are all inert organic solvents, for example aliphatic or aromatic hydrocarbons (such as petroleum ether, toluene, cyclohexane), halogenated hydrocarbons (such as chlorotoluene, dichlorobenzene, dichloromethane, chloroform, 1,2-dichloroethane), ethers (such as diethyl ether, dioxane, tetrahydrofuran, 1,2-dimethoxyethane), esters (such as ethyl or methyl acetate), nitrohydrocarbons (such as nitromethane, nitroethane, nitrobenzene), nitriles (such as acetonitrile, propionitrile, butyronitrile, benzonitrile), amides (such as N,N-dimethylformamide, N,N-dimethylacetamide, N-methylformanilide, N-methylpyrrolidone, hexamethylphosphoramide), and also dimethyl sulphoxide or water or mixtures of the solvents mentioned.

It is also possible to use mixed anhydrides for preparation of compounds of the formula (III) (cf. J. Am. Chem. Soc. 1967, 5012). In this process, it is possible to use chloroformic esters, for example methyl chloroformate, ethyl chloroformate, isobutyl chloroformate and isopropyl chloroformate. Likewise, it is possible for this purpose to use diethylacetyl chloride, trimethylacetyl chloride and similar compounds.

Coupling Process Variant A

The compounds of the formula (I-A) and (I-B) and the intermediates of the formula (VIII) in the processes B, C-2 and E according to the invention can be synthesized using coupling reactions known from the literature, or analogously to the examples explicitly mentioned.

Numerous reaction conditions have been described for the transition metal-catalyzed coupling process variant A, e.g. J. P. Dickens et al.; Journal of Organic Chemistry, 1981, 46, 1781 ff. Harr, Molly S.; Presley, Alice L.; Thorarensen, Atli; Synlett; nb. 10; (1999); p. 1579-158. Babu, S. Ganesh; Karvembu, Tetrahedron Letters, 2013, vol. 54, #13 p. 1677-1680.

The coupling reactions are optionally carried out in the presence of a transition metal, optionally in the presence of an acid acceptor and optionally in the presence of a solvent.

Examples of solvents include: N,N-dimethylformamide, N,N-dimethylacetamide, tetrahydrofuran, toluene.

Examples of metal compounds include: Cu(I) oxide, Cu(II) oxide, tetrakis(triphenylphosphine)palladium(0), tris(dibenzylideneacetone)dipalladium(0).

Examples of bases include: potassium hydroxide, potassium tert-butoxide, triethylamine, also all customary inorganic or organic bases, for example organic amines such as diisopropylethylamine, N-methylmorpholine, pyridine or N,N-dimethylaminopyridine, alkali metal and alkaline earth metal carbonates such as lithium carbonate, sodium carbonate, potassium carbonate or caesium carbonate; alkali metal bicarbonates such as sodium bicarbonate or potassium bicarbonate.

Coupling Process Variant B

The compounds of the formula (I-A) in the processes C-1 and D according to the invention can be synthesized using coupling reactions known from the literature, or analogously to the examples explicitly mentioned.

Numerous reaction conditions have been described for the lithiation coupling process variant B, e.g. Hoechst Aktiengesellschaft, patent: U.S. Pat. No. 4,764,624 A1, 1988. Ohta; Yamamoto; Kawasaki; Yamashita; Katsuma; Nasako; Kobayashi; Ogawa, Chemical and Pharmaceutical Bulletin, 1992, vol. 40, #10 p. 2681-2685. Hara, Kenji; Iwahashi, Keiji; Kanamori, Yoshikazu; Naito, Satoshi; Takakusagi, Satoru; Uosaki, Kohei; Sawamura, Masaya Chemistry Letters, 2006, vol. 35, #8 p. 870-871.

Examples of solvents include: diethyl ether, tetrahydrofuran.

Examples of lithiation agents include: n-butyllithium, lithium diisopropylamine, lithium tert-butoxide.

The reaction temperature for the initial lithiation step is optionally between −100 and −75° C.

Methods and Uses

The invention also relates to methods for controlling animal pests, in which compounds of the formula (I) are allowed to act on animal pests and/or their habitat. The control of the animal pests is preferably carried out in agriculture and forestry, and in material protection. Preferably excluded from this are methods for the surgical or therapeutic treatment of the human or animal body and diagnostic methods carried out on the human or animal body.

The invention further relates to the use of the compounds of the formula (I) as pesticides, especially crop protection agents.

In the context of the present application, the term "pesticide" also always comprises the term "crop protection agent".

The compounds of the formula (I), given good plant tolerance, favourable homeotherm toxicity and good environmental compatibility, are suitable for protecting plants and plant organs against biotic and abiotic stress factors, for increasing harvest yields, for improving the quality of the harvested material and for controlling animal pests, especially insects, arachnids, helminths, nematodes and molluscs, which are encountered in agriculture, in horticulture, in animal husbandry, in aquatic cultures, in forests, in gardens and leisure facilities, in the protection of stored products and of materials, and in the hygiene sector. They can preferably be used as pesticides. They are active against normally sensitive and resistant species and also against all or some stages of development. The abovementioned pests include:

pests from the phylum of the Arthropoda, especially from the class of the Arachnida, for example *Acarus* spp., for example *Acarus siro, Aceria kuko, Aceria sheldoni, Aculops* spp., *Aculus* spp., for example *Aculus fockeui, Aculus schlechtendali, Amblyomma* spp., *Amphitetranychus viennensis, Argas* spp., *Boophilus* spp., *Brevipalpus* spp., for example *Brevipalpus phoenicis, Bryobia graminum, Bryobia praetiosa, Centruroides* spp., *Chorioptes* spp., *Dermanyssus gallinae, Dermatophagoides pteronyssinus, Dermatophagoides farinae, Dermacentor* spp., *Eotetranychus* spp., for example *Eotetranychus hicoriae, Epitrimerus pyri, Eutetranychus* spp., for example *Eutetranychus banksi, Eriophyes* spp., for example *Eriophyes pyri, Glycyphagus domesticus, Halotydeus destructor, Hemitarsonemus* spp., for example *Hemitarsonemus latus* (=*Polyphagotarsonemus latus*), *Hyalomma* spp., *Ixodes* spp., *Latrodectus* spp., *Loxosceles* spp., *Neutrombicula autumnalis, Nuphersa* spp., *Oligonychus* spp., for example *Oligonychus coniferarum, Oligonychus ilicis, Oligonychus indicus, Oligonychus mangiferus, Oligonychus pratensis, Oligonychus punicae, Oligonychus yothersi, Ornithodorus* spp., *Ornithonyssus* spp., *Panonychus* spp., for example *Panonychus citri* (=*Metatetranychus citri*), *Panonychus ulmi* (=*Metatetranychus ulmi*), *Phyllocoptruta oleivora, Platytetranychus multidigituli, Polyphagotarsonemus latus, Psoroptes* spp., *Rhipicephalus* spp., *Rhizoglyphus* spp., *Sarcoptes* spp., *Scorpio maurus, Steneotarsonemus* spp., *Steneotarsonemus spinki, Tarsonemus* spp., for example *Tarsonemus confusus, Tarsonemus pallidus, Tetranychus* spp., for example *Tetranychus canadensis, Tetranychus cinnabarinus, Tetranychus turkestani, Tetranychus urticae, Trombicula alfreddugesi, Vaejovis* spp., *Vasates lycopersici*;

from the class of the Chilopoda, for example *Geophilus* spp., *Scutigera* spp.;

from the order or the class of the Collembola, for example *Onychiurus armatus; Sminthurus viridis*;

from the class of the Diplopoda, for example *Blaniulus guttulatus*;

from the class of the Insecta, for example from the order of the Blattodea, for example *Blatta orientalis, Blattella asahinai, Blattella germanica, Leucophaea maderae, Loboptera decipiens, Neostylopyga rhombifolia, Panchlora* spp., *Parcoblatta* spp., *Periplaneta* spp., for example *Periplaneta americana, Periplaneta australasiae, Pycnoscelus surinamensis, Supella longipalpa*; from the order of the Coleoptera, for example *Acalymma vittatum, Acanthoscelides obtectus, Adoretus* spp., *Aethina tumida, Agelastica alni, Agriotes* spp., for example *Agriotes linneatus, Agriotes mancus, Alphitobius diaperinus, Amphimallon solstitialis, Anobium punctatum, Anoplophora* spp., *Anthonomus* spp., for example *Anthonomus grandis, Anthrenus* spp., *Apion* spp., *Apogonia* spp., *Atomaria* spp., for example *Atomaria linearis, Attagenus* spp., *Baris caerulescens, Bruchidius obtectus, Bruchus* spp., for example *Bruchus pisorum, Bruchus rufimanus, Cassida* spp., *Cerotoma trifurcata, Ceutorrhynchus* spp., for example *Ceutorrhynchus assimilis, Ceutorrhynchus quadridens, Ceutorrhynchus rapae, Chaetocnema* spp., for example *Chaetocnema confinis, Chaetocnema denticulata, Chaetocnema ectypa, Cleonus mendicus, Conoderus* spp., *Cosmopolites* spp., for example *Cosmopolites sordidus, Costelytra zealandica, Ctenicera* spp., *Curculio* spp., for example *Curculio caryae, Curculio caryatrypes, Curculio obtusus, Curculio sayi, Cryptolestes ferrugineus, Cryptolestes pusillus, Cryptorhynchus lapathi, Cryptorhynchus mangiferae, Cylindrocopturus* spp., *Cylindrocopturus adspersus, Cylindrocopturus furnissi, Dermestes* spp., *Diabrotica* spp., for example *Diabrotica balteata, Diabrotica barberi, Diabrotica undecimpunctata howardi, Diabrotica undecimpunctata undecimpunctata, Diabrotica virgifera virgifera, Diabrotica virgifera zeae, Dichocrocis* spp., *Dicladispa armigera, Diloboderus* spp., *Epicaerus* spp., *Epilachna* spp., for example *Epilachna borealis, Epilachna varivestis, Epitrix* spp., for example *Epitrix cucumeris, Epitrix fuscula, Epitrix hirtipennis, Epitrix subcrinita, Epitrix tuberis, Faustinus* spp., *Gibbium psylloides, Gnathocerus cornutus, Hellula undalis, Heteronychus arator, Heteronyx* spp., *Hylamorpha elegans, Hylotrupes bajulus, Hypera postica, Hypomeces squamosus, Hypothenemus* spp., for example *Hypothenemus hampei, Hypothenemus obscurus, Hypothenemus pubescens, Lachnostema consanguinea, Lasioderma serricome, Latheticus oryzae, Lathridius* spp., *Lema* spp., *Leptinotarsa decemlineata, Leucoptera* spp., for example *Leucoptera coffeella, Lissorhoptrus oryzophilus, Listronotus* (=*Hyperodes*) spp., *Lixus* spp., *Luperomorpha xanthodera, Luperodes* spp., *Lyctus* spp., *Megascelis* spp., *Melanotus* spp., for example *Melanotus longulus oregonensis, Meligethes aeneus, Melolontha* spp., for example *Melolontha melolontha, Migdolus* spp., *Monochamus* spp., *Naupactus xanthographus, Necrobia* spp., *Neogalerucella* spp., *Niptus hololeucus, Oryctes rhinoceros, Oryzaephilus surinamensis, Oryzaphagus oryzae, Otiorhynchus* spp., for example *Otiorhynchus cribricollis, Otiorhynchus ligustici, Otiorhynchus ovatus, Otiorhynchus rugosostriarus, Otiorhynchus sulcatus, Oulema* spp., *Oulema oryzae, Oxycetonia jucunda, Phaedon cochleariae, Phyllophaga* spp., *Phyllophaga helleri, Phyllotreta* spp., for example *Phyllotreta armoraciae, Phyllotreta pusilla, Phyllotreta ramosa, Phyllotreta striolata, Popillia japonica, Premnotrypes* spp., *Prostephanus truncatus, Psylliodes* spp., for example *Psylliodes affinis, Psylliodes chrysocephala, Psylliodes punctulata, Ptinus* spp., *Rhizobius ventralis, Rhizopertha dominica, Rhynchophorus* spp., *Rhynchophorus ferrugineus, Rhynchophorus palmarum, Sinoxylon perforans, Sitophilus* spp., for example *Sitophilus granarius, Sitophilus linearis, Sitophilus oryzae, Sitophilus zeamais, Sphenophorus* spp., *Stegobium paniceum, Sternechus* spp., for example *Sternechus paludatus, Symphyletes* spp., *Tanymecus* spp., for example *Tanymecus dilaticollis, Tanymecus indicus, Tanymecus palliatus, Tenebrio molitor, Tenebrioides mauretanicus, Tribolium* spp., for example *Tribolium audax, Tribolium castaneum, Tribolium confusum, Trogoderma* spp., *Tychius* spp., *Xylotrechus* spp., *Zabrus* spp., for example *Zabrus tenebrioides*;

from the order of the Dermaptera, for example *Anisolabis maritime, Forficula auricularia, Labidura riparia*;

from the order of the Diptera, for example *Aedes* spp., for example *Aedes aegypti, Aedes albopictus, Aedes sticticus, Aedes vexans, Agromyza* spp., for example *Agromyza frontella, Agromyza parvicornis, Anastrepha* spp., *Anopheles* spp., for example *Anopheles quadrimaculatus, Anopheles gambiae, Asphondylia* spp., *Bactrocera* spp., for example *Bactrocera cucurbitae, Bactrocera dorsalis, Bactrocera oleae, Bibio hortulanus, Calliphora erythrocephala, Calliphora vicina, Ceratitis capitata, Chironomus* spp., *Chrysomya* spp., *Chrysops* spp., *Chrysozona pluvialis, Cochliomya* spp., *Contarinia* spp., for example *Contarinia johnsoni, Contarinia nasturtii, Contarinia pyrivora, Contarinia schulzi, Contarinia sorghicola, Contarinia tritici, Cordylobia anthropophaga, Cricotopus sylvestris, Culex* spp., for example *Culex pipiens, Culex quinquefasciatus, Culicoides* spp., *Culiseta* spp., *Cuterebra* spp., *Dacus oleae, Dasineura* spp., for example *Dasineura brassicae, Delia* spp., for example *Delia antiqua, Delia coarctata, Delia florilega, Delia platura, Delia radicum, Dermatobia hominis, Drosophila* spp., for example *Drosphila melanogaster, Drosophila suzukii, Echinocnemus* spp., *Euleia heraclei, Fannia* spp., *Gasterophilus* spp., *Glossina* spp., *Haematopota* spp., *Hydrellia* spp., *Hydrellia griseola, Hylemya* spp., *Hippobosca* spp., *Hypoderma* spp., *Liriomyza* spp., for example *Liriomyza brassicae, Liriomyza huidobrensis, Liriomyza sativae, Lucilia* spp., for example *Lucilia cuprina, Lutzomyia* spp., *Mansonia* spp., *Musca* spp., for example *Musca domestica, Musca domestica vicina, Oestrus* spp., *Oscinella frit, Paratanytarsus* spp., *Paralauterbomiella subcincta, Pegomya* spp., for example *Pegomya betae, Pegomya hyoscyami, Pegomya rubivora, Phlebotomus* spp., *Phorbia* spp., *Phormia* spp., *Piophila casei, Platyparea poeciloptera, Prodiplosis* spp., *Psila rosae, Rhagoletis* spp., for example *Rhagoletis cingulata, Rhagoletis completa, Rhagoletis fausta, Rhagoletis indifferens, Rhagoletis mendax, Rhagoletis pomonella, Sarcophaga* spp., *Simulium* spp., for example *Simulium meridionale, Stomoxys* spp., *Tabanus* spp., *Tetanops* spp., *Tipula* spp., for example *Tipula paludosa, Tipula simplex, Toxotrypana curvicauda*;

from the order of the Hemiptera, for example *Acizzia acaciaebaileyanae, Acizzia dodonaeae, Acizzia uncatoides, Acrida turrita, Acyrthosipon* spp., for example *Acyrthosiphon pisum, Acrogonia* spp., *Aeneolamia* spp., *Agonoscena* spp., *Aleurocanthus* spp., *Aleyrodes proletella, Aleurolobus barodensis, Aleurothrixus floccosus, Allocaridara malayensis, Amrasca* spp., for example *Amrasca bigutulla, Amrasca devastans, Anuraphis cardui, Aonidiella* spp., for example *Aonidiella aurantii, Aonidiella citrina, Aonidiella inornata, Aphanostigma piri, Aphis* spp., for example *Aphis citricola, Aphis craccivora, Aphis fabae, Aphis forbesi, Aphis glycines, Aphis gossypii, Aphis hederae, Aphis illinoisensis, Aphis middletoni, Aphis nasturtii, Aphis nerii, Aphis pomi, Aphis spiraecola, Aphis vibumiphila, Arboridia apicalis, Arytainilla* spp., *Aspidiella* spp., *Aspidiotus* spp., for example *Aspidiotus nerii, Atanus* spp., *Aulacorthum solani, Bemisia tabaci, Blastopsylla occidentalis, Boreioglycaspis melaleucae, Brachycaudus helichrysi, Brachycolus* spp., *Brevicoryne brassicae, Cacopsylla* spp., for example *Cacopsylla pyricola, Calligypona marginata, Capulinia* spp., *Carneocephala fulgida, Ceratovacuna lanigera, Cercopidae, Ceroplastes* spp., *Chaetosiphon fragaefolii, Chionaspis tegalensis, Chlorita onukii, Chondracris rosea, Chromaphis juglandicola, Chrysomphalus aonidum, Chrysomphalus ficus, Cicadulina mbila, Coccomytilus halli, Coccus* spp., for example *Coccus hesperidum, Coccus longulus, Coccus pseudomagnoliarum, Coccus viridis, Cryptomyzus ribis, Cryptoneossa* spp., *Ctenarytaina* spp., *Dalbulus* spp., *Dialeurodes chittendeni, Dialeurodes citri, Diaphorina citri, Diaspis* spp., *Diuraphis* spp., *Drosicha* spp., *Dysaphis* spp., for example *Dysaphis apiifolia, Dysaphis plantaginea, Dysaphis tulipae, Dysmicoccus* spp., *Empoasca* spp., for example *Empoasca abrupta, Empoasca fabae, Empoasca maligna, Empoasca solana, Empoasca stevensi, Eriosoma* spp., for example *Eriosoma americanum, Eriosoma lanigerum, Eriosoma pyricola, Erythroneura* spp., *Eucalyptolyma* spp., *Euphyllura* spp., *Euscelis bilobatus, Ferrisia* spp., *Fiorinia* spp., *Furcaspis oceanica, Geococcus coffeae, Glycaspis* spp., *Heteropsylla cubana, Heteropsylla spinulosa, Homalodisca coagulata, Hyalopterus arundinis, Hyalopterus pruni, Icerya* spp., for example *Icerya purchasi, Idiocerus* spp., *Idioscopus* spp., *Laodelphax striatellus, Lecanium* spp., for example *Lecanium comi* (=*Parthenolecanium corni*), *Lepidosaphes* spp., for example *Lepidosaphes ulmi, Lipaphis erysimi, Lopholeucaspis japonica, Lycorma delicatula, Macrosiphum* spp., for example *Macrosiphum euphorbiae, Macrosiphum lilii, Macrosiphum rosae, Macrosteles facifrons, Mahanarva* spp., *Melanaphis sacchari, Metcalfiella* spp., *Metcalfa pruinosa, Metopolophium dirhodum, Monellia costalis, Monelliopsis pecanis, Myzus* spp., for example *Myzus ascalonicus, Myzus cerasi, Myzus ligustri, Myzus ornatus, Myzus persicae, Myzus nicotianae, Nasonovia ribisnigri, Neomaskellia* spp., *Nephotettix* spp., for example *Nephotettix cincticeps, Nephotettix nigropictus, Nettigonicla spectra, Nilaparvata lugens, Oncometopia* spp., *Orthezia praelonga, Oxya chinensis, Pachypsylla* spp., *Parabemisia myricae, Paratrioza* spp., for example *Paratrioza cockerelli, Parlatoria* spp., *Pemphigus* spp., for example *Pemphigus bursarius, Pemphigus populivenae, Peregrinus maidis, Perkinsiella* spp., *Phenacoccus* spp., for example *Phenacoccus madeirensis, Phloeomyzus passerinii, Phorodon humuli, Phylloxera* spp., for example *Phylloxera devastatrix, Phylloxera notabilis, Pinnaspis aspidistrae, Planococcus* spp., for example *Planococcus citri, Prosopidopsylla flava, Protopulvinaria pyriformis, Pseudaulacaspis pentagona, Pseudococcus* spp., for example *Pseudococcus calceolariae, Pseudococcus comstocki, Pseudococcus longispinus, Pseudococcus maritimus, Pseudococcus viburni, Psyllopsis* spp., *Psylla* spp., for example *Psylla buxi, Psylla mali, Psylla pyri, Pteromalus* spp., *Pulvinaria* spp., *Pyrilla* spp., *Quadraspidiotus* spp., for example *Quadraspidiotus juglansregiae, Quadraspidiotus ostreaeformis, Quadraspidiotus perniciosus, Quesada gigas, Rastrococcus* spp., *Rhopalosiphum* spp., for example *Rhopalosiphum maidis, Rhopalosiphum oxyacanthae, Rhopalosiphum padi, Rhopalosiphum rufiabdominale, Saissetia* spp., for example *Saissetia coffeae, Saissetia miranda, Saissetia neglecta, Saissetia oleae, Scaphoideus titanus, Schizaphis graminum, Selenaspidus articulatus, Sitobion avenae, Sogata* spp., *Sogatella furcifera, Sogatodes* spp., *Stictocephala festina, Siphoninus phillyreae, Tenalaphara malayensis, Tetragonocephela* spp., *Tinocallis caryaefoliae, Tomaspis* spp., *Toxoptera* spp., for example *Toxoptera aurantii, Toxoptera citricidus, Trialeurodes vaporariorum, Trioza* spp., for example *Trioza diospyri, Typhlocyba* spp., *Unaspis* spp., *Viteus vitifolii, Zygina* spp.;

from the suborder of the Heteroptera, for example *Aelia* spp., *Anasa tristis, Antestiopsis* spp., *Boisea* spp., *Blissus* spp., *Calocoris* spp., *Campylomma livida, Cavelerius* spp., *Cimex* spp., for example *Cimex adjunctus, Cimex hemipterus, Cimex lectularius, Cimex pilosellus, Collaria* spp., *Creontiades dilutus, Dasynus piperis, Dichelops furcatus, Diconocoris hewetti, Dysdercus* spp., *Euschistus* spp., for example *Euschistus heros, Euschistus servus, Euschistus tristigmus, Euschistus variolarius, Eurydema* spp., *Eurygaster* spp., *Halyomorpha halys, Heliopeltis* spp., *Horcias nobilellus, Leptocorisa* spp., *Leptocorisa varicornis, Leptoglossus occidentalis, Leptoglossus phyllopus, Lygocoris* spp., for example *Lygocoris pabulinus, Lygus* spp., for example *Lygus elisus, Lygus hesperus, Lygus lineolaris, Macropes excavatus, Megacopta cribraria, Miridae, Monalonion atratum, Nezara* spp., for example *Nezara viridula, Nysius* spp., *Oebalus* spp., *Pentomidae, Piesma quadrata, Piezodorus* spp., for example *Piezodorus guildinii, Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.;

from the order of the Hymenoptera, for example *Acromyrmex* spp., *Athalia* spp., for example *Athalia rosae, Atta* spp., *Camponotus* spp., *Dolichovespula* spp., *Diprion* spp., for example *Diprion similis, Hoplocampa* spp., for example *Hoplocampa cookei, Hoplocampa testudinea, Lasius* spp., *Linepithema humile, Monomorium pharaonis, Paratrechina* spp., *Paravespula* spp., *Plagiolepis* spp., *Sirex* spp., *Solenopsis invicta, Tapinoma* spp., *Technomyrmex albipes, Urocerus* spp., *Vespa* spp., for example *Vespa crabro, Wasmannia auropunctata, Xeris* spp.;

from the order of the Isopoda, for example *Armadillidium vulgare, Oniscus asellus, Porcellio scaber;* from the order of the Isoptera, for example *Coptotermes* spp., for example *Coptotermes formosanus, Comitermes cumulans, Cryptotermes* spp., *Incisitermes* spp., *Kalotermes* spp., *Microtermes obesi, Nasutitermes* spp., *Odontotermes* spp., *Porotermes* spp., *Reticulitermes* spp., for example *Reticulitermes flavipes, Reticulitermes hesperus*;

from the order of the Lepidoptera, for example *Achroia grisella, Acronicta major, Adoxophyes* spp., for example *Adoxophyes orana, Aedia leucomelas, Agrotis* spp., for example *Agrotis segetum, Agrotis ipsilon, Alabama* spp., for example *Alabama argillacea, Amyelois transitella, Anarsia* spp., *Anticarsia* spp., for example *Anticarsia gemmatalis, Argyroploce* spp., *Autographa* spp., *Barathra brassicae, Blastodacna atra, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Cheimatobia brumata, Chilo* spp., for example *Chilo plejadellus, Chilo suppressalis, Choreutis pariana, Choristoneura* spp., *Chrysodeixis chalcites, Clysia ambiguella, Cnaphalocerus* spp., *Cnaphalocrocis medinalis, Cnephasia* spp., *Conopomorpha* spp., *Conotrachelus* spp., *Copitarsia* spp., *Cydia* spp., for example *Cydia nigricana, Cydia pomonella, Dalaca noctuides, Diaphania* spp., *Diparopsis* spp., *Diatraea saccharalis, Earias* spp., *Ecdytolopha aurantium, Elasmopalpus lignosellus, Eldana saccharina, Ephestia* spp., for example *Ephestia elutella, Ephestia kuehniella, Epinotia* spp., *Epiphyas postvittana, Erannis* spp., *Erschoviella musculana, Etiella* spp., *Eudocima* spp., *Eulia* spp., *Eupoecilia ambiguella, Euproctis* spp., for example *Euproctis chrysorrhoea, Euxoa* spp., *Feltia* spp., *Galleria mellonella, Gracillaria* spp., *Grapholitha* spp., for example *Grapholita molesta, Grapholita prunivora, Hedylepta* spp., *Helicoverpa* spp., for example *Helicoverpa armigera, Helicoverpa zea, Heliothis* spp., for example *Heliothis virescens, Hofmannophila pseudospretella, Homoeosoma* spp., *Homona* spp., *Hyponomeuta padella, Kakivoria flavofasciata, Lampides* spp., *Laphygma* spp., *Laspeyresia molesta, Leucinodes orbonalis, Leucoptera* spp., for example *Leucoptera coffeella, Lithocolletis* spp., for example *Lithocolletis blancardella, Lithophane antennata, Lobesia* spp., for example *Lobesia botrana, Loxagrotis albicosta, Lymantria* spp., for example *Lymantria dispar, Lyonetia* spp., for example *Lyonetia clerkella, Malacosoma neustria, Maruca testulalis, Mamestra brassicae, Melanitis leda, Mocis* spp., *Monopis obviella, Mythimna separata, Nemapogon cloacellus, Nymphula* spp., *Oiketicus* spp., *Omphisa* spp., *Operophtera* spp., *Oria* spp., *Orthaga* spp., *Ostrinia* spp., for example *Ostrinia nubilalis, Oulema melanopus, Oulema oryzae, Panolis flammea, Parnara* spp., *Pectinophora* spp., for example *Pectinophora gossypiella, Perileucoptera* spp., *Phthorimaea* spp., for example *Phthorimaea operculella, Phyllocnistis citrella, Phyllonorycter* spp., for example *Phyllonorycter blancardella, Phyllonorycter crataegella, Pieris* spp., for example *Pieris rapae, Platynota stultana, Plodia interpunctella, Plusia* spp., *Plutella xylostella* (=*Plutella maculipennis*), *Prays* spp., *Prodenia* spp., *Protoparce* spp., *Pseudaletia* spp., for example *Pseudaletia unipuncta, Pseudoplusia includens, Pyrausta nubilalis, Rachiplusia nu, Schoenobius* spp., for example *Schoenobius bipunctifer, Scirpophaga* spp., for example *Scirpophaga innotata, Scotia segetum, Sesamia* spp., for example *Sesamia inferens, Sparganothis* spp., *Spodoptera* spp., for example *Spodoptera eradiana, Spodoptera exigua, Spodoptera frugiperda, Spodoptera praefica, Stathmopoda* spp., *Stenoma* spp., *Stomopteryx subsecivella, Synanthedon* spp., *Tecia solanivora, Thaumetopoea* spp., *Thermesia gemmatalis, Tinea cloacella, Tinea pellionella, Tineola bisselliella, Tortrix* spp., *Trichophaga tapetzella, Trichoplusia* spp., for example *Trichoplusia ni, Tryporyza incertulas, Tuta absoluta, Virachola* spp.;

from the order of the Orthoptera or Saltatoria, for example *Acheta domesticus, Dichroplus* spp., *Gryllotalpa* spp., for example *Gryllotalpa gryllotalpa, Hieroglyphus* spp.,

*Locusta* spp., for example *Locusta migratoria, Melanoplus* spp., for example *Melanoplus devastator, Paratlanticus ussuriensis, Schistocerca gregaria;* from the order of the Phthiraptera, for example *Damalinia* spp., *Haematopinus* spp., *Linognathus* spp., *Pediculus* spp., *Phylloxera vastatrix, Phthirus pubis, Trichodectes* spp.;

from the order of the Psocoptera, for example *Lepinotus* spp., *Liposcelis* spp.; from the order of the Siphonaptera, for example *Ceratophyllus* spp., *Ctenocephalides* spp., for example *Ctenocephalides canis, Ctenocephalides felis, Pulex irritans, Tunga penetrans, Xenopsylla cheopis;* from the order of the Thysanoptera, for example *Anaphothrips obscurus, Baliothrips biformis, Chaetanaphothrips leeuweni, Drepanothrips reuteri, Enneothrips flavens, Frankliniella* spp., for example *Frankliniella fusca, Frankliniella occidentalis, Frankliniella schultzei, Frankliniella tritici, Frankliniella vaccinii, Frankliniella williamsi, Haplothrips* spp., *Heliothrips* spp., *Hercinothrips femoralis, Rhipiphorothrips cruentatus, Scirtothrips* spp., *Taeniothrips cardamomi, Thrips* spp., for example *Thrips palmi, Thrips tabaci;* from the order of the Zygentoma (=Thysanura), for example *Ctenolepisma* spp., *Lepisma saccharina, Lepismodes inquilinus, Thermobia domestica;* from the class of the Symphyla, for example *Scutigerella* spp., for example *Scutigerella immaculata;* pests from the phylum of the Mollusca, in particular from the class of the Bivalvia, for example *Dreissena* spp.;

and also from the class of the Gastropoda, for example *Arion* spp., for example *Arion ater rufus, Biomphalaria* spp., *Bulinus* spp., *Deroceras* spp., for example *Deroceras laeve, Galba* spp., *Lymnaea* spp., *Oncomelania* spp., *Pomacea* spp., *Succinea* spp.;

animal and human parasites from the phyla of the Platyhelminthes and Nematoda, for example *Aelurostrongylus* spp., *Amidostomum* spp., *Ancylostoma* spp., *Angiostrongylus* spp., *Anisakis* spp., *Anoplocephala* spp., *Ascaris* spp., *Ascaridia* spp., *Baylisascaris* spp., *Brugia* spp., *Bunostomum* spp., *Capillaria* spp., *Chabertia* spp., *Clonorchis* spp., *Cooperia* spp., *Crenosoma* spp., *Cyathostoma* spp., *Dicrocoelium* spp., *Dictyocaulus* spp., *Diphyllobothrium* spp., *Dipylidium* spp., *Dirofilaria* spp., *Dracunculus* spp., *Echinococcus* spp., *Echinostoma* spp., *Enterobius* spp., *Eucoleus* spp., *Fasciola* spp., *Fascioloides* spp., *Fasciolopsis* spp., *Filaroides* spp., *Gongylonema* spp., *Gyrodactylus* spp., *Habronema* spp., *Haemonchus* spp., *Heligmosomoides* spp., *Heterakis* spp., *Hymenolepis* spp., *Hyostrongylus* spp., *Litomosoides* spp., *Loa* spp., *Metastrongylus* spp., *Metorchis* spp., *Mesocestoides* spp., *Moniezia* spp., *Muellerius* spp., *Necator* spp., *Nematodirus* spp., *Nippostrongylus* spp., *Oesophagostomum* spp., *Ollulanus* spp., *Onchocerca* spp., *Opisthorchis* spp., *Oslerus* spp., *Ostertagia* spp., *Oxyuris* spp., *Paracapillaria* spp., *Parafilaria* spp., *Paragonimus* spp., *Paramphistomum* spp., *Paranoplocephala* spp., *Parascaris* spp., *Passalurus* spp., *Protostrongylus* spp., *Schistosoma* spp., *Setaria* spp., *Spirocerca* spp., *Stephanofilaria* spp., *Stephanurus* spp., *Strongyloides* spp., *Strongylus* spp., *Syngamus* spp., *Taenia* spp., *Teladorsagia* spp., *Thelazia* spp., *Toxascaris* spp., *Toxocara* spp., *Trichinella* spp., *Trichobilharzia* spp., *Trichostrongylus* spp., *Trichuris* spp., *Uncinaria* spp., *Wuchereria* spp.;

plant pests from the phylum of the Nematoda, i.e. phytoparasitic nematodes, especially *Aglenchus* spp., for example *Aglenchus agricola, Anguina* spp., for example *Anguina tritici, Aphelenchoides* spp., for example *Aphelenchoides arachidis, Aphelenchoides fragariae, Belonolaimus* spp., for example *Belonolaimus gracilis, Belonolaimus longicaudatus, Belonolaimus nortoni, Bursaphelenchus* spp., for example *Bursaphelenchus cocophilus, Bursaphelenchus eremus, Bursaphelenchus xylophilus, Cacopaurus* spp., for example *Cacopaurus pestis, Criconemella* spp., for example *Criconemella curvata, Criconemella onoensis, Criconemella ornata, Criconemella rusium, Criconemella xenoplax* (=*Mesocriconema xenoplax*), *Criconemoides* spp., for example *Criconemoides ferniae, Criconemoides onoense, Criconemoides ornatum, Ditylenchus* spp., for example *Ditylenchus dipsaci, Dolichodorus* spp., *Globodera* spp., for example *Globodera pallida, Globodera rostochiensis, Helicotylenchus* spp., for example *Helicotylenchus dihystera, Hemicriconemoides* spp., *Hemicycliophora* spp., *Heterodera* spp., for example *Heterodera avenae, Heterodera glycines, Heterodera schachtii, Hoplolaimus* spp., *Longidorus* spp., for example *Longidorus africanus, Meloidogyne* spp., for example *Meloidogyne chitwoodi, Meloidogyne fallax, Meloidogyne hapla, Meloidogyne incognita, Meloinema* spp., *Nacobbus* spp., *Neotylenchus* spp., *Paralongidorus* spp., *Paraphelenchus* spp., *Paratrichodorus* spp., for example *Paratrichodorus minor, Pratylenchus* spp., for example *Pratylenchus penetrans, Pseudohalenchus* spp., *Psilenchus* spp., *Punctodera* spp., *Quinisulcius* spp., *Radopholus* spp., for example *Radopholus citrophilus, Radopholus similis, Rotylenchulus* spp., *Rotylenchus* spp., *Scutellonema* spp., *Subanguina* spp., *Trichodorus* spp., for example *Trichodorus obtusus, Trichodorus primitivus, Tylenchulus* spp., *Tylenchorhynchus* spp., for example *Tylenchorhynchus annulatus, Tylenchulus* spp., for example *Tylenchulus semipenetrans, Xiphinema* spp., for example *Xiphinema index.*

In addition, it is possible to control, from the sub-kingdom of the Protozoa, the order of the Coccidia, for example *Eimeria* spp.

Nematodes

In the present context, the term "nematodes" comprises all species of the phylum Nematoda and here in particular species that act as parasites on plants or fungi (for example species of the order Aphelenchida, Meloidogyne, Tylenchida and others) or else on humans and animals (for example species of the orders Trichinellida, Tylenchida, Rhabditida and Spirurida) or cause damage in or on these living organisms, and also other parasitic helminths.

A nematicide in crop protection, as described herein, is capable of controlling nematodes.

The term "controlling nematodes" means killing the nematodes or preventing or impeding their development or their growth or preventing or impeding their penetration into or their sucking on plant tissue.

Here, the efficacy of the compounds is determined by comparing mortalities, gall formation, cyst formation, nematode density per volume of soil, nematode density per root, number of nematode eggs per volume of soil, mobility of the nematodes between a plant or plant part treated with the compound of the formula (I) or the treated soil and an untreated plant or plant part or the untreated soil (100%). Preferably, the reduction achieved is 25-50% in comparison to an untreated plant, plant part or the untreated soil, more preferably 51-79% and most preferably the complete kill or the complete prevention of development and growth of the nematodes by a reduction of 80 to 100% is achieved. The control of nematodes as described herein also comprises the control of proliferation of the nematodes (development of cysts and/or eggs). Compounds of the formula (I) can likewise be used to maintain the health of the plants or animals, and they can be used for the control of nematodes in a curative, preventative or systemic manner.

The person skilled in the art knows methods for determining mortalities, gall formation, cyst formation, nematode density per volume of soil, nematode density per root, number of nematode eggs per volume of soil, mobility of the nematodes.

The use of a compound of the formula (I) may keep the plant healthy and also comprises a reduction of the damage caused by nematodes and an increase of the harvest yield.

In the present context, the term "nematodes" refers to plant nematodes which comprise all nematodes which damage plants. Plant nematodes comprise phytoparasitic nematodes and soil-borne nematodes. The phytoparasitic nematodes include ectoparasites such as *Xiphinema* spp., *Longidorus* spp. and *Trichodorus* spp.; semiparasites such as *Tylenchulus* spp.; migratory endoparasites such as *Pratylenchus* spp., *Radopholus* spp. and *Scutellonema* spp.; non-migratory parasites such as *Heterodera* spp., *Globodera* spp. and *Meloidogyne* spp., and also stem and leaf endoparasites such as *Ditylenchus* spp., *Aphelenchoides* spp. and *Hirschmaniella* spp. Particularly damaging root-parasitic soil nematodes are, for example, cyst-forming nematodes of the genera *Heterodera* or *Globodera*, and/or root gall nematodes of the genus *Meloidogyne*. Damaging species of these genera are, for example, *Meloidogyne incognita*, *Heterodera glycines* (soya bean cyst nematode), *Globodera pallida* and *Globodera rostochiensis* (yellow potato cyst nematode), these species being controlled effectively by the compounds described in the present text. However, the use of the compounds described in the present text is by no means restricted to these genera or species, but also extends in the same manner to other nematodes.

The plant nematodes include, for example, *Aglenchus agricola, Anguina tritici, Aphelenchoides arachidis, Aphelenchoides fragaria*, and the stem and leaf endoparasites *Aphelenchoides* spp., *Belonolaimus gracilis, Belonolaimus longicaudatus, Belonolaimus nortoni, Bursaphelenchus cocophilus, Bursaphelenchus eremus, Bursaphelenchus xylophilus* and *Bursaphelenchus* spp., *Cacopaurus pestis, Criconemella curvata, Criconemella onoensis, Criconemella ornata, Criconemella rusium, Criconemella xenoplax* (=*Mesocriconema xenoplax*) and *Criconemella* spp., *Criconemoides ferniae, Criconemoides onoense, Criconemoides ornatum* and *Criconemoides* spp., *Ditylenchus destructor, Ditylenchus dipsaci, Ditylenchus myceliophagus* and also the stem and leaf endoparasites *Ditylenchus* spp., *Dolichodorus heterocephalus, Globodera pallida* (=*Heterodera pallida*), *Globodera rostochiensis* (yellow potato cyst nematode), *Globodera solanacearum, Globodera tabacum, Globodera virginia* and the non-migratory cyst-forming parasites *Globodera* spp., *Helicotylenchus digonicus, Helicotylenchus dihystera, Helicotylenchus erythrine, Helicotylenchus multicinctus, Helicotylenchus nannus, Helicotylenchus pseudorobustus* und *Helicotylenchus* spp., *Hemicriconemoides, Hemicycliophora arenaria, Hemicycliophora nudata, Hemicycliophora parvana, Heterodera avenae, Heterodera cruciferae, Heterodera glycines* (soya bean cyst nematode), *Heterodera oryzae, Heterodera schachtii, Heterodera zeae* and the non-migratory cyst-forming parasites *Heterodera* spp., *Hirschmaniella gracilis, Hirschmaniella oryzae, Hirschmaniella spinicaudata* and the stem and leaf endoparasites *Hirschmaniella* spp., *Hoplolaimus aegyptii, Hoplolaimus californicus, Hoplolaimus columbus, Hoplolaimus galeatus, Hoplolaimus indicus, Hoplolaimus magnistylus, Hoplolaimus pararobustus, Longidorus africanus, Longidorus breviannulatus, Longidorus elongatus, Longidorus laevicapitatus, Longidorus vineacola* and the ectoparasites *Longidorus* spp., *Meloidogyne acronea, Meloidogyne africana, Meloidogyne arenaria, Meloidogyne arenaria thamesi, Meloidogyne artiella, Meloidogyne chitwoodi, Meloidogyne coffeicola, Meloidogyne ethiopica, Meloidogyne exigua, Meloidogyne fallax, Meloidogyne graminicola, Meloidogyne graminis, Meloidogyne hapla, Meloidogyne incognita, Meloidogyne incognita acrita, Meloidogyne javanica, Meloidogyne kikuyensis, Meloidogyne minor, Meloidogyne naasi, Meloidogyne paranaensis, Meloidogyne thamesi* and the non-migratory parasites *Meloidogyne* spp., *Meloinema* spp., *Nacobbus aberrans, Neotylenchus vigissi, Paraphelenchus pseudoparietinus, Paratrichodorus allius, Paratrichodorus lobatus, Paratrichodorus minor, Paratrichodorus nanus, Paratrichodorus porosus, Paratrichodorus teres* und *Paratrichodorus* spp., *Paratylenchus hamatus, Paratylenchus minutus, Paratylenchus projectus* und *Paratylenchus* spp., *Pratylenchus agilis, Pratylenchus alleni, Pratylenchus andinus, Pratylenchus brachyurus, Pratylenchus cerealis, Pratylenchus coffeae, Pratylenchus crenatus, Pratylenchus delattrei, Pratylenchus giibbicaudatus, Pratylenchus goodeyi, Pratylenchus hamatus, Pratylenchus hexincisus, Pratylenchus loosi, Pratylenchus neglectus, Pratylenchus penetrans, Pratylenchus pratensis, Pratylenchus scribneri, Pratylenchus teres, Pratylenchus thornei, Pratylenchus vulnus, Pratylenchus zeae* and the migratory endoparasites *Pratylenchus* spp., *Pseudohalenchus minutus, Psilenchus magnidens, Psilenchus tumidus, Punctodera chalcoensis, Quinisulcius acutus, Radopholus citrophilus, Radopholus similis*, the migratory endoparasites *Radopholus* spp., *Rotylenchulus borealis, Rotylenchulus parvus, Rotylenchulus reniformis* and *Rotylenchulus* spp., *Rotylenchus laurentinus, Rotylenchus macrodoratus, Rotylenchus robustus, Rotylenchus uniformis* and *Rotylenchus* spp., *Scutellonema brachyurum, Scutellonema bradys, Scutellonema clathricaudatum* and the migratory endoparasites *Scutellonema* spp., *Subanguina radiciola, Tetylenchus nicotianae, Trichodorus cylindricus, Trichodorus minor, Trichodorus primitivus, Trichodorus proximus, Trichodorus similis, Trichodorus sparsus* and the ectoparasites *Trichodorus* spp., *Tylenchorhynchus agri, Tylenchorhynchus brassicae, Tylenchorhynchus clarus, Tylenchorhynchus claytoni, Tylenchorhynchus digitatus, Tylenchorhynchus ebriensis, Tylenchorhynchus maximus, Tylenchorhynchus nudus, Tylenchorhynchus vulgaris* and *Tylenchorhynchus* spp., *Tylenchulus semipenetrans* and the semiparasites *Tylenchulus* spp., *Xiphinema americanum, Xiphinema brevicolle, Xiphinema dimorphicaudatum, Xiphinema index* and the ectoparasites *Xiphinema* spp.

Nematodes for the control of which a compound of the formula (I) may be used include nematodes of the genus *Meloidogyne* such as the Southern root-knot nematode (*Meloidogyne incognita*), the Javanese root-knot nematode (*Meloidogyne javanica*), the Northern root-knot nematode (*Meloidogyne hapla*) and the peanut root-knot nematode (*Meloidogyne arenaria*); nematodes of the genus *Ditylenchus* such as the potato rot nematode (*Ditylenchus destructor*) and stem and bulb eelworm (*Ditylenchus dipsaci*); nematodes of the genus *Pratylenchus* such as the cob root-lesion nematode (*Pratylenchus penetrans*), the chrysanthemum root-lesion nematode (*Pratylenchus fallax*), the coffee root nematode (*Pratylenchus coffeae*), the tea root nematode (*Pratylenchus loosi*) and the walnut root-lesion nematode (*Pratylenchus vulnus*); nematodes of the genus *Globodera* such as the yellow potato cyst nematode (*Globodera rostochiensis*) and the white potato cyst nematode (*Globodera pallida*); nematodes of the genus *Heterodera* such as the soya bean cyst nematode (*Heterodera glycines*)

and the beet cyst eelworm (*Heterodera schachtii*); nematodes of the genus *Aphelenchoides* such as the rice white-tip nematode (*Aphelenchoides besseyi*), the chrysanthemum nematode (*Aphelenchoides ritzemabosi*) and the strawberry nematode (*Aphelenchoides fragariae*); nematodes of the genus *Aphelenchus* such as the fungivorous nematode (*Aphelenchus avenae*); nematodes of the genus *Radopholus*, such as the burrowing nematode (*Radopholus similis*); nematodes of the genus *Tylenchulus* such as the citrus root nematode (*Tylenchulus semipenetrans*); nematodes of the genus *Rotylenchulus* such as the reniform nematode (*Rotylenchulus reniformis*); tree-dwelling nematodes such as the pine wood nematode (*Bursaphelenchus xylophilus*) and the red ring nematode (*Bursaphelenchus cocophilus*) and the like.

Plants for the protection of which a compound of the formula (I) can be used include plants such as cereals (for example rice, barley, wheat, rye, oats, maize and the like), beans (soya bean, azuki bean, bean, broadbean, peas, peanuts and the like), fruit trees/fruits (apples, citrus species, pears, grapevines, peaches, Japanese apricots, cherries, walnuts, almonds, bananas, strawberries and the like), vegetable species (cabbage, tomato, spinach, broccoli, lettuce, onions, spring onion, pepper and the like), root crops (carrot, potato, sweet potato, radish, lotus root, turnip and the like), plants for industrial raw materials (cotton, hemp, paper mulberry, mitsumata, rape, beet, hops, sugar cane, sugar beet, olive, rubber, palm trees, coffee, tobacco, tea and the like), cucurbits (pumpkin, cucumber, watermelon, melon and the like), meadow plants (cocksfoot, sorghum, timothy-grass, clover, alfalfa and the like), lawn grasses (mascarene grass, bentgrass and the like), spice plants etc. (lavender, rosemary, thyme, parsley, pepper, ginger and the like) and flowers (chrysanthemums, rose, orchid and the like).

The compounds of the formula (I) are particularly suitable for controlling coffee nematodes, in particular *Pratylenchus brachyurus, Pratylenchus coffeae, Meloidogyne exigua, Meloidogyne incognita, Meloidogyne coffeicola, Helicotylenchus* spp. and also *Meloidogyne paranaensis, Rotylenchus* spp., *Xiphinema* spp., *Tylenchorhynchus* spp. and *Scutellonema* spp.

The compounds of the formula (I) are particularly suitable for controlling potato nematodes, in particular *Pratylenchus brachyurus, Pratylenchus pratensis, Pratylenchus scribneri, Pratylenchus penetrans, Pratylenchus coffeae, Ditylenchus dipsaci* and also *Pratylenchus alleni, Pratylenchus andinus, Pratylenchus cerealis, Pratylenchus crenatus, Pratylenchus hexincisus, Pratylenchus loosi, Pratylenchus neglectus, Pratylenchus teres, Pratylenchus thornei, Pratylenchus vulnus, Belonolaimus longicaudatus, Trichodorus cylindricus, Trichodorus primitivus, Trichodorus proximus, Trichodorus similis, Trichodorus sparsus, Paratrichodorus minor, Paratrichodorus allius, Paratrichodorus nanus, Paratrichodorus teres, Meloidogyne arenaria, Meloidogyne fallax, Meloidogyne hapla, Meloidogyne thamesi, Meloidogyne incognita, Meloidogyne chitwoodi, Meloidogyne javanica, Nacobbus aberrans, Globodera rostochiensis, Globodera pallida, Ditylenchus destructor, Radopholus similis, Rotylenchulus reniformis, Neotylenchus vigissi, Paraphelenchus pseudoparietinus, Aphelenchoides fragariae* and *Meloinema* spp.

The compounds of the formula (I) are particularly suitable for controlling tomato nematodes, in particular *Meloidogyne arenaria, Meloidogyne hapla, Meloidogyne javanica, Meloidogyne incognita, Pratylenchus penetrans* and also *Pratylenchus brachyurus, Pratylenchus coffeae, Pratylenchus scribneri, Pratylenchus vulnus, Paratrichodorus minor, Meloidogyne exigua, Nacobbus aberrans, Globodera solanacearum, Dolichodorus heterocephalus* and *Rotylenchulus reniformis*.

The compounds of the formula (I) are particularly suitable for controlling cucumber plant nematodes, in particular *Meloidogyne arenaria, Meloidogyne hapla, Meloidogyne javanica, Meloidogyne incognita, Rotylenchulus reniformis* and *Pratylenchus thornei*.

The compounds of the formula (I) are particularly suitable for controlling cotton nematodes, in particular *Belonolaimus longicaudatus, Meloidogyne incognita, Hoplolaimus columbus, Hoplolaimus galeatus* and *Rotylenchulus reniformis*.

The compounds of the formula (I) are particularly suitable for controlling maize nematodes, in particular *Belonolaimus longicaudatus, Paratrichodorus minor* and also *Pratylenchus brachyurus, Pratylenchus delattrei, Pratylenchus hexincisus, Pratylenchus penetrans, Pratylenchus zeae,* (*Belonolaimus gracilis*), *Belonolaimus nortoni, Longidorus breviannulatus, Meloidogyne arenaria, Meloidogyne arenaria thamesi, Meloidogyne graminis, Meloidogyne incognita, Meloidogyne incognita acrita, Meloidogyne javanica, Meloidogyne naasi, Heterodera avenae, Heterodera oryzae, Heterodera zeae, Punctodera chalcoensis, Ditylenchus dipsaci, Hoplolaimus aegyptii, Hoplolaimus magnistylus, Hoplolaimus galeatus, Hoplolaimus indicus, Helicotylenchus digonicus, Helicotylenchus dihystera, Helicotylenchus pseudorobustus, Xiphinema americanum, Dolichodorus heterocephalus, Criconemella ornata, Criconemella onoensis, Radopholus similis, Rotylenchulus borealis, Rotylenchulus parvus, Tylenchorhynchus agri, Tylenchorhynchus clarus, Tylenchorhynchus claytoni, Tylenchorhynchus maximus, Tylenchorhynchus nudus, Tylenchorhynchus vulgaris, Quinisulcius acutus, Paratylenchus minutus, Hemicycliophora parvana, Aglenchus agricola, Anguina tritici, Aphelenchoides arachidis, Scutellonema brachyurum* and *Subanguina radiciola*.

The compounds of the formula (I) are particularly suitable for controlling soya bean nematodes, in particular *Pratylenchus brachyurus, Pratylenchus pratensis, Pratylenchus penetrans, Pratylenchus scribneri, Belonolaimus longicaudatus, Heterodera glycines, Hoplolaimus columbus* and also *Pratylenchus coffeae, Pratylenchus hexincisus, Pratylenchus neglectus, Pratylenchus crenatus, Pratylenchus alleni, Pratylenchus agilis, Pratylenchus zeae, Pratylenchus vulnus,* (*Belonolaimus gracilis*), *Meloidogyne arenaria, Meloidogyne incognita, Meloidogyne javanica, Meloidogyne hapla, Hoplolaimus columbus, Hoplolaimus galeatus* and *Rotylenchulus reniformis*.

The compounds of the formula (I) are particularly suitable for controlling tobacco nematodes, in particular *Meloidogyne incognita, Meloidogyne javanica* and also *Pratylenchus brachyurus, Pratylenchus pratensis, Pratylenchus hexincisus, Pratylenchus penetrans, Pratylenchus neglectus, Pratylenchus crenatus, Pratylenchus thornei, Pratylenchus vulnus, Pratylenchus zeae, Longidorus elongatu, Paratrichodorus lobatus, Trichodorus* spp., *Meloidogyne arenaria, Meloidogyne hapla, Globodera tabacum, Globodera solanacearum, Globodera virginiae, Ditylenchus dipsaci, Rotylenchus* spp., *Helicotylenchus* spp., *Xiphinema americanum, Criconemella* spp., *Rotylenchulus reniformis, Tylenchorhynchus claytoni, Paratylenchus* spp. and *Tetylenchus nicotianae*.

The compounds of the formula (I) are particularly suitable for controlling citrus nematodes, in particular *Pratylenchus coffeae* and also *Pratylenchus brachyurus, Pratylenchus vulnus, Belonolaimus longicaudatus, Paratrichodorus minor, Paratrichodorus porosus, Trichodorus, Meloidogyne* incognita, Meloidogyne incognita acrita, Meloidogyne javanica, Rotylenchus macrodoratus, Xiphinema americanum, Xiphinema brevicolle, Xiphinema index, Criconemella spp., Hemicriconemoides, Radopholus similis and Radopholus citrophilus, Hemicycliophora arenaria, Hemicycliophora nudata and Tylenchulus semipenetrans.

The compounds of the formula (I) are particularly suitable for controlling banana nematodes, in particular Pratylenchus coffeae, Radopholus similis and also Pratylenchus giibbicaudatus, Pratylenchus loosi, Meloidogyne spp., Helicotylenchus multicinctus, Helicotylenchus dihystera and Rotylenchulus spp.

The compounds of the formula (I) are particularly suitable for controlling pineapple nematodes, in particular Pratylenchus zeae, Pratylenchus pratensis, Pratylenchus brachyurus, Pratylenchus goodeyi., Meloidogyne spp., Rotylenchulus reniformis and also Longidorus elongatus, Longidorus laevicapitatus, Trichodorus primitivus, Trichodorus minor, Heterodera spp., Ditylenchus myceliophagus, Hoplolaimus californicus, Hoplolaimus pararobustus, Hoplolaimus indicus, Helicotylenchus dihystera, Helicotylenchus nannus, Helicotylenchus multicinctus, Helicotylenchus erythrine, Xiphinema dimorphicaudatum, Radopholus similis, Tylenchorhynchus digitatus, Tylenchorhynchus ebriensis, Paratylenchus minutus, Scutellonema clathricaudatum, Scutellonema bradys, Psilenchus tumidus, Psilenchus magnidens, Pseudohalenchus minutus, Criconemoides ferniae, Criconemoides onoense and Criconemoides ornatum.

The compounds of the formula (I) are particularly suitable for controlling grapevine nematodes, in particular Pratylenchus vulnus, Meloidogyne arenaria, Meloidogyne incognita, Meloidogyne javanica, Xiphinema americanum, Xiphinema index and also Pratylenchus pratensis, Pratylenchus scribneri, Pratylenchus neglectus, Pratylenchus brachyurus, Pratylenchus thornei and Tylenchulus semipenetrans.

The compounds of the formula (I) are particularly suitable for controlling nematodes in tree crops—pome fruit, in particular Pratylenchus penetrans and also Pratylenchus vulnus, Longidorus elongatus, Meloidogyne incognita and Meloidogyne hapla.

The compounds of the formula (I) are particularly suitable for controlling nematodes in tree crops—stone fruit, in particular Pratylenchus penetrans, Pratylenchus vulnus, Meloidogyne arenaria, Meloidogyne hapla, Meloidogyne javanica, Meloidogyne incognita, Criconemella xenoplax and also Pratylenchus brachyurus, Pratylenchus coffeae, Pratylenchus scribneri, Pratylenchus zeae, Belonolaimus longicaudatus, Helicotylenchus dihystera, Xiphinema americanum, Criconemella curvata, Tylenchorhynchus claytoni, Paratylenchus hamatus, Paratylenchus projectus, Scutellonema brachyurum and Hoplolaimus galeatus.

The compounds of the formula (I) are particularly suitable for controlling nematodes in tree crops, sugar cane and rice, in particular Trichodorus spp., Criconemella spp. and also Pratylenchus spp., Paratrichodorus spp., Meloidogyne spp., Helicotylenchus spp., Tylenchorhynchus spp., Aphelenchoides spp., Heterodera spp., Xiphinema spp. and Cacopaurus pestis.

In the present context, the term "nematodes" also refers to nematodes damaging humans or animals.

Specific nematode species harmful to humans or to animals are:

Trichinellida, for example: Trichuris spp., Capillaria spp., Paracapillaria spp., Eucoleus spp., Trichomosoides spp., Trichinella spp.

From the order of the Tylenchida, for example: Micronema spp., Strongyloides spp.

From the order of the Rhabditida, for example: Strongylus spp., Triodontophorus spp., Oesophagodontus spp., Trichonema spp., Gyalocephalus spp., Cylindropharynx spp., Poteriostomum spp., Cyclococercus spp., Cylicostephanus spp., Oesophagostomum spp., Chabertia spp., Stephanurus spp., Ancylostoma spp., Uncinaria spp., Necator spp., Bunostomum spp., Globocephalus spp., Syngamus spp., Cyathostoma spp., Metastrongylus spp., Dictyocaulus spp., Muellerius spp., Protostrongylus spp., Neostrongylus spp., Cystocaulus spp., Pneumostrongylus spp., Spicocaulus spp., Elaphostrongylus spp., Parelaphostrongylus spp., Crenosoma spp., Paracrenosoma spp., Oslerus spp., Angiostrongylus spp., Aelurostrongylus spp., Filaroides spp., Parafilaroides spp., Trichostrongylus spp., Haemonchus spp., Ostertagia spp., Teladorsagia spp., Marshallagia spp., Cooperia spp., Nippostrongylus spp., Heligmosomoides spp., Nematodirus spp., Hyostrongylus spp., Obeliscoides spp., Amidostomum spp., Ollulanus spp.

From the order of the Spirurida, for example: Oxyuris spp., Enterobius spp., Passalurus spp., Syphacia spp., Aspiculuris spp., Heterakis spp.; Ascaris spp., Toxascaris spp., Toxocara spp., Baylisascaris spp., Parascaris spp., Anisakis spp., Ascaridia spp.; Gnathostoma spp., Physaloptera spp., Thelazia spp., Gongylonema spp., Habronema spp., Parabronema spp., Draschia spp., Dracunculus spp.; Stephanofilaria spp., Parafilaria spp., Setaria spp., Loa spp., Dirofilaria spp., Litomosoides spp., Brugia spp., Wuchereria spp., Onchocerca spp., Spirocerca spp.;

Many known nematicides also act against other parasitic helminths and are therefore used for controlling worms—not necessarily belonging to the group Nematoda—which are parasites in humans and animals. The present invention also relates to the use of the compounds of the formula (I) as anthelmintic medicaments. The pathogenic endoparasitic helminths include Platyhelmintha (e.g. Monogenea, cestodes and trematodes), Acanthocephala and Pentastoma. The following helminths may be mentioned as being preferred:

Monogenea: for example: Gyrodactylus spp., Dactylogyrus spp., Polystoma spp.

Cestodes: from the order of the Pseudophyllidea, for example: Diphyllobothrium spp., Spirometra spp., Schistocephalus spp., Ligula spp., Bothridium spp., Diplogonoporus spp.

From the order of the Cyclophyllida, for example: Mesocestoides spp., Anoplocephala spp., Paranoplocephala spp., Moniezia spp., Thysanosoma spp., Thysaniezia spp., Avitellina spp., Stilesia spp., Cittotaenia spp., Andyra spp., Bertiella spp., Taenia spp., Echinococcus spp., Hydatigera spp., Davainea spp., Raillietina spp., Hymenolepis spp., Echinolepis spp., Echinocotyle spp., Diorchis spp., Dipylidium spp., Joyeuxiella spp., Diplopylidium spp.

Trematodes: from the class of the Digenea, for example: Diplostomum spp., Posthodiplostomum spp., Schistosoma spp., Trichobilharzia spp., Ornithobilharzia spp., Austrobilharzia spp., Gigantobilharzia spp., Leucochloridium spp., Brachylaima spp., Echinostoma spp., Echinoparyphium spp., Echinochasmus spp., Hypoderaeum spp., Fasciola spp., Fascioloides spp., Fasciolopsis spp., Cyclocoelum spp., Typhlocoelum spp., Paramphistomum spp., Calicophoron spp., Cotylophoron spp., Gigantocotyle spp., Fischoederius spp., Gastrothylacus spp., Notocotylus spp., Catatropis spp., Plagiorchis spp., Prosthogonimus spp., Dicrocoelium spp., Eurytrema spp., Troglotrema spp., Paragonimus spp., Collyriclum spp., Nanophyetus spp., Opisthorchis spp., Clonorchis spp., Metorchis spp., Heterophyes spp., Metagonimus spp.

Acanthocephala: from the order of the Oligacanthorhynchida, for example: *Macracanthorhynchus* spp., *Prosthenorchis* spp.; from the order of the Polymorphida, for example: *Filicollis* spp.; from the order of the Moniliformida, for example: *Moniliformis* spp.

From the order of the Echinorhynchida, for example, *Acanthocephalus* spp., *Echinorhynchus* spp., *Leptorhynchoides* spp.

Pentastoma: from the order of the Porocephalida, for example, *Linguatula* spp.

In the veterinary field and in animal husbandry, the administration of the compounds of the formula (I) is carried out in a known manner, directly or enterally, parenterally, dermally or nasally in the form of suitable use forms. Administration may be prophylactic or therapeutic.

The compounds of the formula (I) can optionally, at certain concentrations or application rates, also be used as herbicides, safeners, growth regulators or agents to improve plant properties, as microbicides or gametocides, for example as fungicides, antimycotics, bactericides, virucides (including agents against viroids) or as agents against MLO (*mycoplasma*-like organisms) and RLO (*rickettsia*-like organisms). If appropriate, they can also be used as intermediates or precursors for the synthesis of other active compounds.

Formulations

The present invention further relates to formulations and use forms prepared therefrom as pesticides, for example drench, drip and spray liquors, comprising at least one compound of the formula (I). In some cases, the use forms comprise further pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates and/or spreaders, for example alkylsiloxanes and/or salts, for example organic or inorganic ammonium or phosphonium salts, for example ammonium sulphate or diammonium hydrogenphosphate and/or retention promoters, for example dioctyl sulphosuccinate or hydroxypropylguar polymers and/or humectants, for example glycerol and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations, in addition to one or more compounds of the formula (I), optionally comprise further agrochemically active compounds.

Preference is given to formulations or use forms comprising auxiliaries, for example extenders, solvents, spontaneity promoters, carriers, emulsifiers, dispersants, frost protection agents, biocides, thickeners and/or further auxiliaries, for example adjuvants. An adjuvant in this context is a component which enhances the biological effect of the formulation, without the component itself having any biological effect. Examples of adjuvants are agents which promote retention, spreading, attachment to the leaf surface or penetration.

These formulations are prepared in a known way, for example by mixing the compounds of the formula (I) with auxiliaries such as, for example, extenders, solvents and/or solid carriers and/or other auxiliaries such as, for example, surfactants. The formulations are produced either in suitable facilities or else before or during application.

The auxiliaries used may be substances suitable for imparting special properties, such as certain physical, technical and/or biological properties, to the formulation of the compounds of the formula (I), or to the use forms prepared from these formulations (for example ready-to-use pesticides such as spray liquors or seed dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender utilized is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and water.

In principle, it is possible to use all suitable solvents. Examples of suitable solvents are aromatic hydrocarbons, such as xylene, toluene or alkylnaphthalenes, chlorinated aromatic or aliphatic hydrocarbons, such as chlorobenzene, chloroethylene or methylene chloride, aliphatic hydrocarbons, such as cyclohexane, paraffins, mineral oil fractions, mineral and vegetable oils, alcohols, such as methanol, ethanol, isopropanol, butanol or glycol and their ethers and esters, ketones such as acetone, methyl ethyl ketone, methyl isobutyl ketone or cyclohexanone, strongly polar solvents, such as dimethyl sulphoxide, and also water.

In principle, it is possible to use all suitable carriers. Useful carriers especially include: for example ammonium salts and ground natural minerals such as kaolins, clays, talc, chalk, quartz, attapulgite, montmorillonite or diatomaceous earth, and ground synthetic minerals such as finely divided silica, alumina and natural or synthetic silicates, resins, waxes and/or solid fertilizers. It is likewise possible to use mixtures of such carriers. Useful carriers for granules include: for example crushed and fractionated natural rocks such as calcite, marble, pumice, sepiolite, dolomite, and synthetic granules of inorganic and organic flours, and also granules of organic material such as sawdust, paper, coconut shells, maize and tobacco stalks.

It is also possible to use liquefied gaseous extenders or solvents. Especially suitable are those extenders or carriers which are gaseous at standard temperature and under atmospheric pressure, for example aerosol propellants such as halogenated hydrocarbons, and also butane, propane, nitrogen and carbon dioxide.

Examples of emulsifiers and/or foam formers, dispersants or wetting agents having ionic or nonionic properties or mixtures of these surface-active substances are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyl taurates), phosphoric esters of polyethoxylated alcohols or phenols, fatty acid esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is advantageous if one of the compounds of the formula (I) and/or one of the inert carriers is insoluble in water and when the application takes place in water.

Further auxiliaries which may be present in the formulations and the use forms derived therefrom are dyes such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc.

Additional components which may be present are stabilizers, such as cold stabilizers, preservatives, antioxidants, light stabilizers, or other agents which improve chemical and/or physical stability. Foam generators or antifoams may also be present.

In addition, the formulations and the use forms derived therefrom may also comprise, as additional auxiliaries, stickers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids. Further auxiliaries may be mineral and vegetable oils.

It is possible if appropriate for still further auxiliaries to be present in the formulations and the use forms derived therefrom. Examples of such additives are fragrances, protective colloids, binders, adhesives, thickeners, thixotropic agents, penetrants, retention promoters, stabilizers, sequestrants, complexing agents, humectants, spreaders. In general, the compounds of the formula (I) can be combined with any solid or liquid additive commonly used for formulation purposes.

Useful retention promoters include all those substances which reduce dynamic surface tension, for example dioctyl sulphosuccinate, or increase viscoelasticity, for example hydroxypropylguar polymers.

Suitable penetrants in the present context are all those substances which are usually used for improving the penetration of agrochemical active compounds into plants. Penetrants are defined in this context by their ability to penetrate from the (generally aqueous) application liquor and/or from the spray coating into the cuticle of the plant and hence increase the mobility of the active compounds in the cuticle. The method described in the literature (Baur et al., 1997, Pesticide Science 51, 131-152) can be used for determining this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulphate or diammonium hydrogenphosphate.

The formulations preferably comprise between 0.00000001% and 98% by weight of the compound of the formula (I), more preferably between 0.01% and 95% by weight of the compound of the formula (I), most preferably between 0.5% and 90% by weight of the compound of the formula (I), based on the weight of the formulation.

The content of the compound of the formula (I) in the use forms prepared from the formulations (in particular pesticides) may vary within wide ranges. The concentration of the compound of the formula (I) in the use forms may typically be between 0.00000001% and 95% by weight of the compound of the formula (I), preferably between 0.00001% and 1% by weight, based on the weight of the use form. Application is accomplished in a customary manner appropriate for the use forms.

Mixtures

The compounds of the formula (I) can also be used in a mixture with one or more suitable fungicides, bactericides, acaricides, molluscicides, nematicides, insecticides, microbiological agents, beneficial organisms, herbicides, fertilizers, bird repellents, phytotonics, sterilants, safeners, semiochemicals and/or plant growth regulators, in order thus, for example, to broaden the spectrum of action, prolong the period of action, enhance the rate of action, prevent repellency or prevent evolution of resistance. In addition, active compound combinations of this kind can improve plant growth and/or tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processability of the harvested products.

In addition, the compounds of the formula (I) may be present in a mixture with other active compounds or semiochemicals such as attractants and/or bird repellents and/or plant activators and/or growth regulators and/or fertilizers. Likewise, the compounds of the formula (I) can be used in mixtures with agents to improve plant properties, for example growth, yield and quality of the harvested material.

In a particular embodiment according to the invention, the compounds of the formula (I) are present in formulations or in the use forms prepared from these formulations in a mixture with further compounds, preferably those as described below.

If one of the compounds mentioned below can occur in different tautomeric forms, these forms are also included even if not explicitly mentioned in each case.

Insecticides/Acaricides/Nematicides

The active compounds specified here with their common names are known and are described for example in "The Pesticide Manual", 16th ed., British Crop Protection Council 2012, or can be searched for on the Internet (e.g. http://www.alanwood.net/pesticides).

(1) Acetylcholinesterase (AChE) inhibitors, such as, for example, carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel antagonists, for example cyclodiene-organochlorines, e.g. chlordane and endosulfan or phenylpyrazoles (fiproles), e.g. ethiprole and fipronil.

(3) Sodium channel modulators/voltage-gated sodium channel blockers, for example pyrethroids, e.g. acrinathrin, allethrin, d-cis-trans allethrin, d-trans allethrin, bifenthrin, bioallethrin, bioallethrin s-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomer], deltamethrin, empenthrin [(EZ)-(1R) isomer], esfenvalerate, etofenprox, fenpropathrin, fenvalerate, flucythrinate, flumethrin, tau-fluvalinate, halfenprox, imiprothrin, kadethrin, momfluorothrin, permethrin, phenothrin [(1R)-trans isomer], prallethrin, pyrethrins (pyrethrum), resmethrin, silafluofen, tefluthrin, tetramethrin, tetramethrin [(1R) isomer)], tralomethrin and transfluthrin or DDT or methoxychlor.

(4) Nicotinergic acetylcholine receptor (nAChR) agonists, for example neonicotinoids, e.g. acetamiprid, clothianidin, dinotefuran, imidacloprid, nitenpyram, thiacloprid and thiamethoxam or nicotine or sulfoxaflor or flupyradifurone.

(5) Allosteric activators of the nicotinergic acetylcholine receptor (nAChR), for example spinosyns, e.g. spinetoram and spinosad.

(6) Chloride channel activators, for example avermectins/milbemycins, e.g. abamectin, emamectin benzoate, lepimectin and milbemectin.

(7) Juvenile hormone imitators, for example, juvenile hormone analogues, e.g. hydroprene, kinoprene and methoprene or fenoxycarb or pyriproxyfen.

(8) Active compounds having unknown or nonspecific mechanisms of action, for example alkyl halides, e.g. methyl bromide and other alkyl halides; or chloropicrine or sulphuryl fluoride or borax or tartar emetic.

(9) Selective antifeedants, e.g. pymetrozine or flonicamid.

(10) Mite growth inhibitors, e.g. clofentezine, hexythiazox and diflovidazin or etoxazole.

(11) Microbial disruptors of the insect gut membrane, e.g. *Bacillus thuringiensis* subspecies *israelensis, Bacillus sphaericus, Bacillus thuringiensis* subspecies *aizawai, Bacillus thuringiensis* subspecies *kurstaki, Bacillus thuringiensis* subspecies *tenebrionis*, and BT plant proteins: Cry1Ab, Cry1Ac, Cry1Fa, Cry2Ab, mCry3A, Cry3Ab, Cry3Bb, Cry34/35Ab1.

(12) Oxidative phosphorylation inhibitors, ATP disruptors, for example diafenthiuron or organotin compounds, e.g. azocyclotin, cyhexatin and fenbutatin oxide or propargite or tetradifon.

(13) Oxidative phosphorylation decouplers that interrupt the H proton gradient, for example chlorfenapyr, DNOC and sulfluramid.

(14) Nicotinergic acetylcholine receptor antagonists, for example bensultap, cartap hydrochloride, thiocyclam, and thiosultap-sodium.

(15) Chitin biosynthesis inhibitors, type 0, for example bistrifluron, chlorfluazuron, diflubenzuron, flucycloxuron, flufenoxuron, hexaflumuron, lufenuron, novaluron, noviflumuron, teflubenzuron and triflumuron.

(16) Chitin biosynthesis inhibitors, type 1, for example buprofezin.

(17) Molting inhibitors (especially for Diptera, i.e. dipterans), for example cyromazine.

(18) Ecdysone receptor agonists, for example chromafenozide, halofenozide, methoxyfenozide and tebufenozide.

(19) Octopaminergic agonists, for example amitraz.

(20) Complex-III electron transport inhibitors, for example hydramethylnon or acequinocyl or fluacrypyrim.

(21) Complex-I electron transport inhibitors, for example METI acaricides, e.g. fenazaquin, fenpyroximate, pyrimidifen, pyridaben, tebufenpyrad and tolfenpyrad or rotenone (Derris).

(22) Voltage-gated sodium channel blockers, for example indoxacarb or metaflumizone.

(23) Inhibitors of acetyl-CoA carboxylase, for example tetronic and tetramic acid derivatives, e.g. spirodiclofen, spiromesifen and spirotetramat.

(24) Complex-IV electron transport inhibitors, for example phosphines, e.g. aluminium phosphide, calcium phosphide, phosphine and zinc phosphide or cyanide.

(25) Complex-II electron transport inhibitors, for example cyenopyrafen and cyflumetofen.

(28) Ryanodine receptor effectors, for example diamides, e.g. chlorantraniliprole, cyantraniliprole and flubendiamide.

Further active compounds having an unknown or unclear mechanism of action, for example afidopyropen, afoxolaner, azadirachtin, benclothiaz, benzoximate, bifenazate, broflanilide, bromopropylate, chinomethionat, cryolite, cyclaniliprole, cycloxaprid, cyhalodiamide, dicloromezotiaz, dicofol, diflovidazin, flometoquin, fluazaindolizine, fluensulfone, flufenerim, flufenoxystrobin, flufiprole, fluhexafon, fluopyram, fluralaner, fluxametamide, fufenozide, guadipyr, heptafluthrin, imidaclothiz, iprodione, lotilaner, meperfluthrin, paichongding, pyflubumide, pyridalyl, pyrifluquinazon, pyriminostrobin, sarolaner, tetramethylfluthrin, tetraniliprole, tetrachlorantraniliprole, tioxazafen, triflumezopyrim and iodomethane; and additionally preparations based on *Bacillus firmus* (I-1582, BioNeem, Votivo), and the following known active compounds: 1-{2-fluoro-4-methyl-5-[(2,2,2-trifluoroethyl)sulphinyl]phenyl}-3-(trifluoromethyl)-1H-1,2,4-triazole-5-amine (known from WO2006/043635), {1'-[(2E)-3-(4-chlorophenyl)prop-2-en-1-yl]-5-fluorospiro[indol-3,4'-piperidin]-1(2H)-yl}(2-chloropyridin-4-yl)methanone (known from WO2003/106457), 2-chloro-N-[2-{1-[(2E)-3-(4-chlorophenyl)prop-2-en-1-yl] piperidin-4-yl}-4-(trifluoromethyl)phenyl]isonicotinamide (known from WO2006/003494), 3-(2,5-dimethylphenyl)-4-hydroxy-8-methoxy-1,8-diazaspiro[4.5]dec-3-en-2-one (known from WO2009/049851), 3-(2,5-dimethylphenyl)-8-methoxy-2-oxo-1,8-diazaspiro[4.5]dec-3-en-4-ylethyl carbonate (known from WO2009/049851), 4-(but-2-yn-1-yloxy)-6-(3,5-dimethylpiperidin-1-yl)-5-fluoropyrimidine (known from WO2004/099160), 4-(but-2-yn-1-yloxy)-6-(3-chlorophenyl)pyrimidine (known from WO2003/076415), PF1364 (CAS Reg. No. 1204776-60-2), methyl 2-[2-({[3-bromo-1-(3-chloropyridin-2-yl)-1H-pyrazol-5-yl] carbonyl}amino)-5-chloro-3-methylbenzoyl]-2-methylhydrazinecarboxylate (known from WO2005/085216), methyl 2-[2-({[3-bromo-1-(3-chloropyridin-2-yl)-1H-pyrazol-5-yl] carbonyl}amino)-5-cyano-3-methylbenzoyl]-2-ethylhydrazinecarboxylate (known from WO2005/085216), methyl 2-[2-({[3-bromo-1-(3-chloropyridin-2-yl)-1H-pyrazol-5-yl]

carbonyl}amino)-5-cyano-3-methylbenzoyl]-2-methylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (known from WO2005/085216), N-[2-(5-amino-1,3,4-thiadiazol-2-yl)-4-chloro-6-methylphenyl]-3-bromo-1-(3-chloropyridin-2-yl)-1H-pyrazole-5-carboxamide (known from CN102057925), 4-[5-(3,5-dichlorophenyl)-5-(trifluoromethyl)-4,5-dihydro-1,2-oxazol-3-yl]-2-methyl-N-(1-oxidothietan-3-yl)benzamide (known from WO2009/080250), N-[(2E)-1-[(6-chloropyridin-3-yl)methyl]pyridin-2(1H)-ylidene]-2,2,2-trifluoroacetamide (known from WO2012/029672), 1-[(2-chloro-1,3-thiazol-5-yl)methyl]-4-oxo-3-phenyl-4H-pyrido[1,2-a]pyrimidin-1-ium-2-olate (known from WO2009/099929), 1-[(6-chloropyridin-3-yl)methyl]-4-oxo-3-phenyl-4H-pyrido[1,2-a]pyrimidin-1-ium-2-olate (known from WO2009/099929), 4-(3-{2,6-dichloro-4-[(3,3-dichloroprop-2-en-1-yl)oxy]phenoxy}propoxy)-2-methoxy-6-(trifluoromethyl)pyrimidine (known from CN101337940), N-[2-(tert-butylcarbamoyl)-4-chloro-6-methylphenyl]-1-(3-chloropyridin-2-yl)-3-(fluoromethoxy)-1H-pyrazole-5-carboxamide (known from WO2008/134969), butyl [2-(2,4-dichlorophenyl)-3-oxo-4-oxaspiro[4.5]dec-1-en-1-yl] carbonate (known from CN 102060818), (3E)-3-[1-[(6-chloro-3-pyridyl)methyl]-2-pyridinylidene]-1,1,1-trifluoropropan-2-one (known from WO2013/144213, N-(methylsulphonyl)-6-[2-(pyridin-3-yl)-1,3-thiazol-5-yl]pyridine-2-carboxamide (known from WO2012/000896), N-[3-(benzylcarbamoyl)-4-chlorophenyl]-1-methyl-3-(pentafluoroethyl)-4-(trifluoromethyl)-1H-pyrazole-5-carboxamide (known from WO2010/051926).

Fungicides

The active compounds specified herein by their common name are known and described, for example, in "Pesticide Manual" or on the Internet (for example: http://www.alanwood.net/pesticides).

All the fungicidal mixing components listed in classes (1) to (15) may optionally form salts with corresponding bases or acids if suitable functional groups are present. In addition, the fungicidal mixing components listed in classes (1) to (15) also include tautomeric forms if tautomerism is possible.

(1) Ergosterol biosynthesis inhibitors, for example (1.01) aldimorph, (1.02) azaconazole, (1.03) bitertanol, (1.04) bromuconazole, (1.05) cyproconazole, (1.06) diclobutrazole, (1.07) difenoconazole, (1.08) diniconazole, (1.09) diniconazole-M, (1.10) dodemorph, (1.11) dodemorph acetate, (1.12) epoxiconazole, (1.13) etaconazole, (1.14) fenarimol, (1.15) fenbuconazole, (1.16) fenhexamid, (1.17) fenpropidin, (1.18) fenpropimorph, (1.19) fluquinconazole, (1.20) flurprimidol, (1.21) flusilazole, (1.22) flutriafole, (1.23) furconazole, (1.24) furconazole-cis, (1.25) hexaconazole, (1.26) imazalil, (1.27) imazalil sulphate, (1.28) imibenconazole, (1.29) ipconazole, (1.30) metconazole, (1.31) myclobutanil, (1.32) naftifin, (1.33) nuarimol, (1.34) oxpoconazole, (1.35) paclobutrazole, (1.36) pefurazoate, (1.37) penconazole, (1.38) piperalin, (1.39) prochloraz, (1.40) propiconazole, (1.41) prothioconazole, (1.42) pyributicarb, (1.43) pyrifenox, (1.44) quinconazole, (1.45) simeconazole, (1.46) spiroxamine, (1.47) tebuconazole, (1.48) terbinafin, (1.49) tetraconazole, (1.50) triadimefon, (1.51) triadimenol, (1.52) tridemorph, (1.53) triflumizole, (1.54) triforine, (1.55) triticonazole, (1.56) uniconazole, (1.57) uniconazole-P, (1.58) viniconazole, (1.59) voriconazole, (1.60) 1-(4-chlorophenyl)-2-(1H-1,2,4-triazol-1-yl)cycloheptanol, (1.61) methyl 1-(2,2-dimethyl-2,3-dihydro-1H-inden-1-yl)-1H-imidazole-5-carboxylate, (1.62) N'-{5-(difluoromethyl)-2-methyl-4-[3-(trimethylsilyl)propoxy]phenyl}-N-ethyl-N-methylimidoformamide, (1.63) N-ethyl-N-methyl-N'-{2-methyl-5-(trifluoromethyl)-4-[3-(trimethylsilyl)propoxy]phenyl}imidoformamide, (1.64)O-[1-(4-methoxyphenoxy)-3,3-dimethylbutan-2-yl]-1H-imidazole 1-carbothioate, (1.65) pyrisoxazole, (1.66) 2-{[3-(2-chlorophenyl)-2-(2,4-difluorophenyl)oxiran-2-yl]methyl}-2,4-dihydro-3H-1,2,4-triazole-3-thione, (1.67) 1-{[3-(2-chlorophenyl)-2-(2,4-difluorophenyl)oxiran-2-yl]methyl}-1H-1,2,4-triazol-5-yl thiocyanate, (1.68) 5-(allylsulphanyl)-1-{[3-(2-chlorophenyl)-2-(2,4-difluorophenyl)oxiran-2-yl]methyl}-1H-1,2,4-triazole, (1.69) 2-[1-(2,4-dichlorophenyl)-5-hydroxy-2,6,6-trimethylheptan-4-yl]-2,4-dihydro-3H-1,2,4-triazole-3-thione, (1.70) 2-{[rel(2R,3S)-3-(2-chlorophenyl)-2-(2,4-difluorophenyl)oxiran-2-yl]methyl}-2,4-dihydro-3H-1,2,4-triazole-3-thione, (1.71) 2-{[rel(2R,3R)-3-(2-chlorophenyl)-2-(2,4-difluorophenyl)oxiran-2-yl]methyl}-2,4-dihydro-3H-1,2,4-triazole-3-thione, (1.72) 1-{[rel(2R,3S)-3-(2-chlorophenyl)-2-(2,4-difluorophenyl)oxiran-2-yl]methyl}-1H-1,2,4-triazol-5-yl thiocyanate, (1.73) 1-{[rel(2R,3R)-3-(2-chlorophenyl)-2-(2,4-difluorophenyl)oxiran-2-yl]methyl}-1H-1,2,4-triazol-5-yl thiocyanate, (1.74) 5-(allylsulphanyl)-1-{[rel(2R,3S)-3-(2-chlorophenyl)-2-(2,4-difluorophenyl)oxiran-2-yl]methyl}-1H-1,2,4-triazole, (1.75) 5-(allylsulphanyl)-1-{[rel(2R,3R)-3-(2-chlorophenyl)-2-(2,4-difluorophenyl)oxiran-2-yl]methyl}-1H-1,2,4-triazole, (1.76) 2-[(2S,4S,5S)-1-(2,4-dichlorophenyl)-5-hydroxy-2,6,6-trimethylheptan-4-yl]-2,4-dihydro-3H-1,2,4-triazole-3-thione, (1.77) 2-[(2R,4S,5 S)-1-(2,4-dichlorophenyl)-5-hydroxy-2,6,6-trimethylheptan-4-yl]-2,4-dihydro-3H-1,2,4-triazole-3-thione, (1.78) 2-[(2R,4R,5R)-1-(2,4-dichlorophenyl)-5-hydroxy-2,6,6-trimethylheptan-4-yl]-2,4-dihydro-3H-1,2,4-triazole-3-thione, (1.79) 2-[(2S,4R,5R)-1-(2,4-dichlorophenyl)-5-hydroxy-2,6,6-trimethylheptan-4-yl]-2,4-dihydro-3H-1,2,4-triazole-3-thione, (1.80) 2-[(2S,4S,5R)-1-(2,4-dichlorophenyl)-5-hydroxy-2,6,6-trimethylheptan-4-yl]-2,4-dihydro-3H-1,2,4-triazole-3-thione, (1.81) 2-[(2R,4S,5R)-1-(2,4-dichlorophenyl)-5-hydroxy-2,6,6-trimethylheptan-4-yl]-2,4-dihydro-3H-1,2,4-triazole-3-thione, (1.82) 2-[(2R,4R,5 S)-1-(2,4-dichlorophenyl)-5-hydroxy-2,6,6-trimethylheptan-4-yl]-2,4-dihydro-3H-1,2,4-triazole-3-thione, (1.83) 2-[(2S,4R,5 S)-1-(2,4-dichlorophenyl)-5-hydroxy-2,6,6-trimethylheptan-4-yl]-2,4-dihydro-3H-1,2,4-triazole-3-thione, (1.84) 2-[4-(4-chlorophenoxy)-2-(trifluoromethyl)phenyl]-1-(1H-1,2,4-triazol-1-yl)propan-2-ol, (1.85) 2-[4-(4-chlorophenoxy)-2-(trifluoromethyl)phenyl]-1-(1H-1,2,4-triazol-1-yl)butan-2-ol, (1.86) 2-[4-(4-chlorophenoxy)-2-(trifluoromethyl)phenyl]-1-(1H-1,2,4-triazol-1-yl)pentan-2-ol, (1.87) 2-[2-chloro-4-(4-chlorophenoxy)phenyl]-1-(1H-1,2,4-triazol-1-yl)butan-2-ol, (1.88) 2-[2-chloro-4-(2,4-dichlorophenoxy)phenyl]-1-(1H-1,2,4-triazol-1-yl)propan-2-ol, (1.89) (2R)-2-(1-chlorocyclopropyl)-4-[(1R)-2,2-dichlorocyclopropyl]-1-(1H-1,2,4-triazol-1-yl)butan-2-ol, (1.90) (2R)-2-(1-chlorocyclopropyl)-4-[(1S)-2,2-dichlorocyclopropyl]-1-(1H-1,2,4-triazol-1-yl)butan-2-ol, (1.91) (2S)-2-(1-chlorocyclopropyl)-4-[(1 S)-2,2-dichlorocyclopropyl]-1-(1H-1,2,4-triazol-1-yl)butan-2-ol, (1.92) (2S)-2-(1-chlorocyclopropyl)-4-[(1R)-2,2-dichlorocyclopropyl]-1-(1H-1,2,4-triazol-1-yl)butan-2-ol, (1.93) (1S,2R,5R)-5-(4-chlorobenzyl)-2-(chloromethyl)-2-methyl-1-(1H-1,2,4-triazol-1-ylmethyl)cyclopentanol, (1.94) (1R,2S,5S)-5-(4-chlorobenzyl)-2-(chloromethyl)-2-methyl-1-(1H-1,2,4-triazol-1-ylmethyl)cyclopentanol, (1.95) 5-(4- chlorobenzyl)-2-(chloromethyl)-2-methyl-1-(1H-1,2,4-triazol-1-ylmethyl)cyclopentanol.

2) Inhibitors of the respiratory chain at complex I or II, for example (2.01) bixafen, (2.02) boscalid, (2.03) carboxin, (2.04) diflumetorim, (2.05) fenfuram, (2.06) fluopyram, (2.07) flutolanil, (2.08) fluxapyroxad, (2.09) furametpyr, (2.10) furmecyclox, (2.11) isopyrazam (mixture of syn-epimeric racemate 1RS,4SR,9RS and anti-epimeric racemate 1RS,4SR,9SR), (2.12) isopyrazam (anti-epimeric racemate 1RS,4SR,9SR), (2.13) isopyrazam (anti-epimeric enantiomer 1R,4S,9S), (2.14) isopyrazam (anti-epimeric enantiomer 1S,4R,9R), (2.15) isopyrazam (syn-epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.18) mepronil, (2.19) oxycarboxin, (2.20) penflufen, (2.21) penthiopyrad, (2.22) sedaxan, (2.23) thifluzamid, (2.24) 1-methyl-N-[2-(1,1,2,2-tetrafluorethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide, (2.28) 5,8-difluoro-N-[2-(2-fluoro-4-{[4-(trifluoromethyl)pyridin-2-yl]oxy}phenyl)ethyl]-quinazoline-4-amine, (2.29) benzovindiflupyr, (2.30) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, (2.31) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.32) 3-(difluoromethyl)-1-methyl-N-(1,1,3-trimethyl-2,3-dihydro-1H-inden-4-yl)-1H-pyrazole-4-carboxamide, (2.33) 1,3,5-trimethyl-N-(1,1,3-trimethyl-2,3-dihydro-1H-inden-4-yl)-1H-pyrazole-4-carboxamide, (2.34) 1-methyl-3-(trifluoromethyl)-N-(1,1,3-trimethyl-2,3-dihydro-1H-inden-4-yl)-1H-pyrazole-4-carboxamide, (2.35) 1-methyl-3-(trifluoromethyl)-N-[(3R)-1,1,3-trimethyl-2,3-dihydro-1H-inden-4-yl]-1H-pyrazole-4-carboxamide, (2.36) 1-methyl-3-(trifluoromethyl)-N-[(3S)-1,1,3-trimethyl-2,3-dihydro-1H-inden-4-yl]-1H-pyrazole-4-carboxamide, (2.37) 3-(difluoromethyl)-1-methyl-N-[(3S)-1,1,3-trimethyl-2,3-dihydro-1H-inden-4-yl]-1H-pyrazole-4-carboxamide, (2.38) 3-(difluoromethyl)-1-methyl-N-[(3R)-1,1,3-trimethyl-2,3-dihydro-1H-inden-4-yl]-1H-pyrazole-4-carboxamide, (2.39) 1,3,5-trimethyl-N-[(3R)-1,1,3-trimethyl-2,3-dihydro-1H-inden-4-yl]-1H-pyrazole-4-carboxamide, (2.40) 1,3,5-trimethyl-N-[(3 S)-1,1,3-trimethyl-2,3-dihydro-1H-inden-4-yl]-1H-pyrazole-4-carboxamide, (2.41) benodanil, (2.42) 2-chloro-N-(1,1,3-trimethyl-2,3-dihydro-1H-inden-4-yl)pyridine-3-carboxamide, (2.43) isofetamid, (2.44) 1-methyl-3-(trifluoromethyl)-N-[2'-(trifluoromethyl)biphenyl-2-yl]-1H-pyrazole-4-carboxamide, (2.45) N-(4'-chlorobiphenyl-2-yl)-3-(difluoromethyl)-1-methyl-1H-pyrazole-4-carboxamide, (2.46) N-(2',4'-dichlorobiphenyl-2-yl)-3-(difluoromethyl)-1-methyl-1H-pyrazole-4-carboxamide, (2.47) 3-(difluoromethyl)-1-methyl-N-[4'-(trifluoromethyl)biphenyl-2-yl]-1H-pyrazole-4-carboxamide, (2.48) N-(2',5'-difluorobiphenyl-2-yl)-1-methyl-3-(trifluoromethyl)-1H-pyrazole-4-carboxamide, (2.49) 3-(difluoromethyl)-1-methyl-N-[4'-(prop-1-yn-1-yl)biphenyl-2-yl]-1H-pyrazole-4-carboxamide, (2.50) 5-fluoro-1,3-dimethyl-N-[4'-(prop-1-yn-1-yl)biphenyl-2-yl]-1H-pyrazole-4-carboxamide, (2.51) 2-chloro-N-[4'-(prop-1-yn-1-yl)biphenyl-2-yl]nicotinamide, (2.52) 3-(difluoromethyl)-N-[4'-(3,3-dimethylbut-1-yn-1-yl)biphenyl-2-yl]-1-methyl-1H-pyrazole-4-carboxamide, (2.53) N-[4'-(3,3-dimethylbut-1-yn-1-yl)biphenyl-2-yl]-5-fluoro-1,3-dimethyl-1H-pyrazole-4-carboxamide, (2.54) 3-(difluoromethyl)-N-(4'-ethynylbiphenyl-2-yl)-1-methyl-1H-pyrazole-4-carboxamide, (2.55) N-(4'-ethynylbiphenyl-2-yl)-5-fluoro-1,3-dimethyl-1H-pyrazole-4-carboxamide, (2.56) 2-chloro-N-(4'-ethynylbiphenyl-2-yl)nicotinamide, (2.57) 2-chloro-N-[4'-(3,3-dimethylbut-1-yn-1-yl)biphenyl-2-yl]nicotinamide, (2.58) 4-(difluoromethyl)-2-methyl-N-[4'-(trifluoromethyl)biphenyl-2-yl]-1,3-thiazole-5-carboxamide, (2.59) 5-fluoro-N-[4'-(3-hydroxy-3-methylbut-1-yn-1-yl)biphenyl-2-yl]-1,3-dimethyl-1H-pyrazole-4-carboxamide, (2.60) 2-chloro-N-[4'-(3-hydroxy-3-methylbut-1-yn-1-yl)biphenyl-2-yl]nicotinamide, (2.61) 3-(difluoromethyl)-N-[4'-(3-methoxy-3-methylbut-1-yn-1-yl)biphenyl-2-yl]-1-methyl-1H-pyrazole-4-carboxamide, (2.62) 5-fluoro-N-[4'-(3-methoxy-3-methylbut-1-yn-1-yl)biphenyl-2-yl]-1,3-dimethyl-1H-pyrazole-4-carboxamide, (2.63) 2-chloro-N-[4'-(3-methoxy-3-methylbut-1-yn-1-yl)biphenyl-2-yl]nicotinamide, (2.64) 1,3-dimethyl-N-(1,1,3-trimethyl-2,3-dihydro-1H-inden-4-yl)-1H-pyrazole-4-carboxamide, (2.65) 1,3-dimethyl-N-[(3R)-1,1,3-trimethyl-2,3-dihydro-1H-inden-4-yl]-1H-pyrazole-4-carboxamide, (2.66) 1,3-dimethyl-N-[(3S)-1,1,3-trimethyl-2,3-dihydro-1H-inden-4-yl]-1H-pyrazole-4-carboxamide, (2.67) 3-(difluoromethyl)-N-methoxy-1-methyl-N-[1-(2,4,6-trichlorophenyl)propan-2-yl]-1H-pyrazole-4-carboxamide, (2.68) 3-(difluoromethyl)-N-(7-fluoro-1,1,3-trimethyl-2,3-dihydro-1H-inden-4-yl)-1-methyl-1H-pyrazole-4-carboxamide, (2.69) 3-(difluoromethyl)-N-[(3R)-7-fluoro-1,1,3-trimethyl-2,3-dihydro-1H-inden-4-yl]-1-methyl-1H-pyrazole-4-carboxamide, (2.70) 3-(difluoromethyl)-N-[(3S)-7-fluoro-1,1,3-trimethyl-2,3-dihydro-1H-inden-4-yl]-1-methyl-1H-pyrazole-4-carboxamide.

3) Inhibitors of the respiratory chain at complex III, for example (3.01) ametoctradin, (3.02) amisulbrom, (3.03) azoxystrobin, (3.04) cyazofamid, (3.05) coumethoxystrobin, (3.06) coumoxystrobin, (3.07) dimoxystrobin, (3.08) enoxastrobin, (3.09) famoxadone, (3.10) fenamidone, (3.11) flufenoxystrobin, (3.12) fluoxastrobin, (3.13) kresoxim-methyl, (3.14) metominostrobin, (3.15) orysastrobin, (3.16) picoxystrobin, (3.17) pyraclostrobin, (3.18) pyrametostrobin, (3.19) pyraoxystrobin, (3.20) pyribencarb, (3.21) triclopyricarb, (3.22) trifloxystrobin, (3.23) (2E)-2-(2-{[6-(3-chloro-2-methylphenoxy)-5-fluoropyrimidin-4-yl]oxy}phenyl)-2-(methoxyimino)-N-methylacetamide, (3.24) (2E)-2-(methoxyimino)-N-methyl-2-(2-{[({(1E)-1-[3-(trifluoromethyl)phenyl]ethylidene}amino)oxy]methyl}phenyl)acetamide, (3.25) (2E)-2-(methoxyimino)-N-methyl-2-{2-[(E)-({1-[3-(trifluoromethyl)phenyl]ethoxy}imino)methyl]-phenyl}acetamide, (3.26) (2E)-2-{2-[({[(1E)-1-(3-{[(E)-1-fluoro-2-phenylvinyl]oxy}phenyl)-ethylidene]amino}oxy)methyl]phenyl}-2-(methoxyimino)-N-methylacetamide, (3.27) fenaminostrobin, (3.28) 5-methoxy-2-methyl-4-(2-{[({(1E)-1-[3-(trifluoromethyl)phenyl]-ethylidene}amino)oxy]methyl}phenyl)-2,4-dihydro-3H-1,2,4-triazol-3-one, (3.29) methyl (2E)-2-{2-[({cyclopropyl[(4-methoxyphenyl)imino]methyl}sulphanyl)methyl]phenyl}-3-methoxyacrylate, (3.30) N-(3-ethyl-3,5,5-trimethylcyclohexyl)-3-formamido-2-hydroxybenzamide, (3.31) 2-{2-[(2,5-dimethylphenoxy)methyl]phenyl}-2-methoxy-N-methylacetamide, (3.32) 2-{2-[(2,5-dimethyl-phenoxy)methyl]phenyl}-2-methoxy-N-methylacetamide, (3.33) (2E, 3Z)-5-{[1-(4-chlorophenyl)-1H-pyrazol-3-yl]oxy}-2-(methoxyimino)-N,3-dimethylpent-3-enamide.

4) Inhibitors of mitosis and cell division, for example (4.01) benomyl, (4.02) carbendazim, (4.03) chlorfenazole, (4.04) diethofencarb, (4.05) ethaboxam, (4.06) fluopicolide, (4.07) fuberidazole, (4.08) pencycuron, (4.09) thiabendazole, (4.10) thiophanate-methyl, (4.11) thiophanate, (4.12) zoxamide, (4.13) 5-chloro-7-(4-methylpiperidin-1-yl)-6-(2,4,6-trifluorophenyl)[1,2,4]triazolo[1,5-a]pyrimidine, (4.14) 3-chloro-5-(6-chloropyridin-3-yl)-6-methyl-4-(2,4,6-trifluorophenyl)pyridazine.

5) Compounds capable of having multisite action, for example (5.01) Bordeaux mixture, (5.02) captafol, (5.03) captan, (5.04) chlorothalonil, (5.05) copper hydroxide, (5.06) copper naphthenate, (5.07) copper oxide, (5.08) copper oxychloride, (5.09) copper (2+) sulphate, (5.10) dichlofluanid, (5.11) dithianon, (5.12) dodine, (5.13) dodine free base, (5.14) ferbam, (5.15) fluorofolpet, (5.16) folpet, (5.17) guazatine, (5.18) guazatine acetate, (5.19) iminoctadine, (5.20) iminoctadine albesilate, (5.21) iminoctadine triacetate, (5.22) mancopper, (5.23) mancozeb, (5.24) maneb, (5.25) metiram, (5.26) metiram zinc, (5.27) oxine-copper, (5.28) propamidine, (5.29) propineb, (5.30) sulphur and sulphur preparations including calcium polysulphide, (5.31) thiram, (5.32) tolylfluanid, (5.33) zineb, (5.34) ziram, (5.35) anilazine.

6) Compounds capable of inducing host defence, for example (6.01) acibenzolar-S-methyl, (6.02) isotianil, (6.03) probenazole, (6.04) tiadinil, (6.05) laminarin.

7) Inhibitors of the amino acid and/or protein biosynthesis, for example (7.01) andoprim, (7.02) blasticidin-S, (7.03) cyprodinil, (7.04) kasugamycin, (7.05) kasugamycin hydrochloride hydrate, (7.06) mepanipyrim, (7.07) pyrimethanil, (7.08) 3-(5-fluoro-3,3,4,4-tetramethyl-3,4-dihydroisoquinolin-1-yl)quinoline, (7.09) oxytetracycline, (7.10) streptomycin.

8) Inhibitors of ATP production, for example (8.01) fentin acetate, (8.02) fentin chloride, (8.03) fentin hydroxide, (8.04) silthiofam.

9) Inhibitors of cell wall synthesis, for example (9.01) benthiavalicarb, (9.02) dimethomorph, (9.03) flumorph, (9.04) iprovalicarb, (9.05) mandipropamid, (9.06) polyoxins, (9.07) polyoxorim, (9.08) validamycin A, (9.09) valifenalate, (9.10) polyoxin B, (9.11) (2E)-3-(4-tert-butylphenyl)-3-(2-chloropyridin-4-yl)-1-(morpholin-4-yl)prop-2-en-1-one, (9.12) (2Z)-3-(4-tert-butylphenyl)-3-(2-chloropyridin-4-yl)-1-(morpholin-4-yl)prop-2-en-1-one.

10) Inhibitors of lipid and membrane synthesis, for example (10.01) biphenyl, (10.02) chloroneb, (10.03) dicloran, (10.04) edifenphos, (10.05) etridiazole, (10.06) iodocarb, (10.07) iprobenfos, (10.08) isoprothiolane, (10.09) propamocarb, (10.10) propamocarb hydrochloride, (10.11) prothiocarb, (10.12) pyrazophos, (10.13) quintozene, (10.14) tecnazene, (10.15) tolclofos-methyl.

11) Inhibitors of melanin biosynthesis, for example (11.01) carpropamid, (11.02) diclocymet, (11.03) fenoxanil, (11.04) phthalide, (11.05) pyroquilon, (11.06) tricyclazole, (11.07) 2,2,2-trifluoroethyl {3-methyl-1-[(4-methylbenzoyl)amino]butan-2-yl}carbamate.

12) Inhibitors of nucleic acid synthesis, for example (12.01) benalaxyl, (12.02) benalaxyl-M (kiralaxyl), (12.03) bupirimate, (12.04) clozylacon, (12.05) dimethirimol, (12.06) ethirimol, (12.07) furalaxyl, (12.08) hymexazole, (12.09) metalaxyl, (12.10) metalaxyl-M (mefenoxam), (12.11) ofurace, (12.12) oxadixyl, (12.13) oxolinic acid, (12.14) octhilinone.

13) Inhibitors of signal transduction, for example (13.01) chlozolinate, (13.02) fenpiclonil, (13.03) fludioxonil, (13.04) iprodione, (13.05) procymidone, (13.06) quinoxyfen, (13.07) vinclozolin, (13.08) proquinazid.

14) Compounds capable of acting as uncouplers, for example (14.01) binapacryl, (14.02) dinocap, (14.03) ferimzone, (14.04) fluazinam, (14.05) meptyldinocap.

15) Further compounds, for example (15.001) benthiazole, (15.002) bethoxazin, (15.003) capsimycin, (15.004) carvone, (15.005) chinomethionat, (15.006) pyriofenone (chlazafenone), (15.007) cufraneb, (15.008) cyflufenamid, (15.009) cymoxanil, (15.010) cyprosulfamide, (15.011) dazomet, (15.012) debacarb, (15.013) dichlorophen, (15.014) diclomezine, (15.015) difenzoquat, (15.016) difenzoquat metilsulphate, (15.017) diphenylamine, (15.018) ecomate, (15.019) fenpyrazamine, (15.020) flumetover, (15.021) fluoroimide, (15.022) flusulfamide, (15.023) flutianil, (15.024) fosetyl-aluminium, (15.025) fosetyl-calcium, (15.026) fosetyl-sodium, (15.027) hexachlorobenzene, (15.028) irumamycin, (15.029) methasulfocarb, (15.030) methyl isothiocyanate, (15.031) metrafenone, (15.032) mildiomycin, (15.033) natamycin, (15.034) nickel dimethyldithiocarbamate, (15.035) nitrothal-isopropyl, (15.036) oxamocarb, (15.037) oxyfenthiin, (15.038) pentachlorophenol and salts, (15.039) phenothrin, (15.040) phosphorous acid and it salts, (15.041) propamocarb-fosetylate, (15.042) propanosin-sodium, (15.043) pyrimorph, (15.044) pyrrolnitrin, (15.045) tebufloquin, (15.046) tecloftalam, (15.047) tolnifanide, (15.048) triazoxide, (15.049) trichlamide, (15.050) zarilamid, (15.051) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (15.052) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.053) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.054) oxathiapiproline, (15.055) 1-(4-methoxyphenoxy)-3,3-dimethylbutan-2-yl 1H-imidazole-1-carboxylate, (15.056) 2,3,5,6-tetrachloro-4-(methylsulphonyl)pyridine, (15.057) 2,3-dibutyl-6-chlorothieno[2,3-d]pyrimidin-4(3H)-one, (15.058) 2,6-dimethyl-1H,5H-[1,4]dithiino[2,3-c:5,6-c']dipyrrole-1,3,5,7(2H,6H)-tetrone, (15.059) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, (15.060) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, (15.061) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, (15.062) 2-butoxy-6-iodo-3-propyl-4H-chromen-4-one, (15.063) 2-chloro-5-[2-chloro-1-(2,6-difluoro-4-methoxyphenyl)-4-methyl-1H-imidazol-5-yl]pyridine, (15.064) 2-phenylphenol and salts, (15.065) 3-(4,4,5-trifluoro-3,3-dimethyl-3,4-dihydroisoquinolin-1-yl)quinoline, (15.066) 3,4,5-trichloropyridine-2,6-dicarbonitrile, (15.067) 3-chloro-5-(4-chlorophenyl)-4-(2,6-difluorophenyl)-6-methylpyridazine, (15.068) 4-(4-chlorophenyl)-5-(2,6-difluorophenyl)-3,6-dimethylpyridazine, (15.069) 5-amino-1,3,4-thiadiazole-2-thiol, (15.070) 5-chloro-N'-phenyl-N'-(prop-2-yn-1-yl)thiophene-2-sulphonohydrazide, (15.071) 5-fluoro-2-[(4-fluorobenzyl)oxy]pyrimidine-4-amine, (15.072) 5-fluoro-2-[(4-methylbenzyl)oxy]pyrimidine-4-amine, (15.073) 5-methyl-6-octyl[1,2,4]triazolo[1,5-a]pyrimidine-7-amine, (15.074) ethyl (2Z)-3-amino-2-cyano-3-phenylacrylate, (15.075) N'-(4-{[3-(4-chlorobenzyl)-1,2,4-thiadiazol-5-yl]oxy}-2,5-dimethylphenyl)-N-ethyl-N-methylimidoformamide, (15.076)N-(4-chlorobenzyl)-3-[3-methoxy-4-(prop-2- yn-1-yloxy)phenyl]propanamide, (15.077)N-[(4-chlorophenyl)(cyano)methyl]-3-[3-methoxy-4-(prop-2-yn-1-yloxy)phenyl]propanamide, (15.078)N-[(5-bromo-3-chloropyridin-2-yl)methyl]-2,4-dichloronicotinamide, (15.079)N-[1-(5-bromo-3-chloropyridin-2-yl)ethyl]-2,4-dichloronicotinamide, (15.080)N-[1-(5-bromo-3-chloropyridin-2-yl)ethyl]-2-fluoro-4-iodonicotinamide, (15.081)N-{(E)-[(cyclopropylmethoxy)imino][6-(difluoromethoxy)-2,3-difluorophenyl]methyl}-2-phenylacetamide, (15.082)N-{(Z)-[(cyclopropylmethoxy)imino][6-(difluoromethoxy)-2,3-difluorophenyl]methyl}-2-phenylacetamide, (15.083) N'-{4-[(3-tert-butyl-4-cyano-1,2-thiazol-5-yl)oxy]-2-chloro-5-methylphenyl}-N-ethyl-N-methylimidoformamide, (15.084)N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, (15.085)N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, (15.086)N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, (15.087) pentyl {6-[({[(1-methyl-1H-tetrazol-5-yl)(phenyl)methylene]amino}oxy)methyl]pyridin-2-yl}carbamate, (15.088) phenazine-1-carboxylic acid, (15.089) quinolin-8-ol, (15.090) quinolin-8-ol sulphate (2:1), (15.091) tert-butyl {6-[({[(1-methyl-1H-tetrazol-5-yl)(phenyl)methylene]amino}oxy)methyl]pyridin-2-yl}carbamate, (15.092) (5-bromo-2-methoxy-4-methylpyridin-3-yl)(2,3,4-trimethoxy-6-methylphenyl)methanone, (15.093)N-[2-(4-{[3-(4-chlorophenyl)prop-2-yn-1-yl]oxy}-3-methoxyphenyl)ethyl]-N2-(methylsulphonyl)valinamide, (15.094) 4-oxo-4-[(2-phenylethyl)amino]butanoic acid, (15.095) but-3-yn-1-yl {6-[({[(Z)-(1-methyl-1H-tetrazol-5-yl)(phenyl)methylene]amino}oxy)methyl]pyridin-2-yl}carbamate, (15.096) 4-amino-5-fluoropyrimidin-2-ol (tautomeric form: 4-amino-5-fluoropyrimidin-2(1H)-one), (15.097) propyl 3,4,5-trihydroxybenzoate, (15.098) [3-(4-chloro-2-fluorophenyl)-5-(2,4-difluorophenyl)-1,2-oxazol-4-yl](pyridin-3-yl)methanol, (15.099) (S)-[3-(4-chloro-2-fluorophenyl)-5-(2,4-difluorophenyl)-1,2-oxazol-4-yl](pyridin-3-yl)methanol, (15.100) (R)-[3-(4-chloro-2-fluorophenyl)-5-(2,4-difluorophenyl)-1,2-oxazol-4-yl](pyridin-3-yl)methanol, (15.101) 2-fluoro-6-(trifluoromethyl)-N-(1,1,3-trimethyl-2,3-dihydro-1H-inden-4-yl)benzamide, (15.102) 2-(6-benzylpyridin-2-yl)quinazoline, (15.103) 2-[6-(3-fluoro-4-methoxyphenyl)-5-methylpyridin-2-yl]quinazoline, (15.104) 3-(4,4-difluoro-3,3-dimethyl-3,4-dihydroisoquinolin-1-yl)quinoline, (15.105) abscisic acid, (15.106) N'-[5-bromo-6-(2,3-dihydro-1H-inden-2-yloxy)-2-methylpyridin-3-yl]-N-ethyl-N-methylimidoformamide, (15.107) N'-{5-bromo-6-[1-(3,5-difluorophenyl)ethoxy]-2-methylpyridin-3-yl}-N-ethyl-N-methylimidoformamide, (15.108) N'-{5-bromo-6-[(1R)-1-(3,5-difluorophenyl)ethoxy]-2-methylpyridin-3-yl}-N-ethyl-N-methylimidoformamide, (15.109) N'-{5-bromo-6-[(1 S)-1-(3,5-difluorophenyl)ethoxy]-2-methylpyridin-3-yl}-N-ethyl-N-methylimidoformamide, (15.110) N'-{5-bromo-6-[(cis-4-isopropylcyclohexyl)oxy]-2-methylpyridin-3-yl}-N-ethyl-N-methylimidoformamide, (15.111) N'-{5-bromo-6-[(trans-4-isopropylcyclohexyl)oxy]-2-methylpyridin-3-yl}-N-ethyl-N-methylimidoformamide, (15.112)N-cyclopropyl-3-(difluoromethyl)-5-fluoro-N-(2-isopropylbenzyl)-1-methyl-1H-pyrazole-4-carboxamide, (15.113)N-cyclopropyl-N-(2-cyclopropylbenzyl)-3-(difluoromethyl)-5-fluoro-1-methyl-1H-pyrazole-4-carboxamide, (15.114) N-(2-tert-butylbenzyl)-N-cyclopropyl-3-(difluoromethyl)-5-fluoro-1-methyl-1H-pyrazole-4-carboxamide, (15.115)N-(5-chloro-2-ethylbenzyl)-N-cyclopropyl-3-(difluoromethyl)-5-fluoro-1-methyl-1H-pyrazole-4-carboxamide, (15.116)N-(5-chloro-2-isopropylbenzyl)-N-cyclopropyl-3-(difluoromethyl)-5-fluoro-1-methyl-1H-pyrazole-4-carboxamide, (15.117)N-cyclopropyl-3-(difluoromethyl)-N-(2-ethyl-5-fluorobenzyl)-5-fluoro-1-methyl-1H-pyrazole-4-carboxamide, (15.118)N-cyclopropyl-3-(difluoromethyl)-5-fluoro-N-(5-fluoro-2-isopropylbenzyl)-1-methyl-1H-pyrazole-4-carboxamide, (15.119)N-cyclopropyl-N-(2-cyclopropyl-5-fluorobenzyl)-3-(difluoromethyl)-5-fluoro-1-methyl-1H-pyrazole-4-carboxamide, (15.120)N-(2-cyclopentyl-5-fluorobenzyl)-N-cyclopropyl-3-(difluoromethyl)-5-fluoro-1-methyl-1H-pyrazole-4-carboxamide, (15.121)N-cyclopropyl-3-(difluoromethyl)-5-fluoro-N-(2-fluoro-6-isopropylbenzyl)-1-methyl-1H-pyrazole-4-carboxamide, (15.122)N-cyclopropyl-3-(difluoromethyl)-N-(2-ethyl-5-methylbenzyl)-5-fluoro-1-methyl-1H-pyrazole-4-carboxamide, (15.123)N-cyclopropyl-3-(difluoromethyl)-5-fluoro-N-(2-isopropyl-5-methylbenzyl)-1-methyl-1H-pyrazole-4-carboxamide, (15.124)N-cyclopropyl-N-(2-cyclopropyl-5-methylbenzyl)-3-(difluoromethyl)-5-fluoro-1-methyl-1H-pyrazole-4-carboxamide, (15.125)N-(2-tert-butyl-5-methylbenzyl)-N-cyclopropyl-3-(difluoromethyl)-5-fluoro-1-methyl-1H-pyrazole-4-carboxamide, (15.126)N-[5-chloro-2-(trifluoromethyl)benzyl]-N-cyclopropyl-3-(difluoromethyl)-5-fluoro-1-methyl-1H-pyrazole-4-carboxamide, (15.127)N-cyclopropyl-3-(difluoromethyl)-5-fluoro-1-methyl-N-[5-methyl-2-(trifluoromethyl)benzyl]-H-pyrazole-4-carboxamide, (15.128)N-[2-chloro-6-(trifluoromethyl)benzyl]-N-cyclopropyl-3-(difluoromethyl)-5-fluoro-1-methyl-1H-pyrazole-4-carboxamide, (15.129)N-[3-chloro-2-fluoro-6-(trifluoromethyl)-benzyl]-N-cyclopropyl-3-(difluoromethyl)-5-fluoro-1-methyl-1H-pyrazole-4-carboxamide, (15.130) N-cyclopropyl-3-(difluoromethyl)-N-(2-ethyl-4,5-dimethylbenzyl)-5-fluoro-1-methyl-1H-pyrazole-4-carboxamide, (15.131)N-cyclopropyl-3-(difluoromethyl)-5-fluoro-N-(2-isopropylbenzyl)-1-methyl-1H-pyrazole-4-carbothioamide, (15.132) N'-(2,5-dimethyl-4-phenoxyphenyl)-N-ethyl-N-methylimidoformamide, (15.133) N'-{4-[(4,5-dichloro-1,3-thiazol-2-yl)oxy]-2,5-dimethylphenyl}-N-ethyl-N-methylimidoformamide, (15.134)N-(4-chloro-2,6-difluorophenyl)-4-(2-chloro-4-fluorophenyl)-1,3-dimethyl-1H-pyrazole-5-amine, (15.135) 9-fluoro-2,2-dimethyl-5-(quinolin-3-yl)-2,3-dihydro-1,4-benzoxazepine, (15.136) 2-{2-fluoro-6-[(8-fluoro-2-methylquinolin-3-yl)oxy]phenyl}propan-2-ol, (15.137) 2-{2-[(7,8-difluoro-2-methylquinolin-3-yl)oxy]-6-fluorophenyl}propan-2-ol, (15.138) 4-(2-chloro-4-fluorophenyl)-N-(2-fluorophenyl)-1,3-dimethyl-1H-pyrazole-5-amine, (15.139) 4-(2-chloro-4-fluorophenyl)-N-(2,6-difluorophenyl)-1,3-dimethyl-1H-pyrazole-5-amine, (15.140) 4-(2-chloro-4-fluorophenyl)-N-(2-chloro-6-fluorophenyl)-1,3-dimethyl-1H-pyrazole-5-amine, (15.141) 4-(2-bromo-4-fluorophenyl)-N-(2-chloro-6-fluorophenyl)-1,3-dimethyl-1H-pyrazole-5-amine, (15.142)N-(2-bromo-6-fluorophenyl)-4-(2-chloro-4-fluorophenyl)-1,3-dimethyl-1H-pyrazole-5-amine, (15.143) 4-(2-bromo-4-fluorophenyl)-N-(2-bromophenyl)-1,3-dimethyl-1H-pyrazole-5-amine, (15.144) 4-(2-bromo-4-fluorophenyl)-N-(2-bromo-6-fluorophenyl)-1,3-dimethyl-1H-pyrazole-5-amine, (15.145) 4-(2-bromo-4-fluorophenyl)-N-(2-chlorophenyl)-1,3-dimethyl-1H-pyrazole-5-amine, (15.146) N-(2-bromophenyl)-4-(2-chloro-4-fluorophenyl)-1,3-dimethyl-1H-pyrazole-5-amine, (15.147) 4-(2-chloro-4- fluorophenyl)-N-(2-chlorophenyl)-1,3-dimethyl-1H-pyrazole-5-amine, (15.148) 4-(2-bromo-4-fluorophenyl)-N-(2,6-difluorophenyl)-1,3-dimethyl-1H-pyrazole-5-amine, (15.149) 4-(2-bromo-4-fluorophenyl)-N-(2-fluorophenyl)-1,3-dimethyl-1H-pyrazole-5-amine, (15.150) N'-(4-{3-[(difluoromethyl)sulphanyl]-phenoxy}-2,5-dimethylphenyl)-N-ethyl-N-methylimidoformamide, (15.151) N'-(2,5-dimethyl-4-{3-[(1,1,2,2-tetrafluoroethyl)sulphanyl]phenoxy}phenyl)-N-ethyl-N-methylimidoformamide, (15.152) N'-(2,5-dimethyl-4-{3-[(2,2,2-trifluoroethyl)sulphanyl]phenoxy}phenyl)-N-ethyl-N-methylimidoformamide, (15.153) N'-(2,5-dimethyl-4-{3-[(2,2,3,3-tetrafluoropropyl)sulphanyl]phenoxy}phenyl)-N-ethyl-N-methylimidoformamide, (15.154) N'-(2,5-dimethyl-4-{3-[(pentafluoroethyl)sulphanyl]-phenoxy}phenyl)-N-ethyl-N-methylimidoformamide, (15.155) N'-(4-{[3-(difluoromethoxy)phenyl]-sulphanyl}-2,5-dimethylphenyl)-N-ethyl-N-methylimidoformamide, (15.156) N'-(2,5-dimethyl-4-{[3-(1,1,2,2-tetrafluoroethoxy)phenyl]sulphanyl}phenyl)-N-ethyl-N-methylimidoformamide, (15.157) N'-(2,5-dimethyl-4-{[3-(2,2,2-trifluoroethoxy)phenyl]sulphanyl}phenyl)-N-ethyl-N-methylimidoformamide, (15.158) N'-(2,5-dimethyl-4-{[3-(2,2,3,3-tetrafluoropropoxy)phenyl]-sulphanyl}phenyl)-N-ethyl-N-methylimidoformamide, (15.159) N'-(2,5-dimethyl-4-{[3-(pentafluoro-ethoxy)phenyl]sulphanyl}phenyl)-N-ethyl-N-methylimidoformamide, (15.160) 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, (15.161) 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.162) 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, (15.163) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulphonate, (15.164) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulphonate, (15.165) 2-[3,5-bis(difluoromethyl)-1H-pyrazol-1-yl]-1-[4-(4-{(5S)-5-[2-(prop-2-yn-1-yloxy)phenyl]-4,5-dihydro-1,2-oxazol-3-yl}-1,3-thiazol-2-yl)-piperidin-1-yl]ethanone, (15.166) 2-[3,5-bis(difluoromethyl)-1H-pyrazol-1-yl]-1-[4-(4-{(5R)-5-[2-(prop-2-yn-1-yloxy)phenyl]-4,5-dihydro-1,2-oxazol-3-yl}-1,3-thiazol-2-yl)piperidin-1-yl]ethanone, (15.167) 2-[3,5-bis(difluoromethyl)-1H-pyrazol-1-yl]-1-[4-(4-{(5S)-5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.168) 2-[3,5-bis(difluoromethyl)-1H-pyrazol-1-yl]-1-[4-(4-{(5R)-5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.169) 2-[3,5-bis(difluoromethyl)-1H-pyrazol-1-yl]-1-[4-(4-{(5 S)-5-[2-chloro-6-(prop-2-yn-1-yloxy)phenyl]-4,5-dihydro-1,2-oxazol-3-yl}-1,3-thiazol-2-yl)piperidin-1-yl]ethanone, (15.170) 2-[3,5-bis(difluoromethyl)-1H-pyrazol-1-yl]-1-[4-(4-{(5R)-5-[2-chloro-6-(prop-2-yn-1-yloxy)phenyl]-4,5-dihydro-1,2-oxazol-3-yl}-1,3-thiazol-2-yl)piperidin-1-yl]ethanone, (15.171) 2-{(5 S)-3-[2-(1-{[3,5-bis-(difluoromethyl)-1H-pyrazol-1-yl]acetyl}piperidin-4-yl)-1,3-thiazol-4-yl]-4,5-dihydro-1,2-oxazol-5-yl}phenyl methanesulphonate, (15.172) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulphonate, (15.173) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulphonate, (15.174) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulphonate.

Biological Pesticides as Mixing Components

The compounds of the formula (I) can be combined with biological pesticides.

Biological pesticides include especially bacteria, fungi, yeasts, plant extracts and products formed by microorganisms, including proteins and secondary metabolites.

Biological pesticides include bacteria such as spore-forming bacteria, root-colonizing bacteria and bacteria which act as biological insecticides, fungicides or nematicides.

Examples of such bacteria which are used or can be used as biological pesticides are:

*Bacillus amyloliquefaciens*, strain FZB42 (DSM 231179), or *Bacillus cereus*, especially *B. cereus* strain CNCM I-1562 or *Bacillus firmus*, strain I-1582 (Accession number CNCM I-1582) or *Bacillus pumilus*, especially strain GB34 (Accession No. ATCC 700814) and strain QST2808 (Accession No. NRRL B-30087), or *Bacillus subtilis*, especially strain GB03 (Accession No. ATCC SD-1397), or *Bacillus subtilis* strain QST713 (Accession No. NRRL B-21661) or *Bacillus subtilis* strain OST 30002 (Accession No. NRRL B-50421) *Bacillus thuringiensis*, especially *B. thuringiensis* subspecies *israelensis* (serotype H-14), strain AM65-52 (Accession No. ATCC 1276), or *B. thuringiensis* subsp. *aizawai*, especially strain ABTS-1857 (SD-1372), or *B. thuringiensis* subsp. *kurstaki* strain HD-1, or *B. thuringiensis* subsp. *tenebrionis* strain NB 176 (SD-5428), *Pasteuria penetrans, Pasteuria* spp. (*Rotylenchulus reniformis* nematode)-PR3 (Accession Number ATCC SD-5834), *Streptomyces microflavus* strain AQ6121 (=QRD 31.013, NRRL B-50550), *Streptomyces galbus* strain AQ 6047 (Accession Number NRRL 30232).

Examples of fungi and yeasts which are used or can be used as biological pesticides are:

*Beauveria bassiana*, in particular strain ATCC 74040, *Coniothyrium minitans*, in particular strain CON/M/91-8 (Accession No. DSM-9660), *Lecanicillium* spp., in particular strain HRO LEC 12, *Lecanicillium lecanii*, (formerly known as *Verticillium lecanii*), in particular strain KV01, *Metarhizium anisopliae*, in particular strain F52 (DSM3884/ATCC 90448), *Metschnikowia fructicola*, in particular strain NRRL Y-30752, *Paecilomyces fumosoroseus* (new: *Isaria fumosorosea*), in particular strain IFPC 200613, or strain Apopka 97 (Accession No. ATCC 20874), *Paecilomyces lilacinus*, in particular *P. lilacinus* strain 251 (AGAL 89/030550), *Talaromyces flavus*, in particular strain V117b, *Trichoderma atroviride*, in particular strain SC1 (Accession Number CBS 122089), *Trichoderma harzianum*, in particular *T. harzianum rifai* T39 (Accession Number CNCM 1-952).

Examples of viruses which are used or can be used as biological pesticides are:

*Adoxophyes orana* (summer fruit *tortrix*) granulosis virus (GV), *Cydia pomonella* (codling moth) granulosis virus (GV), *Helicoverpa armigera* (cotton bollworm) nuclear polyhedrosis virus (NPV), *Spodoptera exigua* (beet armyworm) mNPV, *Spodoptera frugiperda* (fall armyworm) mNPV, *Spodoptera littoralis* (African cotton leafworm) NPV.

Also included are bacteria and fungi which are added as 'inoculant' to plants or plant parts or plant organs and which, by virtue of their particular properties, promote plant growth and plant health. Examples which may be mentioned are:

*Agrobacterium* spp., *Azorhizobium caulinodans, Azospirillum* spp., *Azotobacter* spp., *Bradyrhizobium* spp., *Burkholderia* spp., especially *Burkholderia cepacia* (formerly known as *Pseudomonas cepacia*), *Gigaspora* spp., or *Gigaspora monosporum, Glomus* spp., *Laccaria* spp., *Lactobacillus buchneri, Paraglomus* spp., *Pisolithus tinctorus, Pseudomonas* spp., *Rhizobium* spp., especially *Rhizobium trifolii, Rhizopogon* spp., *Scleroderma* spp., *Suillus* spp., *Streptomyces* spp.

Examples of plant extracts and products formed by microorganisms, including proteins and secondary metabolites, which are used or can be used as biological pesticides are:

*Allium sativum, Artemisia absinthium*, azadirachtin, Biokeeper WP, *Cassia nigricans, Celastrus angulatus, Chenopodium anthelminticum*, chitin, Armour-Zen, *Dryopteris filix-mas, Equisetum arvense*, Fortune Aza, Fungastop, Heads Up (*Chenopodium quinoa* saponin extract), Pyrethrum/Pyrethrins, *Quassia amara, Quercus*, Quillaja, Regalia, "Requiem™ Insecticide", rotenone, ryania/ryanodine, *Symphytum officinale, Tanacetum vulgare*, thymol, Triact 70, TriCon, *Tropaeulum majus, Urtica dioica, Veratrin, Viscum album*, Brassicaceae extract, especially oilseed rape powder or mustard powder.

Safeners as Mixing Components

The compounds of the formula (I) can be combined with safeners, for example benoxacor, cloquintocet (-mexyl), cyometrinil, cyprosulfamide, dichlormid, fenchlorazole (-ethyl), fenclorim, flurazole, fluxofenim, furilazole, isoxadifen (-ethyl), mefenpyr (-diethyl), naphthalic anhydride, oxabetrinil, 2-methoxy-N-({4-[(methylcarbamoyl)amino]phenyl}sulphonyl)benzamide (CAS 129531-12-0), 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4).

Plants and Plant Parts

All plants and plant parts can be treated in accordance with the invention. Plants are understood here to mean all plants and populations of plants, such as desirable and undesirable wild plants or crop plants (including naturally occurring crop plants), for example cereals (wheat, rice, triticale, barley, rye, oats), maize, soya bean, potato, sugar beet, sugar cane, tomatoes, peas and other vegetable species, cotton, tobacco, oilseed rape, and also fruit plants (with the fruits apples, pears, citrus fruits and grapes). Crop plants may be plants which can be obtained by conventional breeding and optimization methods or by biotechnological and genetic engineering methods or combinations of these methods, including the transgenic plants and including the plant cultivars which are protectable or non-protectable by plant breeders' rights. Plant parts shall be understood to mean all parts and organs of the plants above and below ground, such as shoot, leaf, flower and root, examples given being leaves, needles, stalks, stems, flowers, fruit bodies, fruits and seeds, and also roots, tubers and rhizomes. Plant parts also include harvested material and vegetative and generative propagation material, for example cuttings, tubers, rhizomes, slips and seeds.

Treatment according to the invention of the plants and plant parts with the compounds of the formula (I) is carried out directly or by allowing the compounds to act on their surroundings, environment or storage space by the customary treatment methods, for example by immersion, spraying, evaporation, fogging, scattering, painting on, injection and, in the case of propagation material, in particular in the case of seed, also by applying one or more coats.

As already mentioned above, it is possible to treat all plants and parts thereof in accordance with the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. Particular preference is given in accordance with the invention to treating plants of the respective commercially customary plant cultivars or those that are in use. Plant cultivars are understood to mean plants having new properties ("traits") and which have been grown by conventional breeding, by mutagenesis or by recombinant DNA techniques. They may be cultivars, varieties, biotypes or genotypes.

Transgenic Plants, Seed Treatment and Integration Events

The preferred transgenic plants or plant cultivars (those obtained by genetic engineering) which are to be treated in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher harvest yields, higher quality and/or higher nutritional value of the harvested products, better storage life and/or processability of the harvested products. Further and particularly emphasized examples of such properties are increased resistance of the plants against animal and microbial pests, such as insects, arachnids, nematodes, mites, slugs and snails owing, for example, to toxins formed in the plants, in particular those produced in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof), and also increased resistance of the plants against phytopathogenic fungi, bacteria and/or viruses caused, for example, by systemic acquired resistance (SAR), systemin, phytoalexins, elicitors and resistance genes and correspondingly expressed proteins and toxins, and also increased tolerance of the plants to certain herbicidally active compounds, for example imidazolinones, sulphonylureas, glyphosates or phosphinothricin (for example the "PAT" gene). The genes which impart the desired properties ("traits") in question may also be present in combinations with one another in the transgenic plants. Examples of transgenic plants include the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (with the fruits apples, pears, citrus fruits and grapes), particular emphasis being given to maize, soya beans, wheat, rice, potatoes, cotton, sugar cane, tobacco and oilseed rape. Properties ("traits") which are particularly emphasized are the increased resistance of the plants to insects, arachnids, nematodes and slugs and snails.

Crop Protection—Types of Treatment

The plants and plant parts are treated with the compounds of the formula (I) directly or by action on their surroundings, habitat or storage space using customary treatment methods, for example by dipping, spraying, atomizing, irrigating, evaporating, dusting, fogging, broadcasting, foaming, painting, spreading-on, injecting, watering (drenching), drip irrigating and, in the case of propagation material, in particular in the case of seed, additionally by dry seed treatment, liquid seed treatment, slurry treatment, by incrusting, by coating with one or more coats, etc. It is furthermore possible to apply the compounds of the formula (I) by the ultra-low volume method or to inject the application form or the compound of the formula (I) itself into the soil.

A preferred direct treatment of the plants is foliar application, i.e. compounds of the formula (I) are applied to the foliage, where treatment frequency and the application rate should be adjusted according to the level of infestation with the pest in question.

In the case of systemically active compounds, the compounds of the formula (I) also access the plants via the root system. The plants are then treated by the action of the compounds of the formula (I) on the habitat of the plant. This can be accomplished, for example, by drenching, or by mixing into the soil or the nutrient solution, meaning that the locus of the plant (e.g. soil or hydroponic systems) is impregnated with a liquid form of the compounds of the formula (I), or by soil application, meaning that the compounds of the formula (I) are introduced in solid form (e.g. in the form of granules) into the locus of the plants. In the case of paddy rice crops, this can also be accomplished by metering the compound of the formula (I) in a solid application form (for example as granules) into a flooded paddy field.

Seed Treatment

The control of animal pests by the treatment of the seed of plants has long been known and is the subject of constant improvements. However, the treatment of seed entails a series of problems which cannot always be solved in a satisfactory manner. Thus, it is desirable to develop methods for protecting the seed and the germinating plant which dispense with, or at least reduce considerably, the additional application of pesticides during storage, after sowing or after emergence of the plants. It is additionally desirable to optimize the amount of active compound used so as to provide optimum protection for the seed and the germinating plant from attack by animal pests, but without damage to the plant itself by the active compound used. In particular, methods for the treatment of seed should also take account of the intrinsic insecticidal or nematicidal properties of pest-resistant or -tolerant transgenic plants in order to achieve optimal protection of the seed and the germinating plant with a minimum expenditure of pesticides.

The present invention therefore in particular also relates to a method for the protection of seed and germinating plants from attack by pests, by treating the seed with one of the compounds of the formula (I). The method according to the invention for protecting seed and germinating plants against attack by pests further comprises a method in which the seed is treated simultaneously in one operation or sequentially with a compound of the formula (I) and a mixing component. It further also comprises a method where the seed is treated at different times with a compound of the formula (I) and a mixing component.

The invention likewise relates to the use of the compounds of the formula (I) for the treatment of seed for protecting the seed and the resulting plant from animal pests.

The invention further relates to seed which has been treated with a compound of the formula (I) for protection from animal pests. The invention also relates to seed which has been treated simultaneously with a compound of the formula (I) and a mixing component. The invention further relates to seed which has been treated at different times with a compound of the formula (I) and a mixing component. In the case of seed which has been treated at different times with a compound of the formula (I) and a mixing component, the individual substances may be present on the seed in different layers. In this case, the layers comprising a compound of the formula (I) and a mixing component may optionally be separated by an intermediate layer. The invention also relates to seed in which a compound of the formula (I) and a mixing component have been applied as part of a coating or as a further layer or further layers in addition to a coating.

The invention further relates to seed which, after the treatment with a compound of the formula (I), is subjected to a film-coating process to prevent dust abrasion on the seed.

One of the advantages encountered with a systemically acting compound of the formula (I) is the fact that, by treating the seed, not only the seed itself but also the plants resulting therefrom are, after emergence, protected against animal pests. In this way, the immediate treatment of the crop at the time of sowing or shortly thereafter can be dispensed with.

A further advantage is that the treatment of the seed with a compound of the formula (I) can enhance germination and emergence of the treated seed.

It is likewise considered to be advantageous that compounds of the formula (I) can especially also be used for transgenic seed.

Furthermore, compounds of the formula (I) can be employed in combination with compositions of signalling technology, leading to better colonization by symbionts such as, for example, *rhizobia*, mycorrhizae and/or endophytic bacteria or fungi, and/or to optimized nitrogen fixation.

The compounds of the formula (I) are suitable for protection of seed of any plant variety which is used in agriculture, in the greenhouse, in forests or in horticulture. More particularly, this includes seed of cereals (for example wheat, barley, rye, millet and oats), maize, cotton, soya beans, rice, potatoes, sunflowers, coffee, tobacco, canola, oilseed rape, beet (for example sugar beet and fodder beet), peanuts, vegetables (for example tomatoes, cucumbers, beans, cruciferous vegetables, onions and lettuce), fruit plants, lawns and ornamental plants. Of particular significance is the treatment of the seed of cereals (such as wheat, barley, rye and oats), maize, soya beans, cotton, canola, oilseed rape and rice.

As already mentioned above, the treatment of transgenic seed with a compound of the formula (I) is also of particular importance. This involves the seed of plants which generally contain at least one heterologous gene which controls the expression of a polypeptide having insecticidal and/or nematicidal properties in particular. The heterologous genes in transgenic seed may originate in this case from microorganisms such as *Bacillus, Rhizobium, Pseudomonas, Serratia, Trichoderma, Clavibacter, Glomus* or *Gliocladium*. The present invention is particularly suitable for the treatment of transgenic seed containing at least one heterologous gene originating from *Bacillus* sp. The heterologous gene is more preferably derived from *Bacillus thuringiensis*.

In the context of the present invention, the compound of the formula (I) is applied to the seed. The seed is preferably treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content which allows storage. Alternatively, it is also possible to use seed which, after drying, has been treated with, for example, water and then dried again, for example priming. In the case of rice seed, it is also possible to use seed which has been imbibed in water up to a certain stage (pigeon breast stage) for example, which leads to improved germination and more uniform emergence.

When treating the seed, care must generally be taken that the amount of the compound of the formula (I) applied to the seed and/or the amount of further additives is chosen in such a way that the germination of the seed is not adversely affected, or that the resulting plant is not damaged. This has to be ensured particularly in the case of active compounds which can exhibit phytotoxic effects at certain application rates.

In general, the compounds of the formula (I) are applied to the seed in the form of a suitable formulation. Suitable formulations and processes for seed treatment are known to the person skilled in the art.

The compounds of the formula (I) can be converted to the customary seed-dressing formulations, such as solutions, emulsions, suspensions, powders, foams, slurries or other coating compositions for seed, and also ULV formulations.

These formulations are prepared in a known manner, by mixing compounds of the formula (I) with customary additives such as, for example, customary extenders and also solvents or diluents, dyes, wetting agents, dispersants, emulsifiers, antifoams, preservatives, secondary thickeners, adhesives, gibberellins and also water.

Dyes which may be present in the seed-dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed-dressing formulations usable in accordance with the invention are all substances which promote wetting and which are customary for the formulation of active agrochemical compounds. Preference is given to using alkyl naphthalenesulphonates, such as diisopropyl or diisobutyl naphthalenesulphonates.

Suitable dispersants and/or emulsifiers which may be present in the seed-dressing formulations usable in accordance with the invention are all nonionic, anionic and cationic dispersants customary for the formulation of active agrochemical compounds. Preference is given to using nonionic or anionic dispersants or mixtures of nonionic or anionic dispersants. Suitable nonionic dispersants include in particular ethylene oxide/propylene oxide block polymers, alkylphenol polyglycol ethers and tristyrylphenol polyglycol ethers, and the phosphated or sulphated derivatives thereof. Suitable anionic dispersants are especially lignosulphonates, polyacrylic acid salts and arylsulphonate-formaldehyde condensates.

Antifoams which may be present in the seed-dressing formulations usable in accordance with the invention are all foam-inhibiting substances customary for the formulation of active agrochemical compounds. Silicone antifoams and magnesium stearate can be used with preference.

Preservatives which may be present in the seed-dressing formulations usable in accordance with the invention are all substances usable for such purposes in agrochemical compositions. Examples include dichlorophene and benzyl alcohol hemiformal.

Secondary thickeners which may be present in the seed-dressing formulations usable in accordance with the invention are all substances which can be used for such purposes in agrochemical compositions. Preferred examples include cellulose derivatives, acrylic acid derivatives, xanthan, modified clays and finely divided silica.

Useful stickers which may be present in the seed-dressing formulations usable in accordance with the invention are all customary binders usable in seed-dressing products. Preferred examples include polyvinylpyrrolidone, polyvinyl acetate, polyvinyl alcohol and tylose.

Gibberellins which may be present in the seed-dressing formulations usable in accordance with the invention are preferably the gibberellins A1, A3 (=gibberellic acid), A4 and A7; particular preference is given to using gibberellic acid. The gibberellins are known (cf. R. Wegler "Chemie der Pflanzenschutz-und Schadlingsbekampfungsmittel", vol. 2, Springer Verlag, 1970, pp. 401-412).

The seed-dressing formulations usable in accordance with the invention can be used to treat a wide variety of different kinds of seed, either directly or after prior dilution with water. For instance, the concentrates or the preparations obtainable therefrom by dilution with water can be used to dress the seed of cereals, such as wheat, barley, rye, oats, and triticale, and also the seed of maize, rice, oilseed rape, peas, beans, cotton, sunflowers, soya beans and beets, or else a wide variety of different vegetable seed. The seed-dressing formulations usable in accordance with the invention, or the dilute use forms thereof, can also be used to dress seed of transgenic plants.

For the treatment of seed with the seed-dressing formulations usable in accordance with the invention, or use forms prepared therefrom, all mixing units usable customarily for the seed dressing are useful. Specifically, the procedure in seed dressing is to place the seed into a mixer in batchwise or continuous operation, to add the particular desired amount of seed-dressing formulations, either as such or after prior dilution with water, and to mix until the formulation is distributed homogeneously on the seed. If appropriate, this is followed by a drying operation.

The application rate of the seed-dressing formulations usable in accordance with the invention can be varied within a relatively wide range. It is guided by the particular content of the compounds of the formula (I) in the formulations and by the seed. The application rates of the compound of the formula (I) are generally between 0.001 and 50 g per kilogram of seed, preferably between 0.01 and 15 g per kilogram of seed.

Animal Health

In the animal health field, i.e. the field of veterinary medicine, the compounds of the formula (I) are active against animal parasites, in particular ectoparasites or endoparasites. The term "endoparasites" includes especially helminths and protozoa, such as coccidia. Ectoparasites are typically and preferably arthropods, especially insects and acarids.

In the field of veterinary medicine, the compounds of the formula (I) having favourable homeotherm toxicity are suitable for controlling parasites which occur in animal breeding and animal husbandry in livestock, breeding animals, zoo animals, laboratory animals, experimental animals and domestic animals. They are active against all or specific stages of development of the parasites.

Agricultural livestock include, for example, mammals such as sheep, goats, horses, donkeys, camels, buffalo, rabbits, reindeer, fallow deer, and particularly cattle and pigs; poultry such as turkeys, ducks, geese, and particularly chickens; fish and crustaceans, for example in aquaculture, and also insects such as bees.

Domestic animals include, for example, mammals, such as hamsters, guinea pigs, rats, mice, chinchillas, ferrets, and particularly dogs, cats, caged birds, reptiles, amphibians and aquarium fish.

In a preferred embodiment, the compounds of the formula (I) are administered to mammals.

In another preferred embodiment, the compounds of the formula (I) are administered to birds, namely caged birds and particularly poultry.

Use of the compounds of the formula (I) for the control of animal parasites is intended to reduce or prevent illness, cases of death and reductions in performance (in the case of meat, milk, wool, hides, eggs, honey and the like), such that more economical and simpler animal husbandry is enabled and better animal well-being is achievable.

In relation to the field of animal health, the term "control" or "controlling" means that the compounds of the formula (I) are effective in reducing the incidence of the particular parasite in an animal infected with such parasites to an innocuous degree. More specifically, "controlling" in the present context means that the compound of the formula (I) can kill the respective parasite, inhibit its growth, or inhibit its proliferation.

Arthropods include:
from the order of the Anoplurida, for example *Haematopinus* spp., *Linognathus* spp., *Pediculus* spp., *Phtirus* spp., *Solenopotes* spp.; from the order of the Mallophagida and the suborders Amblycerina and Ischnocerina, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; from the order of the Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; from the order of the Siphonapterida, for example *Pulex* spp., *Ctenocephalides* spp., *Tunga* spp., *Xenopsylla* spp., *Ceratophyllus* spp.;
from the order of the Heteropterida, for example *Cimex* spp., *Triatoma* spp., *Rhodnius* spp., *Panstrongylus* spp.; and also nuisance and hygiene pests from the order of the Blattarida.

Arthropods further include:
from the subclass of the Acari (Acarina) and the order of the Metastigmata, for example from the family of Argasidae like *Argas* spp., *Ornithodorus* spp., *Otobius* spp., from the family of Ixodidae like *Ixodes* spp., *Amblyomma* spp., *Rhipicephalus* (*Boophilus*) spp., *Dermacentor* spp., *Haemophysalis* spp., *Hyalomma* spp., *Rhipicephalus* spp. (the original genus of multi-host ticks); from the order of Mesostigmata like *Dermanyssus* spp., *Omithonyssus* spp., *Pneumonyssus* spp., *Raillietia* spp., *Pneumonyssus* spp., *Sternostoma* spp., *Varroa* spp., *Acarapis* spp.; from the order of the Actinedida (Prostigmata), for example *Acarapis* spp., *Cheyletiella* spp., *Omithocheyletia* spp., *Myobia* spp., *Psorergates* spp., *Demodex* spp., *Trombicula* spp., *Neotrombiculla* spp., *Listrophorus* spp.; and from the order of the Acaridida (Astigmata), for example *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

Parasitic protozoa include:
Mastigophora (Flagellata), for example Trypanosomatidae, for example *Trypanosoma b. brucei*, *T. b. gambiense*, *T. b. rhodesiense*, *T. congolense*, *T. cruzi*, *T. evansi*, *T. equinum*, *T. lewisi*, *T. percae*, *T. simiae*, *T. vivax*, *Leishmania brasiliensis*, *L. donovani*, *L. tropica*, for example Trichomonadidae, for example *Giardia lamblia*, *G. canis*;

Sarcomastigophora (Rhizopoda) such as Entamoebidae, for example *Entamoeba histolytica*, Hartmanellidae, for example *Acanthamoeba* sp., *Harmanella* sp.;

Apicomplexa (Sporozoa) such as Eimeridae, for example *Eimeria acervulina*, *E. adenoides*, *E. alabamensis*, *E. anatis*, *E. anserina*, *E. arloingi*, *E. ashata*, *E. auburnensis*, *E. bovis*, *E. brunetti*, *E. canis*, *E. chinchillae*, *E. clupearum*, *E. columbae*, *E. contorta*, *E. crandalis*, *E. debliecki*, *E. dispersa*, *E. ellipsoidales*, *E. falciformis*, *E. faurei*, *E. flavescens*, *E. gallopavonis*, *E. hagani*, *E. intestinalis*, *E. iroquoina*, *E. irresidua*, *E. labbeana*, *E. leucarti*, *E. magna*, *E. maxima*, *E. media*, *E. meleagridis*, *E. meleagrimitis*, *E. mitis*, *E. necatrix*, *E. ninakohlyakimovae*, *E. ovis*, *E. parva*, *E. pavonis*, *E. perforans*, *E. phasani*, *E. piriformis*, *E. praecox*, *E. residua*, *E. scabra*, *E.* spec., *E. stiedai*, *E. suis*, *E. tenella*, *E. truncata*, *E. truttae*, *E. zuernii*, *Globidium* spec., *Isospora belli*, *I. canis*, *I. felis*, *I. ohioensis*, *I. rivolta*, *I.* spec., *I. suis*, *Cystisospora* spec., *Cryptosporidium* spec., in particular *C. parvum*; such as Toxoplasmadidae, for example *Toxoplasma gondii*, *Hammondia heydornii*, *Neospora caninum*, *Besnoitia besnoitii*; such as Sarcocystidae, for example *Sarcocystis bovicanis*, *S. bovihominis*, *S. ovicanis*, *S. ovifelis*, *S. neurona*, *S.* spec., *S. suihominis*, such as Leucozoidae, for example *Leucozytozoon simondi*, such as Plasmodiidae, for example *Plasmodium berghei*, *P. falciparum*, *P. malariae*, *P. ovale*, *P. vivax*, *P.* spec., such as Piroplasmea, for example *Babesia argentina*, *B. bovis*, *B. canis*, *B.* spec., *Theileria parva*, *Theileria* spec., such as Adeleina, for example *Hepatozoon canis*, *H.* spec.

Pathogenic endoparasites which are helminths include Platyhelmintha (e.g. Monogenea, cestodes and trematodes), nematodes, Acanthocephala, and Pentastoma. These include:

Monogenea: for example: *Gyrodactylus* spp., *Dactylogyrus* spp., *Polystoma* spp.;

Cestodes: from the order of the Pseudophyllidea for example: *Diphyllobothrium* spp., *Spirometra* spp., *Schistocephalus* spp., *Ligula* spp., *Bothridium* spp., *Diphlogonoporus* spp.;

from the order of the Cyclophyllida, for example: *Mesocestoides* spp., *Anoplocephala* spp., *Paranoplocephala* spp., *Moniezia* spp., *Thysanosoma* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echinolepis* spp., *Echinocotyle* spp., *Diorchis* spp., *Dipylidium* spp., *Joyeuxiella* spp., *Diplopylidium* spp.;

Trematodes: from the class of the Digenea, for example: *Diplostomum* spp., *Posthodiplostomum* spp., *Schistosoma* spp., *Trichobilharzia* spp., *Ornithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hyporaeum* spp., *Fasciola* spp., *Fasciolides* spp., *Fasciolopsis* spp., *Cyclocoelum* spp., *Typhlocoelum* spp., *Paramphistomum* spp., *Calicophoron* spp., *Cotylophoron* spp., *Gigantocotyle* spp., *Fischoederius* spp., *Gastrothylacus* spp., *Notocotylus* spp., *Catatropis* spp.,

*Plagiorchis* spp., *Prosthogonimus* spp., *Dicrocoelium* spp., *Eurytrema* spp., *Troglotrema* spp., *Paragonimus* spp., *Collyriclum* spp., *Nanophyetus* spp., *Opisthorchis* spp., *Clonorchis* spp., *Metorchis* spp., *Heterophyes* spp., *Metagonimus* spp.;

Nematodes: Trichinellida, for example: *Trichuris* spp., *Capillaria* spp., *Paracapillaria* spp., *Eucoleus* spp., *Trichomosoides* spp., *Trichinella* spp., from the order of the Tylenchida, for example: *Micronema* spp., *Strongyloides* spp.;

from the order of the Rhabditida, for example: *Strongylus* spp., *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Ancylostoma* spp., *Uncinaria* spp., *Necator* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., *Cystocaulus* spp., *Pneumostrongylus* spp., *Spicocaulus* spp., *Elaphostrongylus* spp., *Parelaphostrongylus* spp., *Crenosoma* spp., *Paracrenosoma* spp., *Oslerus* spp., *Angiostrongylus* spp., *Aelurostrongylus* spp., *Filaroides* spp., *Parafilaroides* spp., *Trichostrongylus* spp., *Haemonchus* spp., *Ostertagia* spp., *Teladorsagia* spp., *Marshallagia* spp., *Cooperia* spp., *Nippostrongylus* spp., *Heligmosomoides* spp., *Nematodirus* spp., *Hyostrongylus* spp., *Obeliscoides* spp., *Amidostomum* spp., *Ollulanus* spp;

from the order of the Spirurida, for example: *Oxyuris* spp., *Enterobius* spp., *Passalurus* spp., *Syphacia* spp., *Aspiculuris* spp., *Heterakis* spp.; *Ascaris* spp., *Toxascaris* spp., *Toxocara* spp., *Baylisascaris* spp., *Parascaris* spp., *Anisakis* spp., *Ascaridia* spp.; *Gnathostoma* spp., *Physaloptera* spp., *Thelazia* spp., *Gongylonema* spp., *Habronema* spp., *Parabronema* spp., *Draschia* spp., *Dracunculus* spp.; *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp., *Spirocerca* spp.;

Acanthocephala: from the order of the Oligacanthorhynchida, for example: *Macracanthorhynchus* spp., *Prosthenorchis* spp.; from the order of the Polymorphida, for example: *Filicollis* spp.; from the order of the Moniliformida, for example: *Moniliformis* spp.;

from the order of the Echinorhynchida, for example *Acanthocephalus* spp., *Echinorhynchus* spp., *Leptorhynchoides* spp.;

Pentastoma: from the order of the Porocephalida, for example *Linguatula* spp.

In the veterinary field and in animal husbandry, the compounds of the formula (I) are administered by methods generally known in the art, such as via the enteral, parenteral, dermal or nasal route in the form of suitable preparations. Administration may be prophylactic or therapeutic.

Thus, one embodiment of the present invention refers to the use of a compound of the formula (I) as a medicament.

A further aspect refers to the use of a compound of the formula (I) as an antiendoparasitic agent, in particular a helminthicidal agent or antiprotozoic agent. Compounds of the formula (I) are suitable for use as an antiendoparasitic agent, especially as a helminthicidal agent or antiprotozoic agent, for example in animal breeding, in animal husbandry, in animal houses and in the hygiene sector.

A further aspect in turn relates to the use of a compound of the formula (I) as an antiectoparasitic, in particular an arthropodicide such as an insecticide or an acaricide. A further aspect relates to the use of a compound of the formula (I) as an antiectoparasitic, in particular an arthropodicide such as an insecticide or an acaricide, for example in animal husbandry, in animal breeding, in animal houses or in the hygiene sector.

Anthelmintic Mixing Components

The following anthelmintic mixing components may be mentioned by way of example:

anthelmintically active compounds including trematicidally and cestocidally active compounds:

from the class of the macrocyclic lactones, for example: abamectin, doramectin, emamectin, eprinomectin, ivermectin, milbemycin, moxidectin, nemadectin, selamectin;

from the class of the benzimidazoles and probenzimidazoles, for example: albendazole, albendazole-sulphoxide, cambendazole, cyclobendazole, febantel, fenbendazole, flubendazole, mebendazole, netobimin, oxfendazole, oxibendazole, parbendazole, thiabendazole, thiophanate, triclabendazole;

from the class of the cyclooctadepsipeptides, for example: emodepside, PF1022;

from the class of the aminoacetonitrile derivatives, for example: monepantel;

from the class of the tetrahydropyrimidines, for example: morantel, pyrantel, oxantel;

from the class of the imidazothiazoles, for example: butamisole, levamisole, tetramisole;

from the class of the salicylanilides, for example: bromoxanide, brotianide, clioxanide, closantel, niclosamide, oxyclozanide, rafoxanide, tribromsalan;

from the class of the paraherquamides, for example: derquantel, paraherquamide;

from the class of the aminophenylamidines, for example: amidantel, deacylated amidantel (dAMD), tribendimidine;

from the class of the organophosphates, for example: coumaphos, crufomate, dichlorvos, haloxone, naphthalofos, trichlorfon;

from the class of the substituted phenols, for example: bithionol, disophenol, hexachlorophene, niclofolan, meniclopholan, nitroxynil;

from the class of the piperazinones, for example: praziquantel, epsiprantel;

from various other classes, for example: amoscanate, bephenium, bunamidine, clonazepam, clorsulon, diamfenetid, dichlorophen, diethylcarbamazine, emetine, hetolin, hycanthone, lucanthone, Miracil, mirasan, niclosamide, niridazole, nitroxynil, nitroscanate, oltipraz, omphalotin, oxamniquin, paromomycin, piperazine, resorantel.

Vector Control

The compounds of the formula (I) can also be used in vector control. In the context of the present invention, a vector is an arthropod, especially an insect or arachnid, capable of transmitting pathogens, for example viruses, worms, single-cell organisms and bacteria, from a reservoir (plant, animal, human, etc.) to a host. The pathogens can be transmitted either mechanically (for example trachoma by non-stinging flies) to a host or after injection (for example malaria parasites by mosquitoes) into a host.

Examples of vectors and the diseases or pathogens they transmit are:

1) Mosquitoes

*Anopheles*: malaria, filariasis;

*Culex*: Japanese encephalitis, filariasis, other viral diseases, transmission of worms;

*Aedes*: yellow fever, dengue fever, filariasis, other viral diseases;

*Simuliidae*: transmission of worms, in particular *Onchocerca volvulus*;

2) Lice: skin infections, epidemic typhus;

3) Fleas: plague, endemic typhus;

4) Flies: sleeping sickness (trypanosomiasis); cholera, other bacterial diseases;

5) Mites: acariosis, epidemic typhus, rickettsialpox, tularaemia, Saint Louis encephalitis, tick-borne encephalitis (TBE), Crimean-Congo haemorrhagic fever, borreliosis;

6) Ticks: borellioses such as *Borrelia duttoni*, tick-borne encephalitis, Q fever (*Coxiella burnetii*), babesioses (*Babesia canis canis*).

Examples of vectors in the context of the present invention are insects, such as aphids, flies, leafhoppers or *thrips*, which can transmit plant viruses to plants. Other vectors capable of transmitting plant viruses are spider mites, lice, beetles and nematodes.

Further examples of vectors in the context of the present invention are insects and arachnids such as mosquitoes, especially of the genera *Aedes, Anopheles*, for example *A. gambiae, A. arabiensis, A. funestus, A. dirus* (malaria) and *Culex*, lice, fleas, flies, mites and ticks, which can transmit pathogens to animals and/or humans.

Vector control is also possible if the compounds of the formula (I) are resistance-breaking.

Compounds of the formula (I) are suitable for use in the prevention of diseases and/or pathogens transmitted by vectors. Thus, a further aspect of the present invention is the use of compounds of the formula (I) for vector control, for example in agriculture, in horticulture, in forestry, in gardens and in leisure facilities, and also in the protection of materials and stored products.

Protection of Industrial Materials

The compounds of the formula (I) are suitable for protecting industrial materials against attack or destruction by insects, for example from the orders Coleoptera, Hymenoptera, Isoptera, Lepidoptera, Psocoptera and Zygentoma.

Industrial materials in the present context are understood to mean inanimate materials, such as preferably plastics, adhesives, sizes, papers and cards, leather, wood, processed wood products and coating compositions. The use of the invention for protection of wood is particularly preferred.

In a further embodiment, the compounds of the formula (I) are used together with at least one further insecticide and/or at least one fungicide.

In a further embodiment, the compounds of the formula (I) are present as a ready-to-use pesticide, i.e. it can be applied to the material in question without further modifications. Suitable further insecticides or fungicides are in particular those mentioned above.

Surprisingly, it has also been found that the compounds of the formula (I) can be employed for protecting objects which come into contact with saltwater or brackish water, in particular hulls, screens, nets, buildings, moorings and signalling systems, against fouling. It is equally possible to use the compounds of the formula (I), alone or in combinations with other active compounds, as antifouling agents.

Control of Animal Pests in the Hygiene Sector

The compounds of the formula (I) are suitable for controlling animal pests in the hygiene sector. More particularly, the invention can be used in the domestic protection sector, in the hygiene protection sector and in the protection of stored products, particularly for control of insects, arachnids and mites encountered in enclosed spaces, for example dwellings, factory halls, offices, vehicle cabins. For controlling animal pests, the compounds of the formula (I) are used alone or in combination with other active compounds and/or auxiliaries. They are preferably used in domestic insecticide products. The compounds of the formula (I) are effective against sensitive and resistant species, and against all developmental stages.

These pests include, for example, pests from the class Arachnida, from the orders Scorpiones, Araneae and Opiliones, from the classes Chilopoda and Diplopoda, from the class Insecta the order Blattodea, from the orders Coleoptera, Dermaptera, Diptera, Heteroptera, Hymenoptera, Isoptera, Lepidoptera, Phthiraptera, Psocoptera, Saltatoria or Orthoptera, Siphonaptera and Zygentoma and from the class Malacostraca the order Isopoda.

Application is effected, for example, in aerosols, unpressurized spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or bait stations.

Description of the Processes and Intermediates

The preparation and use examples which follow illustrate the invention without limiting it. The products were characterized by 1H NMR spectroscopy and/or LC-MS (Liquid Chromatography Mass Spectrometry).

The log P values were determined in accordance with OECD Guideline 117 (EC Directive 92/69/EEC) by HPLC (high-performance liquid chromatography) using reversed-phase (RP) columns (C18), by the following methods:

[a] The LC-MS determination in the acidic range was carried out at pH 2.7 with 0.1% aqueous formic acid and acetonitrile (contains 0.1% formic acid) as mobile phases; linear gradient from 10% acetonitrile to 95% acetonitrile.

[b] LC-MS determination in the neutral range was carried out at pH 7.8 with 0.001 molar aqueous ammonium hydrogencarbonate solution and acetonitrile as mobile phases; linear gradient from 10% acetonitrile to 95% acetonitrile.

Calibration was carried out using unbranched alkan-2-ones (having 3 to 16 carbon atoms) with known log P values (log P values determined on the basis of the retention times by linear interpolation between two successive alkanones).

The NMR spectra were determined using a Bruker Avance 400 fitted with a flow probe head (60 µl volume). In individual cases, the NMR spectra were measured with a Bruker Avance II 600.

The NMR data of selected examples are stated in classic form (6 values, multiplet splitting, number of hydrogen atoms). The splitting of the signals was described as follows: s (singlet), d (doublet), t (triplet), q (quartet), quint (quintuplet), m (multiplet), br (for broad signals). Solvents used were CD$_3$CN, CDCl$_3$ or D6-DMSO, and tetramethylsilane (0.00 ppm) was used as reference.

PREPARATION EXAMPLES

Processes A and B

Example (I-A-1)

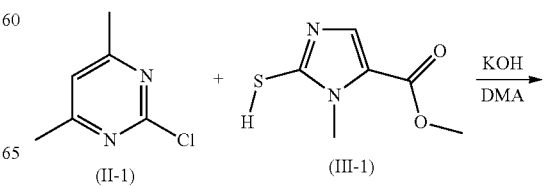

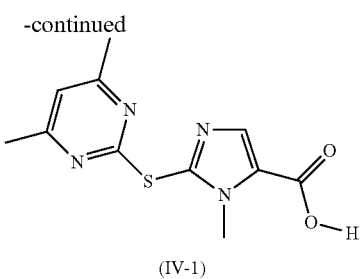

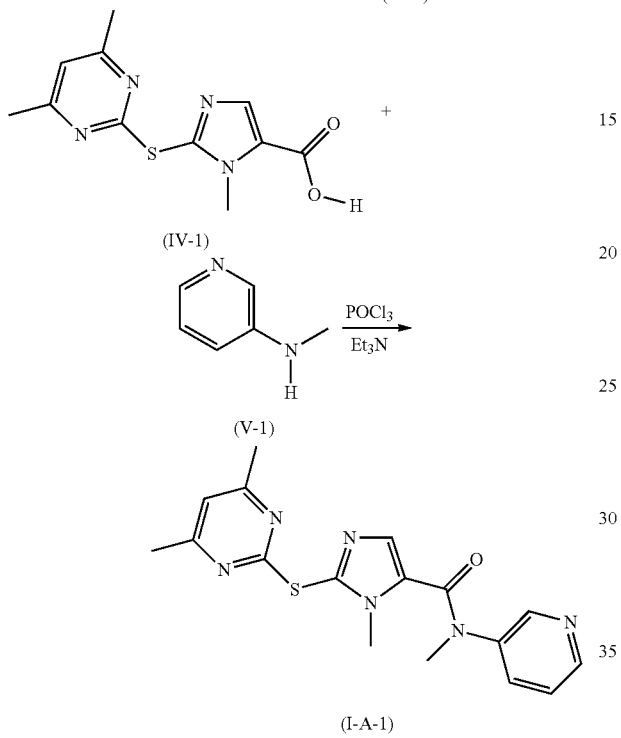

Preparation of the Compound (IV-1)

1.46 g (10 mmol) of 2-chloro-4,6-dimethylpyrimidine, 0.62 g (11 mmol) of powdered potassium hydroxide and 1.72 g (10 mmol) of methyl 1-methyl-2-sulphanylimidazole-5-carboxylate were combined in 30 ml of dimethylacetamide (DMA) and stirred overnight at a temperature of 120° C. The solvent was removed under reduced pressure on a rotary evaporator and the residue was taken up in water and methylene chloride and extracted. The aqueous phase was acidified with 2N hydrochloric acid, and the precipitate was filtered off with suction and dried. Yield: 443 mg (15.8% of theory)

log P[a]: 0.81

$^1$H-NMR (d$_6$-DMSO, 400 MHz); δ=2.30 (s, 6H), 3.34 (s, 3H), 7.07 (s, 1H), 7.75 (s, 1H), 13.19 (s, br, 1H) ppm.

Preparation Example (I-A-1)

At room temperature, 0.339 g (1.18 mmol) of the compound (IV-1) were initially charged in 15 ml of absolute tetrahydrofuran (THF), and 0.17 ml (1.18 mmol) of triethylamine were added. The mixture was stirred for 5 min, 0.14 g (1.3 mmol) of 3-methylaminopyridine was then added and the mixture was stirred for a further 15 min. 0.46 ml (3.31 mmol) of triethylamine was subsequently added, immediately followed by the dropwise addition of 0.11 g (0.71 mmol) of phosphorus oxychloride, and the mixture was then boiled under reflux for 30 min. The mixture was concentrated under reduced pressure and the residue was purified by RP medium pressure column chromatography using a water/acetonitrile mobile phase gradient. Yield: 77 mg (17.7% of theory)

log P[a]: 1.31; log P [n]: 1.41

$^1$H-NMR (CD$_3$CN, 400 MHz); δ=2.32 (s, 6H), 3.43 (s, 3H), 3.79 (s, 3H), 6.43 (s, 1H), 6.90 (s, 1H), 7.36-7.39 (m, 1H), 7.70-7.73 (m, 1H), 8.41-8.42 (d, 1H), 8.45-8.47 (m, 1H) ppm.

Example (I-A-2)

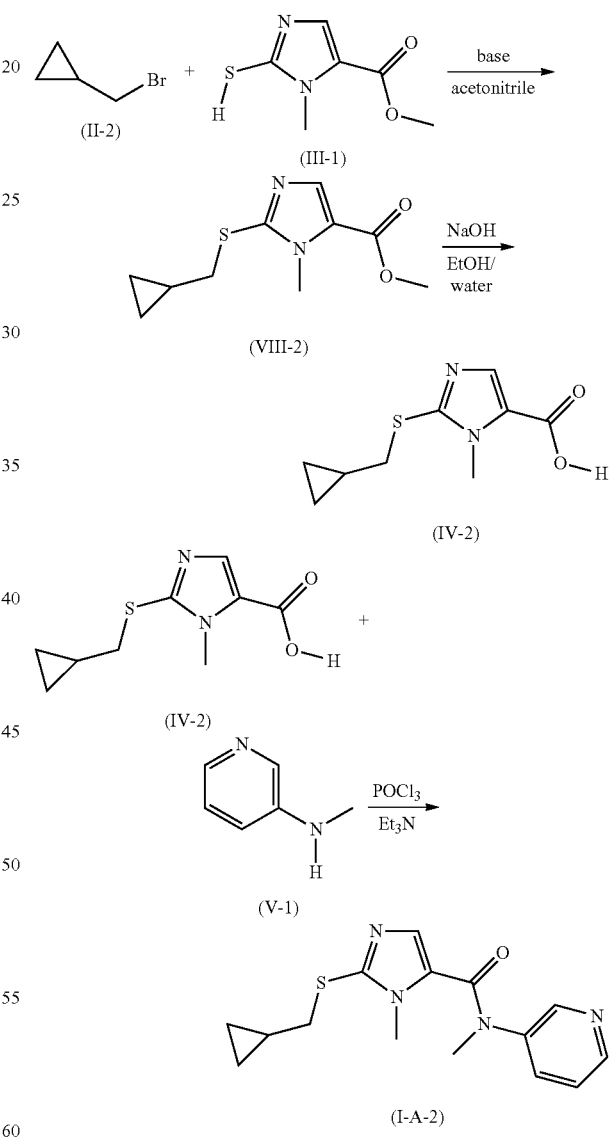

Preparation of the Compound (VIII-2)

0.81 g (6 mmol) of cyclopropylmethyl bromide, 0.83 g (6 mmol) of powdered potassium carbonate and 0.861 g (5 mmol) of methyl 1-methyl-2-sulphanylimidazole-5-carboxylate were combined in 20 ml of acetonitrile, and the mixture was, with stirring, heated under reflux for 5 h. Dissolution in acidic MeOH resulted in the precipitation of a white powder which was filtered off with suction and then purified by MPLC on silica gel using the mobile phase cyclohexane/ethyl acetate 1:1. Yield: 210 mg (18.6% of theory)

log P[a]: 2.06; log P[n]: 2.26

$^1$H-NMR (CD$_3$CN, 400 MHz); δ=0.26-0.30 (m, 2H), 0.56-0.61 (m, 2H), 1.10 (cm, 1H), 3.37-3.47 (m, 2H), 3.88 (s, 3H), 3.96 (s, 3H), 7.97 (s, 1H) ppm.

Preparation of the Compound (IV-2)

0.210 g (0.928 mmol) of the compound (VIII-2) and 0.186 g (0.928 mmol) of 20% strength aqueous sodium hydroxide solution in 5 ml of ethanol were stirred at 40° C. for 1 h. The solvent was evaporated under reduced pressure and the residue was dissolved in 1 ml of water and adjusted to pH 2 using 1N HCl. The solution was concentrated under reduced pressure and the residue was purified by RP-MPLC using a water/acetonitrile gradient. Yield: 155 mg (78.7% of theory)

log P[a]: 0.62; log P[n]: −0.18

$^1$H-NMR (CD$_3$CN, 400 MHz); δ=0.23-0.26 (m, 2H), 0.52-0.56 (m, 2H), 1.12 (cm, 1H), 3.08-3.10 (d, 2H), 3.77 (s, 3H), 7.66 (s, 1H) ppm.

Preparation of Example (I-A-2)

At room temperature, 0.14 g (0.66 mmol) of the compound (IV-2) were initially charged in 10 ml of absolute tetrahydrofuran (THF), and 0.1 ml (0.66 mmol) of triethylamine was added. The mixture was stirred for 5 min, 0.078 g (0.73 mmol) of 3-methylaminopyridine was then added and the mixture was stirred for a further 15 min. 0.26 ml (1.85 mmol) of triethylamine was subsequently added, immediately followed by the dropwise addition of 0.061 g (0.4 mmol) of phosphorus oxychloride, and the mixture was then boiled under reflux for 30 min. The mixture was concentrated under reduced pressure and the residue was purified by MPLC on silica gel using the mobile phase cyclohexane/ethyl acetate 1:1. Yield: 35 mg (14% of theory).

log P[a]: 1.28; log P[n]: 1.81

$^1$H-NMR (CD$_3$CN, 400 MHz); δ=0.12-0.16 (m, 2H), 0.47-0.51 (m, 2H), 1.03 (cm, 1H), 2.94-2.96 (d, 2H), 3.38 (s, 3H), 3.74 (s, 3H), 6.25 (s, 1H), 7.34-7.38 (m, 1H), 7.66-7.69 (m, 1H), 8.410-8.415 (d, 1H), 8.45-8.46 (m, 1H) ppm.

Preparation of the Intermediates for Process B

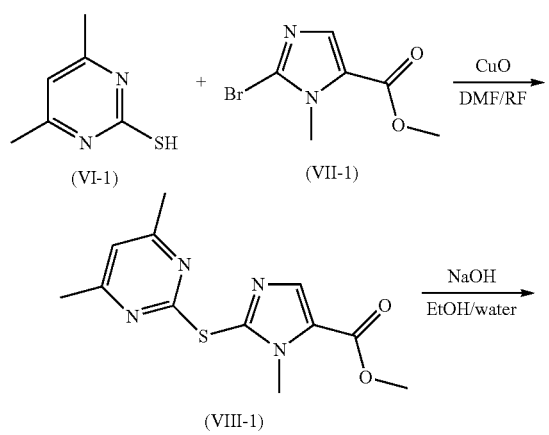

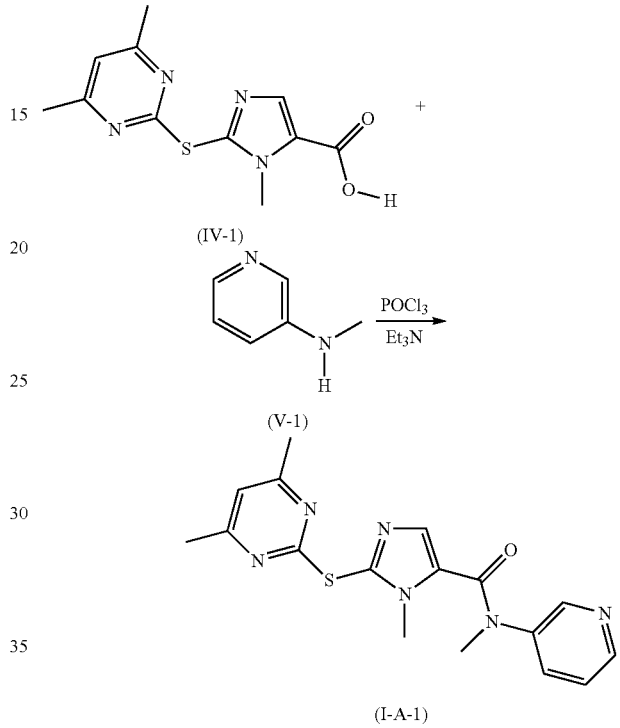

Preparation of the Compound (VIII-1)

Under argon, 0.7 g (5 mmol) of 2-mercapto-4,6-dimethylpyrimidine, 0.75 g (5.25 mmol) of copper (I) oxide and 1.1 g (5 mmol) of methyl 1-methyl-2-bromoimidazole-5-carboxylate were combined in 60 ml of dry dimethylformamide (DMF), and the mixture was heated under reflux overnight. After cooling to room temperature, the reaction mixture was filtered off with suction through Celite, washed with ethyl acetate and hot methanol, the filtrate was extracted with EDTA solution, the organic phase was separated off, the solvent was evaporated under reduced pressure and the residue was purified by MPLC on silica gel using the mobile phase cyclohexane/ethyl acetate 1:1. Yield: 247 mg (17.3% of theory)

log P[a]: 1.78; log P[n]: 1.80

$^1$H-NMR (CD$_3$CN, 400 MHz); δ=2.23 (s, 6H), 3.85 (s, 3H), 3.87 (s, 3H), 6.92 (s, 1H), 7.77 (s, 1H) ppm.

Preparation of the Compound (IV-1)

0.396 g (1.42 mmol) of the compound (VIII-1) and 0.28 g (1.42 mmol) of 20% strength aqueous sodium hydroxide solution in 10 ml of ethanol were stirred at 40° C. for 1 h. The solvent was evaporated under reduced pressure and the residue was dissolved in 2 ml of water and adjusted to pH 2 using 1N HCl. The precipitate was filtered off with suction and dried. Yield: 339 mg (83% of theory)

log P[a]: 0.81

¹H-NMR (CD₃CN, 400 MHz); δ=2.23 (s, 6H), 3.86 (s, 3H), 6.92 (s, 1H), 7.77 (s, 1H) ppm.

Process C-1

Example (I-A-3)

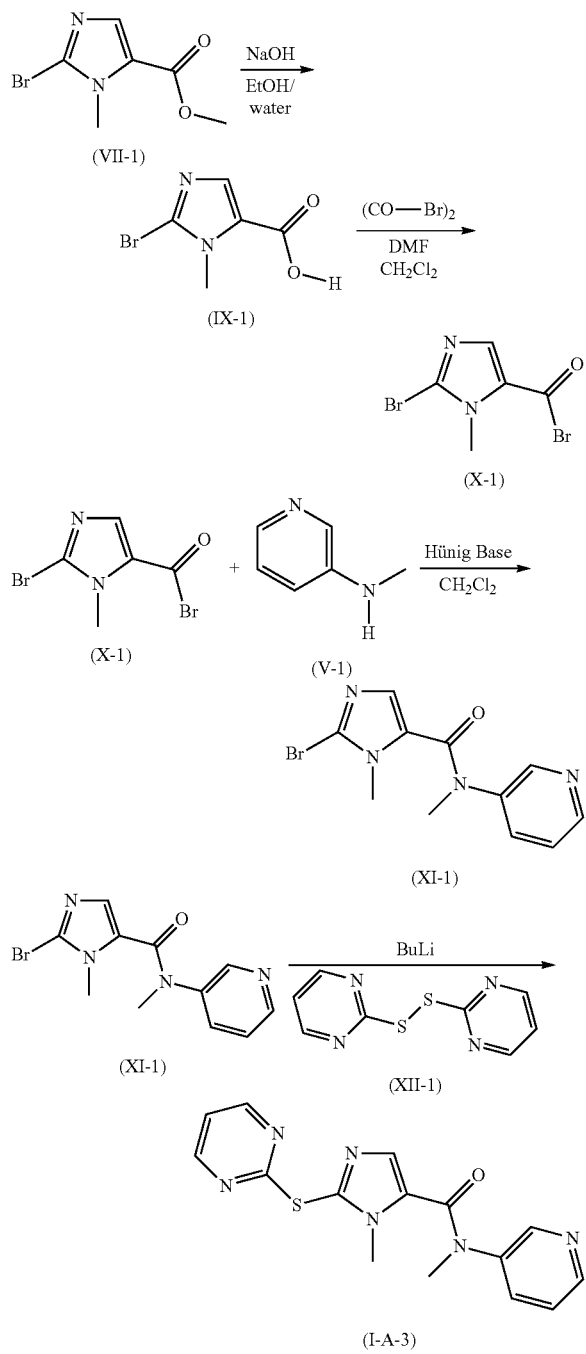

Preparation of the Compound (IX-1)

1 g (4.565 mmol) of methyl 1-methyl-2-bromoimidazole-5-carboxylate (VII-1) was dissolved in 10 ml of ethanol, 5.48 ml of 1N NaOH (aq.) was added and the mixture was stirred at room temperature for 60 min. After addition of 5.5 ml of 1N HCl (aq.) (adjusted to pH ~3), a white precipitate is formed. The mixture was concentrated to dryness and, in an ultrasonic bath, suspended in 6 ml of water. The white crystals were filtered off and washed with 2 ml of water. The mother liquor was concentrated almost to dryness. The crystals were filtered off with suction and washed with a little water. The combined crystals were dried under oil pump vacuum. Yield: 890 mg (95% of theory).

log P[a]: 0.31;

¹H-NMR (d₆-DMSO, 400 MHz); δ=3.82 (s, 3H), 7.60 (s, 1H), 13.15 (s, 1H) ppm.

Preparation of the Compound (X-1)

Using a syringe canula, about 60 mg of DMF were added to a suspension of 890 mg (4.341 mmol) of 1-methyl-2-bromoimidazole-5-carboxylic acid (IX-1) in 15 ml of dichloromethane. At room temperature, 940 mg (4.341 mmol) of oxalyl bromide were added, resulting in an intensive evolution of gas. The next day, a further 10 ml of dichloromethane and 140 mg of oxalyl bromide were added. After 1 h of stirring at room temperature, a further 110 mg of oxalyl bromide and 30 mg of DMF were added, and the mixture was stirred at room temperature for another hour, LC/MS showing 96% conversion. Without further work-up, the suspension was used for the synthesis of compound (XI-1).

Preparation of the Compound (XI-1)

14.02 g (40.19 mmol) of 1-methyl-2-bromoimidazole-5-carbonyl bromide (X-1) were suspended in 80 ml of dichloromethane, and the suspension was cooled to 0° C. A solution of 4.35 g (40.19 mmol) of 3-methylaminopyridine (V-1) and 41 ml (241.2 mmol) of Hünig base dissolved in 40 ml of dichloromethane was added at 0° C. The mixture was stirred at room temperature for 1 h and then boiled under reflux for 4 h and allowed to stand at RT overnight. The mixture was concentrated under reduced pressure. The residue was taken up in 500 ml of dichloromethane and washed 3× with a total of 400 ml of water (2×about 200 ml and 1× about 100 ml). The combined aqueous phases were extracted with about 50 ml of dichloromethane and the organic phases were combined. The combined organic phases were washed 2× with an aqueous NaHCO₃ solution (3.5 g of NaHCO3 in 150 ml of water). The combined aqueous phases were extracted with about 50 ml of dichloromethane and the organic phases were combined, dried and concentrated under reduced pressure. Yield: 10.45 g (81.9% of theory) of a brown viscous oil in an LC/MS purity of 93%.

log P[a] 0.65; log P[n]: 0.93

¹H-NMR (d₆-DMSO, 400 MHz); δ=3.37 (s, 3H), 3.75 (s, 3H), 6.25 (s, 1H), 7.43-7.47 (m, 1H), 7.84-7.87 (m, 1H), 8.48-8.49 (m, 1H), 8.52 (m, 1H) ppm.

Compound (I-A-3)

0.54 g (1.83 mmol) of the compound (XI-1) were dissolved in 5 ml of THF, and the solution was cooled to <−70° C. At this temperature, 0.75 ml (1.83 mmol) of a 2.5 molar solution of n-BuLi in hexane was added dropwise over a period of 10 minutes, and the mixture was stirred for another 15 minutes. 0.407 g of the compound (XII-1), dissolved in 5 ml of THF, was then added dropwise. The mixture was stirred at <−70° C. for a further 45 minutes. At −70° C., the mixture was quenched with ammonium chloride solution, the product was extracted with dichloromethane and the solution was dried and concentrated under reduced pressure. The residue was isolated by MPLC on silica gel using a methylene chloride/ethanol gradient as mobile phase. Yield: 113 mg (17% of theory)

log P[a]: 0.69; log P[n]: 0.98

$^1$H-NMR (d$_6$-DMSO, 400 MHz); δ=3.41 (s, 3H), 3.75 (s, 3H), 6.49 (s, 1H), 6.90 (s, 1H), 7.32-7.34 (t, 1H), 7.45-7.48 (m, 1H), 7.84-7.86 (m, 1H), 8.48-8.50 (m, 1H), 8.51-8.53 (m, 1H), 8.63-8.64 (d, 2H) ppm.

Process C-2

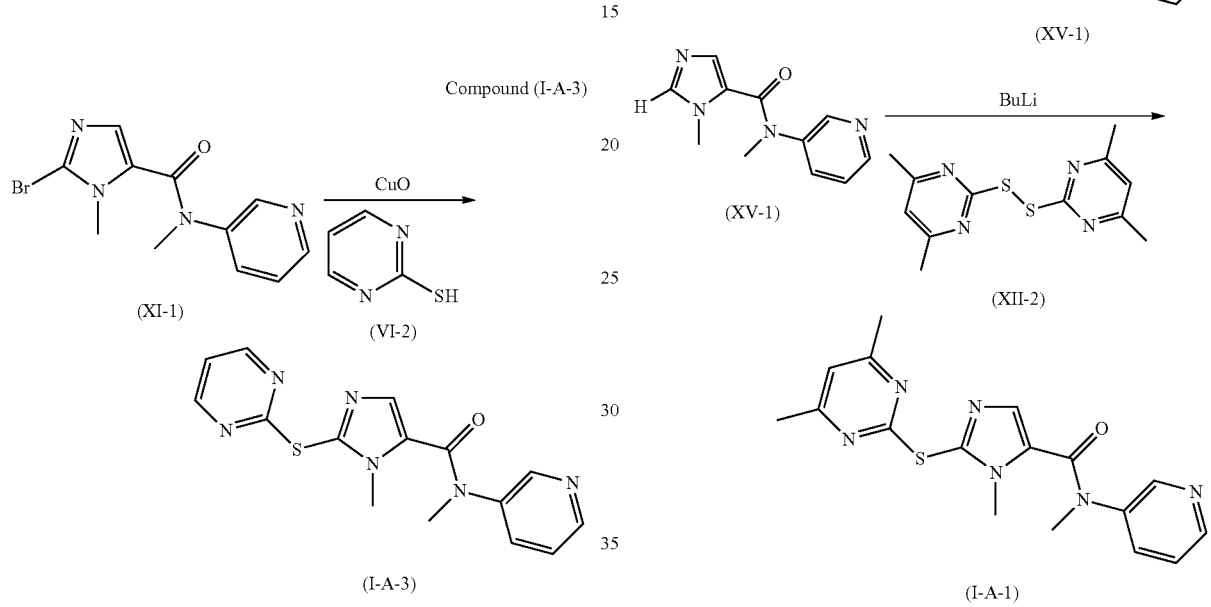

0.456 g (4.066 mmol) of 2-mercaptopyrimidine, 0.64 g (4.473 mmol) of copper (I) oxide and 1.2 g (4.066 mmol) of the compound (XI-1) were combined in 12 ml of dry dimethylformamide (DMF) and heated under reflux for 3 h. After cooling to room temperature, the reaction mixture was filtered through Celite, the solvent was evaporated under reduced pressure and the residue was purified by MPLC on silica gel using a dichloromethane/methanol gradient as mobile phase. Yield: 408 mg (30% of theory).

log P[n]: 0.98

$^1$H-NMR (d$_6$-DMSO, 400 MHz); δ=3.41 (s, 3H), 3.75 (s, 3H), 6.49 (s, 1H), 6.90 (s, 1H), 7.32-7.34 (t, 1H), 7.45-7.48 (m, 1H), 7.84-7.86 (m, 1H), 8.48-8.50 (m, 1H), 8.51-8.53 (m, 1H), 8.63-8.64 (d, 2H) ppm.

Process D

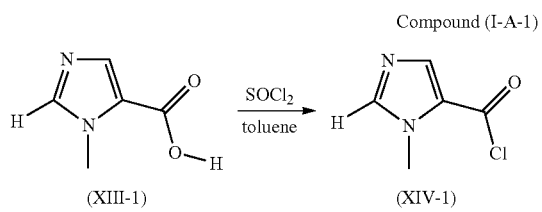

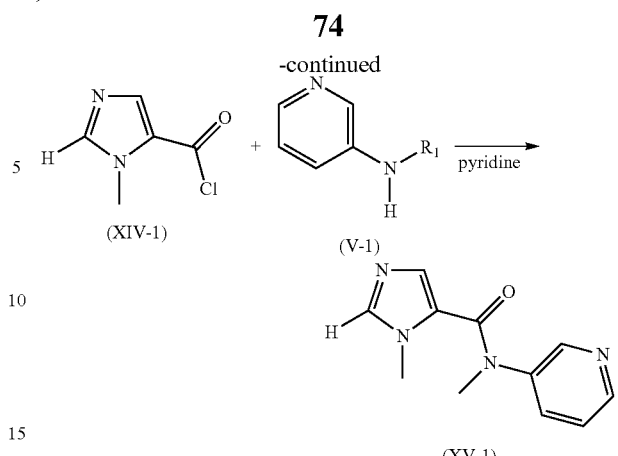

Preparation of the Compound (XV-1)

12.71 g (104.7 mmol) of thionyl chloride were added to a suspension of 12 g (95.2 mmol) of 1-methylimidazole-5-carboxylic acid (XIII-1) in 72 ml of toluene, and the mixture was stirred at 130° C. overnight. The reaction mixture was concentrated under reduced pressure. A solution of 10.3 g (95.2 mmol) of 3-methylaminopyridine (V-1) in 72 ml of pyridine was added to the residue, and the resulting reaction mixture was heated at 115° C. for 4 h. The mixture was then once more concentrated under reduced pressure and the residue was purified by column chromatography on silica gel using the mobile phase acetonitrile/methanol 3:1. This gave 8.1 g (39.3% of theory) of the title compound (XV-1) and 9.5 g (37.1% of theory) of the HCl salt of the title compound.

log P[n]: 0.42

$^1$H-NMR (CD$_3$CN, 400 MHz); δ=3.39 (s, 3H), 3.81 (s, 3H), 6.17 (s, 1H), 7.36-7.40 (m, 2H), 7.67-7.70 (m, 1H), 8.41 (m, 1H) 8.47 (m, 1H) ppm.

Example (I-A-1)

0.500 g (2.31 mmol) of the compound (XV-1) was dissolved in 10 ml of THF, and the mixture was cooled to −85° C. During the reaction, the temperature was kept between −82 and −90° C. At this temperature, 0.91 ml (2.4 mmol) of a 2.5 molar solution of n-BuLi in n-hexane was added dropwise over a period of 5 minutes, and the mixture was stirred for another 10 minutes. 0.407 g of the compound (XII-2), suspended in 5 ml of THF, was then added dropwise over 3 min. The mixture was stirred at <−85° C. for a further 30 minutes. Over 1.5 h, the mixture was warmed to 0° C. and then allowed to stand at room temperature overnight. The solid was filtered off with suction and washed with dichloromethane. The filtrate was concentrated under reduced pressure and the residue was purified by MPLC on silica gel using the mobile phase ethyl acetate/methanol 95:5. This gave 200 mg of product (70% pure) which were purified further by RP-HPLC (acetonitrile/water+0.1% formic acid). Purification gave 105 mg (12.8% of theory).

log P[a]: 1.26; log P[n]: 1.46

$^1$H-NMR (d$_6$-DMSO, 400 MHz); δ=2.31 (s, 6H), 3.41 (s, 3H), 3.74 (s, 3H), 6.46 (s, 1H), 7.06 (s, 1H), 7.43-7.46 (m, 1H), 7.85-7.87 (m, 1H), 8.46-8.49 (m, 2H) ppm.

Preparation of 1-benzyl-N-methyl-N-(pyridin-3-yl)-1H-imidazole-5-carboxamide

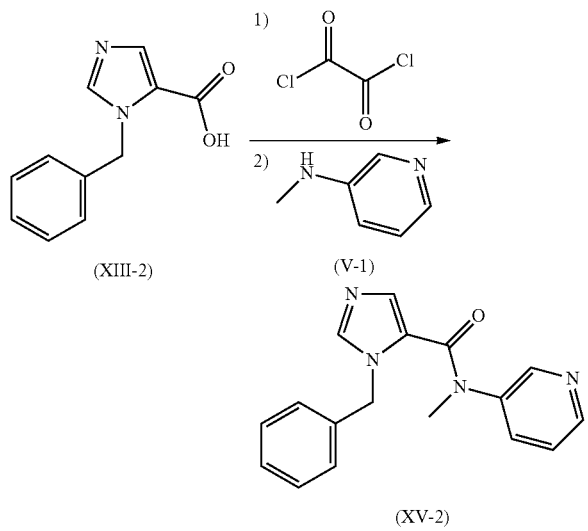

(XIII-2)   (V-1)

(XV-2)

[1-Benzyl-1H-imidazole-5-carboxylic acid hydrochloride (XIII-2) was prepared according to the procedure of *Tetrahedron* 2004, 60, 6079-6083.] 1.00 g (4.94 mmol) of 1-benzyl-1H-imidazole-5-carboxylic acid hydrochloride (XIII-2) was dissolved in 10 ml of dichloromethane with a drop of dimethylformamide. 0.475 ml (5.44 mmol) of oxalyl chloride was added dropwise. The mixture was stirred at room temperature for 3 h. The solvent was evaporated under reduced pressure. A solution of 0.535 g (4.94 mmol) of N-methylpyridine-3-amine (V-1) in 7.2 ml of pyridine was added dropwise to the residue, and the mixture was stirred at 100° C. overnight. The solvent was evaporated under reduced pressure. The residue was dissolved in 8.3 ml of dichloromethane, and 1.57 g (14.8 mmol) of sodium carbonate were added. The mixture was stirred at room temperature for 3 h and then filtered and concentrated. The residue was purified on silica gel by MPLC using the mobile phase ethyl acetate/methanol. Purification gave 0.326 g (21.9% of theory).

log P[a]: 0.85; log P[n]: 1.40;

$^1$H-NMR (d$_6$-DMSO, 400 MHz); δ=3.26 (s, 3H), 5.45 (s, 2H), 6.27 (s, 1H), 7.19-7.21 (m, 2H), 7.30-7.42 (m, 5H), 7.858-7.863 (m, 1H), 7.90 (s, 1H), 8.40-8.41 (m, 1H) ppm.

Example (I-A-111): 1-benzyl-N-methyl-N-(pyridin-3-yl)-2-(pyrimidin-2-ylsulphanyl)-1H-imidazole-5-carboxamide

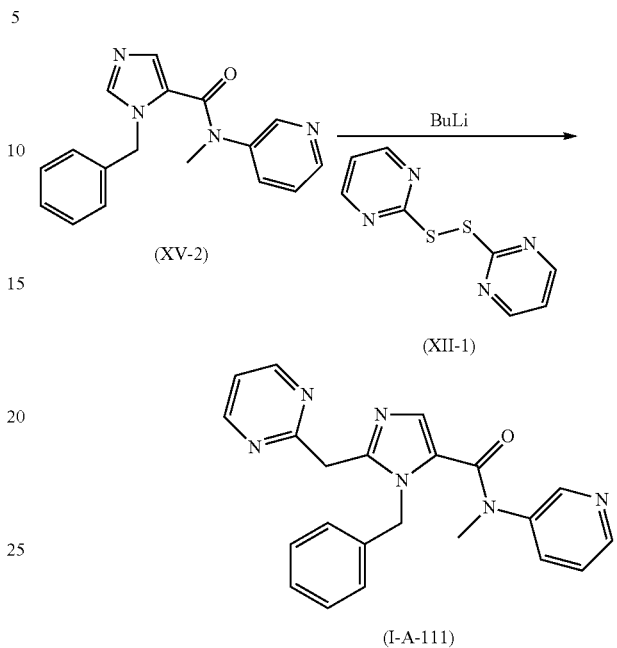

0.272 g (0.930 mmol) of 1-benzyl-N-methyl-N-(pyridin-3-yl)-1H-imidazole-5-carboxamide (XV-2) was dissolved in 11 ml of THF and cooled to −90° C. During the reaction, the temperature was kept between −85° C. and −90° C. 0.39 ml (0.977 mmol) of a 2.5 molar n-BuLi solution in n-hexane was added dropwise at −90° C. over a period of 5 minutes, and the mixture was stirred for another 5 minutes. Subsequently, over a period of 5 minutes, 0.620 g of 2,2'-disulphanediyldipyrimidine (2.79 mmol) (XII-1), dissolved in 1 ml of THF, was added dropwise. The mixture was stirred at −80° C. for a further 30 minutes and then, over 30 minutes, warmed to room temperature. The mixture was extracted with semiconcentrated sodium bicarbonate solution/dichloromethane. The aqueous phase was extracted three more times with dichloromethane. The organic phases were combined, washed with a little water, dried with sodium sulphate, filtered and concentrated. The residue was purified on silica gel by MPLC using the mobile phase ethyl acetate/methanol. The desired fraction was purified on RP18 by HPLC using the mobile phase acetonitrile/water. Purification gave 140 mg (35.1% of theory).

Analysis see Table 2

Process E

Example (I-B-1)

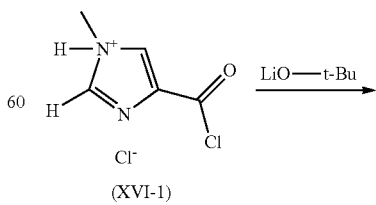

(XVI-1)
Berliner et al. Org. Process Res. Dev., 2011 vol. 15, #5 p. 1052-1062

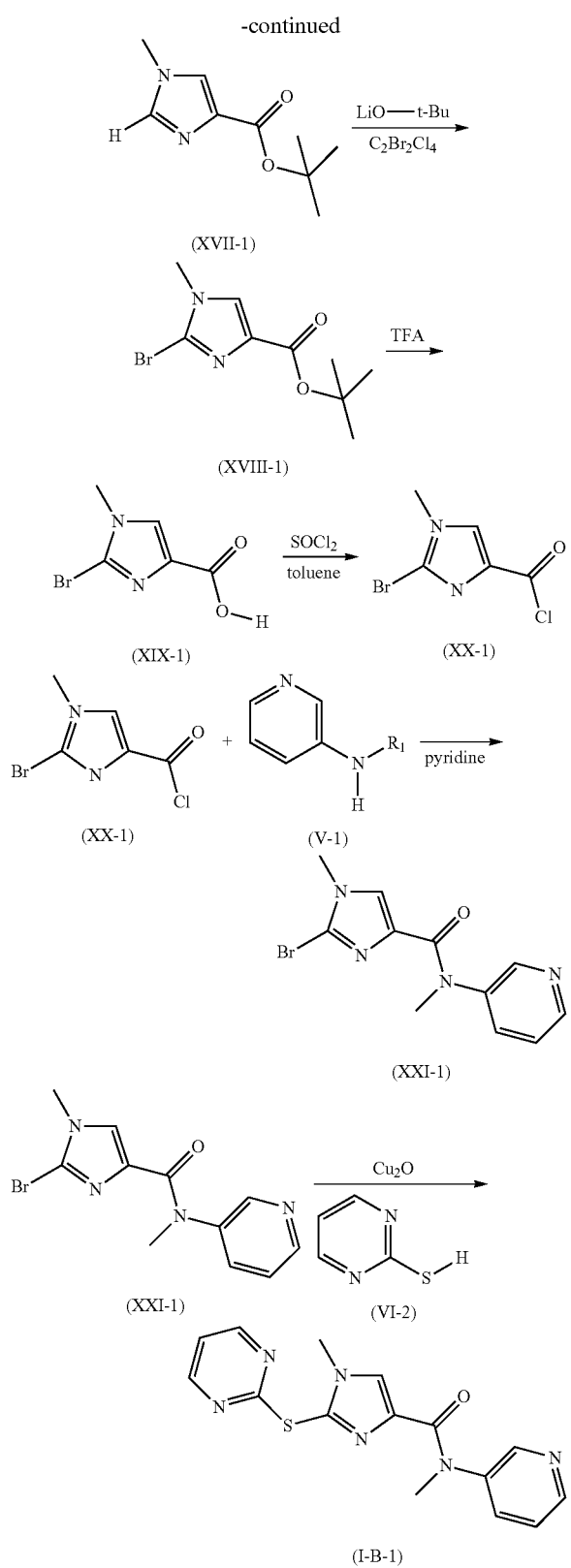

Preparation of the Compound (XVII-1)

Under argon and at −40° C., 33.9 g (0.493 mol) of lithium tert-butoxide were added with stirring to a suspension of 36.5 g (0.201 mol) of 1-methyl-1H-imidazole-4-carbonyl chloride hydrochloride in 400 ml of tetrahydrofuran. Without further cooling, the mixture was then stirred for 12 hours. After addition of 170 g of sodium bicarbonate, the mixture was filtered through a little silica gel, washing with ethyl acetate. The combined organic phases were evaporated and the residue obtained was extracted with dichloromethane. The evaporation residue of the dichloromethane phase was partitioned between saturated sodium bicarbonate solution and ethyl acetate and the organic phase was dried with magnesium sulphate, filtered and evaporated, giving 22.7 g of tert-butyl 1-methyl-1H-imidazole-4-carboxylate (73% yield of theory).

log P[a]: 0.74;
$^1$H-NMR (CD$_3$CN, 400 MHz); δ=1.52 (s, 9H), 3.66 (s, 3H), 7.43 (s, 1H), 7.54 (s, 1H) ppm.

Preparation of the Compound (XVIII-1)

0.5 g (2.744 mmol) of tert-butyl 1-methylimidazole-4-carboxylate (XVII-1) were initially charged in 10 ml of tetrahydrofuran (THF), 0.894 g (2.744 mmol) of 1,2-dibromo-1,1,2,2-tetrachloroethane were added and 0.88 g (11 mmol) of lithium tert-butoxide were added at room temperature. The mixture was stirred at room temperature overnight, the reaction product was concentrated under reduced pressure and the residue was purified by MPLC on RP18 using acetonitrile/water+0.1% formic acid as mobile phase. Yield: 250 mg (34.8% of theory).

log P[a]: 1.27
$^1$H-NMR (CD$_3$CN, 400 MHz); δ=1.51 (s, 9H), 3.60 (s, 3H), 7.65 (s, 1H) ppm.

Preparation of the Compound (XIX-1)

At room temperature, 645 mg (2.47 mmol) of tert-butyl 2-bromo-1-methyl-1H-imidazole-4-carboxylate were stirred in a mixture of 1.7 g of trifluoroacetic acid and 7 ml of dichloromethane for 12 hours. The solvent was removed. The evaporation residue obtained consisted to 95% of the target product 2-bromo-1-methyl-1H-imidazole-4-carboxylic acid, which corresponds to a virtually quantitative yield.

log P[a]: 0.0;
$^1$H-NMR (CD$_3$CN, 400 MHz); δ=3.65 (s, 3H), 7.78 (s, 1H) ppm.

Preparation of the Compound (XXI-1)

0.32 ml of oxalyl chloride (1.2 eq.) were added dropwise to a solution of 681 mg (3.32 mmol) of 2-bromo-1-methyl-1H-imidazole-4-carboxylic acid in 7 ml of dichloromethane and 3 drops of dimethylformamide. After 4 hours, the mixture was evaporated to dryness. 10 ml of dichloromethane, 359 mg (1 eq.) of N-methylpyridine-3-amine and 6 eq. of N,N-diisopropylethylamine were added to the residue and the mixture was then stirred for one hour. The mixture was then evaporated to dryness and the residue was chromatographed by MPLC on silica gel using the mobile phase ethyl acetate/methanol. Yield 411 mg (43% of theory).

log P[n]: 0.76;
$^1$H-NMR (CD$_3$CN, 400 MHz); δ=3.41 (s, 3H); 3.51 (s, 3H), 7.28-7.35 (m, 2H), 7.59-7.61 (m, 1H), 8.37-8.43 (m, 2H) ppm.

Preparation of the Compound (I-B-1)

250 mg (0.618 mmol) of the compound (XXI-1) and 69 mg (0.618 mmol) of 2-mercaptopyrimidine were combined in a rolled flange vessel and stirred at 150° C. for 2 hours. The mixture was washed with saturated EDTA solution and extracted three times with ethyl acetate. The organic solution was dried with magnesium sulphate, filtered and concentrated under reduced pressure. The residue was purified by MPLC on silica gel using an ethyl acetate/methanol gradient as mobile phase. Yield: 65 mg (30.6% of theory).

log P[a]: 0.42; log P[n]: 0.83;

$^1$H-NMR (CD3CN, 400 MHz); δ=3.47 (s, 3H), 3.58 (s, 3H), 7.15 (m, 1H), 7.30 (br. s, 1H), 7.54 (br. s, 1H), 7.60 (br. d, 1H), 8.39 (br. s, 2H), 8.48-8.49 (m, 2H) ppm.

Process F

Example (I-A-45)

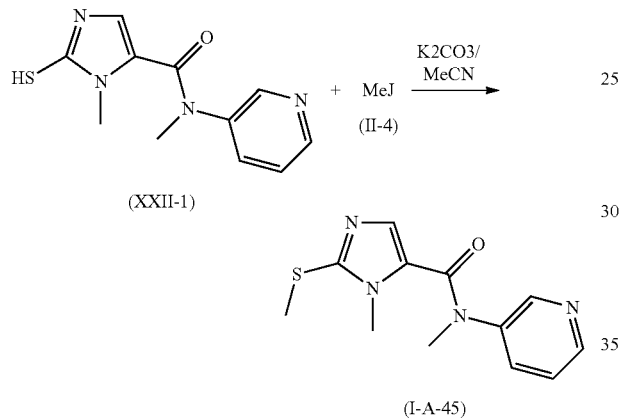

Under argon, 0.496 g (2 mmol) of the compound (XXII-1), 0.332 g (2.4 mmol) of potassium carbonate and 0.125 ml (2 mmol) of methyl iodide in 10 ml of acetonitrile were boiled under reflux for 1 h. The reaction mixture was concentrated under reduced pressure, sodium bicarbonate solution was added, the mixture was concentrated again, the residue was stirred with ethanol, the salts were filtered off and the solvent was evaporated. After reversed phase chromatography, the residue gave 237 mg of the target compound (I-A-45).

Analysis see Table 2

Example (I-A-37)

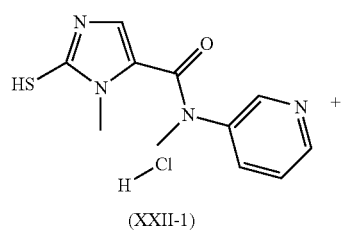

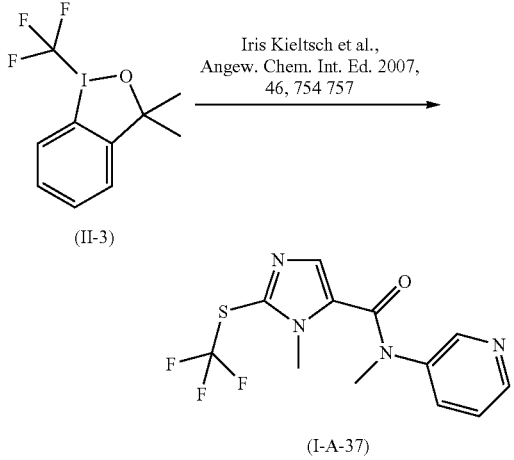

Under argon, 0.420 g (1.47 mmol) of the compound (XXII-1) hydrochloride were dissolved in 5 ml of methanol, and the mixture was cooled to −78° C. After addition of the alkylating agent (11-3) (2 eq.), the mixture was stirred for one hour and then warmed to room temperature, 1 ml of saturated ammonium chloride solution was added and the mixture was concentrated completely. The residue gave, after chromatography on silica gel, 220 mg of the target compound (I-A-37).

Analysis see Table 2

Example (I-A-38)

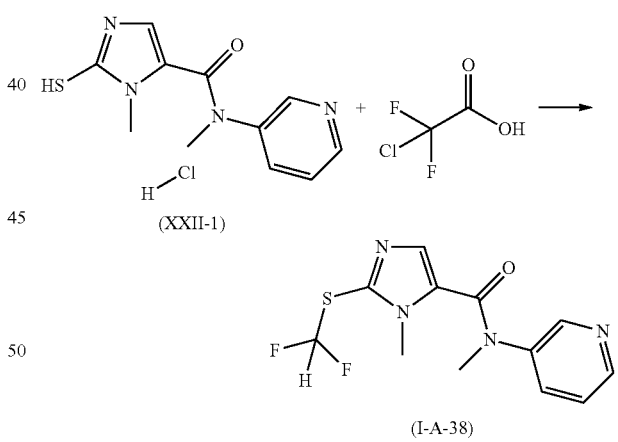

0.200 g (0.70 mmol) of the compound (XXII-1) hydrochloride was dissolved in 10 ml of dimethylformamide, and, with stirring, 3 eq. of potassium carbonate and 2 eq. of sodium chlorodifluoroacetate were added. After 3 hours of heating at 95° C., the mixture was allowed to cool to room temperature and concentrated completely, the residue was taken up in 10 ml of methanol and the mixture was filtered through celite. The filtrate was concentrated completely and chromatographed on silica gel, giving 56 mg of the target compound (I-A-38).

Analysis see Table 2

Synthesis Route to Compound (XXII-1)

Compound (XXIV)

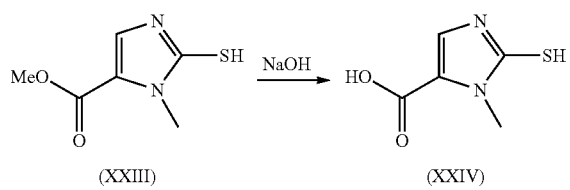

428 g (2.49 mol) of the commercially available compound (XXIII) were stirred in 2.81 of 3 M aqueous sodium hydroxide solution at 15° C. for 30 min. Using 6 M hydrochloride acid, the pH was then adjusted to 1-2 and the precipitate was filtered off with suction. Drying gave 363 g of the compound (XXIV).

1H-NMR (400 MHz, CD$_3$OD): δ=3.82 (s, 3H), 7.58 (s, 1H)

Compound (XXV)

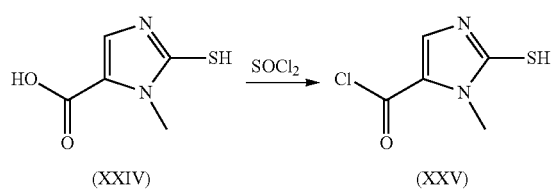

400 g (2.53 mol) of the compound (XXIV) were initially charged in 3.21 of dichloromethane and 30 ml of dimethylformamide. 1.21 of thionyl chloride were added dropwise, and the mixture was then stirred at 50° C. for 2 hours. The reaction mixture was concentrated under reduced pressure. This gave 580 g of crude product as a solid which was directly used for the next reaction.

Compound (XXII-1)

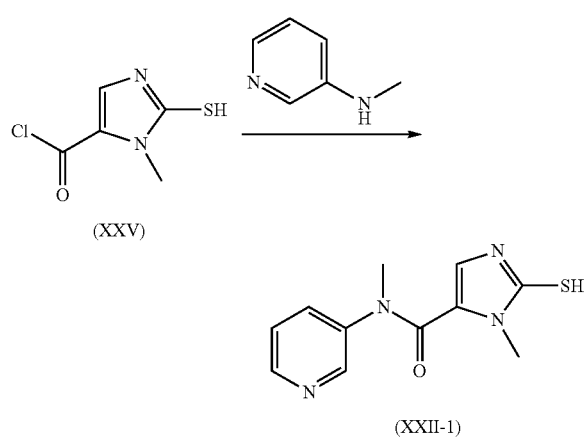

106 g (601 mmol) of the compound (XXV) (1.3 eq.) and 50 g (462 mmol) of 3-methylaminopyridine (1 eq.) were stirred in 750 ml of pyridine at 90° C. for 1 h. The reaction mixture was then concentrated under reduced pressure and the residue was purified on silica gel using a dichloromethane/methanol gradient from 100:1 to 5:1. This gave 67.3 g of the compound (XXII-1).

$^1$H-NMR (DMSO-d6, 400 MHz); δ=3.43 (s, 3H), 3.61 (s, 3H), 6.76 (s, 1H), 7.81-7.84 (m, 1H), 8.33 (d, 1H), 8.67 (d, 1H), 8.91 (d, 1H).

Process G

Example (I-A-43)

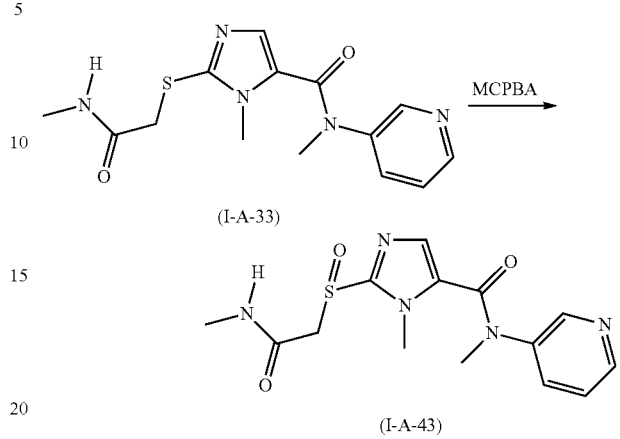

0.18 g (0.564 mmol) of the compound (I-A-33) were dissolved in 30 ml of dichloromethane, and 321 mg (2.82 mmol) of trifluoroacetic acid and 243 mg (1.41 mmol) of 3-chloroperoxybenzoic acid were added successively with stirring at 0° C. The reaction mixture was concentrated. Chromatography on silica gel using an ethyl acetate/methanol gradient gave 62 mg of the target compound (I-A-43).

Analysis see Table 2

Example (I-A-83)

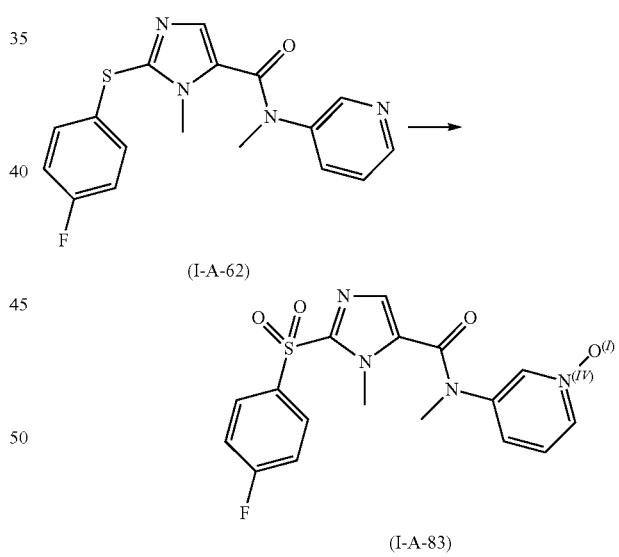

0.100 g (0.29 mmol) of the compound (I-A-62) was dissolved in 15 ml of dichloromethane, and 5 eq. of trifluoroacetic acid and 2 eq. of 3-chloroperoxybenzoic acid were added successively with stirring. After 24 hours of stirring at room temperature, a further eq. of trifluoroacetic acid was added and the mixture was stirred for another hour and concentrated almost completely, giving, after RP chromatography, 59 mg of the target compound (I-A-83).

Analysis see Table 2

Further compounds of the formula (I) prepared in analogous manner according to processes A to D, F and G are listed in the table below.

TABLE 1

Compounds of the formula (I-A)

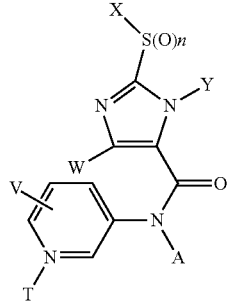

(I-A)

in which the substituents have the meanings given in the table:

| Ex. No. | X | n | W | Y | A | V | T |
|---|---|---|---|---|---|---|---|
| I-A-4 | 2-(4,6-dimethyl)-pyrimidyl- | 0 | H | CH$_3$ | H | H | electron pair |
| I-A-5 | n-butyl- | 0 | H | CH$_3$ | CH$_3$ | H | electron pair |
| I-A-6 | n-pentyl- | 0 | H | CH$_3$ | CH$_3$ | H | electron pair |
| I-A-7 | benzyl- | 0 | H | CH$_3$ | CH$_3$ | H | electron pair |
| I-A-8 | methyl | 2 | H | CH$_3$ | CH$_3$ | H | electron pair |
| I-A-9 | 3-methylthiophenyl- | 0 | H | CH$_3$ | CH$_3$ | H | electron pair |
| I-A-10 | 2,2,2-trifluoroethyl- | 0 | H | CH$_3$ | CH$_3$ | H | electron pair |
| I-A-11 | phenyl- | 0 | H | CH$_3$ | CH$_3$ | H | electron pair |
| I-A-12 | 4-methylphenyl- | 0 | H | CH$_3$ | CH$_3$ | H | electron pair |
| I-A-13 | 2-pyrimidyl- | 0 | Br | CH$_3$ | CH$_3$ | H | electron pair |
| I-A-14 | ethylthioethyl- | 0 | H | CH$_3$ | CH$_3$ | H | electron pair |
| I-A-15 | 2-pyrimidyl- | 0 | Cl | CH$_3$ | CH$_3$ | H | electron pair |
| I-A-16 | 2-nitrophenyl- | 0 | H | CH$_3$ | CH$_3$ | H | electron pair |
| I-A-17 | cyclohexyl | 0 | H | CH$_3$ | CH$_3$ | H | electron pair |
| I-A-18 | —(CH$_2$)$_2$—O—CH$_3$ | 0 | H | CH$_3$ | CH$_3$ | H | electron pair |
| I-A-19 | isopropyl | 0 | H | CH$_3$ | CH$_3$ | H | electron pair |
| I-A-20 | —(CH$_2$)$_3$—O—CH$_3$ | 0 | H | CH$_3$ | CH$_3$ | H | electron pair |
| I-A-21 | n-propyl | 0 | H | CH$_3$ | CH$_3$ | H | electron pair |
| I-A-22 | —(CH$_2$)$_2$—O—C$_2$H$_5$ | 0 | H | CH$_3$ | CH$_3$ | H | electron pair |
| I-A-23 | —CH$_2$—CO—CH$_3$ | 0 | H | CH$_3$ | CH$_3$ | H | electron pair |
| I-A-24 | —CH$_2$—CO$_2$—C$_2$H$_5$ | 0 | H | CH$_3$ | CH$_3$ | H | electron pair |
| I-A-25 | —CH$_2$—CO$_2$—CH$_3$ | 0 | H | CH$_3$ | CH$_3$ | H | electron pair |
| I-A-26 | —(CH$_2$)$_2$—S—CH$_3$ | 0 | H | CH$_3$ | CH$_3$ | H | electron pair |
| I-A-27 | allyl | 0 | H | CH$_3$ | CH$_3$ | H | electron pair |
| I-A-28 | —CH$_2$—CO—C(CH$_3$)$_3$ | 0 | H | CH$_3$ | CH$_3$ | H | electron pair |
| I-A-29 | —CH$_2$—CO$_2$H | 0 | H | CH$_3$ | CH$_3$ | H | electron pair |
| I-A-30 | propargyl | 0 | H | CH$_3$ | CH$_3$ | H | electron pair |
| I-A-31 | —CH$_2$—CO-cyclo-propyl | 0 | H | CH$_3$ | CH$_3$ | H | electron pair |
| I-A-32 | —CH$_2$—CO—NH$_2$ | 0 | H | CH$_3$ | CH$_3$ | H | electron pair |
| I-A-33 | —CH$_2$—CO—NH—CH$_3$ | 0 | H | CH$_3$ | CH$_3$ | H | electron pair |
| I-A-34 | —CH$_2$—CO—N(CH$_3$)$_2$ | 0 | H | CH$_3$ | CH$_3$ | H | electron pair |
| I-A-35 | 3,3-dimethylallyl | 0 | H | CH$_3$ | CH$_3$ | H | electron pair |
| I-A-36 | ethyl | 0 | H | CH$_3$ | CH$_3$ | H | electron pair |
| I-A-37 | CF$_3$ | 0 | H | CH$_3$ | CH$_3$ | H | electron pair |
| I-A-38 | CHF$_2$ | 0 | H | CH$_3$ | CH$_3$ | H | electron pair |
| I-A-39 | —CH$_2$—CNOCH$_3$—CH$_3$ | 0 | H | CH$_3$ | CH$_3$ | H | electron pair |
| I-A-40 | ethyl | 2 | H | CH$_3$ | CH$_3$ | H | electron pair |
| I-A-41 | ethyl | 0 | H | CH$_3$ | H | H | electron pair |
| I-A-42 | —CH$_2$—CO—NH—CH$_3$ | 2 | H | CH$_3$ | CH$_3$ | H | electron pair |
| I-A-43 | —CH$_2$—CO—NH—CH$_3$ | 1 | H | CH$_3$ | CH$_3$ | H | electron pair |
| I-A-44 | methyl | 0 | H | CH$_3$ | C$_2$H$_5$ | H | electron pair |
| I-A-45 | methyl | 0 | H | CH$_3$ | CH$_3$ | H | electron pair |
| I-A-46 | —CH$_2$—CF$_2$—CF$_2$Cl | 0 | H | CH$_3$ | CH$_3$ | H | electron pair |
| I-A-47 | —CH$_2$—CH$_2$—CF$_3$ | 0 | H | CH$_3$ | CH$_3$ | H | electron pair |
| I-A-48 | —CH$_2$—CH$_2$—CH$_2$F | 0 | H | CH$_3$ | CH$_3$ | H | electron pair |
| I-A-49 | —CH$_2$—CF$_2$—CHF$_2$ | 0 | H | CH$_3$ | CH$_3$ | H | electron pair |
| I-A-50 | —(CH$_2$)$_2$—S—CH$_2$—CF$_3$ | 0 | H | CH$_3$ | CH$_3$ | H | electron pair |
| I-A-51 | 4-tetrahydro-thiopyranyl | 0 | H | CH$_3$ | CH$_3$ | H | electron pair |
| I-A-52 | 4-tetrahydro-pyranyl | 0 | H | CH$_3$ | CH$_3$ | H | electron pair |
| I-A-53 | —(CH$_2$)$_2$—i C$_3$H$_7$ | 0 | H | CH$_3$ | CH$_3$ | H | electron pair |
| I-A-54 | 3-oxetanyl | 0 | H | CH$_3$ | CH$_3$ | H | electron pair |
| I-A-55 | 5-oxa-[3.3.0]-bicycloheptane | 0 | H | CH$_3$ | CH$_3$ | H | electron pair |
| I-A-56 | 2,4,5-trichloro-phenyl- | 0 | H | CH$_3$ | CH$_3$ | H | electron pair |
| I-A-57 | 4-chlorophenyl- | 0 | H | CH$_3$ | CH$_3$ | H | electron pair |
| I-A-58 | 4-methoxyphenyl- | 0 | H | CH$_3$ | CH$_3$ | H | electron pair |
| I-A-59 | 4-dimethylamino-phenyl- | 0 | H | CH$_3$ | CH$_3$ | H | electron pair |
| I-A-60 | 2,5-dichloro-phenyl- | 0 | H | CH$_3$ | CH$_3$ | H | electron pair |

TABLE 1-continued

Compounds of the formula (I-A)

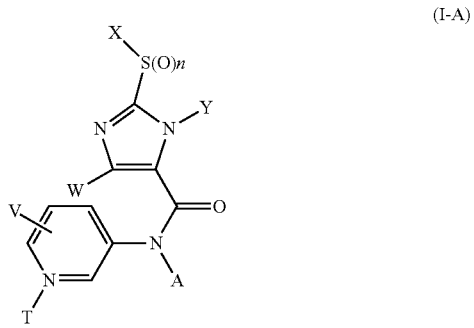

(I-A)

in which the substituents have the meanings given in the table:

| Ex. No. | X | n | W | Y | A | V | T |
|---|---|---|---|---|---|---|---|
| I-A-61 | 3-trifluoromethyl-phenyl- | 0 | H | CH₃ | CH₃ | H | electron pair |
| I-A-62 | 4-fluorophenyl- | 0 | H | CH₃ | CH₃ | H | electron pair |
| I-A-63 | 4-tert-butylphenyl- | 0 | H | CH₃ | CH₃ | H | electron pair |
| I-A-64 | 4-chloro-3-trifluoromethyl-phenyl- | 0 | H | CH₃ | CH₃ | H | electron pair |
| I-A-65 | 2-pyridyl | 0 | H | CH₃ | CH₃ | H | electron pair |
| I-A-66 | 3-chlorophenyl- | 0 | H | CH₃ | CH₃ | H | electron pair |
| I-A-67 | 2-dimethylamino-carbamoylphenyl- | 0 | H | CH₃ | CH₃ | H | electron pair |
| I-A-68 | 3-nitrophenyl- | 0 | H | CH₃ | CH₃ | H | electron pair |
| I-A-69 | 2-dimethylamino-sulphonyl-phenyl- | 0 | H | CH₃ | CH₃ | H | electron pair |
| I-A-70 | 5-(2-chloro)-pyridyl- | 0 | H | CH₃ | CH₃ | H | electron pair |
| I-A-71 | 2-fluorophenyl- | 0 | H | CH₃ | CH₃ | H | electron pair |
| I-A-72 | 2-methoxyphenyl- | 0 | H | CH₃ | CH₃ | H | electron pair |
| I-A-73 | 3-chlorophenyl- | 2 | H | CH₃ | CH₃ | H | electron pair |
| I-A-74 | 3-chlorophenyl- | 1 | H | CH₃ | CH₃ | H | electron pair |
| I-A-75 | 4-tert-butylphenyl- | 1 | H | CH₃ | CH₃ | H | electron pair |
| I-A-76 | 4-tert-butylphenyl- | 2 | H | CH₃ | CH₃ | H | electron pair |
| I-A-77 | 3,5-dichloro- | 1 | H | CH₃ | CH₃ | H | electron pair |
| I-A-78 | 3,5-dichloro- | 2 | H | CH₃ | CH₃ | H | electron pair |
| I-A-79 | 4-chloro-3-trifluoromethyl-phenyl- | 1 | H | CH₃ | CH₃ | H | electron pair |
| I-A-80 | 4-chloro-3-trifluoromethyl-phenyl- | 2 | H | CH₃ | CH₃ | H | electron pair |
| I-A-81 | 4-methoxyphenyl- | 2 | H | CH₃ | CH₃ | H | electron pair |
| I-A-82 | 4-fluorophenyl- | 2 | H | CH₃ | CH₃ | H | electron pair |
| I-A-83 | 4-fluorophenyl- | 2 | H | CH₃ | CH₃ | H | oxygen |
| I-A-84 | 4-fluorophenyl- | 1 | H | CH₃ | CH₃ | H | electron pair |
| I-A-85 | 2-pyridyl- | 2 | H | CH₃ | CH₃ | H | electron pair |
| I-A-86 | 2-pyridyl- | 1 | H | CH₃ | CH₃ | H | electron pair |
| I-A-87 | phenyl- | 1 | H | CH₃ | CH₃ | H | electron pair |
| I-A-88 | phenyl- | 2 | H | CH₃ | CH₃ | H | electron pair |
| I-A-89 | 4-nitrophenyl- | 1 | H | CH₃ | CH₃ | H | electron pair |
| I-A-90 | 4-nitrophenyl- | 2 | H | CH₃ | CH₃ | H | electron pair |
| I-A-91 | 3-dimethylamino-carbamoylphenyl- | 1 | H | CH₃ | CH₃ | H | electron pair |
| I-A-92 | 2-dimethylamino-carbamoylphenyl- | 2 | H | CH₃ | CH₃ | H | electron pair |
| I-A-93 | 4-methoxyphenyl- | 1 | H | CH₃ | CH₃ | H | electron pair |
| I-A-94 | 2-(5-fluoro)pyridyl | 0 | H | CH₃ | CH₃ | H | electron pair |
| I-A-95 | 3-trifluoromethyl-phenyl- | 1 | H | CH₃ | CH₃ | H | oxygen |
| I-A-96 | 3-trifluoromethyl-phenyl- | 1 | H | CH₃ | CH₃ | H | electron pair |
| I-A-97 | 2-pyrimidyl- | 1 | H | CH₃ | CH₃ | H | electron pair |
| I-A-98 | 2-pyrimidyl- | 0 | H | CH₃ | C₂H₅ | H | electron pair |
| I-A-99 | 2-pyrimidyl- | 2 | H | CH₃ | CH₃ | H | electron pair |
| I-A-100 | 2-(4-trifluoro-methyl)pyrimidyl- | 0 | H | CH₃ | CH₃ | H | electron pair |
| I-A-101 | 2-(4-methyl)-pyrimidyl- | 0 | H | CH₃ | CH₃ | H | electron pair |
| I-A-102 | 2-(4,6-dimethoxy)-pyrimidyl- | 0 | H | CH₃ | CH₃ | H | electron pair |
| I-A-103 | 2-(4,5-dimethyl)-pyrimidyl- | 0 | H | CH₃ | CH₃ | H | electron pair |
| I-A-104 | 2-(5-methyl)-pyrimidyl- | 0 | H | CH₃ | CH₃ | H | electron pair |
| I-A-105 | 2-(5-trifluoro-methyl)-pyrimidyl- | 0 | H | CH₃ | CH₃ | H | electron pair |
| I-A-106 | 2-(4-methoxy)-pyrimidyl- | 0 | H | CH₃ | CH₃ | H | electron pair |
| I-A-107 | 2-(5-fluoro)-pyrimidyl- | 0 | H | CH₃ | CH₃ | H | electron pair |
| I-A-108 | 2-(6-methyl)-pyridyl- | 0 | H | CH₃ | CH₃ | H | electron pair |
| I-A-109 | 2-(5-methyl)-pyridyl- | 0 | H | CH₃ | CH₃ | H | electron pair |
| I-A-110 | 2-(3-trifluoro-methyl)-pyridyl- | 0 | H | CH₃ | CH₃ | H | electron pair |
| I-A-111 | 2-pyrimidyl- | 0 | H | Benzyl | CH₃ | H | electron pair |
| I-A-112 | —CH₂-2-pyrimidyl- | 0 | H | CH₃ | CH₃ | H | electron pair |
| I-A-113 | —CH₂-2-pyrazinyl- | 0 | H | CH₃ | CH₃ | H | electron pair |
| I-A-114 | —CH₂-5-(1-methyl)imidazolyl | 0 | H | CH₃ | CH₃ | H | electron pair |
| I-A-115 | —CH₂-3-(1-methyl)pyrazolyl | 0 | H | CH₃ | CH₃ | H | electron pair |
| I-A-116 | —CH₂-4-pyridyl- | 0 | H | CH₃ | CH₃ | H | electron pair |
| I-A-117 | —CH₂-2-pyridyl- | 0 | H | CH₃ | CH₃ | H | electron pair |

TABLE 1-continued

Compounds of the formula (I-A)

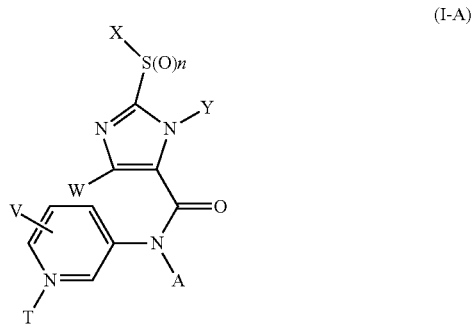

(I-A)

in which the substituents have the meanings given in the table:

| Ex. No. | X | n | W | Y | A | V | T |
|---|---|---|---|---|---|---|---|
| I-A-118 | —$CH_2$-2-(1-methyl)imidazolyl | 0 | H | $CH_3$ | $CH_3$ | H | electron pair |
| I-A-119 | —$CH_2$-3-pyridyl- | 0 | H | $CH_3$ | $CH_3$ | H | electron pair |
| I-A-120 | —$CH_2$-2-furanyl- | 0 | H | $CH_3$ | $CH_3$ | H | electron pair |
| I-A-121 | 3,4-dichlorobenzyl | 0 | H | $CH_3$ | $CH_3$ | H | electron pair |
| I-A-122 | —$CH_2$-5-(2-chloro)-pyridyl- | 0 | H | $CH_3$ | $CH_3$ | H | electron pair |
| I-A-123 | 2,6-difluorobenzyl | 0 | H | $CH_3$ | $CH_3$ | H | electron pair |
| I-A-124 | 2-fluoro-6-methoxybenzyl | 0 | H | $CH_3$ | $CH_3$ | H | electron pair |
| I-A-125 | 2,6-dichlorobenzyl | 0 | H | $CH_3$ | $CH_3$ | H | electron pair |
| I-A-126 | 2-chloro-6-trifluoromethyl-benzyl | 0 | H | $CH_3$ | $CH_3$ | H | electron pair |
| I-A-127 | 2-chloro-6-fluoro-benzyl | 0 | H | $CH_3$ | $CH_3$ | H | electron pair |
| I-A-128 | —$CH_2$-2-(4,6-dimethoxy)-pyrimidyl | 0 | H | $CH_3$ | $CH_3$ | H | electron pair |
| I-A-129 | 2,6-dimethyl-benzyl | 0 | H | $CH_3$ | $CH_3$ | H | electron pair |
| I-A-130 | benzyl | 1 | H | $CH_3$ | $CH_3$ | H | electron pair |
| I-A-131 | —$CH_2$-1-(3-nitro-5-methyl)-pyrazolyl | 0 | H | $CH_3$ | $CH_3$ | H | electron pair |
| I-A-132 | —$CH_2$—CO—NH-cyclopropyl | 0 | H | $CH_3$ | $CH_3$ | H | electron pair |
| I-A-133 | —$CH_2$—CONH—C($CH_3$)$_2$—$CO_2CH_3$ | 0 | H | $CH_3$ | $CH_3$ | H | electron pair |
| I-A-134 | 2-(1-methyl)-benzimidazolyl- | 0 | H | $CH_3$ | $CH_3$ | H | electron pair |
| I-A-135 | 2-(5-methyl)-oxadiazolyl- | 0 | H | $CH_3$ | $CH_3$ | H | electron pair |
| I-A-136 | 2-[3-methyl-6-(trifluoromethyl)-imidazo[4.5]-pyridinyl- | 0 | H | $CH_3$ | $CH_3$ | H | electron pair |
| I-A-137 | 3-[4-ethyl-5-(trifluoromethyl)]-1,2,4-triazolyl- | 0 | H | $CH_3$ | $CH_3$ | H | electron pair |
| I-A-138 | 3-[4-methyl-5-(trifluoromethyl)]-1,2,4-triazolyl- | 0 | H | $CH_3$ | $CH_3$ | H | electron pair |
| I-A-139 | 3-[4-methyl-5-(difluoromethyl)]-1,2,4-triazolyl- | 0 | H | $CH_3$ | $CH_3$ | H | electron pair |
| I-A-140 | 2-(5-phenyl)-1.3.4-thiadiazolyl- | 0 | H | $CH_3$ | $CH_3$ | H | electron pair |
| I-A-141 | 2-(1-methyl-5-phenyl)imidazolyl- | 0 | H | $CH_3$ | $CH_3$ | H | electron pair |
| I-A-142 | 2-(4,5-dimethyl)-oxazolyl- | 0 | H | $CH_3$ | $CH_3$ | H | electron pair |
| I-A-143 | 2-(1-methyl-5-methoxycarbonyl)-imidazolyl | 0 | H | $CH_3$ | $CH_3$ | H | electron pair |
| I-A-144 | 2-(1-methyl)-imidazolyl- | 0 | H | $CH_3$ | $CH_3$ | H | electron pair |
| I-A-145 | 1,2-ethanediyl- | 0 | H | $CH_3$ | $CH_3$ | H | electron pair |
| I-A-146 | 2-pyrimidyl- | 0 | H | $C_2H_5$ | $CH_3$ | H | electron pair |

Table 2

Analytical data for the compounds listed in Table 1

From Example 1-A-17 onwards, the NMR data were compiled using the NMR peak list method.

The 1H NMR data of selected examples are stated in the form of 1H NMR peak lists. For each signal peak, first the δ value in ppm and then the signal intensity in round brackets are listed. The pairs of δ value-signal intensity numbers for different signal peaks are listed with separation from one another by semicolons.

The peak list for one example therefore has the form of:

δ1 (intensity 1); δ2 (intensity 2); . . . ; δi (intensity i); . . . ; δn (intensity n)

The intensity of sharp signals correlates with the height of the signals in a printed example of an NMR spectrum in cm and shows the true ratios of the signal intensities. In the case of broad signals, several peaks or the middle of the signal and the relative intensity thereof may be shown in comparison to the most intense signal in the spectrum.

Calibration of the chemical shift of 1H NMR spectra is accomplished using tetramethylsilane and/or the chemical shift of the solvent, particularly in the case of spectra which are measured in DMSO. Therefore, the tetramethysilane peak may but need not occur in NMR peak lists.

The lists of the 1H NMR peaks are similar to the conventional 1H NMR printouts and thus usually contain all peaks listed in a conventional NMR interpretation.

In addition, like conventional 1H NMR printouts, they may show solvent signals, signals of stereoisomers of the target compounds which likewise form part of the subject-matter of the invention, and/or peaks of impurities.

In the reporting of compound signals within the delta range of solvents and/or water, our lists of 1H NMR peaks show the standard solvent peaks, for example peaks of DMSO in DMSO-D6, and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of a particular preparation process. Their peaks can thus help in this case to identify reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the peak picking in question in conventional 1H NMR interpretation.

Further details of 1H NMR peak lists can be found in the Research Disclosure Database Number 564025.

| Ex. No. | logP[a] | logP[b] | 1H-NMR; δ (ppm) |
|---|---|---|---|
| I-A-4 | 1.55 | 1.97 | $^1$H-NMR (CD$_3$CN, 400 MHz); δ = 2.31 (s, 6H), 3.90 (s, 3H), 6.92 (s, 1H), 7.33-7.37 (m, 1H), 7.85 (s, 1H) 8.12-8.15 (m, 1H), 8.33-8.34 (d, 1H), 8.77 (br, 1H), 8.826-8.831 (d, 1H) ppm. |
| I-A-5 | 1.67 | 1.99 | $^1$H-NMR (CD$_3$CN, 400 MHz); δ = 0.87 (t, 3H), 1.34-1.42 (m, 2H), 1.53-1.61 (m, 2H), 3.02-3.06 (m, 2H), 3.38 (s 3H), 3.70 (s, 3H), 6.24 (s, 1H), 7.35-7.38 (m, 1H), 7.66-7.69 (m, 1H) 8.407-8.413 (d, 1H), 8.45-8.47 (m, 1H) ppm. |
| I-A-6 | 2.03 | 2.33 | $^1$H-NMR (CD$_3$CN, 400 MHz); δ = 0.86 (t, 3H), 1.26-1.36 (m, 4H), 1.57-1.61 (m, 2H), 3.02-3.06 (m, 2H), 3.38 (s 3H), 3.71 (s, 3H), 6.25 (s, 1H), 7.35-7.38 (m, 1H), 7.66-7.69 (m, 1H) 8.41-8.42 (d, 1H), 8.45-8.47 (m, 1H) ppm. |
| I-A-7 | 1.68 | 1.91 | $^1$H-NMR (CD$_3$CN, 400 MHz); δ = 3.37 (s 3H), 3.53 (s, 3H), 4.18 (s, 2H), 6.28 (s, 1H), 7.16-7.18 (m, 2H), 7.25-7.30 (m, 3H), 7.37-7.39 (m, 1H), 7.66-7.68 (m, 1H) 8.380-8.384 (m, 1H), 8.47-8.48 (m, 1H) ppm. |
| I-A-8 | 0.45 | 0.67 | $^1$H-NMR (CD$_3$CN, 400 MHz); δ = 3.25 (s 3H), 3.42 (s, 3H), 4.05 (s, 3H), 6.45 (s, 1H), 7.34-7.39 (m, 1H), 7.68-7.71 (m, 1H), 8.435-8.441 (d, 1H), 8.47-8.49 (m, 1H) ppm. |
| I-A-9 | 2.0 | 2.12 | $^1$H-NMR (d6-DMSO, 400 MHz); δ = 2.41 (s, 3H), 3H), 3.75 (s, 3H), 6.48 (s, 1H), 6.76 (d, 1H), 6.92-6.93 (m, 1H), 7.12-7.14 (m, 1H), 7.25 (t, 1H), 7.43-7.46 (m, 1H), 7.84-7.87 (m, 1H), 8.48-8.53 (m, 2H) ppm. |
| I-A-10 | 1.41 | 1.54 | $^1$H-NMR (CD$_3$CN, 400 MHz); δ = 3.39 (s 3H), 3.76 (s, 3H), 3.80-3.89 (q, 2H), 6.29 (s, 1H), 7.34-7.38 (m, 1H), 7.66-7.69 (m, 1H), 8.406-8.411 (d, 1H), 8.46-8.47 (m, 1H) ppm. |
| I-A-11 | 1.55 | 1.75 | $^1$H-NMR (d$_6$-DMSO, 400 MHz); δ = 3.39 (s, 3H), 3.73 (s, 3H), 6.48 (s, 1H), 7.00-7.16 (m, 2H), 7.26-7.28 (m, 1H), 7.31-7.35 (m, 2H), 7.43-7.46 (m, 1H), 7.83-7.86 (m, 1H), 8.48-8.52 (m, 2 H) ppm |
| I-A-12 | 1.89 | 2.03 | $^1$H-NMR (d$_6$-DMSO, 400 MHz); δ = 2.27 (s, 3H), 3.38 (s, 3H), 3.72 (s, 3H), 6.42 (s, 1H), 7.05-7.07 (m, 4H), 7.42-7.45 (m, 1H), 7.81-7.85 (m, 1H), 8.47-8.50 (m, 2 H) ppm |
| I-A-13 | 1.25 | 1.31 | $^1$H-NMR (d$_6$-DMSO, 400 MHz); δ = 3.46 (s, 3H), 3.68 (s, 3H), 7.34-7.43 (m, 2H), 7.75-7.77 (m, 1H), 8.44-8.47 (m, 2H), 8.66-8.68 (m, 2 H) ppm |
| I-A-14 | 1.61 | 1.87 | $^1$H-NMR (d$_6$-DMSO, 400 MHz); δ = 1.10-1.14 (t, 3H), 2.47-2.50 (m, 2H), 2.71-2.73 (m, 2H), 3.22-3.26 (m, 2H), 3.36 (s, 3H), 3.67 (s, 3H), 6.24 (s, 1H), 7.42-7.45 (m, 1H), 7.82-7.85 (m, 1H), 8.46-8.50 (m, 2H) ppm |
| I-A-15 | 1.24 | 1.34 | $^1$H-NMR (d$_6$-DMSO, 400 MHz); δ = 3.45 (s, 3H), 3.70 (s, 3H), 7.35-7.43 (m, 2H), 7.76-7.78 (m, 1H), 8.44-8.47 (m, 2H), 8.67-8.68 (m, 2H) ppm |
| I-A-16 | 1.68 | 1.78 | $^1$H-NMR (d$_6$-DMSO, 400 MHz); δ = 3.42 (s, 3H), 3.72 (s, 3H), 6.26 (d, 1H), 6.66 (s, 1H), 7.47-7.51 (m, 2H), 7.61-7.65 (m, 1H), 7.87-7.90 (m, 1H), 8.30-8.32 (m, 1H), 8.51-8.55 (m, 2 H) ppm |
| I-A-17 | 1.89 | 2.26 | $^1$H-NMR(400.0 MHz. d$_6$-DMSO): δ = 8.491(2.5); 8.485(2.6); 8.477(1.9); 8.474(1.9); 8.465(1.8); 8.462(1.8); 7.844(0.9); 7.841(1.2); 7.838(1.2); 7.834(1.0); 7.824(1.1); 7.820(1.3); 7.818(1.3); 7.814(1.1); 7.450(1.3); 7.438(1.3); 7.430(1.3); 7.418(1.2); 6.283(4.0); 5.754(1.4); 3.689(16.0); 3.431(0.5); 3.406(0.9); 3.397(0.7); 3.364(15.4); 3.321(4.2); 2.506(23.8); 2.502(30.5); 2.498(23.9); 1.885(1.2); 1.858(1.6); 1.669(1.3); 1.662(1.2); 1.650(1.3); 1.642(1.2); 1.539(0.6); 1.527(0.6); 1.512(0.7); 1.394(0.4); 1.388(0.4); 1.362(1.2); 1.335(1.9); 1.301(1.7); 1.270(1.3); 1.241(1.2); 1.211(0.6); 1.186(0.5); 0.000(27.0) |
| I-A-18 | 0.76 | 1.14 | $^1$H-NMR(400.0 MHz. d$_6$-DMSO): δ = 8.502(1.8); 8.495(1.8); 8.484(1.2); 8.481(1.3); 8.473(1.2); 8.469(1.3); 7.857(0.6); 7.854(0.8); 7.851(0.8); 7.848(0.7); 7.837(0.7); 7.833(0.8); 7.831(0.9); 7.827(0.7); 7.460(1.0); 7.448(1.0); 7.440(0.9); 7.428(0.9); 6.230(3.2); 3.677(12.9); 3.504(1.7); 3.488(4.1); 3.473(2.2); 3.361(12.2); 3.325(12.0); 3.240(2.1); 3.224(3.9); 3.209(16.0); 3.166(0.8); 2.525(0.3); 2.508(16.1); 2.503(21.6); 2.499(16.3); 0.008(0.4); 0.000(11.1); −0.008(0.5) |

| Ex. No. | logP[a] | logP[b] | 1H-NMR; δ (ppm) |
|---|---|---|---|
| I-A-19 | 1.23 | 1.53 | ¹H-NMR(400.0 MHz. $d_6$-DMSO): δ = 8.491(2.1); 8.485(2.2); 8.478(1.6); 8.474(1.7); 8.466(1.6); 8.462(1.6); 7.847(0.8); 7.843(1.0); 7.841(0.9); 7.837(0.8); 7.827(1.0); 7.823(1.1); 7.820(1.1); 7.817(0.9); 7.452(1.1); 7.440(1.2); 7.431(1.1); 7.419(1.0); 6.295(3.7); 3.702(15.9); 3.597(0.4); 3.580(1.1); 3.563(1.5); 3.547(1.1); 3.530(0.5); 3.368(14.9); 3.318(18.5); 2.510(12.4); 2.506(23.6); 2.502(30.4); 2.497(22.5); 1.244(16.0); 1.227(15.8); 0.000(5.4) |
| I-A-20 | 1.04 | 1.35 | ¹H-NMR(400.0 MHz. $d_6$-DMSO): δ = 8.502(1.9); 8.496(1.9); 8.483(1.4); 8.479(1.4); 8.471(1.4); 8.467(1.4); 7.854(0.7); 7.850(0.8); 7.848(0.8); 7.844(0.7); 7.834(0.8); 7.830(0.9); 7.827(0.9); 7.824(0.8); 7.458(1.0); 7.446(1.0); 7.437(1.0); 7.426(0.9); 6.234(3.4); 3.679(14.0); 3.361(14.6); 3.344(4.7); 3.325(7.3); 3.218(0.4); 3.187(16.0); 3.080(1.9); 3.063(3.1); 3.044(2.0); 2.512(7.4); 2.507(14.8); 2.503(19.6); 2.499(14.4); 2.494(7.3); 1.817(0.5); 1.801(1.5); 1.783(2.0); 1.766(1.4); 1.750(0.5); 0.000(8.5); −0.008(0.4) |
| I-A-21 | 1.31 | 1.60 | ¹H-NMR(400.0 MHz. $d_6$-DMSO): δ = 8.500(2.2); 8.494(2.3); 8.483(1.6); 8.480(1.7); 8.471(1.6); 8.468(1.6); 7.852(0.8); 7.848(1.0); 7.846(1.0); 7.842(0.8); 7.831(0.9); 7.828(1.1); 7.825(1.1); 7.822(0.9); 7.457(1.3); 7.445(1.3); 7.437(1.2); 7.425(1.1); 6.230(4.0); 3.677(16.0); 3.361(15.2); 3.320(9.3); 3.034(2.5); 3.016(4.2); 2.999(2.6); 2.687(0.4); 2.674(0.5); 2.507(13.7); 2.502(18.1); 2.498(13.6); 1.596(1.4); 1.578(2.7); 1.560(2.7); 1.542(1.5); 1.524(0.3); 0.922(4.2); 0.904(8.3); 0.885(3.8); 0.000(7.6); −0.008(0.3) |
| I-A-22 | 1.04 | 1.41 | ¹H-NMR(400.0 MHz. $d_6$-DMSO): δ = 8.499(2.2); 8.493(2.2); 8.484(1.6); 8.480(1.6); 8.472(1.6); 8.468(1.6); 7.853(0.8); 7.849(1.0); 7.846(1.0); 7.843(0.8); 7.832(0.9); 7.829(1.1); 7.826(1.1); 7.822(0.9); 7.458(1.2); 7.446(1.2); 7.438(1.1); 7.426(1.0); 6.232(4.0); 3.680(16.0); 3.537(2.1); 3.521(4.8); 3.506(2.5); 3.417(1.4); 3.399(4.4); 3.382(4.5); 3.361(15.2); 3.311(8.2); 3.229(2.4); 3.213(4.6); 3.197(2.0); 2.511(7.8); 2.506(15.6); 2.502(20.5); 2.498(14.9); 2.493(7.4); 1.080(4.5); 1.063(8.9); 1.045(4.3); 0.008(0.4); 0.000(10.1); −0.008(0.4) |
| I-A-23 | 0.67; 0.71 | | ¹H-NMR(400.0 MHz. CD3CN): δ = 8.464(1.6); 8.452(1.6); 8.411(2.2); 8.404(2.3); 7.680(0.8); 7.676(1.1); 7.672(0.8); 7.660(0.9); 7.655(1.2); 7.651(0.9); 7.376(1.3); 7.364(1.3); 7.355(1.2); 7.343(1.2); 6.185(4.3); 3.961(10.2); 3.726(16.0); 3.371(16.0); 2.166(20.2); 1.962(0.4); 1.956(0.5); 1.950(2.5); 1.944(4.5); 1.938(6.1); 1.932(4.2); 1.926(2.1); 0.007(0.4); 0.000(10.5); −0.001(10.5); −0.008(0.5) |
| I-A-24 | 1.20 | 1.34 | ¹H-NMR(400.0 MHz. CD3CN): δ = 8.468(1.4); 8.464(1.5); 8.456(1.5); 8.452(1.5); 8.412(2.0); 8.406(2.1); 7.687(0.8); 7.683(1.0); 7.680(0.9); 7.677(0.8); 7.666(1.0); 7.662(1.1); 7.660(1.1); 7.656(0.9); 7.377(1.2); 7.365(1.2); 7.357(1.1); 7.345(1.0); 6.224(3.9); 4.102(1.4); 4.084(4.0); 4.067(4.1); 4.049(1.4); 3.820(10.7); 3.738(16.0); 3.375(16.0); 2.502(1.1); 2.182(0.3); 1.957(0.3); 1.951(1.8); 1.945(3.2); 1.939(4.3); 1.932(3.0); 1.926(1.6); 1.174(4.5); 1.156(8.5); 1.138(4.3); 0.000(5.4) |
| I-A-25 | 0.88 | 1.09 | ¹H-NMR(400.0 MHz. CD3CN): δ = 8.471(1.3); 8.468(1.3); 8.459(1.3); 8.456(1.3); 8.411(1.8); 8.405(1.8); 7.688(0.8); 7.684(0.9); 7.682(1.0); 7.678(0.8); 7.668(0.9); 7.664(1.0); 7.661(1.0); 7.658(0.8); 7.380(1.0); 7.368(1.0); 7.360(0.9); 7.348(0.8); 6.220(3.4); 3.836(9.5); 3.734(16.0); 3.692(0.3); 3.665(0.5); 3.660(0.5); 3.623(14.8); 3.432(0.5); 3.389(1.0); 3.377(15.4); 2.500(2.2); 2.135(0.4); 2.126(0.4); 2.118(0.5); 2.112(0.5); 2.105(0.5); 2.099(0.4); 1.962(0.8); 1.950(10.0); 1.944(18.1); 1.938(24.1); 1.932(17.0); 1.926(8.9); 0.008(1.3); 0.000(31.4) |
| I-A-26 | 1.23 | 1.55 | ¹H-NMR(400.0 MHz. $d_6$-DMSO): δ = 8.500(1.9); 8.494(1.9); 8.483(1.4); 8.480(1.4); 8.471(1.4); 8.468(1.4); 7.852(0.7); 7.848(0.9); 7.845(0.8); 7.842(0.7); 7.831(0.8); 7.828(0.9); 7.825(0.9); 7.821(0.8); 7.456(1.0); 7.445(1.0); 7.436(1.0); 7.424(0.9); 6.251(3.6); 3.677(14.4); 3.363(13.4); 3.311(7.4); 3.284(1.9); 3.270(1.5); 3.266(2.2); 3.260(1.5); 3.246(2.1); 3.178(0.4); 3.164(0.4); 2.711(2.2); 2.697(1.5); 2.691(2.5); 2.689(2.4); 2.673(2.1); 2.511(4.3); 2.506(8.7); 2.502(11.5); 2.497(8.4); 2.493(4.2); 2.041(16.0); 0.000(2.2) |

-continued

| Ex. No. | logP[a] | logP[b] | 1H-NMR; δ (ppm) |
|---|---|---|---|
| I-A-27 | 1.08; 1.11 | 1.40 | ¹H-NMR(400.0 MHz, CD3CN): δ = 8.463(1.4); 8.460(1.5); 8.451(1.5); 8.448(1.5); 8.400(2.0); 8.394(2.1); 7.673(0.8); 7.669(1.0); 7.666(1.0); 7.663(0.8); 7.652(0.9); 7.648(1.1); 7.646(1.1); 7.642(0.9); 7.374(1.2); 7.362(1.2); 7.353(1.1); 7.342(1.0); 6.264(3.9); 5.911(0.6); 5.904(0.3); 5.893(0.3); 5.886(0.9); 5.869(1.0); 5.861(0.4); 5.851(0.4); 5.844(0.7); 5.826(0.3); 5.096(1.3); 5.093(1.3); 5.054(1.2); 5.051(1.2); 5.026(1.4); 5.024(1.4); 5.001(1.3); 4.999(1.4); 3.725(16.0); 3.658(3.4); 3.641(3.3); 3.379(16.0); 2.166(6.6); 1.957(0.7); 1.951(3.2); 1.945(5.8); 1.939(7.6); 1.933(5.3); 1.926(2.8); 0.000(7.0) |
| I-A-28 | 1.53 | 1.78 | ¹H-NMR(400.0 MHz, CD3CN): δ = 8.463(0.5); 8.460(0.6); 8.451(0.5); 8.448(0.6); 8.408(0.7); 8.402(0.7); 8.034(0.4); 7.677(0.4); 7.674(0.4); 7.670(0.4); 7.656(0.4); 7.653(0.5); 7.650(0.4); 7.372(0.5); 7.361(0.5); 7.352(0.4); 7.340(0.4); 6.188(1.3); 4.259(3.6); 3.741(5.4); 3.705(0.8); 3.390(0.9); 3.371(5.4); 2.502(2.4); 2.138(0.3); 1.956(0.7); 1.950(3.2); 1.944(5.9); 1.938(7.9); 1.932(5.8); 1.926(3.1); 1.118(16.0); 1.093(1.3); 0.000(7.5) |
| I-A-29 | 0.28 | 1.05 | ¹H-NMR(601.6 MHz, d₆-DMSO): δ = 8.506(2.0); 8.502(2.0); 8.482(1.4); 8.480(1.4); 8.475(1.5); 8.472(1.4); 8.139(1.2); 7.843(0.9); 7.841(1.0); 7.839(1.0); 7.837(0.8); 7.830(1.0); 7.827(1.1); 7.826(1.1); 7.823(0.9); 7.452(1.1); 7.444(1.1); 7.438(1.0); 7.430(1.0); 6.202(2.4); 5.754(0.6); 3.884(8.4); 3.697(16.0); 3.358(15.5); 3.340(0.4); 3.333(0.4); 3.327(0.4); 2.541(11.6); 2.507(5.9); 2.504(11.9); 2.501(16.0); 2.498(11.6); 2.495(5.5) |
| I-A-30 | 0.87 | 1.22 | ¹H-NMR(400.0 MHz, CD3CN): δ = 8.469(1.5); 8.466(1.5); 8.457(1.5); 8.454(1.5); 8.412(2.0); 8.406(2.0); 7.689(0.8); 7.685(1.0); 7.682(1.0); 7.679(0.8); 7.668(1.0); 7.665(1.1); 7.662(1.1); 7.658(0.9); 7.380(1.2); 7.379(1.1); 7.368(1.2); 7.367(1.1); 7.360(1.1); 7.359(1.0); 7.348(1.0); 7.347(1.0); 6.302(3.7); 3.781(6.1); 3.775(6.1); 3.757(16.0); 3.386(16.0); 2.466(1.4); 2.459(2.6); 2.453(1.3); 2.170(1.7); 1.957(0.4); 1.952(1.9); 1.946(3.4); 1.939(4.5); 1.933(3.1); 1.927(1.6); 0.000(2.7) |
| I-A-31 | 0.97 | 1.28 | ¹H-NMR(400.0 MHz, CD3CN): δ = 8.466(1.3); 8.463(1.4); 8.455(1.3); 8.451(1.4); 8.404(1.8); 8.398(1.9); 7.682(0.7); 7.678(0.9); 7.676(0.9); 7.672(0.8); 7.661(0.9); 7.658(1.0); 7.655(1.0); 7.651(0.8); 7.378(1.1); 7.366(1.1); 7.357(1.0); 7.345(0.9); 6.202(3.5); 4.107(10.4); 3.737(15.9); 3.384(0.4); 3.373(16.0); 2.354(0.4); 2.129(45.1); 2.096(1.5); 2.085(0.6); 2.078(0.7); 2.066(0.4); 1.963(3.4); 1.957(8.8); 1.951(47.5); 1.945(87.0); 1.939(117.5); 1.933(82.7); 1.927(43.6); 1.774(0.5); 1.767(0.7); 1.761(0.5); 0.901(1.0); 0.893(3.1); 0.875(5.6); 0.864(3.5); 0.856(0.9); 0.008(2.1); 0.000(65.6) |
| I-A-32 | 0.11 | 0.50 | ¹H-NMR(400.0 MHz, CD3CN): δ = 8.475(1.5); 8.472(1.6); 8.463(1.6); 8.460(1.6); 8.418(2.1); 8.412(2.2); 7.695(1.0); 7.690(0.8); 7.673(1.1); 7.388(1.2); 7.376(1.2); 7.368(1.1); 7.356(1.1); 6.258(3.1); 3.734(10.9); 3.654(9.4); 3.383(16.0); 3.280(0.7); 3.269(0.7); 2.149(58.1); 2.119(0.5); 2.113(0.6); 2.106(0.7); 2.101(0.5); 1.963(2.7); 1.957(7.2); 1.951(35.9); 1.945(64.9); 1.939(86.7); 1.933(60.5); 1.927(31.8); 1.774(0.4); 1.768(0.5); 1.762(0.4); 0.007(1.3); 0.000(34.8) |
| I-A-33 | 0.33 | 0.62 | ¹H-NMR(600.1 MHz, CD3CN): δ = 8.472(1.1); 8.470(1.1); 8.464(1.2); 8.462(1.1); 8.4222(1.4); 8.4216(1.4); 8.418(1.5); 7.691(0.7); 7.689(0.8); 7.687(0.8); 7.685(0.7); 7.678(0.7); 7.675(0.8); 7.673(0.8); 7.671(0.7); 7.382(0.9); 7.381(0.9); 7.374(0.9); 7.373(0.9); 7.368(0.9); 7.367(0.8); 7.360(0.8); 7.359(0.8); 6.245(2.1); 3.719(16.0); 3.652(7.8); 3.380(15.5); 2.613(6.4); 2.605(6.4); 2.195(14.1); 1.949(1.7); 1.945(3.1); 1.941(4.5); 1.937(3.0); 1.932(1.5) |
| I-A-34 | 0.59 | 0.81 | ¹H-NMR(400.0 MHz, CD3CN): δ = 8.464(1.6); 8.453(1.6); 8.414(2.2); 8.408(2.3); 7.684(1.1); 7.680(0.9); 7.664(1.2); 7.660(1.0); 7.381(1.3); 7.369(1.3); 7.360(1.2); 7.348(1.1); 6.228(4.1); 4.009(9.2); 3.743(16.0); 3.378(16.0); 3.014(0.4); 2.950(14.7); 2.867(0.4); 2.848(13.5); 2.170(28.7); 1.963(1.0); 1.952(12.6); 1.946(23.5); 1.940(32.2); 1.934(23.6); 1.928(12.9); 0.000(7.7) |

| Ex. No. | logP[a] | logP[b] | 1H-NMR; δ (ppm) |
|---|---|---|---|
| I-A-35 | 1.61 | 1.96 | $^1$H-NMR(400.0 MHz, CD3CN): δ = 8.469(1.3); 8.466(1.4); 8.457(1.4); 8.454(1.4); 8.410(1.9); 8.404(1.9); 7.693(0.8); 7.689(0.9); 7.687(0.9); 7.683(0.7); 7.672(0.9); 7.669(1.1); 7.666(1.1); 7.663(0.8); 7.382(1.1); 7.370(1.1); 7.362(1.1); 7.350(1.0); 6.259(3.6); 5.277(0.5); 5.273(0.4); 5.260(0.8); 5.256(0.9); 5.253(0.8); 5.240(0.4); 5.237(0.5); 3.718(14.7); 3.694(0.5); 3.625(2.9); 3.605(2.8); 3.379(16.0); 2.180(14.8); 1.964(0.4); 1.958(1.2); 1.952(5.8); 1.946(10.5); 1.940(13.9); 1.934(9.7); 1.928(5.0); 1.670(8.1); 1.486(7.9); 0.000(4.5) |
| I-A-36 | 0.95 | 1.31 | $^1$H-NMR(400.0 MHz, CD3CN): δ = 8.466(1.4); 8.463(1.4); 8.454(1.5); 8.451(1.4); 8.415(2.0); 8.409(2.0); 7.688(0.8); 7.685(1.0); 7.682(0.9); 7.678(0.8); 7.668(1.0); 7.664(1.1); 7.662(1.1); 7.658(0.9); 7.379(1.1); 7.367(1.1); 7.359(1.0); 7.347(1.0); 6.254(3.7); 3.748(0.8); 3.703(15.9); 3.380(16.0); 3.069(1.3); 3.051(3.9); 3.033(4.0); 3.014(1.4); 2.759(1.5); 2.193(4.9); 2.119(0.4); 2.113(0.4); 2.107(0.4); 1.963(1.1); 1.952(9.8); 1.946(17.1); 1.940(22.3); 1.933(15.6); 1.927(8.2); 1.322(0.5); 1.269(0.4); 1.259(4.2); 1.241(8.1); 1.223(4.0); 0.000(3.5) |
| I-A-37 | 1.29 | 1.45 | $^1$H-NMR(400.0 MHz, d$_6$-DMSO): δ = 8.501(2.4); 8.494(2.5); 8.483(1.7); 8.480(2.0); 8.472(1.8); 8.468(2.0); 7.864(1.0); 7.861(1.3); 7.858(1.4); 7.854(1.2); 7.844(1.1); 7.840(1.4); 7.838(1.5); 7.834(1.2); 7.450(1.5); 7.438(1.5); 7.429(1.4); 7.418(1.3); 6.592(1.4); 3.867(16.0); 3.402(17.1); 3.372(1.4); 3.321(15.5); 2.506(21.8); 2.502(29.3); 2.498(23.9); 1.621(1.7); 1.236(0.8); 0.000(6.0) |
| I-A-38 | 0.91 | 1.17 | $^1$H-NMR(400.0 MHz, d$_6$-DMSO): δ = 8.504(2.9); 8.498(2.8); 8.486(2.2); 8.474(2.2); 7.926(0.4); 7.919(0.4); 7.856(1.4); 7.835(1.5); 7.582(1.3); 7.456(1.6); 7.444(4.1); 7.437(1.6); 7.424(1.3); 7.305(1.4); 6.468(2.4); 3.820(16.0); 3.600(0.4); 3.390(16.2); 3.360(0.6); 3.319(42.4); 2.687(1.3); 2.674(1.6); 2.505(57.0); 2.501(63.0); 2.328(0.4); 0.003(2.9); 0.000(5.5) |
| I-A-39 | 1.13 | 1.37; 1.45 | $^1$H-NMR(600.1 MHz, CD3CN): δ = 8.465(0.9); 8.463(0.9); 8.457(0.9); 8.455(0.9); 8.412(0.4); 8.407(1.2); 8.403(1.0); 7.679(0.6); 7.676(0.6); 7.675(0.6); 7.672(0.5); 7.665(0.7); 7.663(0.7); 7.661(0.7); 7.659(0.5); 7.373(0.7); 7.372(0.8); 7.365(0.8); 7.364(0.8); 7.359(0.7); 7.358(0.7); 7.3513(0.7); 7.3505(0.7); 6.278(1.5); 6.261(0.5); 3.762(2.4); 3.754(3.8); 3.745(12.4); 3.711(13.1); 3.698(7.3); 3.680(3.9); 3.382(16.0); 2.144(3.4); 1.955(0.6); 1.951(0.6); 1.947(3.7); 1.943(6.4); 1.939(9.4); 1.935(6.4); 1.931(3.2); 1.816(12.2); 1.802(3.7); 0.000(2.6) |
| I-A-40 | 0.68 | 0.88 | $^1$H-NMR(400.0 MHz, CD3CN): δ = 8.479(1.5); 8.476(1.6); 8.467(1.6); 8.464(1.6); 8.431(2.0); 8.426(2.1); 7.695(0.8); 7.692(1.1); 7.689(1.1); 7.686(1.0); 7.675(1.0); 7.671(1.2); 7.669(1.2); 7.665(1.0); 7.379(1.2); 7.367(1.3); 7.358(1.2); 7.346(1.0); 6.495(1.2); 4.062(0.5); 4.047(16.0); 3.423(16.0); 3.391(1.4); 3.372(4.0); 3.354(4.1); 3.335(1.4); 2.755(0.8); 2.176(7.0); 1.952(2.6); 1.946(4.5); 1.940(6.0); 1.934(4.5); 1.928(2.5); 1.227(4.2); 1.209(8.1); 1.190(4.0); 0.000(0.4) |
| I-A-41 | 0.71 | 1.54 | $^1$H-NMR(400.0 MHz, CD3CN): δ = 8.815(2.1); 8.810(2.1); 8.651(0.8); 8.316(1.6); 8.304(1.7); 8.139(1.1); 8.118(1.2); 7.742(4.4); 7.365(1.2); 7.353(1.3); 7.344(1.2); 7.333(1.1); 3.804(16.0); 3.206(1.3); 3.188(3.9); 3.170(4.0); 3.151(1.3); 3.033(0.4); 2.154(170.7); 2.113(2.4); 2.107(2.2); 2.101(1.6); 1.951(60.2); 1.945(107.1); 1.939(142.1); 1.933(100.9); 1.927(53.4); 1.779(0.4); 1.774(0.7); 1.768(0.9); 1.761(0.6); 1.755(0.4); 1.357(4.1); 1.339(8.0); 1.320(3.9); 0.146(3.0); 0.000(555.3); −0.008(49.4); −0.150(3.0) |
| I-A-42 | 0.35 | 0.55 | $^1$H-NMR(400.0 MHz, CD3CN): δ = 8.478(1.4); 8.475(1.4); 8.467(1.5); 8.463(1.5); 8.430(1.8); 8.424(1.9); 7.685(0.8); 7.682(0.9); 7.676(0.8); 7.665(0.9); 7.662(1.1); 7.659(1.1); 7.656(0.8); 7.378(1.1); 7.366(1.1); 7.358(1.1); 7.346(1.0); 6.770(0.3); 6.524(0.8); 4.179(9.3); 4.019(15.9); 3.425(16.0); 2.661(7.6); 2.649(7.6); 2.147(33.0); 2.106(0.3); 1.963(1.3); 1.951(17.8); 1.945(32.6); 1.939(44.6); 1.933(32.1); 1.927(16.9); 0.146(1.1); 0.000(210.5); −0.008(16.6); −0.150(1.1) |
| I-A-43 | 0.27 | 0.22 | $^1$H-NMR(400.0 MHz, CD3CN): δ = 8.480(1.8); 8.470(1.8); 8.427(2.3); 8.421(2.4); 7.703(1.2); 7.682(1.3); 7.389(1.3); 7.377(1.4); 7.369(1.3); 7.357(1.1); 6.727(0.5); 6.439(1.9); 5.446(0.4); 4.167(1.9); 4.132(2.9); 4.010(3.4); 3.998(16.0); 3.975(2.0); 3.816(0.5); 3.413(15.8); 3.389(0.6); 2.652(7.8); 2.640(7.7); 2.178(4.7); 1.951(4.6); 1.945(8.2); 1.939(11.1); 1.933(8.2); 1.927(4.4); 0.000(52.2); −0.001(52.2) |

| Ex. No. | logP[a] | logP[b] | 1H-NMR; δ (ppm) |
|---|---|---|---|
| I-A-44 | 0.80 | 1.30 | $^1$H-NMR(400.0 MHz. CD3CN): δ = 8.488(1.1); 8.485(1.2); 8.476(1.2); 8.473(1.1); 8.386(1.6); 8.380(1.6); 7.679(0.7); 7.675(0.9); 7.672(0.9); 7.669(0.7); 7.658(0.9); 7.655(1.0); 7.652(1.0); 7.648(0.8); 7.395(1.0); 7.383(1.0); 7.375(0.9); 7.363(0.9); 7.345(0.5); 6.170(3.7); 4.608(0.5); 4.521(0.5); 3.898(1.1); 3.880(3.5); 3.862(4.5); 3.844(1.2); 3.801(1.1); 3.687(15.5); 2.499(16.0); 2.209(18.0); 1.958(0.6); 1.953(3.2); 1.946(5.8); 1.940(7.8); 1.934(5.4); 1.928(2.8); 1.162(3.7); 1.144(7.4); 1.126(3.6); 0.008(0.6); 0.000(13.5); −0.008(0.6) |
| I-A-45 | 0.54 | 1.04 | $^1$H-NMR(400.0 MHz. CD3CN): δ = 8.814(2.0); 8.809(1.8); 8.600(1.4); 8.586(1.4); 8.392(1.0); 8.389(1.0); 8.370(1.1); 8.368(1.0); 7.949(1.0); 7.935(1.1); 7.928(1.0); 7.914(0.9); 7.212(3.0); 3.814(15.0); 3.501(15.0); 2.921(16.0); 2.514(1.7); 2.042(0.5); 1.965(0.6); 1.953(7.8); 1.947(14.0); 1.941(18.5); 1.935(12.7); 1.928(6.5); 0.000(49.4); −0.008(2.5) |
| I-A-46 | 2.09 | 2.17 | $^1$H-NMR(400.0 MHz. CD3CN): δ = 8.502(1.4); 8.498(1.5); 8.490(1.4); 8.486(1.4); 8.445(1.9); 8.439(1.9); 7.715(0.8); 7.711(0.9); 7.708(0.9); 7.704(0.8); 7.694(0.9); 7.690(1.0); 7.688(1.0); 7.684(0.8); 7.406(1.1); 7.395(1.1); 7.386(1.0); 7.374(0.9); 6.306(3.2); 5.477(1.2); 4.012(1.5); 3.970(2.6); 3.969(2.6); 3.927(1.6); 3.809(1.1); 3.797(16.0); 3.426(1.2); 3.415(15.9); 2.170(5.5); 1.994(0.4); 1.988(0.8); 1.982(4.0); 1.976(7.1); 1.970(9.7); 1.964(6.7); 1.958(3.4) |
| I-A-47 | 1.65 | 1.84 | $^1$H-NMR(400.0 MHz. CD3CN): δ = 8.506(1.3); 8.502(1.4); 8.494(1.4); 8.490(1.4); 8.453(1.9); 8.447(1.9); 7.724(0.8); 7.720(0.8); 7.718(0.8); 7.714(0.7); 7.704(0.9); 7.700(1.0); 7.697(0.9); 7.694(0.8); 7.414(1.0); 7.402(1.1); 7.394(1.0); 7.382(0.9); 6.293(3.6); 5.477(2.0); 3.730(16.0); 3.413(15.8); 3.272(2.0); 3.253(2.2); 3.248(1.0); 3.233(2.3); 2.646(0.3); 2.638(1.0); 2.626(0.5); 2.623(0.5); 2.619(0.9); 2.611(1.1); 2.599(1.0); 2.591(0.9); 2.584(0.5); 2.572(0.9); 2.564(0.3); 2.173(3.3); 1.994(0.4); 1.988(0.8); 1.982(4.1); 1.976(7.5); 1.970(10.3); 1.964(7.1); 1.958(3.6) |
| I-A-48 | 1.11 | 1.40 | $^1$H-NMR(400.0 MHz. CD3CN): δ = 8.497(1.4); 8.495(1.6); 8.486(1.5); 8.483(1.6); 8.446(2.2); 8.440(2.2); 7.718(0.8); 7.714(1.0); 7.708(0.8); 7.697(0.9); 7.693(1.1); 7.409(1.2); 7.397(1.2); 7.388(1.1); 7.376(1.1); 6.282(4.1); 5.478(2.5); 4.594(1.3); 4.579(2.5); 4.565(1.3); 4.475(1.3); 4.461(2.5); 4.446(1.3); 3.741(16.0); 3.410(16.0); 3.181(2.4); 3.163(4.4); 3.145(2.6); 2.204(17.0); 2.078(0.3); 2.063(0.8); 2.045(1.2); 2.028(0.8); 2.013(0.6); 1.995(1.1); 1.982(5.2); 1.976(9.0); 1.970(11.4); 1.964(8.6); 1.958(4.2); 1.948(0.4) |
| I-A-49 | 1.55 | 1.71 | $^1$H-NMR(400.0 MHz. CD3CN): δ 8.501(1.9); 8.498(1.7); 8.489(1.6); 8.486(1.3); 8.444(2.3); 8.438(2.0); 7.714(1.1); 7.710(1.2); 7.708(1.1); 7.704(1.0); 7.694(1.2); 7.690(1.2); 7.684(0.8); 7.407(1.4); 7.396(1.4); 7.387(1.2); 7.375(1.0); 6.305(3.4); 6.278(0.4); 6.268(0.6); 6.146(0.8); 6.136(1.3); 6.125(0.6); 6.014(0.4); 6.004(0.6); 5.478(3.9); 3.826(1.6); 3.796(16.0); 3.784(3.0); 3.742(1.7); 3.414(15.2); 2.198(8.5); 2.194(8.2); 1.982(6.0); 1.976(8.6); 1.970(10.0); 1.964(6.5); 1.958(3.1) |
| I-A-50 | 1.94 | 2.10 | $^1$H-NMR(400.0 MHz. CD3CN): δ 8.498(1.4); 8.495(1.4); 8.486(1.4); 8.483(1.4); 8.446(2.0); 8.440(2.1); 7.720(0.7); 7.716(0.9); 7.714(0.9); 7.710(0.8); 7.699(0.9); 7.695(1.1); 7.693(1.0); 7.689(0.9); 7.409(1.2); 7.397(1.1); 7.388(1.0); 7.376(1.0); 6.276(3.9); 5.478(0.8); 3.730(16.0); 3.410(15.9); 3.344(1.2); 3.318(5.8); 3.300(2.6); 3.292(4.3); 3.280(2.6); 3.266(1.3); 2.936(1.9); 2.917(2.2); 2.899(1.6); 2.195(17.4); 1.995(0.4); 1.988(0.7); 1.983(4.5); 1.976(8.3); 1.970(11.5); 1.964(8.0); 1.958(4.1) |
| I-A-51 | 1.47 | 1.73 | $^1$H-NMR(400.0 MHz. CD3CN): δ 8.493(1.3); 8.489(1.3); 8.481(1.4); 8.477(1.4); 8.437(1.8); 8.431(1.9); 7.706(0.8); 7.702(0.9); 7.700(0.8); 7.696(0.7); 7.686(0.9); 7.682(1.0); 7.679(0.9); 7.676(0.8); 7.403(1.1); 7.391(1.1); 7.382(1.0); 7.370(0.9); 6.328(3.7); 5.478(3.9); 3.762(16.0); 3.505(0.5); 3.487(0.5); 3.479(1.0); 3.470(0.5); 3.452(0.5); 3.429(0.4); 3.414(15.8); 2.686(2.4); 2.677(4.9); 2.663(2.7); 2.655(1.9); 2.628(0.3); 2.261(0.4); 2.251(0.8); 2.241(0.9); 2.229(0.6); 2.218(1.2); 2.208(1.2); 2.181(4.9); 1.994(0.4); 1.988(0.7); 1.983(4.1); 1.976(7.6); 1.970(10.5); 1.964(7.2); 1.958(3.7); 1.806(0.5); 1.793(0.5); 1.781(0.6); 1.772(0.9); 1.760(0.7); 1.747(0.9); 1.738(0.6); 1.724(0.4); 1.712(0.4) |
| I-A-52 | 0.90 | 1.25 | $^1$H-NMR(400.0 MHz. CD3CN): δ 8.488(1.7); 8.477(1.7); 8.436(2.4); 8.430(2.5); 7.708(0.8); 7.706(1.0); 7.704(1.1); 7.700(0.9); 7.688(0.9); 7.686(1.1); 7.684(1.3); 7.680(1.0); 7.401(1.4); 7.390(1.4); 7.381(1.3); 7.369(1.2); 6.329(4.3); |

| Ex. No. | logP[a] | logP[b] | 1H-NMR; δ (ppm) |
|---|---|---|---|
| | | | 5.478(1.8); 5.477(1.6); 3.894(1.0); 3.885(1.7); 3.876(1.1); 3.865(1.2); 3.856(1.9); 3.846(1.1); 3.769(16.0); 3.768(15.2); 3.617(0.6); 3.607(0.3); 3.600(0.6); 3.590(1.3); 3.580(0.6); 3.573(0.4); 3.562(0.6); 3.434(1.4); 3.429(1.5); 3.416(16.0); 3.414(15.2); 3.406(2.8); 3.400(2.4); 3.377(1.2); 3.372(1.2); 2.199(18.1); 1.993(0.4); 1.983(4.0); 1.982(4.0); 1.977(7.4); 1.976(7.1); 1.971(10.1); 1.969(9.5); 1.965(7.2); 1.963(6.6); 1.958(3.8); 1.903(1.1); 1.867(1.5); 1.673(0.6); 1.662(0.6); 1.645(1.2); 1.635(1.3); 1.613(1.1); 1.602(1.0); 1.585(0.5); 1.575(0.5) |
| I-A-53 | 2.68 | 2.76 | $^1$H-NMR(400.0 MHz. CD3CN): δ 8.505(1.3); 8.502(1.3); 8.494(1.3); 8.490(1.3); 8.453(1.7); 8.447(1.8); 7.723(0.7); 7.719(0.8); 7.716(0.8); 7.712(0.7); 7.702(0.8); 7.698(0.9); 7.696(0.9); 7.692(0.8); 7.412(1.0); 7.411(1.0); 7.400(1.0); 7.399(0.9); 7.392(0.9); 7.391(0.9); 7.380(0.8); 6.282(3.5); 5.478(1.0); 3.731(16.0); 3.412(15.6); 3.304(1.2); 3.284(1.2); 3.263(1.4); 2.694(0.5); 2.672(0.5); 2.653(0.5); 2.643(0.5); 2.621(0.5); 2.602(0.5); 2.181(7.5); 1.988(0.7); 1.983(3.7); 1.976(6.8); 1.970(9.4); 1.964(6.5); 1.958(3.3) |
| I-A-54 | 0.63 | 0.98 | $^1$H-NMR(400.0 MHz. CD3CN): δ 8.469(1.4); 8.466(1.4); 8.457(1.4); 8.454(1.4); 8.411(1.9); 8.405(1.9); 7.687(0.8); 7.683(0.9); 7.680(0.9); 7.676(0.8); 7.666(0.9); 7.662(1.0); 7.660(1.0); 7.656(0.8); 7.380(1.1); 7.378(1.0); 7.368(1.1); 7.366(1.0); 7.360(1.0); 7.348(1.0); 7.346(0.9); 6.223(3.6); 5.448(1.2); 4.940(2.1); 4.923(4.1); 4.905(2.3); 4.602(0.7); 4.584(1.3); 4.569(1.0); 4.564(0.4); 4.551(0.5); 4.507(2.8); 4.491(4.0); 4.475(1.8); 3.716(16.0); 3.377(16.0); 2.175(18.4); 1.964(0.4); 1.958(0.9); 1.952(4.4); 1.946(8.0); 1.940(10.8); 1.934(7.4); 1.927(3.7); 0.008(1.0); 0.000(21.4); −0.008(0.7) |
| I-A-55 | 1.01 | 1.27 | 1H-NMR(601.6 MHz. d6-DMSO): δ = 8.632(0.5); 8.629(0.5); 8.546(0.4); 8.539(0.4); 8.486(2.2); 8.481(2.2); 8.478(1.7); 8.475(1.5); 8.470(1.6); 8.467(1.4); 7.842(0.8); 7.840(1.0); 7.838(0.9); 7.836(0.8); 7.829(0.9); 7.826(1.0); 7.825(1.0); 7.822(0.8); 7.448(1.1); 7.440(1.1); 7.434(1.1); 7.426(1.0); 6.256(2.7); 4.536(8.2); 4.427(8.1); 4.244(0.7); 3.900(3.3); 3.790(1.2); 3.778(1.8); 3.771(3.8); 3.765(1.2); 3.675(16.0); 3.449(2.9); 3.361(14.7); 3.338(0.9); 3.330(1.3); 3.306(255.1); 3.280(0.3); 3.173(0.7); 3.164(0.7); 2.660(1.3); 2.655(0.7); 2.646(1.4); 2.642(1.3); 2.637(1.5); 2.628(0.7); 2.624(1.4); 2.615(1.0); 2.612(1.3); 2.609(0.9); 2.521(2.4); 2.518(3.0); 2.515(3.1); 2.506(79.7); 2.503(156.7); 2.500(210.1); 2.497(156.0); 2.494(76.4); 2.387(0.9); 2.384(1.3); 2.381(0.9); 2.169(1.5); 2.165(0.7); 2.157(1.5); 2.152(1.3); 2.147(1.4); 2.139(0.7); 2.134(1.3); 2.033(0.4); 2.010(0.4); 0.000(1.3) |
| I-A-56 | 2.86 | 2.92 | $^1$H-NMR(400.0 MHz. $d_6$-DMSO): δ = 8.559(2.4); 8.552(2.5); 8.499(1.7); 8.496(1.8); 8.487(1.8); 8.484(1.7); 7.974(5.6); 7.862(0.9); 7.858(1.1); 7.855(1.0); 7.852(0.9); 7.841(1.1); 7.837(1.2); 7.835(1.2); 7.831(1.0); 7.452(1.4); 7.440(1.4); 7.431(1.3); 7.420(1.2); 6.721(5.0); 6.558(2.3); 5.754(2.1); 3.800(16.0); 3.758(0.5); 3.409(15.5); 3.318(23.4); 2.671(0.4); 2.507(46.4); 2.502(60.3); 2.498(45.2); 2.329(0.4); 1.989(0.5); 0.008(2.5); 0.000(62.0) |
| I-A-57 | 2.02 | 2.14 | $^1$H-NMR(400.0 MHz. $d_6$-DMSO): δ = 8.515(2.4); 8.509(2.6); 8.495(1.7); 8.493(1.8); 8.484(1.7); 8.481(1.8); 8.135(1.5); 7.855(0.9); 7.851(1.1); 7.850(1.1); 7.846(1.0); 7.834(1.0); 7.831(1.3); 7.829(1.3); 7.825(1.0); 7.466(1.4); 7.454(1.4); 7.446(1.3); 7.434(1.3); 7.423(0.5); 7.416(4.3); 7.399(1.6); 7.394(4.9); 7.115(0.6); 7.108(4.8); 7.087(4.1); 6.475(2.9); 5.754(2.7); 3.741(16.0); 3.392(15.6); 3.321(2.5); 2.507(15.4); 2.503(20.1); 2.499(15.7); 2.086(8.1); 0.008(1.2); 0.000(26.8) |
| I-A-58 | 1.62 | 1.79 | $^1$H-NMR(400.0 MHz. $d_6$-DMSO): δ = 8.496(1.9); 8.489(2.0); 8.478(1.4); 8.475(1.5); 8.467(1.4); 8.463(1.4); 7.839(0.7); 7.835(0.9); 7.832(0.8); 7.829(0.7); 7.818(0.8); 7.814(1.0); 7.812(0.9); 7.808(0.8); 7.448(1.1); 7.436(1.1); 7.428(1.0); 7.416(1.0); 7.218(3.3); 7.213(1.1); 7.201(1.1); 7.196(3.9); 7.188(0.4); 6.944(0.4); 6.936(3.9); 6.931(1.3); 6.919(1.1); 6.914(3.3); 6.906(0.3); 6.344(2.6); 4.108(0.4); 4.095(1.3); 4.082(1.3); 4.069(0.5); 3.741(16.0); 3.736(14.8); 3.369(13.3); 3.320(9.1); 3.177(5.7); 3.163(5.5); 2.688(0.9); 2.675(1.0); 2.506(15.5); 2.502(20.5); 2.497(15.3); 0.008(1.1); 0.000(27.6); −0.009(1.1) |
| I-A-59 | 1.55 | 2.11 | $^1$H-NMR(400.0 MHz. $d_6$-DMSO): δ 8.486(1.2); 8.480(1.3); 8.469(0.9); 8.466(0.9); 8.458(0.9); 8.454(0.9); 8.140(1.9); 7.830(0.5); 7.827(0.6); 7.824(0.6); 7.821(0.5); 7.810(0.5); 7.806(0.6); 7.804(0.6); 7.800(0.5); 7.441(0.7); 7.429(0.7); 7.421(0.6); 7.409(0.6); 7.180(2.0); 7.175(0.8); 7.158(2.1); 6.676(2.0); 6.654(1.9); 6.263(1.7); 3.732(8.0); 3.357(9.0); |

| Ex. No. | logP[a] | logP[b] | 1H-NMR; δ (ppm) |
|---|---|---|---|
| | | | 2.891(16.0); 2.506(13.5); 2.502(17.4); 2.498(13.4); 2.073(0.7); 0.007(0.9); 0.000(16.4) |
| I-A-60 | 2.55 | 2.58 | ¹H-NMR(400.0 MHz. d₆-DMSO): δ = 8.548(2.3); 8.542(2.3); 8.495(1.6); 8.491(1.7); 8.483(1.7); 8.479(1.7); 7.853(0.9); 7.850(1.1); 7.847(1.0); 7.843(0.9); 7.833(1.0); 7.829(1.2); 7.827(1.2); 7.823(1.0); 7.517(1.7); 7.512(3.1); 7.508(1.7); 7.446(1.3); 7.434(1.3); 7.425(1.2); 7.414(1.1); 7.078(6.4); 7.074(6.3); 6.542(2.3); 5.754(1.8); 3.784(16.0); 3.403(15.3); 3.318(15.9); 2.524(0.7); 2.511(12.8); 2.507(24.6); 2.502(31.9); 2.498(24.0); 2.086(1.3); 0.000(0.4) |
| I-A-61 | | | ¹H-NMR(400.0 MHz. d₆-DMSO): δ = 8.531(3.6); 8.525(3.7); 8.493(2.5); 8.481(2.5); 7.928(1.0); 7.921(1.0); 7.860(1.3); 7.856(1.7); 7.854(1.7); 7.840(1.4); 7.837(1.6); 7.758(0.8); 7.747(0.9); 7.638(1.2); 7.619(2.3); 7.591(1.6); 7.571(2.2); 7.552(0.9); 7.459(3.2); 7.446(2.1); 7.434(1.9); 7.425(1.5); 7.413(1.4); 7.315(1.7); 7.295(1.5); 7.090(0.5); 7.079(0.5); 7.070(0.7); 7.058(0.6); 6.862(0.6); 6.859(0.6); 6.855(0.6); 6.838(0.5); 6.515(3.0); 6.209(1.0); 5.843(0.4); 5.755(1.1); 3.774(16.0); 3.750(5.7); 3.398(15.7); 3.377(5.8); 3.353(0.5); 3.321(30.3); 2.688(3.8); 2.675(4.0); 2.502(54.8); 2.328(0.4); 0.032(0.3); 0.000(38.1) |
| I-A-62 | 1.66 | 1.87 | ¹H-NMR(400.0 MHz. d₆-DMSO): δ = 8.509(2.4); 8.503(2.6); 8.489(1.8); 8.486(1.8); 8.477(1.9); 8.474(1.8); 7.929(0.4); 7.923(0.4); 7.849(0.9); 7.845(1.2); 7.843(1.2); 7.839(1.0); 7.828(1.1); 7.825(1.3); 7.822(1.3); 7.819(1.0); 7.762(0.3); 7.751(0.3); 7.458(1.4); 7.446(1.4); 7.438(1.3); 7.426(1.3); 7.222(10.5); 7.207(5.0); 7.202(5.1); 7.186(0.3); 7.179(0.4); 6.427(3.0); 5.755(3.7); 3.747(16.0); 3.384(15.4); 3.323(5.6); 2.689(1.3); 2.677(1.4); 2.507(16.7); 2.503(20.8); 0.008(0.9); 0.000(18.4) |
| I-A-63 | 2.75 | 2.92 | ¹H-NMR(400.0 MHz. d₆-DMSO): δ = 8.516(0.8); 8.509(0.8); 8.490(0.6); 8.487(0.6); 8.478(0.6); 8.475(0.6); 7.854(0.4); 7.837(0.3); 7.833(0.4); 7.831(0.4); 7.460(0.5); 7.448(0.5); 7.440(0.4); 7.428(0.4); 7.367(1.4); 7.346(1.6); 7.071(1.6); 7.050(1.4); 6.424(1.0); 3.740(5.6); 3.384(5.5); 3.320(5.7); 3.177(0.4); 3.163(0.4); 2.506(7.0); 2.502(9.2); 2.498(6.8); 1.246(16.0); 1.074(0.4); 1.057(0.9); 1.039(0.4); 0.000(5.8) |
| I-A-64 | 2.63 | 2.71 | ¹H-NMR(400.0 MHz. d₆-DMSO): δ = 8.526(2.8); 8.520(2.9); 8.493(2.2); 8.482(2.2); 7.854(1.5); 7.852(1.4); 7.834(1.6); 7.832(1.5); 7.702(2.3); 7.681(2.5); 7.592(2.9); 7.589(2.9); 7.448(1.5); 7.436(1.6); 7.428(1.5); 7.416(1.4); 7.330(1.6); 7.309(1.5); 6.514(3.0); 5.756(3.5); 5.755(4.1); 3.778(16.0); 3.398(15.7); 3.322(15.0); 2.503(30.6); 0.000(22.0) |
| I-A-65 | 1.01 | 1.18 | ¹H-NMR(400.0 MHz. d₆-DMSO): δ = 8.535(2.3); 8.529(2.4); 8.505(1.6); 8.502(1.7); 8.493(1.7); 8.490(1.7); 8.397(1.3); 8.387(1.3); 8.384(1.3); 7.878(0.8); 7.874(1.0); 7.873(1.0); 7.869(0.9); 7.858(1.0); 7.854(1.1); 7.852(1.1); 7.848(0.9); 7.727(0.8); 7.722(0.8); 7.707(1.4); 7.703(1.5); 7.688(0.9); 7.683(0.9); 7.479(1.3); 7.468(1.3); 7.459(1.3); 7.447(1.2); 7.229(1.1); 7.217(1.2); 7.211(1.2); 7.198(1.0); 6.814(2.0); 6.794(1.9); 6.542(2.2); 3.753(16.0); 3.414(15.4); 3.320(14.3); 2.507(21.1); 2.502(27.9); 2.498(21.2); 0.008(0.6); 0.000(13.8) |
| I-A-66 | 1.97 | 2.11 | ¹H-NMR(400.0 MHz. d₆-DMSO): δ = 8.532(2.3); 8.526(2.4); 8.495(1.6); 8.491(1.7); 8.483(1.7); 8.479(1.7); 7.858(0.8); 7.854(1.0); 7.852(1.0); 7.848(0.9); 7.838(0.9); 7.834(1.1); 7.832(1.1); 7.828(1.0); 7.456(1.3); 7.444(1.3); 7.435(1.2); 7.423(1.2); 7.380(0.7); 7.360(2.2); 7.341(3.1); 7.335(2.7); 7.332(1.7); 7.320(0.5); 7.315(0.7); 7.312(0.4); 7.136(1.5); 7.131(2.8); 6.993(0.9); 6.989(1.7); 6.986(1.0); 6.976(0.9); 6.971(1.5); 6.967(0.9); 6.512(2.5); 5.755(1.2); 3.760(16.0); 3.398(15.4); 3.321(12.6); 2.507(17.4); 2.502(23.0); 2.498(17.5); 2.086(1.8); 0.007(0.5); 0.000(13.1) |
| I-A-67 | 1.17 | 1.25 | ¹H-NMR(400.0 MHz. d₆-DMSO): δ = 8.513(2.1); 8.506(2.2); 8.490(1.5); 8.487(1.6); 8.478(1.5); 8.475(1.5); 8.137(1.7); 7.859(0.8); 7.855(1.0); 7.853(1.0); 7.849(0.9); 7.839(1.0); 7.835(1.1); 7.832(1.1); 7.829(0.9); 7.460(1.3); 7.448(1.3); 7.439(1.2); 7.428(1.2); 7.342(2.1); 7.334(2.2); 7.327(2.4); 7.319(3.7); 7.309(0.9); 7.297(2.1); 7.290(1.0); 7.287(0.8); 7.283(1.1); 7.274(0.7); 6.823(1.3); 6.815(1.3); 6.810(1.0); 6.801(1.3); 6.450(2.7); 5.754(5.4); 3.712(16.0); 3.700(0.4); 3.388(15.4); 3.319(3.8); 2.988(11.2); 2.722(11.2); 2.671(0.3); 2.524(0.7); 2.510(18.9); 2.506(38.0); 2.502(50.3); 2.497(37.5); 2.328(0.3); 0.008(1.9); 0.000(48.7); −0.008(2.3) |
| I-A-68 | 1.71 | 1.77 | ¹H-NMR(400.0 MHz. d₆-DMSO): δ = 8.539(2.1); 8.534(2.2); 8.493(1.6); 8.490(1.7); 8.482(1.7); 8.478(1.6); 8.136(0.5); 8.108(1.0); 8.106(1.1); 8.102(1.1); 8.100(1.0); 8.087(1.1); |

| Ex. No. | logP[a] | logP[b] | 1H-NMR; δ (ppm) |
|---|---|---|---|
| | | | 8.085(1.2); 8.082(1.3); 8.080(1.1); 7.881(1.5); 7.876(2.6); 7.871(1.5); 7.857(0.9); 7.853(1.1); 7.850(1.0); 7.847(0.9); 7.836(1.0); 7.833(1.1); 7.830(1.1); 7.826(1.0); 7.653(1.3); 7.633(2.6); 7.613(1.5); 7.513(1.3); 7.511(1.5); 7.509(1.5); 7.507(1.3); 7.494(1.0); 7.491(1.1); 7.489(1.1); 7.487(0.9); 7.454(1.2); 7.453(1.2); 7.443(1.2); 7.441(1.2); 7.434(1.1); 7.433(1.1); 7.422(1.1); 7.421(1.0); 6.544(2.3); 3.783(16.0); 3.404(15.3); 3.311(4.4); 2.524(0.4); 2.511(8.9); 2.507(17.7); 2.502(23.0); 2.498(17.0); 2.073(10.4); 0.000(1.9) |
| I-A-69 | 1.56 | 1.63 | $^1$H-NMR(400.0 MHz, $d_6$-DMSO): δ = 8.529(1.0); 8.522(1.1); 8.513(0.7); 8.510(0.8); 8.502(0.8); 8.498(0.8); 8.151(0.3); 7.886(0.4); 7.882(0.5); 7.880(0.5); 7.876(0.4); 7.866(0.5); 7.862(0.5); 7.859(0.5); 7.856(0.5); 7.851(0.7); 7.847(0.7); 7.831(0.8); 7.828(0.8); 7.528(0.3); 7.513(0.6); 7.510(0.6); 7.494(0.5); 7.489(0.8); 7.476(0.6); 7.467(0.5); 7.455(0.6); 7.451(0.6); 7.448(0.6); 7.429(0.8); 6.598(1.0); 6.354(0.8); 6.334(0.7); 5.754(1.0); 3.708(7.2); 3.414(6.8); 3.318(4.7); 2.815(16.0); 2.524(0.6); 2.510(11.6); 2.506(23.5); 2.502(31.1); 2.497(23.2); 2.493(11.8); 0.008(1.1); 0.000(29.5); −0.008(1.3) |
| I-A-70 | 1.45 | 1.52 | $^1$H-NMR(400.0 MHz, $d_6$-DMSO): δ = 8.513(2.0); 8.508(2.1); 8.485(1.5); 8.482(1.6); 8.473(1.6); 8.470(1.6); 8.233(2.1); 8.227(2.1); 8.226(2.1); 8.141(0.4); 7.853(0.8); 7.849(1.0); 7.847(1.0); 7.843(0.9); 7.833(1.0); 7.829(1.1); 7.826(1.1); 7.823(1.0); 7.648(1.4); 7.641(1.4); 7.627(1.9); 7.620(1.9); 7.521(2.5); 7.520(2.6); 7.500(1.8); 7.499(1.8); 7.452(1.1); 7.441(1.1); 7.440(1.1); 7.433(1.1); 7.431(1.1); 7.421(1.0); 7.419(1.0); 6.435(2.6); 5.751(1.2); 3.786(16.0); 3.388(15.3); 3.309(13.5); 2.524(0.7); 2.510(17.8); 2.506(35.9); 2.501(47.4); 2.497(35.8); 0.000(3.7) |
| I-A-71 | 1.68 | 1.78 | $^1$H-NMR(400.0 MHz, $d_6$-DMSO): δ = 8.513(2.5); 8.507(2.4); 8.498(0.9); 8.487(2.1); 8.484(2.1); 8.475(1.7); 8.472(1.6); 7.855(1.2); 7.851(1.3); 7.849(1.3); 7.845(1.3); 7.835(1.3); 7.831(1.3); 7.828(1.2); 7.825(1.0); 7.456(1.7); 7.444(1.6); 7.435(1.5); 7.423(1.2); 7.397(0.4); 7.392(0.5); 7.383(0.6); 7.376(1.0); 7.358(1.1); 7.354(0.8); 7.344(0.6); 7.340(0.5); 7.312(1.1); 7.309(1.1); 7.292(0.9); 7.288(1.5); 7.285(1.1); 7.267(0.7); 7.264(0.6); 7.188(1.1); 7.185(1.1); 7.169(1.7); 7.166(1.6); 7.151(0.9); 7.147(0.8); 6.920(0.9); 6.916(1.0); 6.900(1.6); 6.896(1.5); 6.881(0.7); 6.877(0.7); 6.438(2.9); 6.237(0.4); 3.779(3.2); 3.767(16.0); 3.674(1.6); 3.400(3.2); 3.389(15.6); 3.373(0.4); 3.360(1.6); 3.322(3.5); 3.311(12.5); 3.037(0.4); 2.510(27.1); 2.506(37.5); 2.501(41.6); 2.497(28.4); 0.858(0.5); 0.840(0.9); 0.821(0.4); 0.011(0.5); 0.000(2.8) |
| I-A-72 | 1.59 | 1.74 | $^1$H-NMR(400.0 MHz, $d_6$-DMSO): δ = 8.522(3.3); 8.492(2.4); 8.481(2.4); 7.867(1.6); 7.847(1.8); 7.467(1.5); 7.455(1.7); 7.447(1.5); 7.435(1.3); 7.249(1.0); 7.229(2.2); 7.210(1.3); 7.051(2.7); 7.031(2.2); 6.879(1.3); 6.860(2.5); 6.841(1.3); 6.475(3.7); 6.421(2.3); 6.402(2.2); 5.754(1.3); 3.819(16.0); 3.732(16.0); 3.398(15.7); 3.321(8.9); 2.502(36.3); 0.000(2.8) |
| I-A-73 | 1.81 | 1.87 | $^1$H-NMR(400.0 MHz, $d_6$-DMSO): δ = 8.509(2.2); 8.503(2.2); 8.460(1.6); 8.457(1.7); 8.448(1.7); 8.445(1.7); 7.927(1.2); 7.923(2.5); 7.918(2.0); 7.907(1.4); 7.888(2.4); 7.873(1.4); 7.868(1.3); 7.850(0.9); 7.846(1.1); 7.844(1.0); 7.840(0.9); 7.830(1.0); 7.826(1.1); 7.824(1.2); 7.820(1.0); 7.725(1.7); 7.705(2.7); 7.685(1.2); 7.420(1.3); 7.408(1.3); 7.399(1.2); 7.387(1.1); 6.583(0.6); 4.030(16.0); 4.016(0.3); 3.388(15.2); 3.315(50.4); 2.675(0.4); 2.670(0.6); 2.666(0.5); 2.510(36.0); 2.506(69.7); 2.501(93.6); 2.497(72.1); 2.333(0.5); 2.328(0.6); 2.324(0.5); 0.146(0.5); 0.008(4.9); 0.000(99.4); −0.008(4.9); −0.019(0.4); −0.150(0.5) |
| I-A-74 | 1.45 | 1.55 | $^1$H-NMR(400.0 MHz, $d_6$-DMSO): δ = 8.505(2.3); 8.499(2.4); 8.476(1.7); 8.472(1.8); 8.464(1.8); 8.461(1.9); 8.137(2.6); 7.842(0.9); 7.839(1.1); 7.836(1.1); 7.832(1.0); 7.822(1.1); 7.818(1.3); 7.816(1.3); 7.812(1.1); 7.661(0.9); 7.657(1.2); 7.654(1.7); 7.650(3.3); 7.645(4.2); 7.642(2.9); 7.629(2.0); 7.610(2.5); 7.601(0.5); 7.598(0.4); 7.589(1.2); 7.551(1.3); 7.547(2.1); 7.543(1.3); 7.532(0.9); 7.528(1.3); 7.525(0.8); 7.431(1.3); 7.419(1.3); 7.411(1.3); 7.399(1.2); 6.471(1.1); 3.907(16.0); 3.376(15.3); 3.316(5.7); 2.670(0.4); 2.666(0.3); 2.506(46.5); 2.501(62.9); 2.497(50.5); 2.328(0.4); 2.324(0.3); 0.008(2.8); 0.000(63.9) |
| I-A-75 | 2.14 | 2.19 | $^1$H-NMR(400.0 MHz, $d_6$-DMSO): δ = 8.504(0.8); 8.498(0.8); 8.481(0.6); 8.478(0.6); 8.470(0.6); 8.466(0.6); 8.139(0.6); 7.839(0.4); 7.837(0.4); 7.833(0.3); 7.823(0.3); 7.819(0.4); 7.816(0.4); 7.813(0.3); 7.626(1.1); 7.604(1.7); 7.519(1.7); 7.498(1.1); 7.437(0.4); 7.425(0.5); 7.417(0.4); 7.405(0.4); |

-continued

| Ex. No. | logP[a] | logP[b] | 1H-NMR; δ (ppm) |
|---|---|---|---|
| | | | 6.459(0.4); 3.845(5.4); 3.369(5.1); 3.316(8.7); 2.510(11.9); 2.506(23.5); 2.501(31.8); 2.497(24.8); 1.298(16.0); 0.008(1.7); 0.000(35.6); −0.008(1.8) |
| I-A-76 | 2.53 | 2.55 | ¹H-NMR(400.0 MHz. d₆-DMSO): δ 8.515(0.9); 8.509(0.9); 8.461(0.7); 8.449(0.7); 7.852(1.6); 7.831(2.1); 7.697(1.7); 7.675(1.3); 7.424(0.5); 7.412(0.5); 7.404(0.6); 7.392(0.5); 5.752(1.9); 4.017(5.4); 3.383(5.2); 3.371(0.3); 3.316(5.0); 2.502(9.5); 1.300(16.0); 0.000(6.2) |
| I-A-77 | | | ¹H-NMR(400.0 MHz. CD3CN): δ = 8.467(1.2); 8.464(1.3); 8.455(1.3); 8.452(1.3); 8.400(1.7); 8.394(1.7); 7.651(0.7); 7.647(0.9); 7.645(0.8); 7.641(0.7); 7.630(1.0); 7.626(2.2); 7.621(3.2); 7.617(1.6); 7.515(5.3); 7.511(4.8); 7.355(1.0); 7.343(1.0); 7.334(0.9); 7.322(0.9); 6.424(1.2); 3.918(16.0); 3.391(16.0); 2.142(23.5); 2.113(1.1); 2.106(0.9); 2.100(0.7); 2.094(0.4); 1.963(2.1); 1.957(4.1); 1.951(26.4); 1.945(48.5); 1.939(66.8); 1.933(46.1); 1.926(23.8); 1.767(0.4); 0.146(1.2); 0.008(10.3); 0.000(243.1); −0.009(11.1); −0.033(0.6); −0.150(1.2) |
| I-A-78 | 2.37 | 2.53 | ¹H-NMR(400.0 MHz. d₆-DMSO): δ = 8.512(2.5); 8.506(2.5); 8.462(1.8); 8.460(1.9); 8.451(1.9); 8.448(1.9); 8.118(1.8); 8.114(2.9); 8.110(1.8); 7.933(6.3); 7.928(6.0); 7.848(1.3); 7.827(1.4); 7.422(1.4); 7.410(1.4); 7.401(1.3); 7.390(1.2); 6.625(0.8); 5.753(1.7); 4.042(16.0); 3.394(15.4); 3.315(45.2); 2.671(0.6); 2.501(97.2); 2.328(0.7); 0.000(22.3) |
| I-A-79 | 2.16 | 2.29 | ¹H-NMR(400.0 MHz. d₆-DMSO): δ = 8.503(2.9); 8.498(2.9); 8.467(2.3); 8.455(2.3); 8.072(3.7); 7.973(0.8); 7.952(5.1); 7.922(0.6); 7.845(1.5); 7.824(1.7); 7.425(1.5); 7.413(1.6); 7.405(1.5); 7.393(1.4); 6.450(1.5); 5.752(3.7); 3.985(16.0); 3.380(15.6); 3.313(43.1); 2.891(0.7); 2.731(0.7); 2.670(0.9); 2.501(137.8); 2.327(0.9); 0.000(30.9) |
| I-A-80 | 2.56 | 2.72 | ¹H-NMR(400.0 MHz. d₆-DMSO): δ = 8.503(2.8); 8.498(2.8); 8.455(2.2); 8.444(2.2); 8.256(1.5); 8.235(1.8); 8.192(3.3); 8.063(2.7); 8.042(2.2); 7.848(1.5); 7.829(1.6); 7.419(1.5); 7.407(1.6); 7.399(1.4); 7.387(1.3); 6.604(0.9); 4.043(16.0); 3.390(15.6); 3.314(43.1); 2.671(0.8); 2.501(125.8); 2.328(0.8); 0.000(25.2) |
| I-A-81 | 1.53 | 1.58 | ¹H-NMR(400.0 MHz. d₆-DMSO): δ = 8.506(2.4); 8.500(2.5); 8.463(1.7); 8.460(2.0); 8.451(1.8); 8.448(1.9); 7.861(4.1); 7.852(1.6); 7.839(5.0); 7.832(1.8); 7.828(1.6); 7.825(1.5); 7.822(1.2); 7.428(1.4); 7.417(1.4); 7.408(1.3); 7.396(1.2); 7.185(0.7); 7.178(4.4); 7.155(4.2); 6.486(0.9); 5.754(4.5); 4.002(15.6); 3.862(16.0); 3.820(0.4); 3.379(14.9); 3.330(1.5); 3.319(33.0); 2.687(0.7); 2.674(1.0); 2.506(54.0); 2.502(71.2); 2.497(57.9); 2.328(0.5); 2.086(3.8); 0.008(2.6); 0.000(38.0) |
| I-A-82 | 1.53 | 1.62 | ¹H-NMR(400.0 MHz. d₆-DMSO): δ = 8.506(1.8); 8.501(1.9); 8.460(1.5); 8.448(1.4); 8.314(0.5); 8.027(2.0); 8.014(2.1); 8.009(1.5); 8.004(2.2); 7.996(1.1); 7.992(2.0); 7.901(1.2); 7.898(1.1); 7.882(0.6); 7.851(0.9); 7.847(1.1); 7.845(1.1); 7.841(0.9); 7.831(1.0); 7.827(1.2); 7.824(1.2); 7.821(1.0); 7.530(2.3); 7.508(4.0); 7.486(2.0); 7.426(1.2); 7.414(1.2); 7.406(1.1); 7.394(1.0); 6.536(0.7); 4.021(16.0); 3.384(15.2); 3.317(96.9); 2.675(1.0); 2.670(1.4); 2.666(1.1); 2.506(159.2); 2.501(207.5); 2.497(158.2); 2.333(1.0); 2.328(1.3); 2.324(1.0); 0.000(5.0) |
| I-A-83 | 1.12 | 1.23 | ¹H-NMR(400.0 MHz. d₆-DMSO): δ = 8.464(2.9); 8.136(0.9); 8.132(1.6); 8.126(1.1); 8.123(1.1); 8.119(1.6); 8.114(1.0); 8.058(2.1); 8.053(1.0); 8.045(2.3); 8.040(1.5); 8.035(2.4); 8.027(1.1); 8.023(2.3); 7.543(2.3); 7.521(4.3); 7.503(0.8); 7.499(2.1); 7.421(0.4); 7.417(0.4); 7.401(4.9); 7.389(2.2); 7.368(0.4); 6.788(3.0); 4.099(0.9); 4.085(0.9); 4.072(0.3); 4.032(16.0); 3.348(15.6); 3.323(27.4); 3.176(3.4); 3.163(3.3); 2.507(23.5); 2.503(30.9); 2.498(23.6); 0.000(0.5) |
| I-A-84 | 1.22 | 1.27 | ¹H-NMR(400.0 MHz. d₆-DMSO): δ = 8.497(2.2); 8.491(2.3); 8.478(1.6); 8.475(1.7); 8.466(1.6); 8.463(1.6); 7.842(0.9); 7.838(1.1); 7.832(0.9); 7.821(1.0); 7.818(1.2); 7.815(1.1); 7.812(0.9); 7.684(1.9); 7.679(1.0); 7.671(2.1); 7.667(1.5); 7.662(2.4); 7.654(1.1); 7.649(2.2); 7.472(0.3); 7.465(2.3); 7.460(0.9); 7.442(4.4); 7.426(2.0); 7.420(2.6); 7.406(1.2); 6.452(1.1); 5.754(2.0); 3.880(16.0); 3.372(15.2); 3.318(34.3); 2.671(0.4); 2.506(49.2); 2.502(63.2); 2.497(47.1); 2.328(0.4); 2.086(0.5); 0.008(0.5); 0.000(7.4) |
| I-A-85 | 1.01 | 1.10 | ¹H-NMR(400.0 MHz. d₆-DMSO): δ = 8.744(1.4); 8.742(1.2); 8.736(1.0); 8.733(1.6); 8.730(1.1); 8.514(1.9); 8.508(2.0); 8.461(1.4); 8.458(1.6); 8.449(1.5); 8.446(1.6); 8.208(0.4); 8.204(0.5); 8.189(1.4); 8.185(1.4); 8.172(3.3); 8.168(3.7); 8.153(0.5); 8.151(0.5); 7.854(0.8); 7.851(1.0); 7.848(1.0); 7.844(0.9); 7.834(1.0); 7.830(1.1); 7.828(1.1); 7.824(0.9); |

| Ex. No. | logP[a] | logP[b] | 1H-NMR; δ (ppm) |
|---|---|---|---|
| | | | 7.790(0.9); 7.785(0.9); 7.778(0.9); 7.773(1.6); 7.768(0.9); 7.762(0.9); 7.757(0.8); 7.430(1.2); 7.418(1.2); 7.410(1.1); 7.398(1.0); 6.628(0.5); 5.754(2.5); 4.095(16.0); 3.402(15.1); 3.317(19.4); 2.675(0.3); 2.670(0.5); 2.666(0.4); 2.510(26.1); 2.506(51.0); 2.501(68.0); 2.497(51.7); 2.492(26.7); 2.328(0.4); 0.000(0.4) |
| I-A-86 | 0.59 | 0.80 | $^1$H-NMR(400.0 MHz. $d_6$-DMSO): δ = 8.591(1.8); 8.581(1.8); 8.501(2.6); 8.495(2.8); 8.474(2.1); 8.462(2.1); 8.171(0.8); 8.155(1.7); 8.152(1.9); 8.136(4.8); 8.035(2.5); 8.016(1.8); 7.839(1.3); 7.835(1.2); 7.819(1.5); 7.815(1.2); 7.584(1.3); 7.573(1.4); 7.566(1.3); 7.554(1.2); 7.439(1.5); 7.427(1.5); 7.419(1.5); 7.407(1.3); 6.433(1.3); 3.857(16.0); 3.370(16.0); 3.320(3.9); 2.671(0.4); 2.501(55.8); 2.329(0.4) |
| I-A-87 | 1.04 | 1.20 | $^1$H-NMR(400.0 MHz. $d_6$-DMSO): δ = 8.494(2.3); 8.487(2.3); 8.480(1.7); 8.476(1.7); 8.468(1.7); 8.464(1.8); 8.138(1.2); 7.836(0.9); 7.832(1.0); 7.831(1.0); 7.827(0.9); 7.816(1.1); 7.812(1.1); 7.810(1.1); 7.806(0.9); 7.605(0.7); 7.601(0.8); 7.597(1.1); 7.584(8.1); 7.578(7.3); 7.568(1.6); 7.557(0.8); 7.435(1.3); 7.423(1.3); 7.415(1.2); 7.403(1.2); 7.395(0.3); 6.466(1.0); 5.754(3.4); 4.021(0.9); 4.012(0.8); 3.832(16.0); 3.382(1.0); 3.367(15.2); 3.343(1.4); 3.320(10.5); 2.510(18.0); 2.506(33.9); 2.502(43.7); 2.497(32.5); 2.493(16.2); 0.000(2.1) |
| I-A-88 | 1.37 | 1.47 | $^1$H-NMR(400.0 MHz. $d_6$-DMSO): δ = 8.507(2.2); 8.500(2.2); 8.460(1.6); 8.457(1.6); 8.448(1.7); 8.445(1.6); 7.927(2.9); 7.908(3.5); 7.847(0.9); 7.843(1.1); 7.838(0.9); 7.827(1.0); 7.822(1.2); 7.817(1.0); 7.809(0.7); 7.790(1.9); 7.772(1.2); 7.691(2.6); 7.671(3.6); 7.652(1.5); 7.420(1.3); 7.408(1.3); 7.400(1.3); 7.388(1.2); 6.544(0.7); 5.754(4.3); 4.012(16.0); 3.382(15.3); 3.320(33.6); 2.506(34.7); 2.501(44.4); 2.497(33.4); 0.000(1.9); −0.001(2.0) |
| I-A-89 | 1.20 | 1.38 | $^1$H-NMR(400.0 MHz. $d_6$-DMSO): δ = 8.495(2.5); 8.489(2.7); 8.463(1.8); 8.460(2.0); 8.447(2.7); 8.441(2.9); 8.436(2.3); 8.418(1.5); 8.398(1.5); 8.394(1.3); 8.039(1.5); 8.019(1.9); 7.892(1.7); 7.872(2.8); 7.852(1.3); 7.844(1.0); 7.838(1.3); 7.835(1.1); 7.824(1.1); 7.818(1.4); 7.814(1.1); 7.424(1.4); 7.412(1.4); 7.404(1.4); 7.392(1.4); 6.462(1.2); 5.754(8.3); 3.957(16.0); 3.376(15.3); 3.349(0.6); 3.319(46.3); 2.671(0.4); 2.666(0.3); 2.506(48.2); 2.502(63.4); 2.497(51.2); 2.328(0.4); 0.000(13.5) |
| I-A-90 | 1.58 | 1.68 | $^1$H-NMR(400.0 MHz. $d_6$-DMSO): δ = 8.610(1.4); 8.606(1.5); 8.604(1.5); 8.589(1.4); 8.586(1.6); 8.584(1.7); 8.550(2.9); 8.502(2.3); 8.497(2.4); 8.449(1.9); 8.438(1.9); 8.377(1.7); 8.357(1.8); 7.988(1.6); 7.968(2.8); 7.948(1.3); 7.848(1.3); 7.845(1.4); 7.827(1.4); 7.825(1.5); 7.418(1.4); 7.406(1.4); 7.397(1.4); 7.385(1.2); 6.610(0.8); 5.754(10.9); 4.049(16.0); 3.387(15.5); 3.330(29.8); 2.670(0.5); 2.501(69.6); 2.328(0.5); 0.000(11.9) |
| I-A-91 | 0.76 | 0.96 | $^1$H-NMR(400.0 MHz. $d_6$-DMSO): δ = 8.539(2.4); 8.533(2.4); 8.480(1.7); 8.477(1.8); 8.469(1.8); 8.465(1.7); 8.142(0.4); 8.053(1.8); 8.033(2.0); 7.902(0.9); 7.898(1.1); 7.892(0.9); 7.882(1.1); 7.877(1.2); 7.872(1.0); 7.756(0.9); 7.754(0.9); 7.735(1.8); 7.718(1.0); 7.715(1.0); 7.607(1.0); 7.590(1.9); 7.588(1.9); 7.572(1.0); 7.569(1.0); 7.458(1.5); 7.447(3.1); 7.437(1.5); 7.428(2.0); 6.362(1.2); 5.754(5.1); 3.978(16.0); 3.384(15.4); 3.321(46.6); 2.743(4.1); 2.675(0.4); 2.670(0.5); 2.506(54.4); 2.501(71.4); 2.497(54.1); 2.439(4.0); 2.333(0.3); 2.328(0.5); 2.324(0.3); 0.000(7.4) |
| I-A-92 | 1.12 | 1.29 | $^1$H-NMR(400.0 MHz. $d_6$-DMSO): δ = 8.522(2.3); 8.516(2.3); 8.453(1.8); 8.443(1.8); 8.134(1.2); 8.034(1.8); 8.014(2.1); 7.839(1.3); 7.819(2.1); 7.802(2.0); 7.783(1.3); 7.710(1.3); 7.691(1.9); 7.673(0.8); 7.455(2.1); 7.436(1.9); 7.416(1.4); 7.404(1.4); 7.396(1.3); 7.384(1.3); 6.548(0.7); 5.754(6.4); 3.986(15.8); 3.395(15.4); 3.321(37.3); 2.958(16.0); 2.670(0.5); 2.646(14.9); 2.506(45.7); 2.502(58.2); 2.498(45.4); 2.329(0.4); 0.000(4.4) |
| I-A-93 | 1.12 | 1.28 | $^1$H-NMR(400.0 MHz. $d_6$-DMSO): δ = 8.497(0.6); 8.313(1.0); 8.134(0.8); 8.016(0.5); 7.855(0.9); 7.834(1.0); 7.634(0.4); 7.629(0.4); 7.554(0.4); 7.546(3.2); 7.524(3.6); 7.459(0.6); 7.447(0.7); 7.438(0.7); 7.427(0.6); 7.142(3.6); 7.120(3.3); 6.447(1.0); 4.432(0.3); 4.349(0.5); 4.002(3.7); 3.972(3.3); 3.961(3.3); 3.863(3.1); 3.852(15.2); 3.820(16.0); 3.749(1.3); 3.742(1.2); 3.671(0.8); 3.637(0.6); 3.605(0.5); 3.544(0.4); 3.510(0.4); 3.381(1.0); 3.370(12.8); 2.789(3.7); 2.675(1.3); 2.671(1.8); 2.666(1.3); 2.510(112.8); 2.506(220.1); 2.501(293.3); 2.497(224.0); 2.437(0.6); 2.400(0.4); 2.385(0.3); 2.370(0.4); 2.333(1.5); 2.328(2.0); 2.324(1.6); 0.008(0.6); 0.000(14.9); −0.008(0.6) |

| Ex. No. | logP[a] | logP[b] | 1H-NMR; δ (ppm) |
|---|---|---|---|
| I-A-94 | 1.18 | 1.39 | $^1$H-NMR(400.0 MHz. CD3CN): δ = 8.484(1.3); 8.481(1.4); 8.473(1.4); 8.469(1.4); 8.430(1.9); 8.424(2.0); 8.287(1.9); 8.280(2.0); 7.705(0.7); 7.702(0.9); 7.699(0.8); 7.696(0.7); 7.685(0.8); 7.681(1.0); 7.679(1.0); 7.675(0.8); 7.473(0.7); 7.465(0.6); 7.451(1.2); 7.444(1.2); 7.430(0.7); 7.422(0.7); 7.396(1.1); 7.384(1.1); 7.376(1.0); 7.364(0.9); 6.957(1.2); 6.947(1.2); 6.935(1.1); 6.925(1.1); 6.487(2.5); 5.447(5.3); 3.779(16.0); 3.423(15.8); 2.763(0.7); 2.751(0.7); 2.165(8.4); 1.958(0.5); 1.952(3.2); 1.946(5.8); 1.940(7.9); 1.934(5.4); 1.927(2.8); 0.008(0.7); 0.000(17.4); −0.009(0.7) |
| I-A-95 | 1.41 | 1.39 | $^1$H-NMR(400.0 MHz. d$_6$-DMSO): δ = 8.449(2.9); 8.138(0.9); 8.134(1.7); 8.129(1.1); 8.124(1.1); 8.120(1.7); 8.116(1.0); 8.020(2.5); 7.984(1.2); 7.965(1.6); 7.941(1.2); 7.921(1.8); 7.854(1.4); 7.834(1.9); 7.815(0.8); 7.419(0.5); 7.415(0.4); 7.398(4.7); 7.383(2.0); 7.362(0.5); 6.740(3.7); 5.755(8.3); 3.962(16.0); 3.375(0.4); 3.340(15.9); 3.320(34.9); 2.671(0.4); 2.506(49.1); 2.502(64.8); 2.497(49.9); 2.328(0.4); 0.008(0.8); 0.000(16.2); −0.008(0.6) |
| I-A-96 | 1.74 | 1.80 | $^1$H-NMR(400.0 MHz. d$_6$-DMSO): δ = 8.502(2.4); 8.496(2.4); 8.468(1.7); 8.465(1.9); 8.456(1.8); 8.453(1.9); 7.971(3.7); 7.955(1.6); 7.915(1.1); 7.895(1.8); 7.841(2.1); 7.823(2.6); 7.814(1.2); 7.803(0.6); 7.539(0.4); 7.422(1.4); 7.410(2.1); 7.402(1.3); 7.390(1.3); 6.807(0.8); 6.457(1.0); 5.754(1.7); 3.953(16.0); 3.774(2.5); 3.375(15.4); 3.364(2.8); 3.349(0.6); 3.318(96.5); 2.675(0.7); 2.671(0.9); 2.666(0.7); 2.506(102.8); 2.501(134.3); 2.497(102.4); 2.333(0.6); 2.328(0.9); 0.008(1.5); 0.000(31.3); −0.008(1.3) |
| I-A-97 | 0.45 | 0.48 | $^1$H-NMR(400.0 MHz. d$_6$-DMSO): δ = 8.661(6.4); 8.649(6.5); 8.423(2.7); 8.163(0.9); 8.159(1.1); 8.156(1.1); 8.153(1.6); 8.146(1.3); 8.141(1.0); 7.436(2.6); 7.427(4.1); 7.424(3.8); 7.340(1.7); 7.328(3.2); 7.316(1.7); 6.802(4.7); 3.740(16.0); 3.380(15.7); 3.320(12.1); 2.506(21.1); 2.502(28.0); 2.498(21.3); 1.236(0.5); 0.008(0.9); 0.000(26.2) |
| I-A-98 | 1.04 | 1.22 | $^1$H-NMR(400.0 MHz. CD3CN): δ = 8.518(4.6); 8.506(4.7); 8.499(1.4); 8.495(1.4); 8.487(1.3); 8.483(1.4); 8.402(1.7); 8.396(1.9); 7.697(0.6); 7.693(0.8); 7.691(0.8); 7.687(0.7); 7.677(0.8); 7.673(1.0); 7.671(0.9); 7.667(0.8); 7.409(1.0); 7.397(1.0); 7.388(0.9); 7.376(0.9); 7.177(1.3); 7.165(2.5); 7.152(1.2); 6.433(1.8); 3.950(1.1); 3.932(3.4); 3.914(3.5); 3.896(1.3); 3.883(0.4); 3.874(0.4); 3.868(0.5); 3.860(0.5); 3.853(0.4); 3.844(0.4); 3.771(15.0); 2.527(0.7); 2.164(4.4); 1.958(0.7); 1.952(3.9); 1.946(7.1); 1.940(9.5); 1.934(6.7); 1.928(3.5); 1.197(3.7); 1.179(7.4); 1.161(3.6); 1.099(16.0); 1.084(15.7); 0.000(4.6) |
| I-A-99 | 0.66 | 0.87 | $^1$H-NMR(400.0 MHz. CD3CN): δ = 8.553(1.9); 8.543(6.2); 8.531(5.7); 7.924(0.9); 7.904(1.1); 7.575(0.9); 7.563(1.0); 7.555(1.0); 7.542(0.9); 7.209(1.3); 7.197(2.5); 7.185(1.2); 6.700(2.3); 4.099(0.5); 4.073(1.2); 4.040(0.8); 3.986(0.8); 3.951(0.7); 3.907(0.6); 3.878(0.6); 3.853(0.5); 3.810(15.8); 3.760(0.4); 3.654(1.0); 3.467(16.0); 3.453(0.8); 3.409(1.0); 3.337(0.5); 3.277(6.0); 1.964(0.6); 1.958(1.5); 1.952(8.2); 1.946(15.0); 1.940(20.2); 1.934(14.1); 1.928(7.4); 0.000(7.2) |
| I-A-100 | 1.58 | | $^1$H-NMR(400.0 MHz. CD3CN): δ = 9.012(1.2); 8.999(1.3); 8.913(1.2); 8.908(1.2); 8.677(0.9); 8.663(1.0); 8.540(0.6); 8.537(0.6); 8.516(0.7); 8.078(0.7); 8.063(0.7); 8.057(0.7); 8.043(0.8); 7.953(2.1); 7.724(1.5); 7.711(1.5); 7.549(0.9); 3.995(9.5); 3.554(9.5); 2.970(0.3); 2.919(16.0); 2.834(0.6); 2.799(15.7); 2.769(0.8); 2.745(0.9); 2.623(1.5); 2.607(3.8); 2.593(6.2); 2.578(3.9); 2.545(1.7); 2.500(1.6); 2.485(1.5); 2.276(0.5); 2.201(0.4); 2.120(0.3); 2.114(0.4); 2.108(0.5); 2.101(0.4); 1.965(1.2); 1.958(2.8); 1.953(16.1); 1.947(29.7); 1.940(40.5); 1.934(28.2); 1.928(14.8); 1.769(0.3); 1.285(0.4); 1.272(1.0); 0.008(2.3); 0.000(63.5); −0.008(3.0) |
| I-A-101 | 1.00 | | $^1$H-NMR(400.0 MHz. CD3CN): δ = 8.471(1.0); 8.461(1.1); 8.428(1.4); 8.423(1.4); 8.342(1.1); 8.329(1.2); 8.032(0.8); 7.719(0.7); 7.716(0.9); 7.713(0.8); 7.709(0.9); 7.699(0.9); 7.695(1.0); 7.693(0.9); 7.689(0.8); 7.398(0.9); 7.385(0.9); 7.377(0.9); 7.365(0.8); 7.040(1.7); 7.027(1.6); 6.458(1.3); 3.780(16.0); 3.428(16.0); 2.380(12.8); 2.153(65.7); 2.119(0.5); 2.113(0.5); 2.107(0.5); 2.100(0.4); 1.963(1.9); 1.957(4.5); 1.952(24.5); 1.945(44.5); 1.939(59.8); 1.933(40.8); 1.927(20.7); 1.768(0.3); 0.146(0.7); 0.008(6.5); 0.000(147.6); −0.009(6.1); −0.150(0.7) |
| I-A-102 | 1.61 | 1.79 | $^1$H-NMR(400.0 MHz. CD3CN): δ = 8.474(0.7); 8.471(0.7); 8.462(0.7); 8.459(0.8); 8.406(1.0); 8.400(1.0); 7.726(0.4); 7.722(0.5); 7.720(0.5); 7.716(0.4); 7.706(0.4); 7.702(0.5); 7.700(0.5); 7.696(0.4); 7.390(0.6); 7.378(0.6); 7.369(0.5); |

| Ex. No. | logP[a] | logP[b] | 1H-NMR; δ (ppm) |
|---|---|---|---|
| | | | 7.357(0.5); 6.428(1.2); 5.849(2.9); 5.447(3.7); 3.845(8.1); 3.737(16.0); 3.411(8.1); 2.158(11.4); 1.958(0.5); 1.952(3.0); 1.946(5.4); 1.940(7.3); 1.934(5.0); 1.927(2.6); 0.008(0.6); 0.000(14.9); −0.008(0.6) |
| I-A-103 | 1.23 | | $^1$H-NMR(400.0 MHz. CD3CN): δ = 8.474(1.1); 8.463(1.1); 8.428(1.3); 8.174(1.9); 7.717(0.8); 7.714(0.9); 7.708(0.7); 7.697(0.9); 7.693(1.0); 7.691(1.0); 7.687(0.8); 7.398(1.0); 7.387(1.0); 7.378(0.9); 7.366(0.8); 6.449(1.0); 4.089(0.5); 3.915(0.4); 3.774(15.5); 3.451(0.5); 3.427(16.0); 2.467(0.4); 2.340(12.4); 2.179(265.0); 2.159(12.3); 2.113(0.4); 2.107(0.4); 2.101(0.3); 1.964(2.2); 1.952(27.8); 1.946(50.3); 1.940(67.5); 1.934(46.1); 1.928(23.7); 1.769(0.4); 0.146(0.7); 0.008(6.8); 0.000(150.8); −0.008(6.8); −0.150(0.8) |
| I-A-104 | 0.97 | | $^1$H-NMR(400.0 MHz. CD3CN): δ = 8.501(0.3); 8.474(0.4); 8.462(0.4); 8.449(0.4); 8.408 (0.5); 8.403(0.5); 7.703(0.9); 7.683(1.1); 7.407(0.4); 3.864 (0.4); 3.806(0.4); 3.763(12.8); 3.427(16.0); 3.382(0.7); 2.216(7.9); 2.162(45.1); 1.972(0.7); 1.964(1.0); 1.958(2.3); 1.952(13.3); 1.946(24.2); 1.940(32.8); 1.933(22.3); 1.927(11.3); 1.204(0.3); 1.100(5.4); 1.085(5.3); 0.008(2.1); 0.000(56.9); −0.009(2.0) |
| I-A-105 | 1.64 | 1.73 | $^1$H-NMR(400.0 MHz. d$_6$-DMSO): δ = 9.087(6.0); 9.085(6.0); 8.529(2.0); 8.523(2.1); 8.500(1.6); 8.497(1.7); 8.488(1.7); 8.485(1.7); 7.865(0.8); 7.861(0.9); 7.858(0.9); 7.855(0.7); 7.844(0.9); 7.841(1.0); 7.838(1.0); 7.834(0.9); 7.488(1.1); 7.476(1.1); 7.468(1.0); 7.456(1.0); 6.522(1.2); 5.754(9.2); 3.770(16.0); 3.417(15.1); 3.321(12.8); 2.520(0.5); 2.511(8.3); 2.507(17.5); 2.502(23.5); 2.498(16.9); 2.493(8.1); 0.008(1.2); 0.000(36.7); −0.009(1.2) |
| I-A-106 | 1.20 | | $^1$H-NMR(601.6 MHz. d$_6$-DMSO): δ = 8.512(1.5); 8.508(1.6); 8.490(1.2); 8.483(1.2); 8.337(3.1); 8.328(3.1); 7.881(0.8); 7.879(1.0); 7.877(0.9); 7.875(0.8); 7.868(0.9); 7.865(1.1); 7.864(1.0); 7.861(0.9); 7.466(1.0); 7.458(1.0); 7.453(1.0); 7.445(0.9); 6.726(3.3); 6.716(3.3); 6.467(1.1); 3.900(2.4); 3.791(15.7); 3.697(16.0); 3.401(14.9); 3.358(1.0); 3.328(672.2); 3.304(2.7); 3.282(0.5); 3.174(1.0); 3.165(1.0); 2.617(0.6); 2.614(0.8); 2.611(0.5); 2.523(1.4); 2.520(1.8); 2.517(2.0); 2.508(46.4); 2.505(93.3); 2.502(127.2); 2.499(96.7); 2.496(49.0); 2.389(0.6); 2.386(0.8); 2.383(0.6); 1.909(0.5); 0.000(0.9) |
| I-A-107 | 1.04 | 1.20 | $^1$H-NMR(400.0 MHz. CD3CN): δ = 8.490(4.7); 8.436(0.4); 7.710(0.5); 7.706(0.7); 7.704(0.6); 7.700(0.5); 7.689(0.6); 7.686(0.7); 7.683(0.7); 7.680(0.6); 7.406(0.4); 7.394(0.5); 7.386(0.5); 7.374(0.4); 6.491(0.6); 5.446(3.5); 3.776(15.9); 3.430(16.0); 1.958(0.5); 1.952(3.8); 1.946(7.1); 1.939(9.8); 1.933(6.7); 1.927(3.4); 1.538(0.4); 0.008(0.8); 0.000(25.5); −0.009(0.9) |
| I-A-108 | 1.28 | 1.43 | $^1$H-NMR(400.0 MHz. CD3CN): δ = 8.481(1.1); 8.477(1.1); 8.469(1.1); 8.466(1.1); 8.434(1.5); 8.428(1.5); 7.716(0.7); 7.712(0.8); 7.709(0.8); 7.706(0.7); 7.695(0.8); 7.692(0.9); 7.689(0.9); 7.685(0.8); 7.509(1.1); 7.490(2.1); 7.470(1.2); 7.396(0.9); 7.394(0.9); 7.384(1.0); 7.382(0.9); 7.375(0.9); 7.374(0.8); 7.363(0.8); 7.362(0.8); 7.005(1.6); 6.986(1.4); 6.564(1.5); 6.544(1.4); 6.486(2.1); 5.446(0.4); 3.788(16.0); 3.426(15.9); 2.401(10.8); 2.152(13.0); 1.964(0.5); 1.957(1.0); 1.952(7.1); 1.945(13.4); 1.939(18.5); 1.933(12.7); 1.927(6.5); 1.270(0.4); 0.008(1.3); 0.000(40.6); −0.009(1.7) |
| I-A-109 | | | $^1$H-NMR(400.0 MHz. CD3CN): δ = 8.483(0.7); 8.473(0.7); 8.429(0.8); 8.202(0.6); 7.705(0.6); 7.701(0.7); 7.698(0.7); 7.694(0.6); 7.684(0.7); 7.681(0.8); 7.678(0.8); 7.674(0.7); 7.463(0.6); 7.459(0.6); 7.443(0.7); 7.439(0.7); 7.397(0.7); 7.385(0.7); 7.376(0.7); 7.364(0.6); 6.767(0.7); 6.747(0.7); 6.482(0.5); 5.447(1.3); 3.767(15.6); 3.421(16.0); 2.249(7.3); 2.158(11.1); 1.958(0.6); 1.952(4.5); 1.945(8.5); 1.939(11.8); 1.933(8.0); 1.927(4.1); 0.008(1.1); 0.000(33.1); −0.009(1.1) |
| I-A-110 | 1.77 | 1.93 | $^1$H-NMR(400.0 MHz. CD3CN): δ = 8.475(1.1); 8.472(1.2); 8.463(1.2); 8.460(1.4); 8.442(1.1); 8.423(1.6); 8.417(1.6); 8.034(1.1); 8.015(1.1); 7.718(0.7); 7.714(0.8); 7.711(0.8); 7.708(0.7); 7.697(0.8); 7.693(1.0); 7.691(1.0); 7.687(0.8); 7.402(1.0); 7.390(1.1); 7.381(1.0); 7.369(0.9); 7.327(0.8); 7.315(0.8); 7.307(0.8); 7.295(0.7); 6.490(1.8); 5.447(3.1); 3.763(0.6); 3.756(0.6); 3.734(0.6); 3.429(15.9); 3.388(1.1); 2.190(31.2); 1.958(0.5); 1.952(3.9); 1.946(7.3); 1.940(10.1); 1.934(6.8); 1.928(3.5); 0.007(0.6); 0.000(17.0); −0.009(0.6) |
| I-A-111 | 1.73 | 1.78 | $^1$H-NMR(400.0 MHz. d$_6$-DMSO): δ = 8.609(14.5); 8.597(14.9); 8.564(0.6); 8.552(0.6); 8.447(3.8); 8.442(4.5); 8.436(4.2); 8.432(4.3); 8.314(0.5); 8.082(0.6); 7.914(5.5); 7.866(0.3); |

-continued

| Ex. No. | logP[a] | logP[b] | 1H-NMR; δ (ppm) |
|---|---|---|---|
| | | | 7.420(1.4); 7.414(1.1); 7.404(3.8); 7.399(6.5); 7.394(7.9); 7.382(4.8); 7.363(4.0); 7.346(8.0); 7.328(7.5); 7.313(6.9); 7.301(8.8); 7.293(4.8); 7.290(5.3); 7.276(1.3); 7.219(0.4); 7.201(0.6); 7.184(0.5); 7.158(8.1); 7.140(7.1); 7.078(0.3); 6.637(3.6); 5.685(0.5); 5.597(0.5); 5.485(16.0); 3.392(0.8); 3.375(0.8); 3.357(0.5); 3.319(142.2); 3.287(36.5); 3.266(0.7); 3.212(0.4); 2.671(1.1); 2.506(140.0); 2.502(186.0); 2.498(152.0); 2.329(1.1); 1.355(0.4); 1.109(0.7); 1.091(1.5); 1.074(0.7); 0.146(0.8); 0.000(164.9); −0.150(0.8) |
| I-A-112 | 0.56 | 0.85 | $^1$H-NMR(400.0 MHz. $d_6$-DMSO): δ = 8.740(5.4); 8.728(5.6); 8.485(3.5); 8.480(3.7); 8.472(1.7); 8.469(1.7); 7.842(0.8); 7.838(0.9); 7.835(0.9); 7.831(0.9); 7.821(0.9); 7.817(1.1); 7.815(1.1); 7.811(0.9); 7.458(1.2); 7.446(1.2); 7.438(1.1); 7.425(1.1); 7.410(1.4); 7.398(2.6); 7.385(1.3); 6.224(3.6); 4.469(9.4); 4.098(0.6); 4.085(0.6); 3.642(16.0); 3.357(15.2); 3.321(16.5); 3.176(2.7); 3.163(2.7); 2.525(0.4); 2.511(10.4); 2.507(21.6); 2.502(29.1); 2.498(21.8); 2.493(11.3); 0.008(0.5); 0.000(16.5); −0.008(0.7) |
| I-A-113 | 0.66 | 0.93 | $^1$H-NMR(400.0 MHz. $d_6$-DMSO): δ = 8.919(0.4); 8.693(0.3); 8.551(2.4); 8.547(2.3); 8.526(3.7); 8.516(3.3); 8.510(2.5); 8.496(2.9); 8.490(4.6); 8.478(2.0); 7.823(1.3); 7.805(1.3); 7.802(1.5); 7.459(1.5); 7.447(1.5); 7.439(1.4); 7.427(1.3); 6.249(4.0); 5.953(0.9); 4.413(9.6); 4.102(0.5); 4.089(0.5); 3.603(16.0); 3.355(15.6); 3.327(21.3); 3.175(2.5); 3.163(2.4); 2.784(0.9); 2.771(0.9); 2.505(33.7); 0.008(0.7); 0.000(13.8) |
| I-A-114 | 0.20 | 0.85 | $^1$H-NMR(400.0 MHz. $d_6$-DMSO): δ = 8.497(3.9); 8.492(3.3); 8.485(2.0); 8.482(1.8); 7.815(0.8); 7.809(1.0); 7.805(0.9); 7.795(1.0); 7.791(1.1); 7.789(1.2); 7.785(1.0); 7.551(3.3); 7.470(1.3); 7.458(1.3); 7.450(1.2); 7.438(1.1); 6.567(3.2); 6.285(3.8); 4.279(8.4); 4.098(0.9); 4.085(0.9); 3.560(16.0); 3.540(15.9); 3.360(15.8); 3.342(0.6); 3.321(9.3); 3.303(0.6); 3.175(4.2); 3.163(4.2); 2.506(26.0); 2.502(34.4); 2.497(25.8); 0.008(0.6); 0.000(16.9); −0.008(0.7) |
| I-A-115 | 0.76 | 1.12 | $^1$H-NMR(400.0 MHz. $d_6$-DMSO): δ = 8.496(2.7); 8.490(3.8); 8.481(1.8); 8.478(1.6); 7.854(0.9); 7.850(1.1); 7.847(1.0); 7.843(0.9); 7.833(1.0); 7.829(1.2); 7.827(1.1); 7.823(0.9); 7.557(2.6); 7.552(2.5); 7.468(1.3); 7.456(1.3); 7.448(1.2); 7.436(1.2); 6.278(3.8); 5.939(2.8); 5.934(2.7); 4.174(8.9); 4.101(0.5); 4.088(0.5); 3.763(16.0); 3.599(15.8); 3.364(15.1); 3.322(13.8); 3.176(2.2); 3.162(2.1); 2.524(0.5); 2.506(20.9); 2.502(26.4); 2.498(18.9); 0.008(0.4); 0.000(11.8); −0.009(0.4) |
| I-A-116 | 0.16 | 1.11 | $^1$H-NMR(400.0 MHz. $d_6$-DMSO): δ = 8.500(1.6); 8.497(1.8); 8.488(1.8); 8.485(1.8); 8.472(2.6); 8.464(4.8); 8.460(2.9); 8.448(4.3); 8.439(0.5); 8.435(0.5); 7.843(0.8); 7.837(1.1); 7.833(0.9); 7.823(1.0); 7.817(1.2); 7.813(1.0); 7.467(1.3); 7.455(1.3); 7.447(1.3); 7.435(1.2); 7.237(0.4); 7.222(0.4); 7.194(3.6); 7.179(3.6); 6.269(3.8); 4.246(8.1); 3.681(0.4); 3.600(0.4); 3.580(16.0); 3.385(0.5); 3.353(15.5); 3.321(33.9); 2.506(38.1); 2.502(50.4); 2.498(38.7); 2.329(0.3); 1.236(0.4); 0.007(1.0); 0.000(25.1) |
| I-A-117 | 0.63 | 1.16 | $^1$H-NMR(400.0 MHz. $d_6$-DMSO): δ = 8.495(1.8); 8.492(2.7); 8.484(2.7); 8.477(4.1); 8.472(3.1); 7.846(0.8); 7.843(1.0); 7.840(1.0); 7.836(0.9); 7.826(0.9); 7.822(1.1); 7.820(1.1); 7.816(0.9); 7.728(0.8); 7.723(0.8); 7.708(1.6); 7.704(1.6); 7.689(0.9); 7.685(0.9); 7.561(0.6); 7.467(1.3); 7.456(1.3); 7.447(1.2); 7.435(1.1); 7.282(1.1); 7.270(1.2); 7.266(1.1); 7.251(1.0); 7.231(1.9); 7.211(1.7); 6.257(3.8); 4.416(1.1); 4.345(9.1); 4.249(0.3); 3.644(1.8); 3.638(0.7); 3.580(16.0); 3.383(0.6); 3.356(15.4); 3.319(53.6); 2.708(0.8); 2.697(0.8); 2.671(0.5); 2.666(0.4); 2.506(62.1); 2.502(81.5); 2.497(61.2); 2.333(0.4); 2.328(0.5); 2.324(0.4); 1.236(0.8); 0.008(1.3); 0.000(34.7); −0.008(1.6) |
| I-A-118 | | 0.89 | $^1$H-NMR(400.0 MHz. $d_6$-DMSO): δ = 8.495(2.2); 8.489(3.7); 8.480(1.6); 8.476(1.7); 7.839(0.8); 7.835(0.9); 7.832(1.0); 7.829(0.9); 7.818(0.9); 7.815(1.0); 7.812(1.1); 7.808(0.9); 7.464(1.1); 7.452(1.2); 7.444(1.0); 7.432(1.0); 7.074(2.9); 7.072(3.2); 6.787(2.9); 6.784(3.1); 6.283(3.5); 4.307(9.3); 3.574(15.6); 3.480(16.0); 3.362(14.8); 3.315(3.7); 3.173(1.1); 3.163(1.1); 2.524(0.7); 2.511(15.9); 2.506(33.8); 2.502(46.0); 2.497(34.9); 2.493(18.1); 0.008(0.7); 0.000(22.2); −0.008(1.0) |
| I-A-119 | 0.39 | 1.15 | $^1$H-NMR(400.0 MHz. $d_6$-DMSO): δ = 8.500(1.5); 8.496(1.8); 8.491(2.5); 8.485(3.8); 8.444(1.3); 8.440(1.4); 8.432(1.5); 8.428(1.5); 8.413(1.9); 8.408(2.0); 7.831(0.8); 7.827(1.0); 7.825(0.9); 7.821(0.8); 7.811(0.9); 7.807(1.0); 7.804(1.0); 7.801(0.9); 7.596(0.7); 7.592(1.1); 7.587(0.7); 7.577(0.8); 7.572(1.2); 7.567(0.8); 7.470(1.2); 7.457(1.2); 7.450(1.1); 7.437(1.1); 7.314(1.1); 7.303(1.1); 7.295(1.0); 7.283(0.9); |

| Ex. No. | logP[a] | logP[b] | 1H-NMR; δ (ppm) |
|---|---|---|---|
| | | | 6.281(3.7); 4.269(7.6); 3.553(16.0); 3.355(15.2); 3.317(44.0); 2.677(0.5); 2.672(0.6); 2.668(0.5); 2.525(1.8); 2.512(38.7); 2.508(79.5); 2.503(106.6); 2.499(79.6); 2.334(0.5); 2.330(0.7); 2.325(0.5); 0.008(0.7); 0.000(22.6); −0.008(1.0) |
| I-A-120 | 1.34 | 1.55 | $^1$H-NMR(400.0 MHz. d$_6$-DMSO): δ = 8.491(1.9); 8.479(1.9); 8.468(2.6); 8.461(2.7); 8.132(0.7); 7.830(1.2); 7.826(1.1); 7.809(1.1); 7.805(1.1); 7.574(2.7); 7.571(2.9); 7.569(2.9); 7.467(1.4); 7.455(1.4); 7.446(1.4); 7.435(1.3); 6.361(1.5); 6.354(2.1); 6.349(1.8); 6.297(4.1); 6.060(2.3); 6.052(2.3); 5.751(2.0); 4.269(9.4); 3.570(16.0); 3.360(15.6); 3.310(7.8); 2.501(26.9); 2.497(21.9); −0.001(1.7) |
| I-A-121 | 2.51 | 2.62 | $^1$H-NMR(400.0 MHz. d$_6$-DMSO): δ = 8.496(1.6); 8.492(1.7); 8.484(3.9); 8.480(3.3); 8.136(0.8); 7.842(0.8); 7.838(1.0); 7.836(1.0); 7.832(0.9); 7.822(0.9); 7.818(1.1); 7.816(1.1); 7.812(0.9); 7.553(2.6); 7.548(2.7); 7.536(2.7); 7.516(2.9); 7.460(1.2); 7.448(1.2); 7.440(1.2); 7.428(1.1); 7.178(1.5); 7.173(1.5); 7.157(1.3); 7.152(1.3); 6.280(3.8); 5.751(2.6); 4.258(7.7); 3.600(16.0); 3.358(15.4); 3.310(8.4); 2.524(0.6); 2.506(30.2); 2.501(39.9); 2.497(29.9); 0.000(3.0) |
| I-A-122 | 1.37 | 1.58 | $^1$H-NMR(400.0 MHz. CD3CN): δ = 8.481(1.7); 8.472(1.9); 8.469(1.8); 8.394(2.3); 8.388(2.6); 8.172(2.0); 8.166(2.3); 7.654(1.2); 7.651(1.1); 7.640(1.1); 7.634(1.4); 7.630(1.2); 7.577(1.2); 7.570(1.4); 7.556(1.4); 7.550(1.5); 7.394(1.3); 7.382(1.5); 7.374(1.4); 7.362(1.2); 7.310(2.3); 7.290(2.0); 6.268(3.7); 4.186(8.5); 3.701(0.4); 3.584(15.6); 3.370(16.0); 2.501(1.2); 2.163(40.1); 2.113(0.5); 2.106(0.4); 2.100(0.4); 1.951(13.0); 1.945(23.4); 1.939(32.0); 1.933(25.9); 1.927(16.2); 1.270(0.4); 0.000(24.1); −0.008(5.9) |
| I-A-123 | 1.69 | 1.92 | $^1$H-NMR(400.0 MHz. CD3CN): δ = 8.487(1.3); 8.484(1.3); 8.475(1.3); 8.472(1.3); 8.391(1.7); 8.386(1.7); 7.675(0.7); 7.671(0.8); 7.668(0.8); 7.664(0.7); 7.654(0.9); 7.650(1.0); 7.648(0.9); 7.644(0.8); 7.395(1.0); 7.393(1.0); 7.383(1.0); 7.381(1.0); 7.375(0.9); 7.373(0.9); 7.363(0.9); 7.361(0.8); 7.331(0.6); 7.327(0.6); 7.314(0.4); 7.310(1.2); 7.306(0.4); 7.293(0.6); 7.289(0.7); 7.272(0.3); 6.956(1.6); 6.936(2.6); 6.927(0.3); 6.916(1.5); 6.264(3.2); 5.447(2.6); 4.156(5.1); 3.628(15.2); 3.376(16.0); 2.178(21.3); 1.958(0.5); 1.952(3.5); 1.946(6.5); 1.940(8.9); 1.934(6.1); 1.927(3.1); 0.008(0.6); 0.000(16.4); −0.009(0.6) |
| I-A-124 | 1.72 | 2.03 | $^1$H-NMR(400.0 MHz. CD3CN): δ = 8.479(1.3); 8.476(1.3); 8.467(1.3); 8.464(1.2); 8.406(1.5); 8.404(1.6); 8.399(1.5); 8.398(1.4); 7.682(0.8); 7.678(0.9); 7.675(0.8); 7.671(0.8); 7.661(1.0); 7.658(1.0); 7.655(0.9); 7.651(0.8); 7.391(1.0); 7.389(1.0); 7.379(1.0); 7.377(1.0); 7.371(0.9); 7.369(0.9); 7.359(0.8); 7.357(0.8); 7.286(0.5); 7.269(0.7); 7.265(1.2); 7.248(1.2); 7.244(0.7); 7.227(0.6); 6.770(1.3); 6.749(1.1); 6.712(0.7); 6.689(1.3); 6.668(0.6); 6.666(0.6); 6.268(3.0); 5.451(0.4); 5.447(5.1); 4.150(4.4); 4.147(4.2); 3.754(14.4); 3.619(15.8); 3.379(16.0); 2.170(42.1); 1.964(0.4); 1.958(0.9); 1.952(4.1); 1.946(7.2); 1.940(9.5); 1.933(6.4); 1.927(3.2); 0.008(1.0); 0.004(1.6); 0.000(15.8); −0.009(0.6) |
| I-A-125 | 2.09 | 2.28 | $^1$H-NMR(400.0 MHz. CD3CN): δ = 8.484(1.2); 8.481(1.3); 8.472(1.3); 8.469(1.3); 8.428(1.6); 8.422(1.7); 7.696(0.7); 7.693(0.8); 7.690(0.7); 7.686(0.7); 7.676(0.8); 7.672(0.9); 7.670(0.9); 7.666(0.8); 7.396(1.0); 7.394(0.9); 7.384(1.0); 7.382(0.9); 7.375(1.1); 7.3704(2.7); 7.3698(2.7); 7.364(1.0); 7.350(4.5); 7.259(1.7); 7.240(1.4); 7.237(1.2); 7.219(0.9); 6.271(3.1); 5.448(5.4); 4.362(8.2); 3.754(0.3); 3.633(16.0); 3.382(16.0); 2.181(32.5); 1.964(0.3); 1.958(0.7); 1.952(5.1); 1.946(9.5); 1.940(13.1); 1.934(8.9); 1.928(4.6); 0.008(0.7); 0.000(22.2); −0.009(0.7) |
| I-A-126 | 2.47 | 2.54 | $^1$H-NMR(400.0 MHz. CD3CN): δ = 8.485(1.2); 8.482(1.3); 8.474(1.2); 8.470(1.3); 8.430(1.6); 8.424(1.6); 7.709(1.1); 7.690(2.8); 7.688(2.7); 7.670(2.0); 7.664(0.8); 7.481(0.7); 7.461(1.2); 7.441(0.5); 7.393(0.9); 7.391(0.9); 7.381(0.9); 7.380(0.9); 7.373(0.8); 7.371(0.8); 7.361(0.8); 7.359(0.8); 6.295(3.3); 5.446(5.7); 4.461(4.7); 3.756(0.6); 3.659(16.0); 3.388(15.9); 3.274(0.6); 2.141(8.8); 1.958(0.7); 1.952(5.1); 1.946(9.5); 1.939(13.1); 1.933(8.9); 1.927(4.5); 0.008(0.8); 0.000(24.1); −0.009(0.7) |
| I-A-127 | 1.89 | 2.09 | $^1$H-NMR(400.0 MHz. CD3CN): δ = 8.487(1.4); 8.483(1.5); 8.475(1.4); 8.472(1.5); 8.404(2.0); 8.397(2.0); 7.685(0.8); 7.681(0.9); 7.679(1.0); 7.675(0.9); 7.665(0.9); 7.661(1.0); 7.658(1.1); 7.655(0.9); 7.395(1.2); 7.383(1.2); 7.375(1.1); 7.363(1.0); 7.314(0.5); 7.299(0.5); 7.293(1.2); 7.279(1.2); 7.273(1.1); 7.259(1.2); 7.245(2.1); 7.226(0.8); 7.072(0.9); 7.052(1.4); 7.032(0.6); 7.028(0.6); 6.267(3.5); 5.448(6.5); |

-continued

| Ex. No. | logP[a] | logP[b] | 1H-NMR; δ (ppm) |
|---|---|---|---|
| | | | 4.238(5.1); 4.235(5.2); 3.625(16.0); 3.378(16.0); 2.189(25.7); 1.953(3.9); 1.947(6.8); 1.940(9.0); 1.934(6.1); 1.928(3.1); 0.008(0.8); 0.000(13.5); −0.009(0.5) |
| I-A-128 | 1.41 | 1.68 | $^1$H-NMR(400.0 MHz. CD3CN): δ = 8.465(0.6); 8.461(0.6); 8.453(0.6); 8.449(0.6); 8.402(0.8); 8.396(0.8); 7.676(0.4); 7.673(0.4); 7.670(0.4); 7.666(0.4); 7.656(0.4); 7.652(0.4); 7.650(0.4); 7.646(0.4); 7.374(0.5); 7.372(0.5); 7.362(0.5); 7.360(0.5); 7.354(0.4); 7.352(0.4); 7.342(0.4); 7.340(0.4); 6.257(1.7); 5.958(2.3); 5.447(0.5); 4.217(4.4); 3.813(16.0); 3.696(8.0); 3.689(0.4); 3.375(8.0); 2.169(14.8); 1.958(0.4); 1.952(2.7); 1.946(5.0); 1.940(6.9); 1.934(4.7); 1.928(2.4); 0.000(9.7); −0.009(0.4) |
| I-A-129 | 2.32 | 2.44 | $^1$H-NMR(400.0 MHz. CD3CN): δ = 8.488(1.2); 8.484(1.3); 8.476(1.3); 8.472(1.3); 8.411(1.6); 8.405(1.7); 7.696(0.7); 7.692(0.8); 7.689(0.8); 7.686(0.7); 7.675(0.8); 7.672(0.9); 7.669(0.9); 7.665(0.7); 7.402(1.0); 7.400(0.9); 7.390(1.0); 7.388(0.9); 7.381(0.9); 7.380(0.8); 7.370(0.8); 7.368(0.8); 7.100(0.5); 7.084(0.9); 7.078(1.0); 7.063(1.8); 7.031(3.3); 7.012(1.2); 6.306(3.5); 5.446(6.4); 4.259(7.8); 3.764(0.6); 3.552(16.0); 3.376(15.8); 3.268(0.6); 2.416(0.3); 2.340(0.3); 2.328(0.4); 2.255(20.5); 2.169(23.9); 1.972(0.7); 1.963(0.3); 1.957(0.7); 1.952(4.9); 1.945(9.1); 1.939(12.6); 1.933(8.6); 1.927(4.4); 0.008(0.5); 0.000(16.5); −0.009(0.6) |
| I-A-130 | 1.18 | | $^1$H-NMR(400.0 MHz. CD3CN): δ = 8.514(1.8); 8.511(1.7); 8.503(1.9); 8.384(2.5); 8.378(2.2); 7.715(1.1); 7.711(1.2); 7.695(1.3); 7.691(1.4); 7.427(1.2); 7.414(1.4); 7.406(1.2); 7.395(1.1); 7.362(5.2); 7.356(5.1); 7.351(3.6); 7.349(3.7); 7.056(2.4); 7.051(2.5); 7.041(2.6); 6.448(2.3); 4.422(8.2); 3.544(16.0); 3.387(16.0); 2.134(175.3); 2.125(19.2); 2.106(1.4); 2.100(0.9); 1.951(85.8); 1.945(141.2); 1.939(167.4); 1.933(116.4); 1.927(58.6); 1.773(0.8); 1.767(0.9); 1.761(0.7); 1.286(0.4); 1.273(0.5); 0.146(0.4); 0.080(0.8); 0.000(68.9); −0.009(7.5); −0.149(0.4); −0.383(6.2) |
| I-A-131 | 1.28 | 1.40 | $^1$H-NMR(400.0 MHz. d$_6$-DMSO): δ = 8.501(2.5); 8.494(2.8); 8.488(1.9); 8.480(1.7); 8.476(1.8); 7.831(0.8); 7.827(1.0); 7.825(1.0); 7.821(0.9); 7.810(0.9); 7.804(1.2); 7.800(1.0); 7.455(1.4); 7.443(1.4); 7.434(1.3); 7.422(1.2); 6.819(3.8); 6.355(3.1); 5.667(8.2); 4.109(0.6); 4.096(1.7); 4.083(1.7); 4.070(0.6); 3.544(16.0); 3.361(15.8); 3.321(18.5); 3.176(8.0); 3.163(7.7); 2.525(0.5); 2.507(20.5); 2.502(27.6); 2.498(20.8); 2.003(12.4); 0.008(0.5); 0.000(14.7); −0.008(0.7) |
| I-A-132 | 0.59 | 0.94 | $^1$H-NMR(601.6 MHz. d$_6$-DMSO): δ = 8.504(2.0); 8.500(2.0); 8.480(1.5); 8.478(1.5); 8.473(1.6); 8.470(1.5); 8.165(0.8); 8.160(0.8); 7.842(0.9); 7.839(1.0); 7.838(1.0); 7.835(0.9); 7.828(1.0); 7.826(1.1); 7.824(1.1); 7.822(0.9); 7.449(1.1); 7.448(1.1); 7.441(1.1); 7.440(1.1); 7.436(1.1); 7.435(1.0); 7.428(1.0); 7.427(1.0); 6.218(2.3); 3.710(0.6); 3.699(16.0); 3.694(9.2); 3.361(14.9); 3.315(18.1); 3.173(0.5); 3.164(0.5); 2.578(0.4); 2.572(0.6); 2.566(0.9); 2.560(0.9); 2.554(0.6); 2.548(0.4); 2.507(6.8); 2.504(14.0); 2.501(18.8); 2.498(13.9); 2.495(6.6); 0.596(0.6); 0.587(1.8); 0.584(2.3); 0.576(2.3); 0.572(1.9); 0.564(0.7); 0.337(0.7); 0.329(2.0); 0.325(2.1); 0.322(1.9); 0.319(2.0); 0.311(0.6); 0.000(0.5) |
| I-A-133 | 1.06 | 1.22 | $^1$H-NMR(400.0 MHz. CD3CN): δ = 8.464(0.9); 8.425(0.4); 7.897(0.4); 7.719(0.6); 7.701(0.9); 7.385(0.6); 6.340(1.0); 6.245(0.7); 3.982(0.4); 3.843(2.2); 3.739(10.6); 3.640(4.0); 3.625(4.7); 3.610(0.7); 3.567(9.3); 3.389(8.2); 3.380(4.0); 2.308(16.0); 1.964(1.1); 1.952(13.8); 1.946(25.4); 1.940(34.5); 1.933(24.6); 1.927(13.0); 1.849(0.5); 1.832(0.4); 1.774(0.5); 1.768(0.5); 1.762(0.5); 1.756(0.5); 1.305(15.6); 0.146(0.3); 0.008(3.6); 0.000(78.1); −0.150(0.4) |
| I-A-134 | 1.27 | 1.56 | $^1$H-NMR(400.0 MHz. CD3CN): δ = 8.438(1.2); 8.434(1.2); 8.426(1.3); 8.422(1.5); 8.419(1.7); 8.412(1.6); 7.685(0.7); 7.681(0.8); 7.679(0.8); 7.675(0.7); 7.665(0.8); 7.661(0.9); 7.658(0.9); 7.654(0.8); 7.559(1.2); 7.539(1.3); 7.434(1.0); 7.414(1.4); 7.357(0.9); 7.356(0.9); 7.345(0.9); 7.344(0.9); 7.337(0.9); 7.335(0.8); 7.325(0.8); 7.324(0.8); 7.307(0.6); 7.305(0.7); 7.289(1.2); 7.287(1.3); 7.269(0.9); 7.266(0.8); 7.243(1.0); 7.240(1.0); 7.222(1.2); 7.220(1.0); 7.205(0.5); 7.202(0.5); 6.392(1.8); 5.447(3.0); 3.855(15.7); 3.764(16.0); 3.404(15.8); 3.388(0.4); 2.184(70.5); 1.972(0.9); 1.964(0.6); 1.958(1.2); 1.952(7.8); 1.946(14.5); 1.940(19.8); 1.934(13.5); 1.927(6.9); 1.269(0.5); 1.204(0.5); 0.008(0.5); 0.000(16.6); −0.009(0.6) |
| I-A-135 | 0.62 | 0.89 | $^1$H-NMR(400.0 MHz. CD3CN): δ = 8.470(0.5); 8.407(0.5); 7.699(0.6); 7.696(0.7); 7.693(0.7); 7.690(0.6); 7.679(0.7); 7.675(0.8); 7.673(0.8); 7.669(0.7); 7.386(0.6); 7.374(0.6); |

| Ex. No. | logP[a] | logP[b] | 1H-NMR; δ (ppm) |
|---|---|---|---|
| | | | 7.366(0.5); 7.354(0.5); 6.435(1.1); 5.447(1.5); 3.880(15.2); 3.847(0.7); 3.411(15.1); 2.649(0.7); 2.436(16.0); 2.163(23.5); 1.964(0.4); 1.958(0.7); 1.952(4.6); 1.946(8.5); 1.940(11.8); 1.934(8.1); 1.928(4.1); 0.008(0.5); 0.000(13.5); −0.009(0.5) |
| I-A-136 | | | $^1$H-NMR(400.0 MHz. CD3CN): δ = 8.637(1.7); 8.635(1.6); 8.473(0.8); 8.463(0.8); 8.440(0.9); 8.158(1.4); 7.718(0.6); 7.714(0.7); 7.711(0.7); 7.708(0.6); 7.697(0.7); 7.694(0.9); 7.691(0.9); 7.687(0.8); 7.395(0.7); 7.383(0.8); 7.374(0.8); 7.363(0.7); 6.481(0.5); 6.222(0.5); 5.447(5.0); 3.849(15.1); 3.808(14.9); 3.763(3.8); 3.427(16.0); 3.388(3.9); 2.171(32.3); 1.965(0.5); 1.959(1.0); 1.953(6.7); 1.947(12.4); 1.940(17.2); 1.934(11.7); 1.928(5.9); 0.008(0.6); 0.000(18.6); −0.009(0.6) |
| I-A-137 | 1.41 | 1.46 | $^1$H-NMR(400.0 MHz. CD3CN): δ = 8.453(0.6); 8.442(0.7); 8.396(0.8); 7.673(0.7); 7.670(0.8); 7.667(0.7); 7.663(0.6); 7.653(0.7); 7.649(0.8); 7.647(0.8); 7.643(0.7); 7.356(0.8); 7.345(0.7); 7.336(0.7); 7.324(0.6); 6.357(1.3); 5.446(4.8); 4.263(0.7); 4.245(2.2); 4.227(2.2); 4.208(0.7); 3.926(16.0); 3.756(1.9); 3.393(15.7); 3.388(2.5); 2.142(12.3); 1.963(0.5); 1.957(1.0); 1.952(5.6); 1.945(10.4); 1.939(14.4); 1.933(9.9); 1.927(5.0); 1.295(2.7); 1.277(5.6); 1.259(2.7); 0.000(2.0) |
| I-A-138 | 1.12 | 1.26 | $^1$H-NMR(400.0 MHz. CD3CN): δ = 8.455(0.9); 8.444(0.9); 8.395(1.1); 7.676(0.7); 7.672(0.9); 7.670(0.9); 7.666(0.7); 7.656(0.8); 7.652(1.0); 7.650(1.0); 7.646(0.8); 7.362(0.9); 7.350(1.0); 7.341(0.9); 7.330(0.8); 6.339(1.8); 5.446(3.6); 3.902(16.0); 3.733(10.1); 3.390(16.0); 3.021(0.3); 2.141(17.9); 1.963(0.5); 1.957(1.0); 1.951(5.7); 1.945(10.6); 1.939(14.5); 1.933(10.1); 1.927(5.1); 0.000(0.5) |
| I-A-139 | 0.87 | 1.00 | $^1$H-NMR(400.0 MHz. CD3CN): δ = 8.452(1.2); 8.441(1.2); 8.395(1.6); 8.390(1.5); 7.673(0.8); 7.668(1.0); 7.664(0.8); 7.652(0.9); 7.647(1.2); 7.643(0.9); 7.359(1.1); 7.347(1.1); 7.339(1.0); 7.327(1.0); 7.103(1.3); 6.973(2.7); 6.843(1.3); 6.321(2.2); 5.447(4.0); 4.103(0.7); 3.923(0.7); 3.894(16.0); 3.718(13.2); 3.388(15.8); 3.021(1.7); 2.162(23.5); 1.964(0.7); 1.958(1.7); 1.952(8.0); 1.946(14.1); 1.940(18.8); 1.934(12.8); 1.928(6.4); 1.271(0.4); 0.882(0.6) |
| I-A-140 | 1.92 | 1.96 | $^1$H-NMR(400.0 MHz. CD3CN): δ = 8.482(0.9); 8.473(0.9); 8.470(0.9); 8.411(1.1); 8.406(1.0); 7.931(0.4); 7.924(2.0); 7.920(2.1); 7.916(1.0); 7.915(1.0); 7.910(0.9); 7.904(2.0); 7.900(2.2); 7.727(0.8); 7.723(0.9); 7.720(0.8); 7.716(0.8); 7.706(0.9); 7.703(0.9); 7.700(0.9); 7.696(0.8); 7.572(0.4); 7.568(0.3); 7.554(0.9); 7.552(1.0); 7.545(0.8); 7.541(1.6); 7.536(2.9); 7.535(2.8); 7.530(1.6); 7.524(0.9); 7.520(1.3); 7.516(2.2); 7.509(0.4); 7.505(0.5); 7.501(0.7); 7.494(0.5); 7.394(0.8); 7.392(0.9); 7.382(0.9); 7.380(0.9); 7.372(0.8); 7.361(0.7); 7.360(0.7); 6.530(1.6); 5.447(2.7); 3.886(16.0); 3.870(0.7); 3.425(15.8); 3.410(0.7); 2.156(9.3); 1.964(1.3); 1.958(1.9); 1.952(7.0); 1.946(11.8); 1.940(15.9); 1.934(11.1); 1.927(6.1); 0.000(2.5) |
| I-A-141 | 1.39 | 1.84 | $^1$H-NMR(400.0 MHz. CD3CN): δ = 8.438(1.4); 8.390(1.2); 7.687(0.4); 7.666(1.4); 7.646(1.3); 7.489(2.5); 7.472(2.0); 7.393(3.4); 7.353(1.3); 7.344(1.4); 5.446(5.4); 4.057(0.4); 3.861(2.4); 3.805(2.7); 3.763(0.5); 3.602(2.4); 3.433(0.5); 3.387(16.0); 2.156(30.0); 1.963(0.8); 1.951(8.5); 1.945(15.3); 1.939(20.4); 1.933(14.6); 1.927(7.7); 1.269(0.7); 0.823(0.3); 0.000(1.9) |
| I-A-142 | 1.31 | 1.47 | $^1$H-NMR(400.0 MHz. CD3CN): δ = 8.464(1.0); 8.454(1.0); 8.405(1.3); 8.399(1.2); 7.688(0.8); 7.684(0.9); 7.682(0.9); 7.678(0.8); 7.668(0.8); 7.664(0.9); 7.662(0.9); 7.658(0.8); 7.375(1.0); 7.363(1.0); 7.355(0.9); 7.343(0.8); 6.391(1.3); 5.447(6.3); 3.845(16.0); 3.763(0.3); 3.405(16.0); 3.388(0.5); 2.174(22.0); 1.983(7.9); 1.982(8.1); 1.964(0.7); 1.958(1.1); 1.952(4.0); 1.946(6.8); 1.940(9.0); 1.934(6.0); 1.928(3.0); 1.270(0.4); 0.000(0.5) |
| I-A-143 | 1.12 | 1.27 | $^1$H-NMR(400.0 MHz. CD3CN): δ = 8.450(1.0); 8.447(1.0); 8.438(1.0); 8.435(1.0); 8.392(1.3); 8.386(1.3); 7.666(0.7); 7.662(0.8); 7.660(0.8); 7.656(0.6); 7.646(0.8); 7.642(0.9); 7.639(0.9); 7.636(0.7); 7.611(0.7); 7.358(0.9); 7.347(0.9); 7.338(0.8); 7.326(0.7); 6.325(0.5); 5.447(5.2); 3.863(10.4); 3.830(8.8); 3.810(0.5); 3.799(16.0); 3.763(0.8); 3.386(15.7); 2.164(26.8); 1.964(0.6); 1.958(1.2); 1.952(6.7); 1.946(12.4); 1.940(17.0); 1.934(11.6); 1.928(5.8); 1.270(0.4); 0.000(1.5) |
| I-A-144 | | 0.86 | $^1$H-NMR(400.0 MHz. CD3CN): δ = 8.447(1.4); 8.443(1.5); 8.435(1.4); 8.432(1.5); 8.386(2.0); 8.379(2.0); 7.659(0.7); 7.655(0.9); 7.650(0.8); 7.639(0.8); 7.634(1.0); 7.630(0.8); 7.351(1.1); 7.339(1.1); 7.331(1.0); 7.319(1.0); 7.129(2.9); 6.962(2.8); 6.259(2.8); 5.447(4.1); 3.853(16.0); 3.806(1.4); 3.647(15.2); 3.386(1.9); 3.375(15.7); 2.170(4.9); 1.964(0.5); |

-continued

| Ex. No. | logP[a] | logP[b] | 1H-NMR; δ (ppm) |
|---|---|---|---|
| I-A-145 | 0.31 | 0.85 | 1.958(1.0); 1.952(4.8); 1.946(8.7); 1.939(11.8); 1.933 (8.3); 1.927(4.3); 0.000(1.0) <br> $^1$H-NMR(600.1 MHz. $d_6$-DMSO): δ = 8.587(5.5); 8.585(5.8); 8.580(6.0); 8.577(6.0); 8.571(7.7); 8.568(7.8); 7.894(3.4); 7.891(4.0); 7.890(3.9); 7.887(3.5); 7.880(3.8); 7.878(4.2); 7.876(4.3); 7.874(3.7); 7.5254(4.5); 7.5245(4.4); 7.5174(4.5); 7.5166(4.4); 7.512(4.4); 7.511(4.4); 7.504(4.2); 7.503(4.1); 5.718(5.0); 4.449(8.6); 4.437(15.3); 4.424(9.6); 3.948(10.1); 3.935(16.0); 3.923(9.0); 3.790(0.4); 3.686(0.5); 3.494(0.5); 3.459(0.6); 3.450(0.7); 3.370(4.4); 3.346(7.9); 3.335(73.5); 3.216(0.6); 2.794(0.4); 2.787(0.4); 2.720(2.5); 2.614(0.5); 2.611(0.3); 2.523(0.7); 2.520(0.9); 2.517(0.8); 2.508(23.1); 2.505(50.2); 2.502(69.7); 2.499(51.5); 2.496(25.3); 2.389(0.3); 2.386(0.5); 2.383(0.3); 1.194(0.4); 1.182(0.7); 1.170(0.4); 0.000(2.5) |
| I-A-146 | 1.11 | 1.27 | $^1$H-NMR(400.0 MHz. $d_6$-DMSO): δ = 8.632(15.5); 8.620(16.0); 8.505(3.7); 8.502(4.1); 8.493(4.1); 8.490(4.6); 8.485(5.6); 8.479(5.4); 8.313(0.5); 7.842(1.9); 7.838(2.3); 7.835(2.3); 7.831(2.1); 7.821(2.2); 7.817(2.5); 7.815(2.7); 7.811(2.2); 7.492(2.9); 7.480(2.9); 7.471(2.7); 7.459(2.6); 7.329(4.1); 7.317(7.8); 7.304(4.0); 6.535(4.3); 5.754(1.0); 4.306(1.7); 4.288(5.9); 4.271(6.0); 4.253(1.8); 3.417(36.1); 3.317(141.0); 2.675(1.1); 2.670(1.4); 2.666(1.0); 2.524(3.5); 2.510(74.8); 2.506(159.0); 2.501(224.8); 2.497(171.3); 2.492(84.5); 2.333(0.9); 2.328(1.3); 2.324(1.0); 1.310(6.5); 1.292(14.9); 1.274(6.4); 0.146(0.6); 0.008(4.5); 0.000(133.6); −0.008(5.1); −0.150(0.6) |

BIOLOGICAL EXAMPLES

*Meloidogyne incognita* Test

Solvent: 125.0 parts by weight of acetone

To produce a suitable preparation of active compound, 1 part by weight of active compound is mixed with the stated amount of solvent and the concentrate is diluted with water to the desired concentration.

Vessels are filled with sand, active compound solution, an egg/larvae suspension of the southern root-knot nematode (*Meloidogyne incognita*) and lettuce seeds. The lettuce seeds germinate and the plants develop. The galls develop on the roots.

After 14 days, the nematicidal efficacy in % is determined by the formation of galls. 100% means that no galls were found; 0% meant that the number of galls on the treated plants corresponds to the untreated control.

In this test, for example, the following compounds from the preparation examples show an efficacy of 90% at an application rate of 20 ppm: I-A-7; I-A-35

*Myzus persicae*—Spray Test

Solvent: 78 parts by weight of acetone 1.5 parts by weight of dimethylformamide

Emulsifier: alkylaryl polyglycol ether

To produce a suitable active compound preparation, 1 part by weight of active compound is dissolved using the stated parts by weight of solvent and made up with water containing an emulsifier concentration of 1000 ppm until the desired concentration is attained. To produce further test concentrations, the preparation is diluted with emulsifier-containing water.

Discs of Chinese cabbage leaves (*Brassica pekinensis*) infested by all stages of the green peach aphid (*Myzus persicae*) are sprayed with an active compound preparation of the desired concentration.

After 5 or 6 days, the efficacy in % is determined. 100% means that all the aphids were killed; 0% means that no aphids were killed.

In this test, for example, the following compounds from the preparation examples show an efficacy of 100% at an application rate of 500 g/ha: I-A-1, I-A-2, I-A-3, I-A-8, I-A-10; I-A-11, I-A-18, I-A-19, I-A-21, I-A-22, I-A-26, I-A-37, I-A-40, I-A-45, I-A-46, I-A-47, I-A-48, I-A-49, I-A-50, I-A-51, I-A-52, I-A-53, I-A-54, I-A-65, I-A-68, I-A-69, I-A-70, I-A-71, I-A-94, I-A-95, I-A-96, I-A-101, I-A-102, I-A-103, I-A-104, I-A-105, I-A-106, I-A-108, I-A-110, I-A-112, I-A-116, I-A-122, I-A-126, I-A-134, I-A-135, I-A-136, I-A-138, I-A-139, I-A-140, I-A-141, I-A-144, I-A-145, I-B-1

In this test, for example, the following compounds from the preparation examples show an efficacy of 90% at an application rate of 500 g/ha: I-A-5, I-A-6, I-A-7, I-A-12, I-A-14, I-A-16, I-A-23, I-A-24, I-A-25, I-A-27, I-A-28, I-A-30, I-A-31, I-A-36, I-A-38, I-A-39, I-A-41, I-A-55, I-A-58, I-A-59, I-A-60, I-A-61, I-A-62, I-A-64, I-A-67, I-A-73, I-A-74, I-A-75, I-A-77, I-A-79, I-A-82, I-A-83, I-A-84, I-A-86, I-A-87, I-A-97, I-A-98, I-A-100, I-A-107, I-A-109, I-A-113, I-A-117, I-A-119, I-A-120, I-A-123, I-A-124, I-A-125, I-A-127, I-A-128, I-A-130, I-A-131, I-A-132, I-A-137, I-A-142

In this test, for example, the following compounds from the preparation examples show an efficacy of 90% at an application rate of 100 g/ha: I-A-78, I-A-146

In this test, for example, the following compounds from the preparation examples show an efficacy of 90% at an application rate of 20 g/ha: I-A-9

*Tetranychus urticae*—Spray Test, OP-Resistant

Solvent: 78.0 parts by weight of acetone 1.5 parts by weight of dimethylformamide Emulsifier: alkylaryl polyglycol ether To produce a suitable active compound preparation, 1 part by weight of active compound is dissolved using the stated parts by weight of solvent and made up with water containing an emulsifier concentration of 1000 ppm until the desired concentration is attained. To produce further test concentrations, the preparation is diluted with emulsifier-containing water.

Discs of bean leaves (*Phaseolus vulgaris*) infested with all stages of the greenhouse red spider mite (*Tetranychus urticae*) are sprayed with an active compound preparation of the desired concentration.

After 6 days, the efficacy in % is determined. 100% means that all the spider mites had been killed; 0% means that no spider mites had been killed.

In this test, for example, the following compounds from the preparation examples show an efficacy of 90% at an application rate of 500 g/ha: I-A-6, I-A-78, I-A-105

*Phaedon cochleariae*—Spray Test

Solvents: 78.0 parts by weight of acetone
1.5 parts by weight of dimethylformamide
Emulsifier: alkylaryl polyglycol ether To produce a suitable active compound preparation, 1 part by weight of active compound is dissolved using the stated parts by weight of solvent and made up with water containing an emulsifier concentration of 1000 ppm until the desired concentration is attained. To produce further test concentrations, the preparation is diluted with emulsifier-containing water.

Discs of Chinese cabbage leaves (*Brassica pekinensis*) are sprayed with an active compound preparation of the desired concentration and, after drying, populated with larvae of the mustard beetle (*Phaedon cochleariae*).

After 7 days, the efficacy in % is determined. 100% means that all beetle larvae were killed; 0% means that no beetle larvae were killed.

In this test, for example, the following compounds from the preparation examples show an efficacy of 100% at an application rate of 500 g/ha: I-A-79, I-A-80

In this test, for example, the following compounds from the preparation examples show an efficacy of 83% at an application rate of 500 g/ha: I-A-15

*Myzus persicae*—Spray Test

Solvent: 14 parts by weight of dimethylformamide
Emulsifier: alkylaryl polyglycol ether To produce a suitable active compound preparation, 1 part by weight of active compound is dissolved using the stated parts by weight of solvent and made up with water containing an emulsifier concentration of 1000 ppm until the desired concentration is attained. To produce further test concentrations, the preparation is diluted with emulsifier-containing water. If the addition of ammonium salts and/or penetrants is required, these are each added in a concentration of 1000 ppm to the formulation solution.

Bell pepper plants (*Capsicum annuum*) severely infested with the green peach aphid (*Myzus persicae*) are treated by spraying with the active compound preparation in the desired concentration.

After 6 days, the kill in % is determined. 100% means that all of the aphids have been killed; 0% means that none of the aphids have been killed.

In this test, for example, the following compounds from the preparation examples show an efficacy of 99% at an application rate of 100 ppm: I-A-66

In this test, for example, the following compounds from the preparation examples show an efficacy of 100% at an application rate of 20 ppm: I-A-44, I-A-99

In this test, for example, the following compounds from the preparation examples show an efficacy of 99% at an application rate of 20 ppm: I-A-4, I-A-20, I-A-57, I-A-89

In this test, for example, the following compounds from the preparation examples show an efficacy of 95% at an application rate of 20 ppm: I-A-93

CONTRASTING EXAMPLES

*Myzus persicae*—Spray Test (MYZUPE)

Solvents: 78.0 parts by weight of acetone
1.5 parts by weight of dimethylformamide
Emulsifier: alkylaryl polyglycol ether To produce a suitable active compound preparation, 1 part by weight of active compound is dissolved using the stated parts by weight of solvent and made up with water containing an emulsifier concentration of 1000 ppm until the desired concentration is attained. To produce further test concentrations, the preparation is diluted with emulsifier-containing water.

Discs of Chinese cabbage leaves (*Brassica pekinensis*), infested by all stages of the green peach aphid (*Myzus persicae*) are sprayed with an active compound preparation of the desired concentration.

After the desired period of time, the efficacy in % is determined. 100% means that all aphids were killed; 0% means that no aphids were killed.

In this test, for example, the following compounds from the preparation examples show superior efficacy compared to the prior art: see table

*Tetranychus urticae*—Spray Test; OP Resistant (TETRUR)

Solvents: 78.0 parts by weight of acetone
1.5 parts by weight of dimethylformamide
Emulsifier: alkylaryl polyglycol ether To produce a suitable active compound preparation, 1 part by weight of active compound is dissolved using the stated parts by weight of solvent and made up with water containing an emulsifier concentration of 1000 ppm until the desired concentration is attained. To produce further test concentrations, the preparation is diluted with emulsifier-containing water.

Discs of bean leaves (*Phaseolus vulgaris*), infested by all stages of the greenhouse red spider mite (*Tetranychus urticae*) are sprayed with an active compound preparation of the desired concentration.

After the desired period of time, the efficacy in % is determined. 100% means that all spider mites were killed; 0% means that no spider mites were killed.

In this test, for example, the following compounds from the preparation examples show superior efficacy compared to the prior art: see table

*Phaedon cochleariae*—Spray Test (PHAECO)

Solvents: 78.0 parts by weight of acetone
1.5 parts by weight of dimethylformamide
Emulsifier: alkylaryl polyglycol ether To produce a suitable active compound preparation, 1 part by weight of active compound is dissolved using the stated parts by weight of solvent and made up with water containing an emulsifier concentration of 1000 ppm until the desired concentration is attained. To produce further test concentrations, the preparation is diluted with emulsifier-containing water.

Discs of Chinese cabbage leaves (*Brassica pekinensis*) are sprayed with an active compound preparation of the desired concentration and, after drying, populated with larvae of the mustard beetle (*Phaedon cochleariae*).

After the desired period of time, the efficacy in % is determined. 100% means that all beetle larvae were killed; 0% means that no beetle larvae were killed.

In this test, for example, the following compounds from the preparation examples show superior efficacy compared to the prior art: see table

| Substance | Structure | Animal species | Concentration | % efficacy | dat |
|---|---|---|---|---|---|
| Ex. No. 13 Prior art WO2011/009804 | | PHAECO TETRUR MYZUPE | 500 g ai/ha 500 g ai/ha 100 g ai/ha | 0 0 0 | 7 dat 6 dat 6 dat |
| Ex. No. 14 Prior art WO2011/009804 | | PHAECO TETRUR MYZUPE | 500 g ai/ha 500 g ai/ha 100 g ai/ha | 0 0 0 | 7 dat 6 dat 6 dat |
| Ex. No. I-A-79 According to the invention | | PHAECO | 500 g ai/ha | 100 | 7 dat |
| Ex. No. I-A-80 According to the invention | | PHAECO | 500 g ai/ha | 100 | 7 dat |
| Ex. No. I-A-15 According to the invention | | PHAECO | 500 g ai/ha | 83 | 7 dat |
| Ex. No. I-A-6 According to the invention | | TETRUR MYZUPE | 500 g ai/ha 100 g ai/ha | 90 90 | 6 dat 6 dat |

-continued

| Substance | Structure | Animal species | Concentration | % efficacy | dat |
|---|---|---|---|---|---|
| Ex. No. I-A-78 According to the invention | 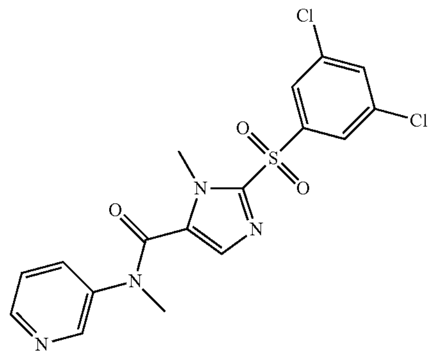 [SMILES: CN(C(=O)c1cnc(S(=O)(=O)c2cc(Cl)cc(Cl)c2)n1C)c1cccnc1] | TETRUR MYZUPE | 500 g ai/ha 100 g ai/ha | 90 90 | 6 dat 6 dat |
| Ex. No. I-A-105 According to the invention | 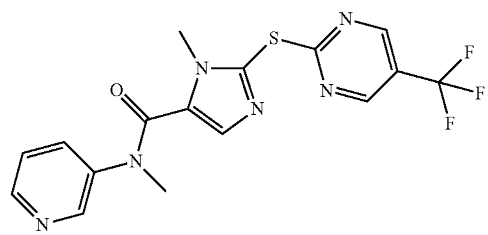 [SMILES: CN(C(=O)c1cnc(Sc2ncc(C(F)(F)F)cn2)n1C)c1cccnc1] | TETRUR MYZUPE | 500 g ai/ha 100 g ai/ha | 90 100 | 6 dat 6 dat |
| Ex. No. I-A-39 According to the invention | 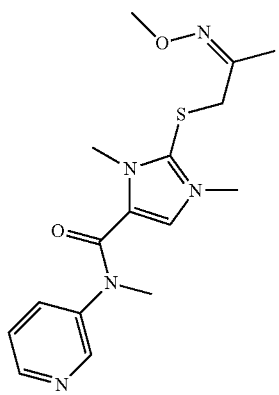 | TETRUR | 500 g ai/ha | 70 | 6 dat |
| Ex. No. I-A-107 According to the invention | 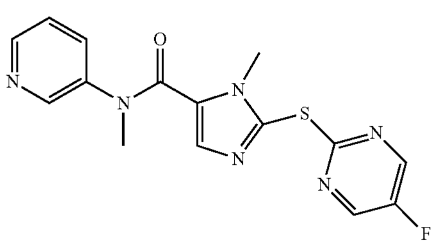 [SMILES: CN(C(=O)c1cnc(Sc2ncc(F)cn2)n1C)c1cccnc1] | TETRUR MYZUPE | 500 g ai/ha 100 g ai/ha | 70 90 | 6 dat 6 dat |
| Ex. No. I-A-110 According to the invention | 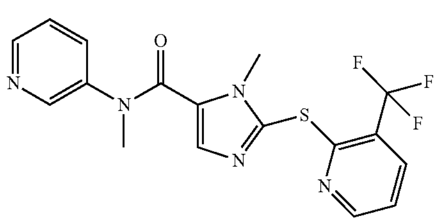 [SMILES: CN(C(=O)c1cnc(Sc2ncccc2C(F)(F)F)n1C)c1cccnc1] | TETRUR MYZUPE | 500 g ai/ha 100 g ai/ha | 70 100 | 6 dat 6 dat |

-continued

| Substance | Structure | Animal species | Concentration | % efficacy | dat |
|---|---|---|---|---|---|
| Ex. No. I-A-125 According to the invention | 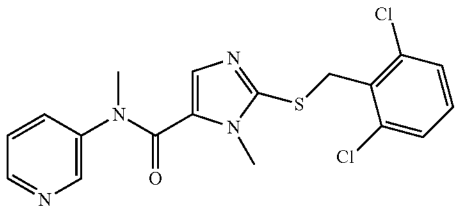 [SMILES: CN(C(=O)c1cnc(SCc2c(Cl)cccc2Cl)n1C)c1cccnc1] | TETRUR MYZUPE | 500 g ai/ha 100 g ai/ha | 70 70 | 6 dat 6 dat |
| Ex. No. I-A-1 According to the invention | 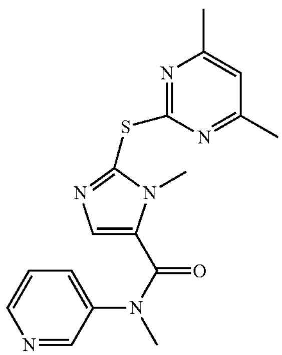 [SMILES: Cc1cc(C)nc(Sc2ncc(C(=O)N(C)c3cccnc3)n2C)n1] | MYZUPE | 100 g ai/ha | 100 | 6 dat |
| Ex. No. I-A-5 According to the invention | 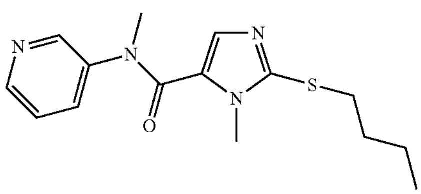 [SMILES: CCCCSc1ncc(C(=O)N(C)c2cccnc2)n1C] | MYZUPE | 100 g ai/ha | 100 | 6 dat |
| Ex. No. I-A-10 According to the invention | 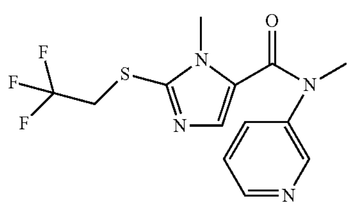 [SMILES: CN(C(=O)c1cnc(SCC(F)(F)F)n1C)c1cccnc1] | MYZUPE | 100 g ai/ha | 100 | 6 dat |
| Ex. No. I-A-21 According to the invention | 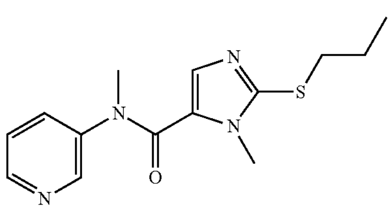 [SMILES: CCCSc1ncc(C(=O)N(C)c2cccnc2)n1C] | MYZUPE | 100 g ai/ha | 100 | 6 dat |
| Ex. No. I-A-37 According to the invention | 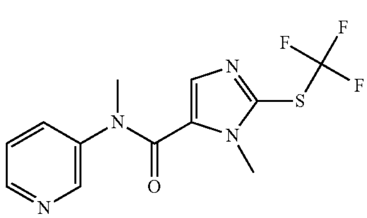 [SMILES: CN(C(=O)c1cnc(SC(F)(F)F)n1C)c1cccnc1] | MYZUPE | 100 g ai/ha | 100 | 6 dat |

-continued

| Substance | Structure | Animal species | Concentration | % efficacy | dat |
|---|---|---|---|---|---|
| Ex. No. I-A-50 According to the invention | 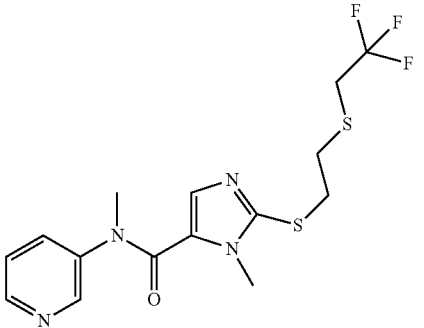 [SMILES: CN(C(=O)c1cnc(SCCSCC(F)(F)F)n1C)c1cccnc1] | MYZUPE | 100 g ai/ha | 100 | 5 dat |
| Ex. No. I-A-51 According to the invention | 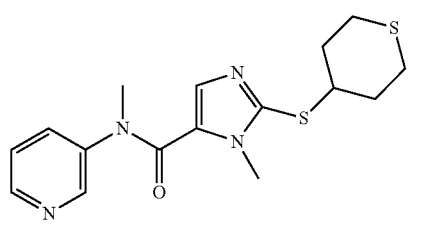 [SMILES: CN(C(=O)c1cnc(SC2CCSCC2)n1C)c1cccnc1] | MYZUPE | 100 g ai/ha | 100 | 5 dat |
| Ex. No. I-A-52 According to the invention | 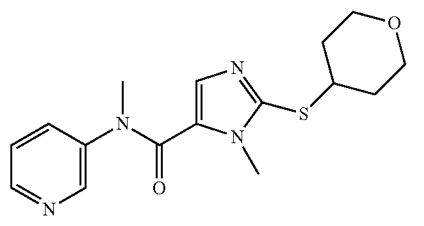 [SMILES: CN(C(=O)c1cnc(SC2CCOCC2)n1C)c1cccnc1] | MYZUPE | 100 g ai/ha | 100 | 5 dat |
| Ex. No. I-A-53 According to the invention | 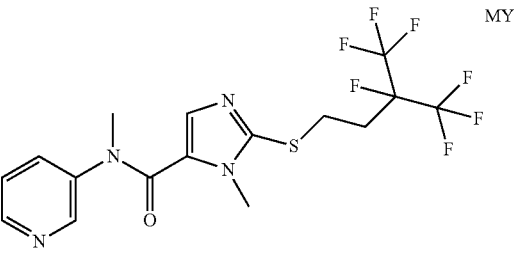 | MYZUPE | 100 g ai/ha | 100 | 5 dat |
| Ex. No. I-A-65 According to the invention | 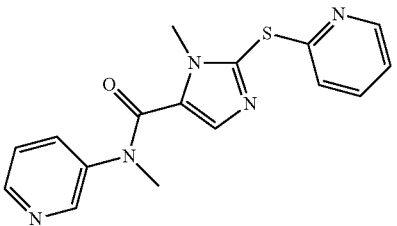 [SMILES: CN(C(=O)c1cnc(Sc2ccccn2)n1C)c1cccnc1] | MYZUPE | 100 g ai/ha | 100 | 6 dat |
| Ex. No. I-A-134 According to the invention | 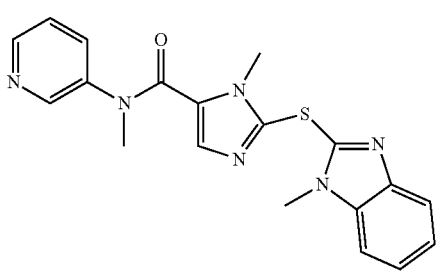 [SMILES: CN(C(=O)c1cnc(Sc2nc3ccccc3n2C)n1C)c1cccnc1] | MYZUPE | 100 g ai/ha | 100 | 5 dat |

-continued

| Substance | Structure | Animal species | Concentration | % efficacy | dat |
|---|---|---|---|---|---|
| Ex. No. I-A-2 According to the invention | 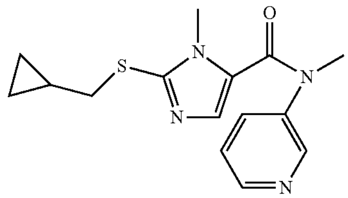 [SMILES: CN(C(=O)c1cnc(SCC2CC2)n1C)c1cccnc1] | MYZUPE | 100 g ai/ha | 90 | 6 dat |
| Ex. No. I-A-3 According to the invention | 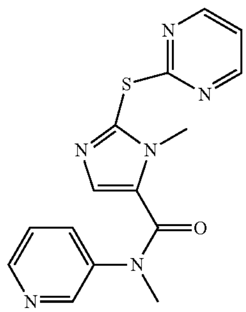 [SMILES: CN(C(=O)c1cnc(Sc2ncccn2)n1C)c1cccnc1] | MYZUPE | 100 g ai/ha | 90 | 6 dat |
| Ex. No. I-A-8 According to the invention | 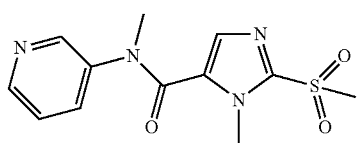 [SMILES: CN(C(=O)c1cnc(S(C)(=O)=O)n1C)c1cccnc1] | MYZUPE | 100 g ai/ha | 90 | 6 dat |
| Ex. No. I-A-11 According to the invention | 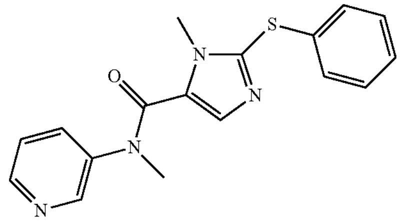 [SMILES: CN(C(=O)c1cnc(Sc2ccccc2)n1C)c1cccnc1] | MYZUPE | 100 g ai/ha | 90 | 6 dat |
| Ex. No. I-A-14 According to the invention | 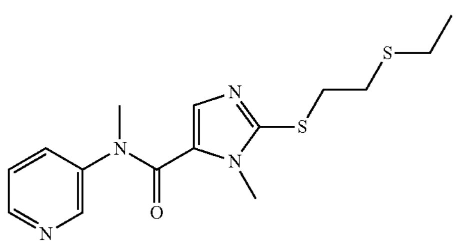 [SMILES: CCSCCSc1ncc(C(=O)N(C)c2cccnc2)n1C] | MYZUPE | 100 g ai/ha | 90 | 6 dat |
| Ex. No. I-A-18 According to the invention | 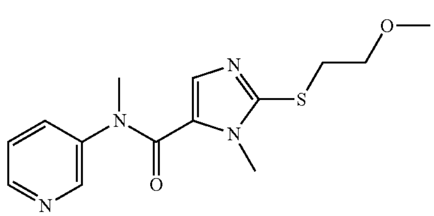 [SMILES: COCCSc1ncc(C(=O)N(C)c2cccnc2)n1C] | MYZUPE | 100 g ai/ha | 90 | 6 dat |
| Ex. No. I-A-19 According to the invention | 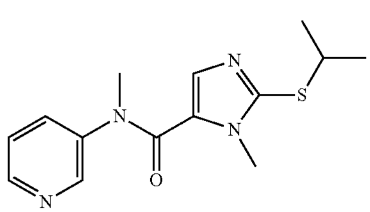 [SMILES: CC(C)Sc1ncc(C(=O)N(C)c2cccnc2)n1C] | MYZUPE | 100 g ai/ha | 90 | 6 dat |

-continued

| Substance | Structure | Animal species | Concentration | % efficacy | dat |
|---|---|---|---|---|---|
| Ex. No. I-A-22 According to the invention | 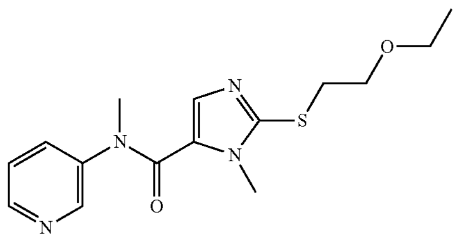 [SMILES: CCOCCSc1ncc(C(=O)N(C)c2cccnc2)n1C] | MYZUPE | 100 g ai/ha | 90 | 6 dat |
| Ex. No. I-A-30 According to the invention | 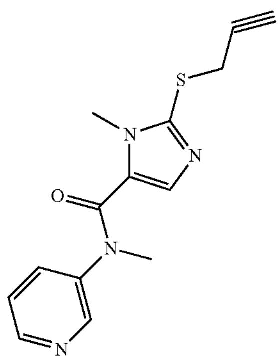 [SMILES: C#CCSc1ncc(C(=O)N(C)c2cccnc2)n1C] | MYZUPE | 100 g ai/ha | 90 | 6 dat |
| Ex. No. I-A-36 According to the invention | 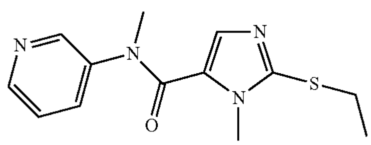 [SMILES: CCSc1ncc(C(=O)N(C)c2cccnc2)n1C] | MYZUPE | 100 g ai/ha | 90 | 6 dat |
| Ex. No. I-A-40 According to the invention | 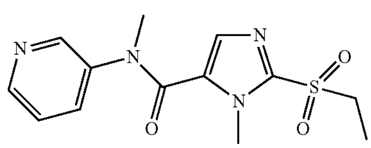 [SMILES: CCS(=O)(=O)c1ncc(C(=O)N(C)c2cccnc2)n1C] | MYZUPE | 100 g ai/ha | 90 | 6 dat |
| Ex. No. I-A-45 According to the invention | 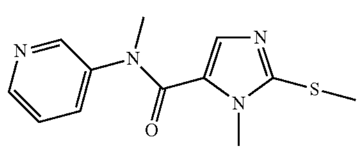 [SMILES: CSc1ncc(C(=O)N(C)c2cccnc2)n1C] | MYZUPE | 100 g ai/ha | 90 | 6 dat |
| Ex. No. I-A-46 According to the invention | 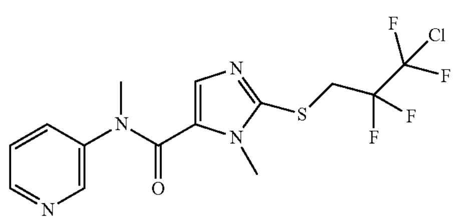 [SMILES: CN(C(=O)c1cnc(SCC(F)(F)C(F)(F)Cl)n1C)c1cccnc1] | MYZUPE | 100 g ai/ha | 90 | 5 dat |
| Ex. No. I-A-47 According to the invention | 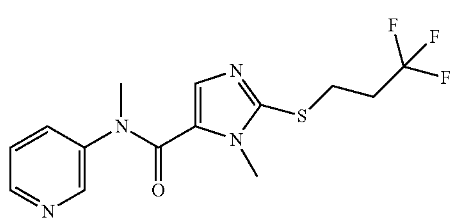 [SMILES: CN(C(=O)c1cnc(SCCC(F)(F)F)n1C)c1cccnc1] | MYZUPE | 100 g ai/ha | 90 | 5 dat |

-continued

| Substance | Structure | Animal species | Concentration | % efficacy | dat |
|---|---|---|---|---|---|
| Ex. No. I-A-48 According to the invention | 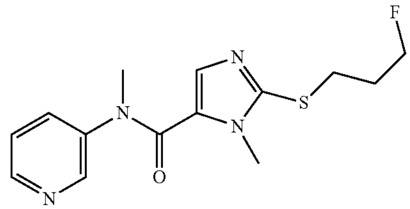 [SMILES: CN(C(=O)c1cnc(SCCCF)n1C)c1cccnc1] | MYZUPE | 100 g ai/ha | 90 | 5 dat |
| Ex. No. I-A-49 According to the invention | 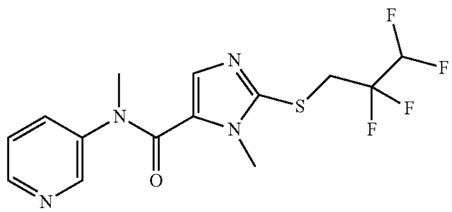 [SMILES: CN(C(=O)c1cnc(SCC(F)(F)C(F)F)n1C)c1cccnc1] | MYZUPE | 100 g ai/ha | 90 | 5 dat |
| Ex. No. I-A-54 According to the invention | 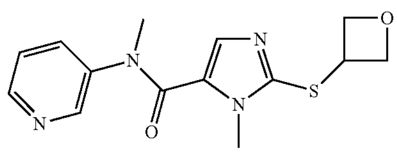 [SMILES: CN(C(=O)c1cnc(SC2COC2)n1C)c1cccnc1] | MYZUPE | 100 g ai/ha | 90 | 5 dat |
| Ex. No. I-A-55 According to the invention | 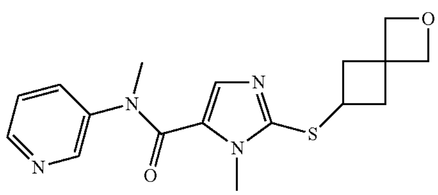 [SMILES: CN(C(=O)c1cnc(SC2CC3(COC3)C2)n1C)c1cccnc1] | MYZUPE | 100 g ai/ha | 90 | 5 dat |
| Ex. No. I-A-59 According to the invention | 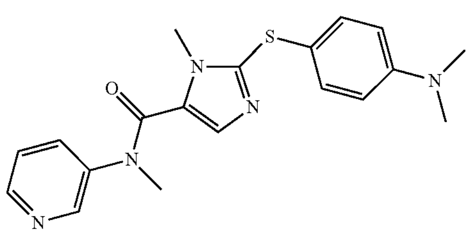 [SMILES: CN(C)c1ccc(Sc2ncc(C(=O)N(C)c3cccnc3)n2C)cc1] | MYZUPE | 100 g ai/ha | 90 | 6 dat |
| Ex. No. I-A-61 According to the invention | 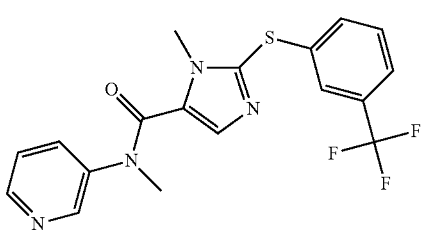 [SMILES: CN(C(=O)c1cnc(Sc2cccc(C(F)(F)F)c2)n1C)c1cccnc1] | MYZUPE | 100 g ai/ha | 90 | 6 dat |
| Ex. No. I-A-82 According to the invention | 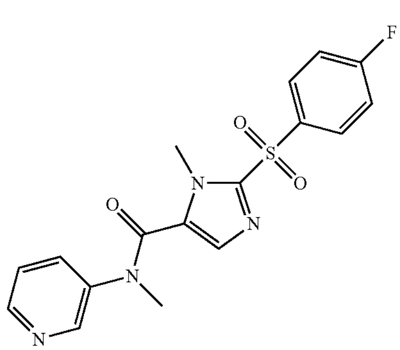 [SMILES: CN(C(=O)c1cnc(S(=O)(=O)c2ccc(F)cc2)n1C)c1cccnc1] | MYZUPE | 100 g ai/ha | 90 | 6 dat |

-continued

| Substance | Structure | Animal species | Concentration | % efficacy | dat |
|---|---|---|---|---|---|
| Ex. No. I-A-86 According to the invention | 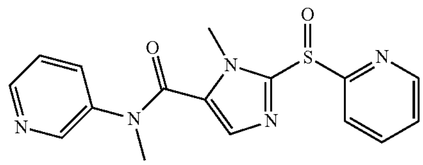 [SMILES: CN(C(=O)c1cnc(S(=O)c2ccccn2)n1C)c1cccnc1] | MYZUPE | 100 g ai/ha | 90 | 6 dat |
| Ex. No. I-A-87 According to the invention | 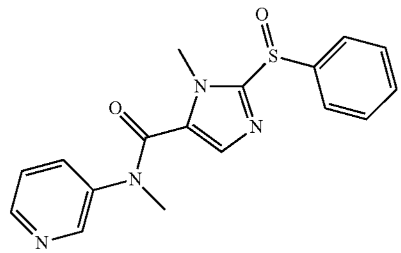 [SMILES: CN(C(=O)c1cnc(S(=O)c2ccccc2)n1C)c1cccnc1] | MYZUPE | 100 g ai/ha | 90 | 6 dat |
| Ex. No. I-A-94 According to the invention | 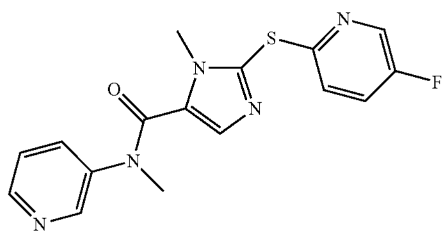 [SMILES: CN(C(=O)c1cnc(Sc2ccc(F)cn2)n1C)c1cccnc1] | MYZUPE | 100 g ai/ha | 90 | 6 dat |
| Ex. No. I-A-95 According to the invention | 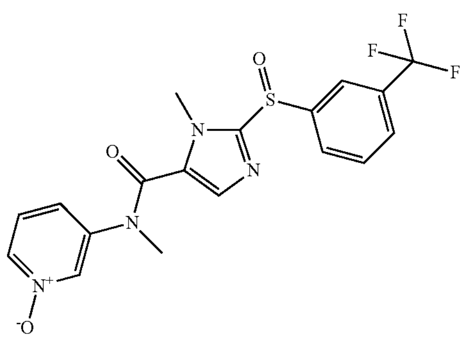 | MYZUPE | 100 g ai/ha | 90 | 5 dat |
| Ex. No. I-A-96 According to the invention | 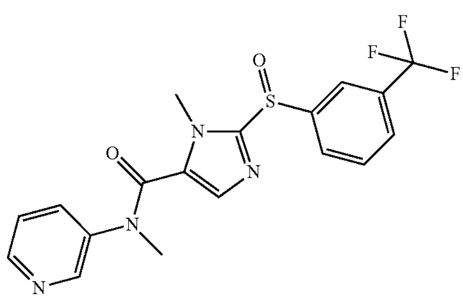 [SMILES: CN(C(=O)c1cnc(S(=O)c2cccc(C(F)(F)F)c2)n1C)c1cccnc1] | MYZUPE | 100 g ai/ha | 90 | 5 dat |
| Ex. No. I-A-100 According to the invention | 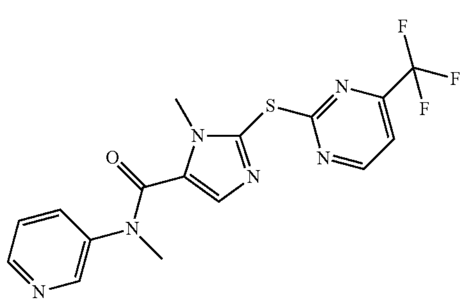 [SMILES: CN(C(=O)c1cnc(Sc2nccc(C(F)(F)F)n2)n1C)c1cccnc1] | MYZUPE | 100 g ai/ha | 90 | 6 dat |

-continued

| Substance | Structure | Animal species | Concentration | % efficacy | dat |
|---|---|---|---|---|---|
| Ex. No. I-A-101 According to the invention | 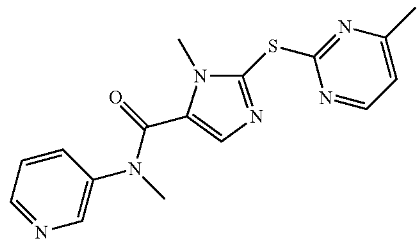 [SMILES: Cc1ccnc(Sc2ncc(C(=O)N(C)c3cccnc3)n2C)n1] | MYZUPE | 100 g ai/ha | 90 | 6 dat |
| Ex. No. I-A-102 According to the invention | 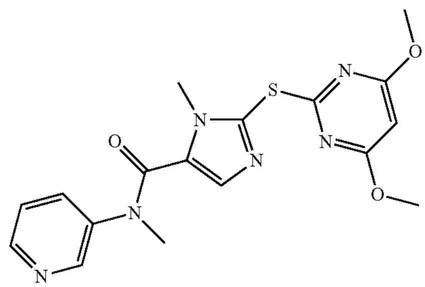 [SMILES: COc1cc(OC)nc(Sc2ncc(C(=O)N(C)c3cccnc3)n2C)n1] | MYZUPE | 100 g ai/ha | 90 | 6 dat |
| Ex. No. I-A-104 According to the invention | 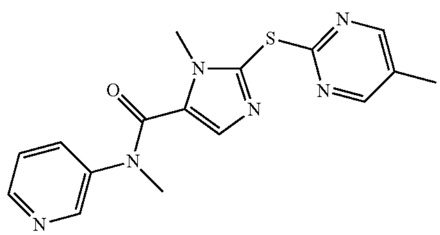 [SMILES: Cc1cnc(Sc2ncc(C(=O)N(C)c3cccnc3)n2C)nc1] | MYZUPE | 100 g ai/ha | 90 | 6 dat |
| Ex. No. I-A-106 According to the invention | 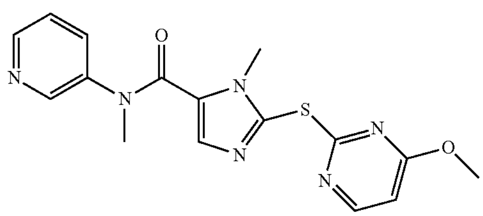 [SMILES: COc1ccnc(Sc2ncc(C(=O)N(C)c3cccnc3)n2C)n1] | MYZUPE | 100 g ai/ha | 90 | 6 dat |
| Ex. No. I-A-112 According to the invention | 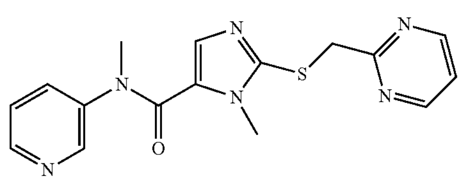 [SMILES: CN(C(=O)c1cnc(SCc2ncccn2)n1C)c1cccnc1] | MYZUPE | 100 g ai/ha | 90 | 6 dat |
| Ex. No. I-A-113 According to the invention | 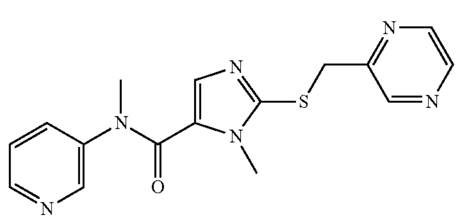 [SMILES: CN(C(=O)c1cnc(SCc2cnccn2)n1C)c1cccnc1] | MYZUPE | 100 g ai/ha | 90 | 6 dat |
| Ex. No. I-A-116 According to the invention | 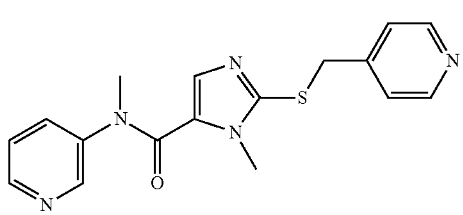 [SMILES: CN(C(=O)c1cnc(SCc2ccncc2)n1C)c1cccnc1] | MYZUPE | 100 g ai/ha | 90 | 6 dat |

-continued

| Substance | Structure | Animal species | Concentration | % efficacy | dat |
|---|---|---|---|---|---|
| Ex. No. I-A-117 According to the invention | 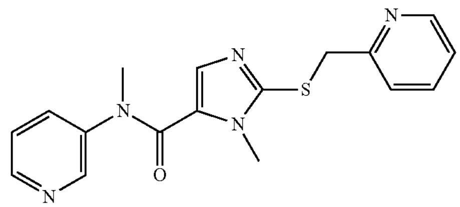 [SMILES: CN(C(=O)c1cnc(SCc2ccccn2)n1C)c1cccnc1] | MYZUPE | 100 g ai/ha | 90 | 6 dat |
| Ex. No. I-A-122 According to the invention | 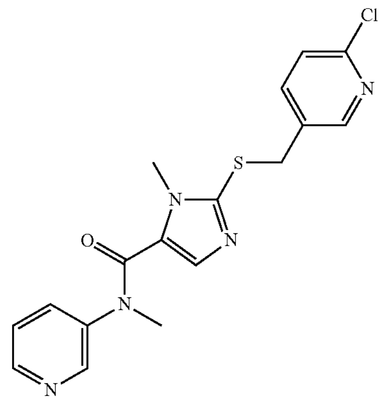 [SMILES: CN(C(=O)c1cnc(SCc2ccc(Cl)nc2)n1C)c1cccnc1] | MYZUPE | 100 g ai/ha | 90 | 6 dat |
| Ex. No. I-A-128 According to the invention | 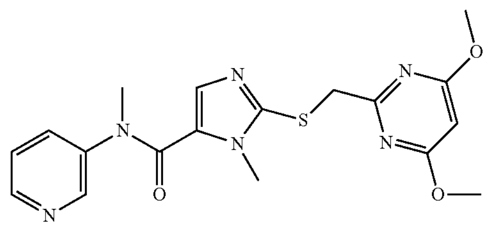 [SMILES: COc1cc(OC)nc(CSc2ncc(C(=O)N(C)c3cccnc3)n2C)n1] | MYZUPE | 100 g ai/ha | 90 | 6 dat |
| Ex. No. I-A-130 According to the invention | 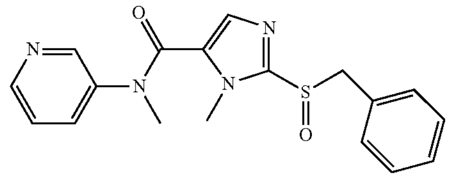 [SMILES: CN(C(=O)c1cnc(S(=O)Cc2ccccc2)n1C)c1cccnc1] | MYZUPE | 100 g ai/ha | 90 | 5 dat |
| Ex. No. I-A-135 According to the invention | 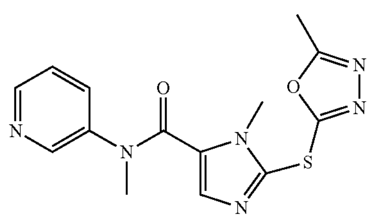 [SMILES: Cc1nnc(Sc2ncc(C(=O)N(C)c3cccnc3)n2C)o1] | MYZUPE | 100 g ai/ha | 90 | 5 dat |
| Ex. No. I-A-136 According to the invention | 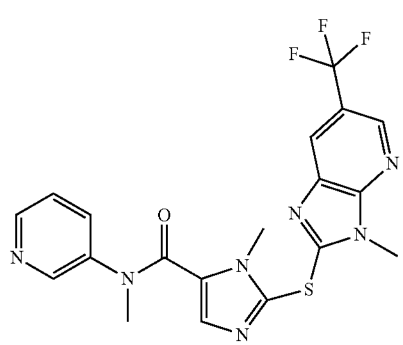 [SMILES: CN(C(=O)c1cnc(Sc2nc3cc(C(F)(F)F)cnc3n2C)n1C)c1cccnc1] | MYZUPE | 100 g ai/ha | 90 | 5 dat |

-continued

| Substance | Structure | Animal species | Concentration | % efficacy | dat |
|---|---|---|---|---|---|
| Ex. No. I-A-137 According to the invention | 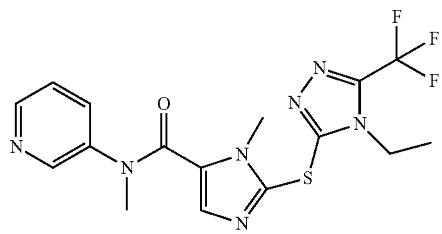 [SMILES: CCn1c(Sc2ncc(C(=O)N(C)c3cccnc3)n2C)nnc1C(F)(F)F] | MYZUPE | 100 g ai/ha | 90 | 5 dat |
| Ex. No. I-A-138 According to the invention | 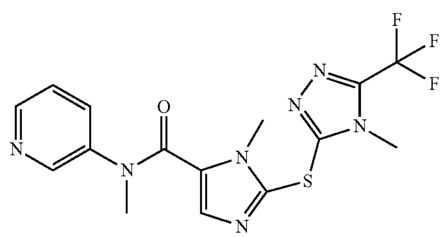 [SMILES: CN(C(=O)c1cnc(Sc2nnc(C(F)(F)F)n2C)n1C)c1cccnc1] | MYZUPE | 100 g ai/ha | 90 | 5 dat |
| Ex. No. I-A-139 According to the invention | 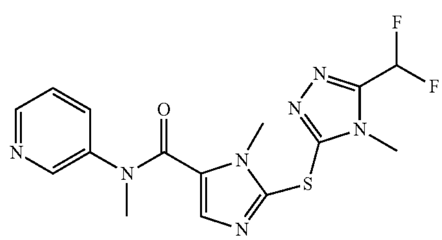 [SMILES: CN(C(=O)c1cnc(Sc2nnc(C(F)F)n2C)n1C)c1cccnc1] | MYZUPE | 100 g ai/ha | 90 | 5 dat |
| Ex. No. I-A-142 According to the invention | 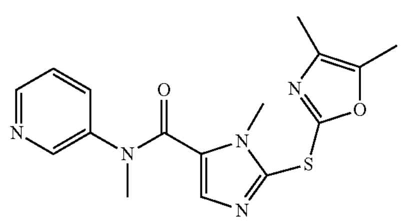 [SMILES: Cc1nc(Sc2ncc(C(=O)N(C)c3cccnc3)n2C)oc1C] | MYZUPE | 100 g ai/ha | 90 | 5 dat |
| Ex. No. I-A-144 According to the invention | 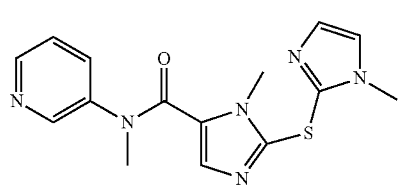 [SMILES: CN(C(=O)c1cnc(Sc2nccn2C)n1C)c1cccnc1] | MYZUPE | 100 g ai/ha | 90 | 5 dat |
| Ex. No. I-B-1 According to the invention | 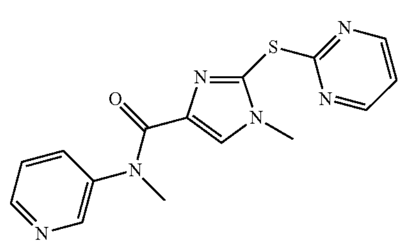 [SMILES: CN(C(=O)c1cn(C)c(Sc2ncccn2)n1)c1cccnc1] | MYZUPE | 100 g ai/ha | 90 | 6 dat |

-continued

| Substance | Structure | Animal species | Concentration | % efficacy | dat |
|---|---|---|---|---|---|
| Ex. No. I-A-4 According to the invention | 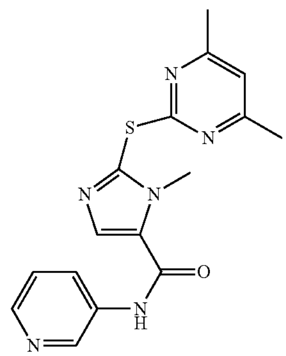 [SMILES: Cc1cc(C)nc(Sc2ncc(C(=O)Nc3cccnc3)n2C)n1] | MYZUPE | 100 g ai/ha | 70 | 6 dat |
| Ex. No. I-A-7 According to the invention | 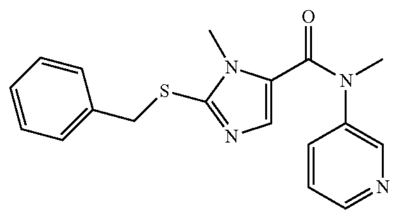 [SMILES: CN(C(=O)c1cnc(SCc2ccccc2)n1C)c1cccnc1] | MYZUPE | 100 g ai/ha | 70 | 6 dat |
| Ex. No. I-A-9 According to the invention | 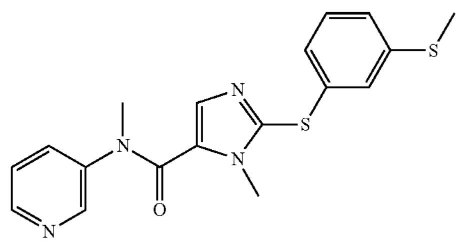 [SMILES: CSc1cccc(Sc2ncc(C(=O)N(C)c3cccnc3)n2C)c1] | MYZUPE | 100 g ai/ha | 70 | 6 dat |
| Ex. No. I-A-12 According to the invention | 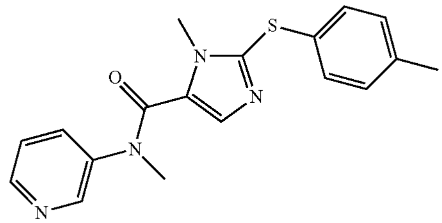 [SMILES: Cc1ccc(Sc2ncc(C(=O)N(C)c3cccnc3)n2C)cc1] | MYZUPE | 100 g ai/ha | 70 | 6 dat |
| Ex. No. I-A-26 According to the invention | 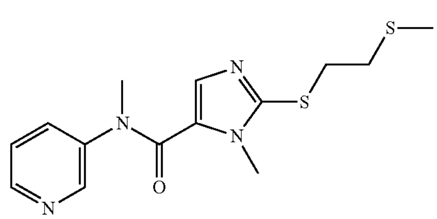 [SMILES: CSCCSc1ncc(C(=O)N(C)c2cccnc2)n1C] | MYZUPE | 100 g ai/ha | 70 | 6 dat |
| Ex. No. I-A-27 According to the invention | 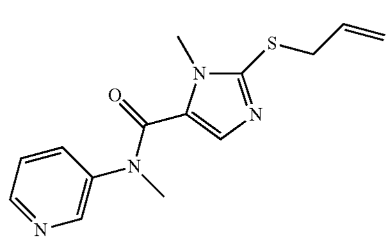 [SMILES: C=CCSc1ncc(C(=O)N(C)c2cccnc2)n1C] | MYZUPE | 100 g ai/ha | 70 | 6 dat |

-continued

| Substance | Structure | Animal species | Concentration | % efficacy | dat |
|---|---|---|---|---|---|
| Ex. No. I-A-38 According to the invention | 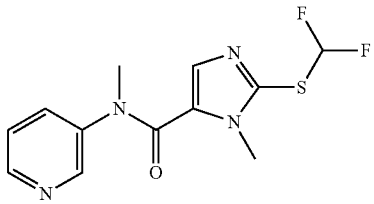 [SMILES: CN(C(=O)c1cnc(SC(F)F)n1C)c1cccnc1] | MYZUPE | 100 g ai/ha | 70 | 6 dat |
| Ex. No. I-A-43 According to the invention | 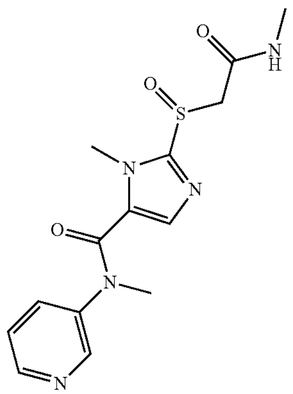 [SMILES: CNC(=O)CS(=O)c1ncc(C(=O)N(C)c2cccnc2)n1C] | MYZUPE | 100 g ai/ha | 70 | 6 dat |
| Ex. No. I-A-56 According to the invention | 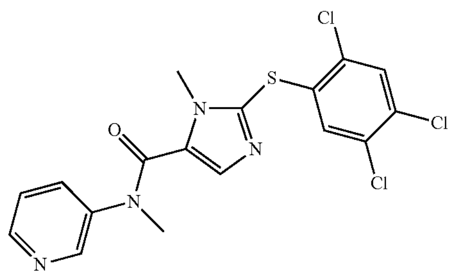 [SMILES: CN(C(=O)c1cnc(Sc2cc(Cl)c(Cl)cc2Cl)n1C)c1cccnc1] | MYZUPE | 100 g ai/ha | 70 | 6 dat |
| Ex. No. I-A-58 According to the invention | 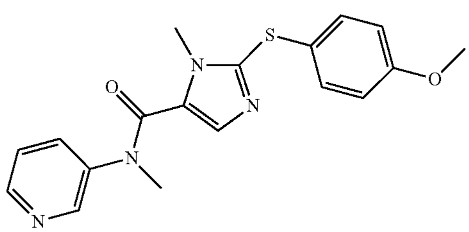 [SMILES: COc1ccc(Sc2ncc(C(=O)N(C)c3cccnc3)n2C)cc1] | MYZUPE | 100 g ai/ha | 70 | 6 dat |
| Ex. No. I-A-60 According to the invention | 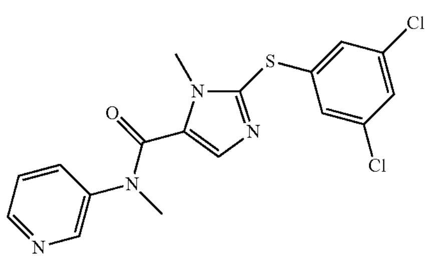 [SMILES: CN(C(=O)c1cnc(Sc2cc(Cl)cc(Cl)c2)n1C)c1cccnc1] | MYZUPE | 100 g ai/ha | 70 | 6 dat |
| Ex. No. I-A-62 According to the invention | 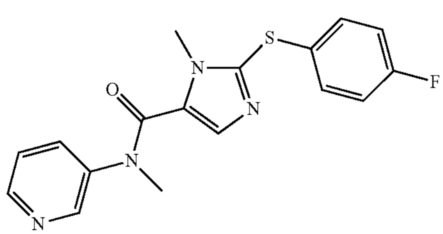 [SMILES: CN(C(=O)c1cnc(Sc2ccc(F)cc2)n1C)c1cccnc1] | MYZUPE | 100 g ai/ha | 70 | 6 dat |

-continued

| Substance | Structure | Animal species | Concentration | % efficacy | dat |
|---|---|---|---|---|---|
| Ex. No. I-A-64 According to the invention | 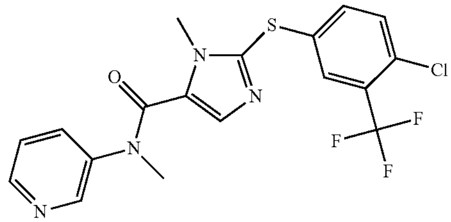 [SMILES: CN(C(=O)c1cnc(Sc2ccc(Cl)c(C(F)(F)F)c2)n1C)c1cccnc1] | MYZUPE | 100 g ai/ha | 70 | 6 dat |
| Ex. No. I-A-69 According to the invention | 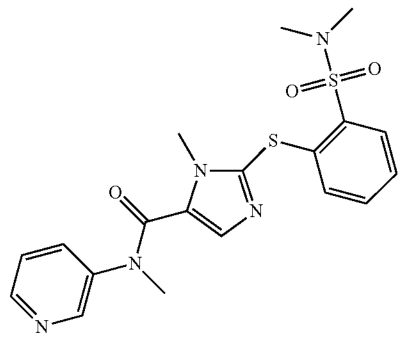 [SMILES: CN(C(=O)c1cnc(Sc2ccccc2S(=O)(=O)N(C)C)n1C)c1cccnc1] | MYZUPE | 100 g ai/ha | 70 | 6 dat |
| Ex. No. I-A-70 According to the invention | 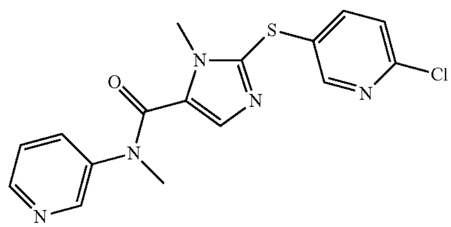 [SMILES: CN(C(=O)c1cnc(Sc2ccc(Cl)nc2)n1C)c1cccnc1] | MYZUPE | 100 g ai/ha | 70 | 6 dat |
| Ex. No. I-A-71 According to the invention | 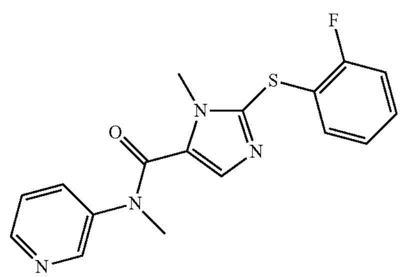 [SMILES: CN(C(=O)c1cnc(Sc2ccccc2F)n1C)c1cccnc1] | MYZUPE | 100 g ai/ha | 70 | 6 dat |
| Ex. No. I-A-77 According to the invention | 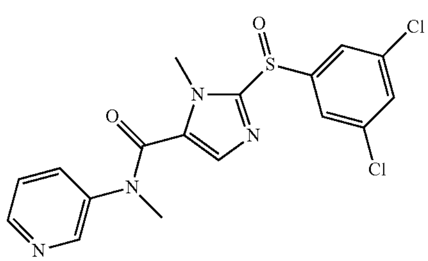 [SMILES: CN(C(=O)c1cnc(S(=O)c2cc(Cl)cc(Cl)c2)n1C)c1cccnc1] | MYZUPE | 100 g ai/ha | 70 | 6 dat |
| Ex. No. I-A-84 According to the invention | 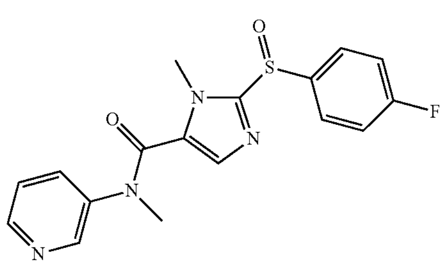 [SMILES: CN(C(=O)c1cnc(S(=O)c2ccc(F)cc2)n1C)c1cccnc1] | MYZUPE | 100 g ai/ha | 70 | 6 dat |

-continued

| Substance | Structure | Animal species | Concentration | % efficacy | dat |
|---|---|---|---|---|---|
| Ex. No. I-A-89 According to the invention | 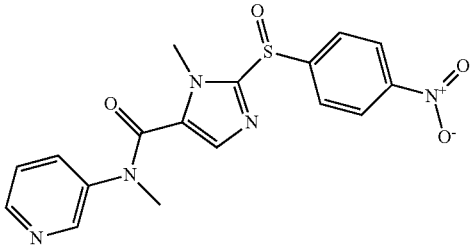 [SMILES: CN(C(=O)c1cnc(S(=O)c2ccc([N+](=O)[O-])cc2)n1C)c1cccnc1] | MYZUPE | 100 g ai/ha | 70 | 6 dat |
| Ex. No. I-A-93 According to the invention | 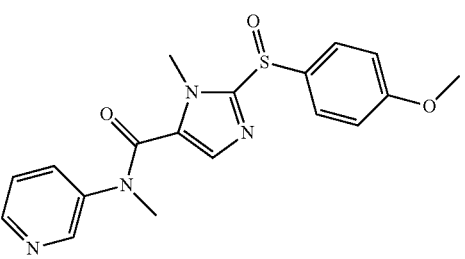 [SMILES: COc1ccc(S(=O)c2ncc(C(=O)N(C)c3cccnc3)n2C)cc1] | MYZUPE | 100 g ai/ha | 70 | 6 dat |
| Ex. No. I-A-97 According to the invention | 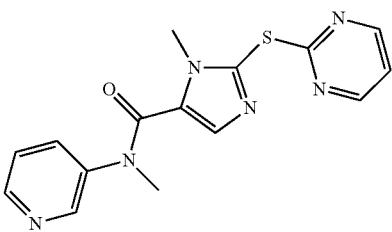 [SMILES: CN(C(=O)c1cnc(Sc2ncccn2)n1C)c1cccnc1] | MYZUPE | 100 g ai/ha | 70 | 6 dat |
| Ex. No. I-A-99 According to the invention | 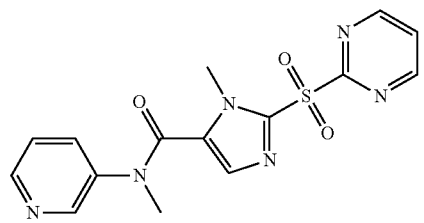 [SMILES: CN(C(=O)c1cnc(S(=O)(=O)c2ncccn2)n1C)c1cccnc1] | MYZUPE | 100 g ai/ha | 70 | 6 dat |
| Ex. No. I-A-108 According to the invention | 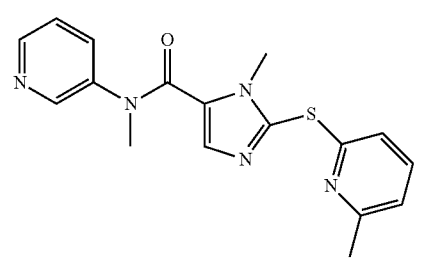 [SMILES: Cc1cccc(Sc2ncc(C(=O)N(C)c3cccnc3)n2C)n1] | MYZUPE | 100 g ai/ha | 70 | 6 dat |
| Ex. No. I-A-109 According to the invention | 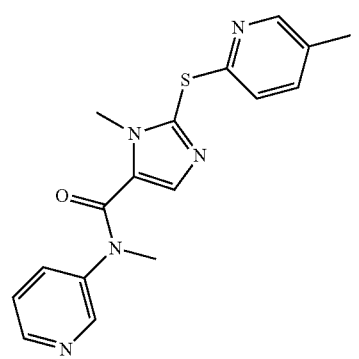 [SMILES: Cc1ccc(Sc2ncc(C(=O)N(C)c3cccnc3)n2C)nc1] | MYZUPE | 100 g ai/ha | 70 | 6 dat |

-continued

| Substance | Structure | Animal species | Concentration | % efficacy | dat |
|---|---|---|---|---|---|
| Ex. No. I-A-126 According to the invention | 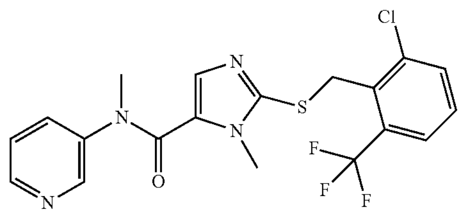 [SMILES: CN(C(=O)c1cnc(SCc2c(Cl)cccc2C(F)(F)F)n1C)c1cccnc1] | MYZUPE | 100 g ai/ha | 70 | 6 dat |
| Ex. No. I-A-140 According to the invention | 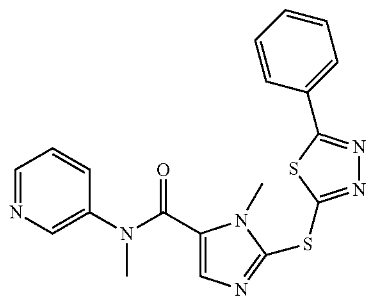 [SMILES: CN(C(=O)c1cnc(Sc2nnc(-c3ccccc3)s2)n1C)c1cccnc1] | MYZUPE | 100 g ai/ha | 70 | 5 dat |
| Ex. No. I-A-141 According to the invention | 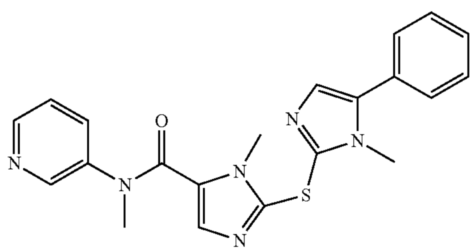 [SMILES: CN(C(=O)c1cnc(Sc2ncc(-c3ccccc3)n2C)n1C)c1cccnc1] | MYZUPE | 100 g ai/ha | 70 | 5 dat |
| Ex. No. I-A-145 According to the invention | 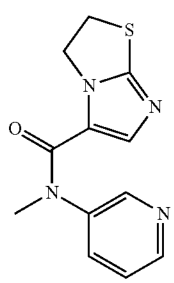 [SMILES: CN(C(=O)c1cnc2n1CCS2)c1cccnc1] | MYZUPE | 100 g ai/ha | 70 | 5 dat |
| Ex. No. I-A-146 According to the invention | 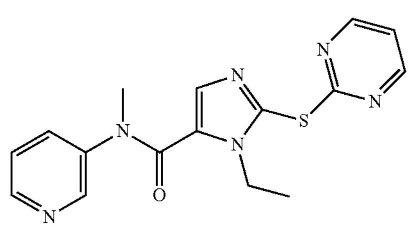 [SMILES: CCn1c(C(=O)N(C)c2cccnc2)cnc1Sc1ncccn1] | MYZUPE | 100 g ai/ha | 90 | 5 dat |

The invention claimed is:
1. A compound of formula (I)

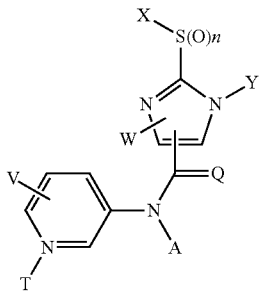

wherein
Q represents oxygen or sulphur,
V represents a radical selected from the group consisting of hydrogen, halogen, alkyl, haloalkyl, alkoxy, haloalkoxy and cyano,
W represents a radical selected from the group consisting of hydrogen, halogen, alkyl, haloalkyl, alkoxy, haloalkoxy and cyano,
X represents a radical selected from the group consisting of optionally substituted alkyl, alkenyl, alkynyl, optionally substituted cycloalkyl which is saturated or unsaturated and optionally interrupted by heteroatoms, optionally substituted cycloalkylalkyl which is saturated or unsaturated and optionally interrupted by heteroatoms, optionally substituted aryl, hetaryl, optionally substituted arylalkyl, hetarylalkyl and cyano,
Y represents a radical selected from the group consisting of hydrogen, optionally substituted alkyl, alkenyl, alkynyl, optionally substituted cycloalkyl which is optionally interrupted by heteroatoms, optionally substituted cycloalkylalkyl which is optionally interrupted by heteroatoms, arylalkyl, hetarylalkyl and cyano,
n represents a number 0, 1 or 2,
A represents a radical selected from the group consisting of hydrogen, optionally substituted alkyl, alkenyl, alkynyl and optionally substituted cycloalkyl and cycloalkylalkyl which are optionally interrupted by heteroatoms,
T represents oxygen or an electron pair,
and/or a salt thereof.
2. The compound according to claim 1, wherein
Q represents oxygen or sulphur,
V represents a radical selected from the group consisting of hydrogen, halogen, $C_1$-$C_4$-alkyl, $C_1$-$C_4$-haloalkyl, $C_1$-$C_4$-alkoxy, $C_1$-$C_4$-haloalkoxy and cyano,
W represents a radical selected from the group consisting of hydrogen, halogen, $C_1$-$C_4$-alkyl, $C_1$-$C_4$-haloalkyl, $C_1$-$C_4$-alkoxy, $C_1$-$C_4$-haloalkoxy and cyano,
X represents a radical selected from the group consisting of $C_1$-$C_8$-alkyl, $C_3$-$C_8$-alkenyl or $C_3$-$C_8$-alkynyl, optionally mono- or polysubstituted independently of one another by halogen, $C_1$-$C_4$-alkoxy, $C_1$-$C_4$-alkyl-S(O)$_m$—, cyano, C(O)OR$^2$, CONR$^2$R$^3$, and/or C(G)R$^2$; $C_3$-$C_8$-cycloalkyl or $C_5$-$C_8$-cycloalkenyl, optionally interrupted once or twice independently of one another by O, S(O)$_m$, C(G)R$^2$, NR$^4$ and optionally mono- to tetrasubstituted independently of one another by halogen, $C_1$-$C_4$-alkyl, $C_1$-$C_4$-haloalkyl, $C_1$-$C_4$-alkoxy, and/or cyano; straight-chain or branched $C_3$-$C_8$-cycloalkyl-$C_1$-$C_4$-alkyl or $C_5$-$C_8$-cycloalkenyl-$C_1$-$C_4$-alkyl, optionally interrupted once or twice independently of one another by O, S(O)$_m$, C(G)R$^2$, NR$^4$ and optionally mono- to tetrasubstituted independently of one another by halogen, $C_1$-$C_4$-alkyl, $C_1$-$C_4$-haloalkyl, $C_1$-$C_4$-alkoxy, and/or cyano; aryl, optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-S(O)$_m$—, $C_1$-$C_4$-haloalkoxy, $C_1$-$C_4$-haloalkyl-S(O)$_m$—, nitro and/or cyano; hetaryl, which can be optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-S(O)$_m$—, $C_1$-$C_4$-haloalkoxy, $C_1$-$C_4$-haloalkyl-S(O)$_m$—, nitro and/or cyano; and straight-chain or branched aryl-$C_1$-$C_4$-alkyl or hetaryl-$C_1$-$C_4$-alkyl, optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-S(O)$_m$—, $C_1$-$C_4$-haloalkoxy, $C_1$-$C_4$-haloalkyl-S(O)$_m$—, nitro and/or cyano,
G represents O, N—CN, or N—OR$^2$,
Y represents a radical selected from the group consisting of hydrogen; $C_1$-$C_6$-alkyl, $C_3$-$C_6$-alkenyl or $C_3$-$C_6$-alkynyl, optionally mono- or polysubstituted independently of one another by halogen, $C_1$-$C_4$-alkoxy, $C_1$-$C_4$-alkyl-S(O)$_m$—, and/or cyano; $C_3$-$C_8$-cycloalkyl, optionally mono- or disubstituted independently of one another by halogen, $C_1$-$C_4$-alkyl, $C_1$-$C_4$-haloalkyl, $C_1$-$C_4$-alkoxy, and/or cyano; straight-chain or branched $C_3$-$C_8$-cycloalkyl-$C_1$-$C_4$-alkyl, optionally interrupted once or twice independently of one another by O, S(O)$_m$, CO, NR$^4$ and optionally mono- to tetrasubstituted independently of one another by halogen, $C_1$-$C_4$-alkyl, $C_1$-$C_4$-haloalkyl, $C_1$-$C_4$-alkoxy, and/or cyano; arylalkyl or hetarylalkyl, optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-S(O)$_m$—, $C_1$-$C_4$-haloalkoxy, $C_1$-$C_4$-haloalkyl-S(O)$_m$—, nitro and/or cyano; and cyano,
m represents a number 0, 1 or 2,
n represents a number 0, 1 or 2,
A represents a radical selected from the group consisting of hydrogen; $C_1$-$C_6$-alkyl, $C_3$-$C_6$-alkenyl or $C_3$-$C_6$-alkynyl, optionally mono- or polysubstituted independently of one another by halogen, $C_1$-$C_4$-alkoxy, $C_1$-$C_4$-alkyl-S(O)$_m$—, and/or cyano; $C_3$-$C_6$-cycloalkyl, optionally mono- or disubstituted independently of one another by halogen, $C_1$-$C_4$-alkyl, $C_1$-$C_4$-haloalkyl, $C_1$-$C_4$-alkoxy, and/or cyano; and straight-chain or branched $C_3$-$C_8$-cycloalkyl-$C_1$-$C_4$-alkyl, optionally mono- or disubstituted independently of one another by halogen, $C_1$-$C_4$-alkyl, $C_1$-$C_4$-haloalkyl, $C_1$-$C_4$-alkoxy, and/or cyano,
R$^2$ represents a radical selected from the group consisting of hydrogen; $C_1$-$C_8$-alkyl, $C_3$-$C_8$-alkenyl or $C_3$-$C_8$-alkynyl, optionally mono- or polysubstituted independently of one another by halogen, $C_1$-$C_4$-alkoxy, and/or $C_1$-$C_4$-alkyl-S(O)$_m$—; $C_3$-$C_8$-cycloalkyl, optionally interrupted once by O, S(O)$_m$ and optionally mono- or disubstituted independently of one another by halogen, $C_1$-$C_4$-alkyl, $C_1$-$C_4$-haloalkyl, $C_1$-$C_4$-alkoxy, and/or cyano; straight-chain or branched $C_3$-$C_8$-cycloalkyl-$C_1$-$C_4$-alkyl, optionally interrupted once by O, S(O)$_n$ and optionally mono- or disubstituted independently of one another by halogen, $C_1$-$C_4$-alkyl, $C_1$-$C_4$-haloalkyl, $C_1$-$C_4$-alkoxy, and/or cyano; aryl or hetaryl, optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-S(O)$_m$—, $C_1$-$C_4$-haloalkoxy, $C_1$-$C_4$-haloalkyl-S(O)$_m$—, nitro and/or cyano; and straight-chain or branched aryl-$C_1$-$C_4$-alkyl or hetaryl-$C_1$-$C_4$-alkyl, optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-S(O)$_m$—, $C_1$-$C_4$-haloalkoxy, $C_1$-$C_4$-haloalkyl-S(O)$_m$—, nitro and/or cyano, $R^3$ represents a radical selected from the group consisting of hydrogen; $C_1$-$C_6$-alkyl, $C_3$-$C_6$-alkenyl or $C_3$-$C_6$-alkynyl, optionally mono- or polysubstituted independently of one another by halogen, $C_1$-$C_4$-alkoxy, $C_1$-$C_4$-alkyl-S(O)$_m$—, and/or cyano, $R^4$ represents a radical selected from the group consisting of hydrogen; and $C_1$-$C_6$-alkyl, $C_3$-$C_6$-alkenyl or $C_3$-$C_6$-alkynyl, optionally mono- or polysubstituted independently of one another by halogen, $C_1$-$C_4$-alkoxy, $C_1$-$C_4$-alkyl-S(O)$_m$—, and/or cyano, or represents the radical CONR$^2$R$^3$ COR$^2$, wherein $R^2$ and $R^3$ are as defined above, T represents oxygen or an electron pair, and/or a salt thereof.

3. The compound according to claim 1, wherein

Q represents oxygen,

Y represents a radical selected from the group consisting of hydrogen, fluorine, chlorine, bromine, methyl, ethyl, difluoromethyl, trifluoromethyl, methoxy, ethoxy, difluoromethoxy, trifluoromethoxy and cyano, W represents a radical selected from the group consisting of hydrogen, fluorine, chlorine, bromine, methyl, ethyl, difluoromethyl, trifluoromethyl, methoxy, ethoxy, difluoromethoxy, trifluoromethoxy and cyano, X represents a radical selected from the group consisting of $C_1$-$C_6$-alkyl, $C_3$-$C_6$-alkenyl or $C_3$-$C_6$-alkynyl, optionally mono- to heptasubstituted independently of one another by fluorine, chlorine, bromine, methoxy, ethoxy, methyl-S(O)$_m$—, ethyl-S(O)$_m$—, cyano, C(O)OR$^2$, CONR$^2$R$^3$, and/or C(G)R$^2$; $C_3$-$C_6$-cycloalkyl, optionally interrupted once or twice independently of one another by O, S(O)$_m$, CO, NR$^4$ and optionally mono- or disubstituted independently of one another by fluorine, chlorine, bromine, methyl, ethyl, trifluoromethyl, methoxy, ethoxy, and/or cyano; straight-chain or branched $C_3$-$C_6$-cycloalkyl-$C_1$-$C_2$-alkyl, optionally interrupted once or twice independently of one another by O, S(O)$_m$, CO, NR$^4$ and optionally mono- or disubstituted independently of one another by fluorine, chlorine, bromine, methyl, ethyl, trifluoromethyl, methoxy, ethoxy, and/or cyano; phenyl, naphthyl, pyridyl, pyrimidyl, pyridazinyl, pyrazinyl, triazinyl, furanyl, thienyl, oxazolyl, isoxazolyl, thiazolyl, isothiazolyl, pyrazolyl, imidazolyl, oxadiazolyl, thiadiazolyl, triazolyl, benzimidazolyl or imidazopyridinyl, which may optionally be substituted by phenyl which is mono- to trisubstituted independently of one another by fluorine, chlorine, methyl, ethyl, difluoromethyl, trifluoromethyl, methoxy, ethoxy, methyl-S(O)m-, ethyl-S(O)m-, difluoromethoxy, trifluoromethoxy, trifluoromethyl-S(O)m-, difluoroethyl-S(O)m-, trifluoromethyl-S(O)m-, nitro and/or cyano, or which may optionally be mono- or disubstituted independently of one another by fluorine, chlorine, bromine, methyl, ethyl, difluoromethyl, trifluoromethyl, methoxy, ethoxy, methyl-S(O)$_m$—, ethyl-S(O)$_n$—, difluoromethoxy, trifluoromethoxy, trifluoromethyl-S(O)$_m$—, difluoroethyl-S(O)$_m$—, trifluoroethyl-S(O)$_m$—, nitro and/or cyano; straight-chain or branched phenyl-$C_1$-$C_2$-alkyl, pyridyl-$C_1$-$C_2$-alkyl, pyrimidyl-$C_1$-$C_2$-alkyl, thiazolyl-$C_1$-$C_2$-alkyl or pyrazolyl-$C_1$-$C_2$-alkyl, optionally mono- or disubstituted independently of one another by fluorine, chlorine, bromine, methyl, ethyl, difluoromethyl, trifluoromethyl, methoxy, ethoxy, Me-S(O)$_m$—, Et-S(O)$_m$—, difluoromethoxy, trifluoromethoxy, trifluoromethyl-S(O)$_m$—, difluoroethyl-S(O)$_m$—, trifluoroethyl-S(O)$_m$—, nitro and/or cyano; and cyano, G represents O or N—OR$^2$, Y represents a radical selected from the group consisting of hydrogen; $C_1$-$C_4$-alkyl, $C_3$-$C_4$-alkenyl or $C_3$-$C_4$-alkynyl, optionally mono- to pentasubstituted independently of one another by fluorine, chlorine, bromine, methoxy, ethoxy, methyl-S(O)$_m$—, ethyl-S(O)$_m$—, and/or cyano; $C_3$-$C_6$-cycloalkyl, optionally mono- or disubstituted independently of one another by fluorine, chlorine, bromine, methyl, ethyl, trifluoromethyl, methoxy, ethoxy, and/or cyano; straight-chain or branched $C_3$-$C_6$-cycloalkyl-$C_1$-$C_2$-alkyl, optionally interrupted once or twice independently of one another by O, S(O)$_m$, CO, NR$^4$ and optionally mono- to tetrasubstituted independently of one another by fluorine, chlorine, bromine, methyl, ethyl, trifluoromethyl, methoxy, ethoxy, and/or cyano; aryl-$C_1$-$C_2$-alkyl or hetaryl-$C_1$-$C_2$-alkyl, optionally mono- or disubstituted independently of one another by fluorine, chlorine, bromine, methyl, ethyl, $C_1$-$C_4$-haloalkyl, trifluoromethyl, methoxy, ethoxy, cyano, nitro and/or cyano; and cyano, m represents a number 0, 1 or 2, n represents a number 0, 1 or 2, A represents a radical selected from the group consisting of hydrogen; $C_1$-$C_6$-alkyl, $C_3$-$C_6$-alkenyl or $C_3$-$C_6$-alkynyl, optionally mono- to pentasubstituted independently of one another by fluorine, chlorine, bromine, methoxy, ethoxy, methyl-S(O)$_m$—, ethyl-S(O)$_m$—, and/or cyano; $C_3$-$C_6$-cycloalkyl, optionally mono- or disubstituted independently of one another by fluorine, chlorine, bromine, methyl, ethyl, trifluoromethyl, methoxy, ethoxy, and/or cyano; and straight-chain or branched $C_3$-$C_6$-cycloalkyl-$C_1$-$C_2$-alkyl, optionally mono- or disubstituted independently of one another by fluorine, chlorine, bromine, methyl, ethyl, trifluoromethyl, methoxy, ethoxy, and/or cyano, R$^2$ represents a radical selected from the group consisting of hydrogen; $C_1$-$C_6$-alkyl, $C_3$-$C_6$-alkenyl or $C_3$-$C_6$-alkynyl, optionally mono- to pentasubstituted independently of one another by fluorine, chlorine, bromine, methoxy, ethoxy, methyl-S(O)$_m$—, and/or ethyl-S(O)$_m$—; $C_3$-$C_6$-cycloalkyl, optionally interrupted once by O, S(O)$_m$, and optionally mono- or disubstituted independently of one another by fluorine, chlorine, bromine, methyl, ethyl, trifluoromethyl, methoxy, ethoxy, and/or cyano; straight-chain or branched $C_3$-$C_6$-cycloalkyl-$C_1$-$C_2$-alkyl, optionally interrupted once by O, S(O)$_m$ and optionally mono- or disubstituted independently of one another by fluorine, chlorine, bromine, methyl, ethyl, trifluoromethyl, methoxy, ethoxy, and/or cyano; phenyl or pyridyl, optionally mono- or disubstituted independently of one another by fluorine, chlorine, bromine, methyl, ethyl, difluoromethyl, trifluoromethyl, methoxy, ethoxy, methyl-S(O)$_m$—, ethyl-S(O)$_m$—, difluoromethoxy, trifluoromethoxy, trifluoromethyl-S(O)$_m$—, difluoroethyl-S(O)$_m$—, trifluoroethyl-S(O)$_m$—, nitro and/or cyano;

and straight-chain or branched phenyl-$C_1$-$C_2$-alkyl, pyridyl-$C_1$-$C_2$-alkyl, pyrimidyl-$C_1$-$C_2$-alkyl or thiazolyl-$C_1$-$C_2$-alkyl, optionally mono- or disubstituted independently of one another by fluorine, chlorine, bromine, methyl, ethyl, difluoromethyl, trifluoromethyl, methoxy, ethoxy, methyl-$S(O)_m$—, ethyl-$S(O)_m$—, difluoromethoxy, trifluoromethoxy, trifluoromethyl-$S(O)_n$—, difluoroethyl-$S(O)_n$—, trifluoroethyl-$S(O)_n$—, nitro and/or cyano, $R^3$ represents a radical selected from the group consisting of hydrogen; and $C_1$-$C_4$-alkyl, $C_3$-$C_4$-alkenyl or $C_3$-$C_4$-alkynyl, optionally mono- to pentasubstituted independently of one another by fluorine, chlorine, bromine, methoxy, ethoxy, methyl-$S(O)_m$—, ethyl-$S(O)_m$—, and/or cyano, $R^4$ represents a radical selected from the group consisting of hydrogen; and $C_1$-$C_4$-alkyl, $C_3$-$C_4$-alkenyl or $C_3$-$C_4$-alkynyl, optionally mono- to pentasubstituted independently of one another by fluorine, chlorine, bromine, methoxy, ethoxy, methyl-$S(O)_m$—, ethyl-$S(O)_m$—, cyano, and/or represents the radical $CONR^2R^3$ or $COR^2$, wherein $R^2$ and $R^3$ are as defined above, T represents oxygen or an electron pair, and/or a salt thereof.

4. The compound of formula (I-A)

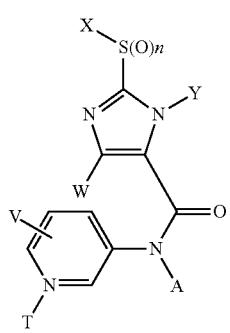

(I-A)

according to claim 1, and/or salt thereof.

5. The compound of formula (I-B)

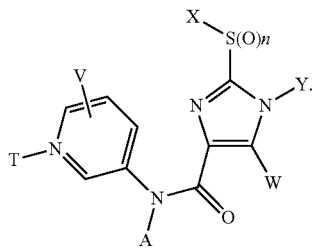

(I-B)

according to claim 1, and/or salt thereof.

6. The compound according to claim 4 wherein

V represents a radical selected from the group consisting of hydrogen, fluorine, chlorine, methyl and cyano, W represents a radical selected from the group consisting of hydrogen, fluorine, chlorine, bromine, methyl, ethyl and cyano, X represents a radical selected from the group consisting of $C_1$-$C_6$-alkyl, $C_3$-$C_4$-alkenyl or $C_3$-$C_4$-alkynyl, which are optionally mono-, di-, tri-, tetra-, pentasubstituted independently of one another by fluorine, chlorine, bromine, methoxy, ethoxy, methyl-$S(O)_m$—, ethyl-$S(O)_m$—, and/or cyano and may optionally be mono-substituted by the groups $C(O)OR^2$, $CONR^2R^3$, $C(G)R^2$; $C_3$-$C_6$-cycloalkyl, optionally interrupted once or twice independently of one another by O, $S(O)_m$, CO, $NR^4$ and optionally mono- or disubstituted independently of one another by fluorine, chlorine, methyl, ethyl, trifluoromethyl, methoxy, and/or cyano; $C_3$-$C_6$-cycloalkyl-methyl, optionally interrupted once or twice independently of one another by O, $S(O)_m$, CO, $NR^4$ and optionally mono- or disubstituted independently of one another by fluorine, chlorine, methyl, ethyl, trifluoromethyl, methoxy, and/or cyano; phenyl, pyridyl, pyrimidyl, thienyl, thiazolyl, oxazolyl, imidazolyl, oxadiazolyl, thiadiazolyl, triazolyl, benzimidazolyl or imidazopyridinyl, which may optionally be substituted by phenyl which is mono- or disubstituted independently of one another by fluorine, chlorine, methyl, ethyl, difluoromethyl, trifluoromethyl, methoxy, ethoxy, methyl-S(O)m-, ethyl-S(O)n-, difluoromethoxy, trifluoromethoxy, trifluoromethyl-S(O)m-, difluoroethyl-S(O)m-, trifluoroethyl-S(O)m-, nitro and/or cyano, or which may optionally be mono- or disubstituted independently of one another by fluorine, chlorine, bromine, methyl, ethyl, difluoromethyl, trifluoromethyl, methoxy, ethoxy, methyl-$S(O)_m$—, ethyl-$S(O)_m$—, difluoromethoxy, trifluoromethoxy, trifluoromethyl-$S(O)_m$—, difluoroethyl-$S(O)_m$—, trifluoroethyl-$S(O)_m$—, nitro and/or cyano; benzyl, pyridylmethyl, pyrimidylmethyl, thiazolylmethyl or pyrazolyl-$C_1$-$C_2$-alkyl, optionally mono- or disubstituted independently of one another by fluorine, chlorine, bromine, methyl, ethyl, difluoromethyl, trifluoromethyl, methoxy, ethoxy, Me-$S(O)_m$—, Et-$S(O)_m$—, difluoromethoxy, trifluoromethoxy, trifluoromethyl-S(O)$_n$—, difluoroethyl-$S(O)_m$—, trifluoroethyl-$S(O)_m$—, nitro and/or cyano; and cyano, G represents O or N—$OR^2$, Y represents a radical selected from the group consisting of hydrogen; and methyl, ethyl, propyl, allyl, propargyl or benzyl, optionally mono- to trisubstituted independently of one another by fluorine, methoxy, ethoxy, and/or cyano, m represents a number 0, 1 or 2, n represents a number 0, 1 or 2, A represents a radical selected from the group consisting of hydrogen; and methyl, ethyl, propyl, allyl, propargyl, cyclopropyl or cyclopropylmethyl, optionally mono- to trisubstituted independently of one another by fluorine, methoxy, ethoxy, and/or cyano, $R^2$ represents a radical selected from the group consisting of hydrogen; $C_1$-$C_6$-alkyl, $C_3$-$C_6$-alkenyl or $C_3$-$C_6$-alkynyl, optionally mono- to trisubstituted independently of one another by fluorine, chlorine, methoxy, ethoxy, methyl-$S(O)_m$—, and/or ethyl-$S(O)_m$—; $C_3$-$C_6$-cycloalkyl, optionally interrupted once by O, $S(O)_m$ and optionally mono- or disubstituted independently of one another by fluorine, chlorine, methyl, ethyl, trifluoromethyl, methoxy, and/or cyano; $C_3$-$C_6$-cycloalkylmethyl, optionally interrupted once by O, $S(O)_m$ and optionally mono- or disubstituted independently of one another by fluorine, chlorine, methyl, ethyl, trifluoromethyl, methoxy, and/or cyano; phenyl or pyridyl, optionally mono- or disubstituted independently of one another by fluorine, chlorine, bromine, methyl, ethyl, difluoromethyl, trifluoromethyl, methoxy, ethoxy, methyl-$S(O)_m$—, ethyl-$S(O)_m$—, difluoromethoxy, trifluoromethoxy, trifluoromethyl-$S(O)_m$—, difluoroethyl-$S(O)_m$—, trifluoroethyl-$S(O)_m$—, nitro and/or cyano; and benzyl, pyridylmethyl, pyrimidylmethyl or thiazolylmethyl, optionally mono- or disubstituted independently of one another by fluorine, chlorine, bromine, methyl, ethyl, difluoromethyl, trifluoromethyl, methoxy, ethoxy, methyl-$S(O)_m$—, ethyl-$S(O)_m$—, difluoromethoxy, trifluoromethoxy, trifluoromethyl-$S(O)_m$—, difluoroethyl-$S(O)_m$—, trifluoroethyl-$S(O)_m$—, nitro and/or cyano, $R^3$ represents a radical selected from the group consisting of hydrogen; and $C_1$-$C_4$-alkyl, $C_3$-$C_4$-alkenyl or $C_3$-$C_4$-alkynyl, optionally mono- to trisubstituted independently of one another by fluorine, chlorine, bromine, methoxy, ethoxy, methyl-$S(O)_m$—, ethyl-$S(O)_m$—, and/or cyano, $R^4$ represents a radical selected from the group consisting of hydrogen; and $C_1$-$C_4$-alkyl, $C_3$-$C_4$-alkenyl or $C_3$-$C_4$-alkynyl, optionally mono- to trisubstituted independently of one another by fluorine, chlorine, bromine, methoxy, ethoxy, methyl-$S(O)_m$—, ethyl-$S(O)_m$—, and/or cyano; or represents the radical $CONR^2R^3$ or $COR^2$, wherein $R^2$ and $R^3$ are as defined above, T represents oxygen or an electron pair, and/or a salt thereof.

7. The compound according to claim 4 wherein

V represents hydrogen or fluorine,

W represents a radical selected from the group consisting of hydrogen, chlorine, bromine and methyl, X represents a radical selected from the group consisting of methyl, ethyl, propyl, isopropyl, butyl, isobutyl, sec-butyl, tert-butyl, pentyl, isopentyl, 2,2-dimethylpropyl, hexyl, neohexyl, allyl, methallyl, 2-butenyl, propargyl, and 2-butynyl, which are optionally mono- to trisubstituted independently of one another by fluorine, chlorine, bromine, methoxy, ethoxy, methylsulphanyl, ethylsulphanyl, methylsulphinyl, ethylsulphinyl, methylsulphonyl, and/or ethylsulphonyl and may optionally be monosubstituted by the groups $C(O)OR^2$, $CONR^2R^3$, and/or $C(G)R^2$; cyclopropyl, cyclobutyl, cyclopentyl or cyclohexyl, optionally interrupted once or twice independently of one another by O, $S(O)_m$, CO, $NR^4$ and optionally mono- or disubstituted independently of one another by fluorine, chlorine, methyl, ethyl, trifluoromethyl, methoxy, and/or cyano; cyclopropylmethyl, cyclobutylmethyl, cyclopentylmethyl or cyclohexylmethyl, optionally interrupted once or twice independently of one another by O, $S(O)_m$, CO, $NR^4$ and optionally mono- or disubstituted independently of one another by fluorine, chlorine, methyl, ethyl, trifluoromethyl, methoxy, and/or cyano; phenyl, pyridyl, pyrimidyl, thienyl, thiazolyl, oxazolyl, imidazolyl, oxadiazolyl, thiadiazolyl, triazolyl, benzimidazolyl or imidazopyridinyl, which may optionally be substituted by phenyl, optionally mono- or disubstituted independently of one another by fluorine, chlorine, bromine, methyl, ethyl, difluoromethyl, trifluoromethyl, methoxy, ethoxy, methylsulphanyl, ethylsulphanyl, methylsulphinyl, ethylsulphinyl, methylsulphonyl, ethylsulphonyl, difluoromethoxy, trifluoromethoxy, trifluoromethylsulphanyl, trifluoromethylsulphinyl, trifluoromethylsulphonyl, difluoromethylsulphanyl, difluoromethylsulphinyl, difluoromethylsulphonyl, trifluoroethylsulphanyl, trifluoroethylsulphinyl trifluoroethylsulphonyl, nitro and/or cyano; benzyl, pyridylmethyl, pyrimidylmethyl, thiazolylmethyl or pyrazolyl-$C_1$-$C_2$-alkyl, optionally mono- or disubstituted independently of one another by fluorine, chlorine, bromine, methyl, ethyl, difluoromethyl, trifluoromethyl, methoxy, ethoxy, methylsulphanyl, ethylsulphanyl, methylsulphinyl, ethylsulphinyl, methylsulphonyl, ethylsulphonyl, difluoromethoxy, trifluoromethoxy, trifluoromethylsulphanyl, trifluoromethylsulphinyl, trifluoromethylsulphonyl, difluoromethylsulphanyl, difluoromethylsulphinyl, difluoromethylsulphonyl, trifluoroethylsulphanyl, trifluoroethylsulphinyl trifluoroethylsulphonyl, nitro and/or cyano; and cyano, G represents O or N—$OR^2$, Y represents a radical selected from the group consisting of hydrogen, methyl, ethyl, propyl, difluoroethyl, trifluoroethyl, methoxymethyl, ethoxymethyl, cyanomethyl and benzyl, m represents a number 0, 1 or 2, n represents a number 0, 1 or 2, A represents a radical selected from the group consisting of hydrogen, methyl, ethyl, propyl, difluoroethyl, trifluoroethyl, methoxymethyl, ethoxymethyl, cyanomethyl, allyl, propargyl, cylopropyl and cyclopropylmethyl, $R^2$ represents a radical selected from the group consisting of hydrogen; methyl, ethyl, propyl, isopropyl, n-butyl, isobutyl, sec-butyl, tert-butyl, allyl, methallyl, 2-butenyl, propargyl or 2-butynyl, optionally mono- to trisubstituted independently of one another by fluorine, chlorine, methoxy, and/or ethoxy; cyclopropyl, cyclobutyl, cyclopentyl or cyclohexyl, optionally interrupted once by O or $S(O)_m$ and optionally mono- or disubstituted independently of one another by fluorine, chlorine, methyl, ethyl, trifluoromethyl, methoxy, and/or cyano; cyclopropylmethyl, cyclobutylmethyl, cyclopentylmethyl or cyclohexylmethyl, optionally interrupted once by O or $S(O)_m$ and optionally mono- or disubstituted independently of one another by fluorine, chlorine, methyl, ethyl, trifluoromethyl, methoxy, and/or cyano; phenyl or pyridyl, optionally mono- or disubstituted independently of one another by fluorine, chlorine, bromine, methyl, ethyl, difluoromethyl, trifluoromethyl, methoxy, ethoxy, methylsulphanyl, ethylsulphanyl, methylsulphinyl, ethylsulphinyl, methylsulphonyl, ethylsulphonyl, difluoromethoxy, trifluoromethoxy, trifluoromethylsulfanyl, trifluoromethylsulphinyl, trifluoromethylsulphonyl, difluoromethylsulphanyl, difluoromethylsulphinyl, difluoromethylsulphonyl, trifluoroethylsulphanyl, trifluoroethylsulphinyl, trifluoroethylsulphonyl, nitro and/or cyano; and benzyl, pyridylmethyl, pyrimidylmethyl or thiazolylmethyl, optionally mono- or disubstituted independently of one another by fluorine, chlorine, bromine, methyl, ethyl, difluoromethyl, trifluoromethyl, methoxy, ethoxy, difluoromethoxy, trifluoromethoxy, nitro and/or cyano, $R^3$ represents a radical selected from the group consisting of hydrogen, methyl, ethyl, propyl, isopropyl, butyl, isobutyl and allyl, $R^4$ represents a radical selected from the group consisting of hydrogen; and methyl, ethyl, propyl, isopropyl, butyl, isobutyl, or allyl, which may optionally be substituted once to three times independently of one another by fluorine, methoxy, ethoxy, or cyano; or represents the radical $CONR^2R^3$ or $COR^2$, wherein $R^2$ and $R^3$ are as defined above, T represents oxygen or an electron pair, and/or a salt thereof.

8. The compound of formula (I-A)

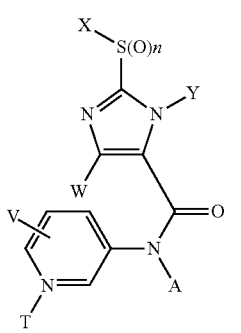

(I-A)

according to claim 1, wherein
V represents hydrogen,
W represents a radical selected from the group consisting of hydrogen, chlorine and bromine,
X represents a radical selected from the group consisting of methyl, ethyl, n-butyl, n-pentyl, n-propyl, isopropyl, allyl, 3,3-dimethylallyl, propargyl, cyclohexyl, tetrahydropyranyl, tetrahydrothiopyranyl, 3-oxetanyl, 5-oxa-[3.3.0]-bicycloheptanyl, methoxyethyl, methoxypropyl, ethoxyethyl, ethylthioethyl, methylthioethyl, difluoromethyl, trifluoromethyl, 2,2,2-trifluoroethyl, 3,3,3-trifluoropropyl, 3-chloro-2,2,3,3-tetrafluoropropyl, 3-fluoropropyl, 3,3-difluoropropyl, 2,2,2-trifluoroethylthioethyl, methylcarbonylmethyl, cyclopropylcarbonylmethyl, tert-butylcarbonylmethyl, methoxycarbonylmethyl, ethoxycarbonylmethyl, hydroxycarbonylmethyl, carbamoylmethyl, N-methylcarbamoylmethyl, N-cyclopropylcarbamoylmethyl, N,N-dimethylcarbamoylmethyl, 2-methoximinopropyl, cyclopropylmethyl, phenyl, 4-methylphenyl, 2-nitrophenyl, 3-methylthiophenyl, 4-chlorophenyl, 4-fluorophenyl, 4-tert-butylphenyl, 4-methoxyphenyl, 4-nitrophenyl, 4-diemethylaminophenyl, 2-fluorophenyl, 2-methoxyphenyl, 2-dimethylaminosulphonylphenyl, 2-dimethylaminocarbamoylphenyl, 3-nitrophenyl, 3-trifluoromethylphenyl, 3-chlorophenyl, 2,5-dichlorophenyl, 3,5-dichlorophenyl, 4-chloro-3-trifluoromethylphenyl, 2,4,5-trichlorophenyl, 2-pyridyl, 5-(2-chloro)pyridyl, 2-(5-methyl)pyridyl, 2-(6-methyl)pyridyl, 2-(3-trifluoromethyl)pyridyl, 2-pyrimidyl, 2-(4-methyl)pyrimidyl, 2-(5-methyl)pyrimidyl, 2-(4-methoxy)pyrimidyl, 2-(5-fluoro)pyrimidyl, 2-(4-trifluoromethyl)pyrimidyl, 2-(5-trifluoromethyl)pyrimidyl, 2-(4,6-dimethyl)pyrimidyl, 2-(4,5-dimethyl)pyrimidyl, 2-(4,6-dimethoxy)pyrimidyl, —CH$_2$-2-pyrimidyl, —CH$_2$-2-pyrazinyl, —CH$_2$-5-(1-methyl)imidazolyl, —CH$_2$-3-(1-methyl)pyrazolyl, —CH$_2$-4-pyridyl, —CH$_2$-2-pyridyl, —CH$_2$-2-(1-methyl)imidazolyl, —CH$_2$-3-pyridyl, —CH$_2$-2-furanyl, —CH$_2$-5-(2-chloro)pyridyl, benzyl, 3,4-dichlorobenzyl, 2,6-difluorobenzyl, 2-fluoro-6-methoxybenzyl, 2,6-dichlorobenzyl, 2-chloro-6-trifluoromethylbenzyl, 2-chloro-6-fluorobenzyl, —CH$_2$-2-(4,6-dimethoxy)pyrimidyl, 2,6-dimethylbenzyl, —CH$_2$-1-(3-nitro-5-methyl)pyrazolyl, 2-(1-methyl)benzimidazolyl, 2-(5-methyl)oxadiazolyl, 2-[3-methyl-6-(trifluoromethyl)imidazo[4.5]pyridinyl, 3-[4-ethyl-5-(trifluoromethyl)]-1,2,4-triazolyl, 3-[4-methyl-5-(trifluoromethyl)]-1,2,4-triazolyl, 3-[4-methyl-5-(difluoromethyl)]-1,2,4-triazolyl, 2-(5-phenyl)-1,3,4-thiadiazolyl, 2-(1-methyl-5-phenyl)imidazolyl, 2-(4,5-dimethyl)oxazolyl, 2-(1-methyl-5-methoxycarbonyl)imidazolyl, 2-(1-methyl)imidazolyl, and 1,2-ethanediyl,
Y represents methyl, ethyl or benzyl,
n represents a number 0 or 2,
A represents hydrogen or methyl,
T represents an electron pair,
and/or a salt thereof;
or
a compound of formula (I-B)

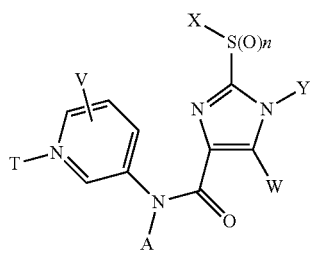

(I-B)

according to claim 1, where
V represents hydrogen,
W represents a radical selected from the group consisting of hydrogen, chlorine and bromine
X represents a radical selected from the group consisting of 4,6-dimethylpyrimidyl, n-butyl, n-pentyl, benzyl, methyl, 3-methylthiophenyl, 2,2,2-trifluoroethyl, phenyl, 4-methylphenyl, pyrimidyl, ethylthioethyl, 2-nitrophenyl, and cyclopropylmethyl,
Y represents methyl,
n represents a number 0 or 2,
A represents hydrogen or methyl,
T represents an electron pair,
and/or a salt thereof.

9. The compound of formula (I-A) or (I-B) according to claim 8, wherein
W represents hydrogen and
A represents methyl.

10. The compound according to claim 1, wherein W is hydrogen, Y is $C_1$-$C_6$-alkyl, and A is $C_1$-$C_6$-alkyl.

11. A composition, comprising at least one compound according to claim 1 and one or more customary extenders and/or surfactants optionally for controlling one or more animal pests.

12. An agrochemical formulation comprising at least one compound according to claim 1 in a biologically effective amount of from 0.00000001 to 98% by weight based on the weight of the agrochemical formulation, and one or more extenders and/or surfactants.

13. The agrochemical formulation according to claim 12, additionally comprising a further agrochemically active compound.

14. A method for controlling one or more animal pests, comprising allowing at least one compound according to claim 1 or a composition thereof to act on the animal pests and/or a habitat thereof.

15. A method according to claim 14, where surgical, therapeutic and diagnostic treatment of the human or animal body is excluded.

16. A product comprising at least one compound according to claim 1 for controlling one or more animal pests.

17. A product comprising at least one compound according to claim 1 for protecting propagation material of one or more plants.

* * * * *